(12) United States Patent
Cagle et al.

(10) Patent No.: US 11,185,455 B2
(45) Date of Patent: *Nov. 30, 2021

(54) TABLE ADAPTERS FOR MOUNTING ROBOTIC ARMS TO A SURGICAL TABLE

(71) Applicant: Verb Surgical Inc., Mountain View, CA (US)

(72) Inventors: David Cagle, Belmont, CA (US); Pablo E. Garcia Kilroy, Menlo Park, CA (US); Karen Shakespear Koenig, San Jose, CA (US); Jacob Spencer Gee, Cincinnati, OH (US); Wayne Grout, San Francisco, CA (US); Michael P. Schaller, Redwood City, CA (US)

(73) Assignees: Verb Surgical Inc., Santa Clara, CA (US); Maquet GmbH, Rastatt (DE)

( * ) Notice: Subject to any disclaimer, the term of this patent is extended or adjusted under 35 U.S.C. 154(b) by 159 days.

This patent is subject to a terminal disclaimer.

(21) Appl. No.: 15/706,087

(22) Filed: Sep. 15, 2017

(65) Prior Publication Data
US 2018/0078439 A1    Mar. 22, 2018

Related U.S. Application Data

(60) Provisional application No. 62/417,211, filed on Nov. 3, 2016, provisional application No. 62/395,807, filed on Sep. 16, 2016.

(51) Int. Cl.
*A61G 13/10* (2006.01)
*A61B 34/30* (2016.01)
(Continued)

(52) U.S. Cl.
CPC ............ *A61G 13/101* (2013.01); *A61B 34/30* (2016.02); *A61B 34/32* (2016.02); *A61B 34/70* (2016.02);
(Continued)

(58) Field of Classification Search
CPC .. A61G 13/101; A61G 2210/50; A61B 34/70; A61B 34/57; A61B 34/32;
(Continued)

(56) References Cited

U.S. PATENT DOCUMENTS

| | | | | |
|---|---|---|---|---|
| 5,855,583 A | * | 1/1999 | Wang | A61B 17/11 318/568.11 |
| 5,876,325 A | * | 3/1999 | Mizuno | A61B 1/00048 600/102 |

(Continued)

FOREIGN PATENT DOCUMENTS

| | | |
|---|---|---|
| CN | 102006834 | 4/2011 |
| CN | 104783900 A | 7/2015 |

(Continued)

OTHER PUBLICATIONS

Written Opinion of the International Search Authority dated Nov. 16, 2017 for WO Application No. PCT/US17/051805.

(Continued)

*Primary Examiner* — Nicholas F Polito
*Assistant Examiner* — Morgan J McClure
(74) *Attorney, Agent, or Firm* — Womble Bond Dickinson (US) LLP

(57) ABSTRACT

In some embodiments, an apparatus can include a surgical table and an adapter coupled thereto. The adapter includes an interface structure, a first link member pivotally coupled to the interface structure at a first joint, and coupled to a second link member of the adapter at a second joint. The second link member can also be coupleable to a robotic arm via a coupling. The first joint can allow the first link member to rotate about a first axis defined in a vertical direction relative to the table top, and the second joint can allow the second link member and a robotic arm coupled thereto to move in a vertical direction relative to the table top. The first (Continued)

link member and the second link member collectively provide for movement of the robotic arm in at least one of a lateral, longitudinal or vertical direction relative to the table top.

35 Claims, 98 Drawing Sheets

(51) Int. Cl.
| | |
|---|---|
| *A61B 34/32* | (2016.01) |
| *A61B 34/00* | (2016.01) |
| *A61B 90/57* | (2016.01) |
| *A61B 17/00* | (2006.01) |

(52) U.S. Cl.
CPC .... *A61B 90/57* (2016.02); *A61B 2017/00305* (2013.01); *A61B 2017/00477* (2013.01); *A61B 2090/571* (2016.02); *A61G 2210/50* (2013.01)

(58) Field of Classification Search
CPC .......... A61B 34/30; A61B 2017/00305; A61B 2017/00477; A61B 2090/571
See application file for complete search history.

(56) References Cited

U.S. PATENT DOCUMENTS

| | | | | |
|---|---|---|---|---|
| 6,246,200 | B1* | 6/2001 | Blumenkranz | B25J 9/1689 128/DIG. 7 |
| 6,788,018 | B1 | 9/2004 | Blumenkranz | |
| 7,027,892 | B2 | 4/2006 | Wang et al. | |
| 7,979,157 | B2* | 7/2011 | Anvari | A61G 13/10 700/245 |
| 8,738,181 | B2* | 5/2014 | Greer | B25J 9/1671 600/130 |
| 9,119,653 | B2 | 9/2015 | Amat Girbau et al. | |
| 9,119,655 | B2 | 9/2015 | Bowling et al. | |
| 10,022,192 | B1* | 7/2018 | Ummalaneni | A61B 34/20 |
| 10,145,747 | B1 | 12/2018 | Lin et al. | |
| 10,492,874 | B2 | 12/2019 | Hasegawa | |
| 2006/0149418 | A1 | 7/2006 | Anvari | |
| 2006/0161136 | A1* | 7/2006 | Anderson | A61B 90/57 606/1 |
| 2007/0137371 | A1* | 6/2007 | Devengenzo | B25J 15/04 74/490.01 |
| 2007/0293734 | A1* | 12/2007 | Coste-Maniere | B25J 9/1671 600/300 |
| 2008/0218770 | A1 | 9/2008 | Moll et al. | |
| 2009/0041565 | A1* | 2/2009 | Rodriguez Y Baena | A61B 34/70 414/431 |
| 2009/0046146 | A1 | 2/2009 | Hoyt | |
| 2010/0069920 | A1* | 3/2010 | Naylor | A61N 5/1049 606/130 |
| 2010/0152749 | A1* | 6/2010 | von Pechmann | A61B 90/50 606/130 |
| 2010/0217991 | A1 | 8/2010 | Choi | |
| 2010/0286712 | A1* | 11/2010 | Won | A61B 34/30 606/130 |
| 2012/0277764 | A1* | 11/2012 | Cooper | A61B 90/10 606/130 |
| 2013/0041219 | A1* | 2/2013 | Hasegawa | B25J 13/02 600/109 |
| 2013/0269109 | A1 | 10/2013 | Yu | |
| 2013/0310639 | A1* | 11/2013 | Omori | A61B 1/00149 600/102 |
| 2014/0018960 | A1 | 1/2014 | Itkowitz | |
| 2014/0249546 | A1* | 9/2014 | Shvartsberg | B25J 5/02 606/130 |
| 2015/0119637 | A1* | 4/2015 | Alvarez | G16H 40/63 600/102 |
| 2015/0150635 | A1* | 6/2015 | Kilroy | B25J 15/0286 606/130 |
| 2016/0037998 | A1 | 2/2016 | Kawashima | |
| 2016/0157942 | A1* | 6/2016 | Gombert | A61B 34/30 606/130 |
| 2016/0220324 | A1 | 8/2016 | Tesar | |
| 2016/0296294 | A1* | 10/2016 | Moll | A61G 13/06 |
| 2016/0331477 | A1* | 11/2016 | Yu | A61B 34/30 |
| 2017/0071685 | A1* | 3/2017 | Crawford | A61B 34/25 |
| 2018/0078439 | A1* | 3/2018 | Cagle | A61B 34/32 |
| 2018/0078440 | A1 | 3/2018 | Koenig et al. | |
| 2018/0279992 | A1* | 10/2018 | Frankel | B25J 9/1689 |
| 2018/0362060 | A1* | 12/2018 | Schaller | B62B 3/10 |
| 2019/0216555 | A1* | 7/2019 | DiMaio | A61B 34/00 |
| 2019/0216576 | A1* | 7/2019 | Eyre | A61B 1/00149 |
| 2019/0223291 | A1* | 7/2019 | Seow | A61B 34/30 |
| 2019/0223966 | A1* | 7/2019 | Holop | A61B 17/3476 |
| 2019/0239889 | A1* | 8/2019 | Stokes | A61B 17/122 |

FOREIGN PATENT DOCUMENTS

| | | |
|---|---|---|
| DE | 102013111935 A1 | 4/2015 |
| KR | 101448201 | 10/2014 |
| WO | 2010/068005 A2 | 6/2010 |
| WO | 2018/053281 A1 | 3/2018 |
| WO | 2018067611 | 4/2018 |
| WO | WO2018067611 A1 | 4/2018 |

OTHER PUBLICATIONS

Outgoing—ISA/210—International Search Report dated Nov. 16, 2017 for WO Application No. PCT/US17/051805.
Australian Full Examination Report dated Apr. 23, 2019 for related Australian Appln. No. 2017339943 3 Pages.
International Preliminary Report on Patentability for International Application No. PCT/US2017/051805 dated Mar. 28, 2019, 12 pages.
Examination Report for Australian Application No. 2017326014 dated Apr. 16, 2019, 3 pages.
Office Action for Chinese Application No. 201780003865.5 dated Apr. 14, 2020, 25 pages.
Non-Final Office Action for U.S. Appl. No. 15/706,112 dated Sep. 26, 2019, 24 pages.
Final Office Action for U.S. Appl. No. 15/706,112 dated May 14, 2020, 15 pages.
Office Action for Korean Application No. 10-2019-7006149 dated Aug. 20, 2020, 17 pages.
Extended European Search Report for European Application No. 17851615.9 dated Apr. 20, 2020, 14 pages.
Examiner's Report for Canadian Application No. 3035245 dated Feb. 10, 2020, 4 pages.
Notice of Reasons for Rejection for Japanese Application No. 2019-512243 dated Feb. 25, 2020, 10 pages.
Advisory Action of the U.S. Patent Office dated Sep. 2, 2020 for related U.S. Appl. No. 15/706,112.
Decision to Grant a Patent of the Japanese Patent Office dated Dec. 25, 2020 for related Japanese Patent Application No. 2019-512243.
Search Report of the Chinese Patent Office dated Apr. 5, 2020 for related Chinese Patent Application No. 201780003865.5.
Non-Final Office Action of the U.S. Patent Office dated Jan. 19, 2021 for related U.S. Appl. No. 15/706,112.
Office Action of the Canadian Patent Office dated Nov. 19, 2020 for related Canadian Patent Application No. 3035245.
Office Action of the Chinese Patent Office dated Jan. 5, 2021 for related Chinese Patent Application No. 201780003865.5.
Final Office Action of the U.S. Patent Office dated Jul. 7, 2021 for related U.S. Appl. No. 15/706,112.
Decision on Rejection of the Chinese Patent Office dated Jun. 24, 2021 for related Chinese Patent Application No. 201780003865.5.
Verb Surgical Inc., "Examination Report" for Australian Application No. 2020202497, dated Aug. 20, 2021 (7 pages).

* cited by examiner

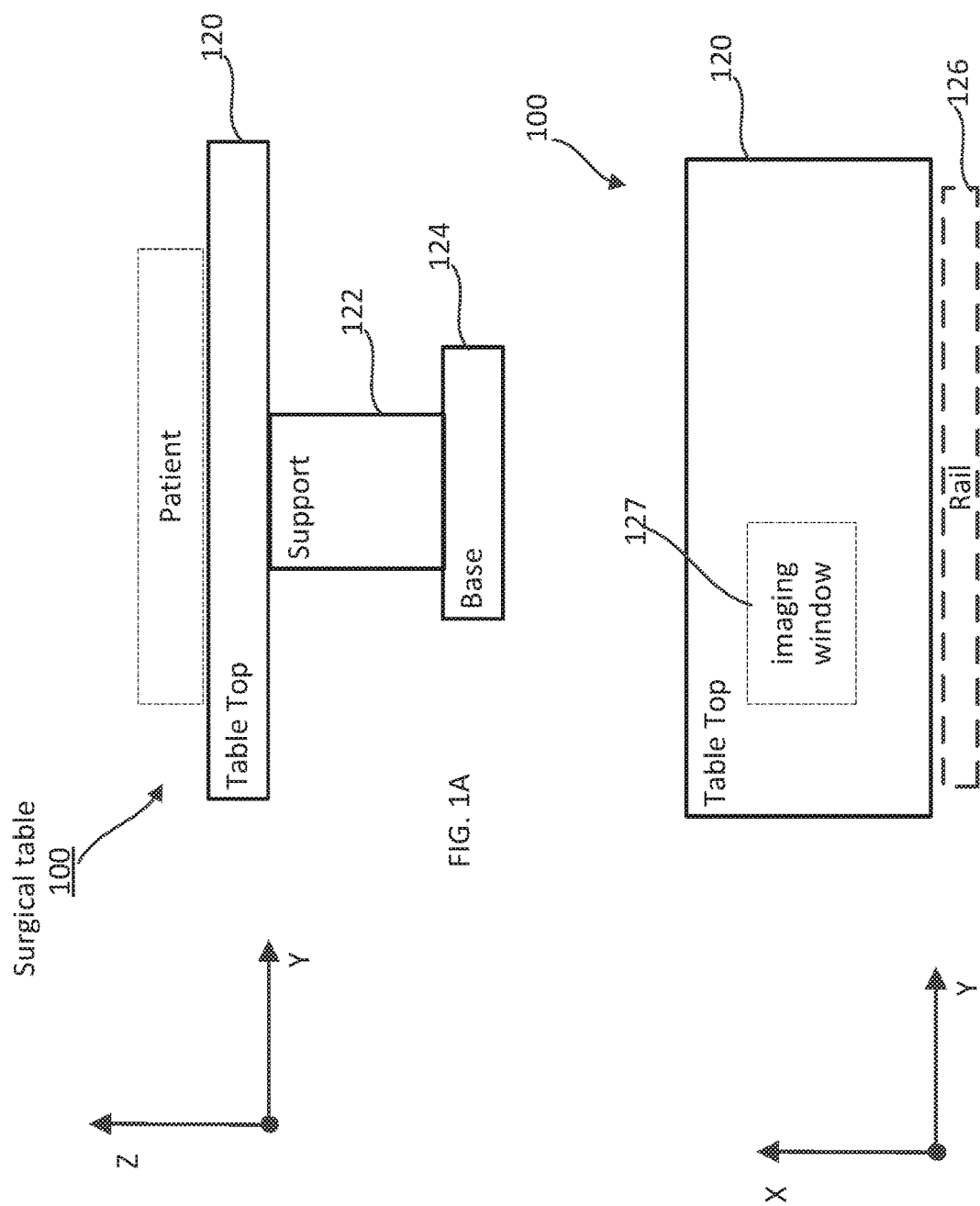

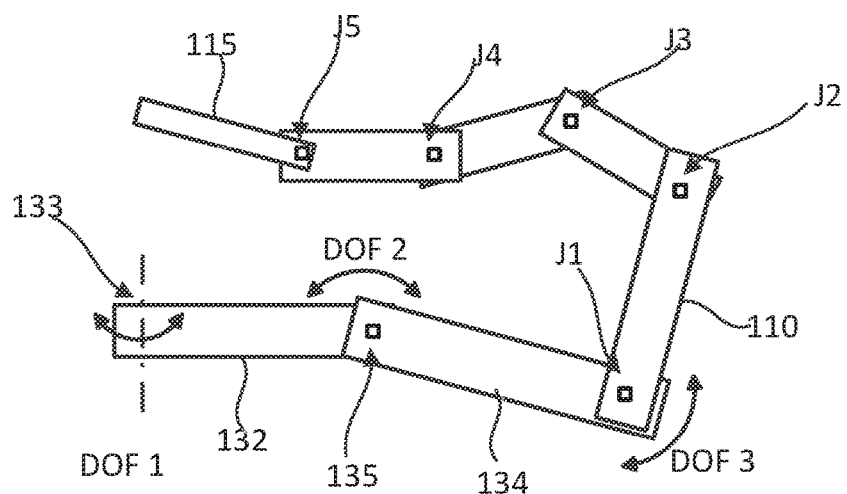
FIG. 2F
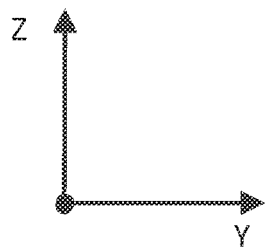
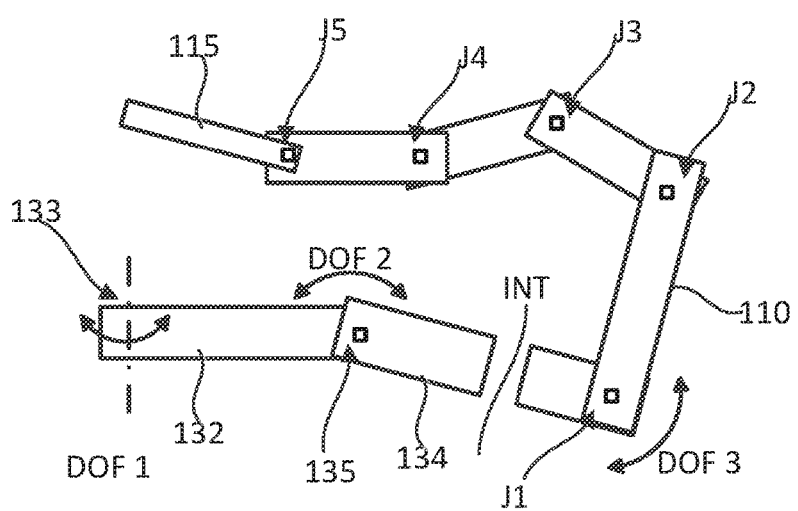
FIG. 2G
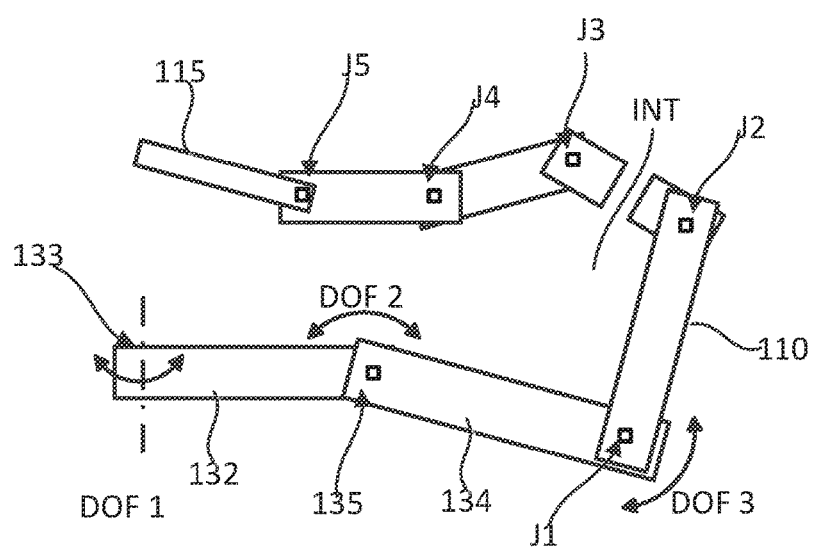
FIG. 2H

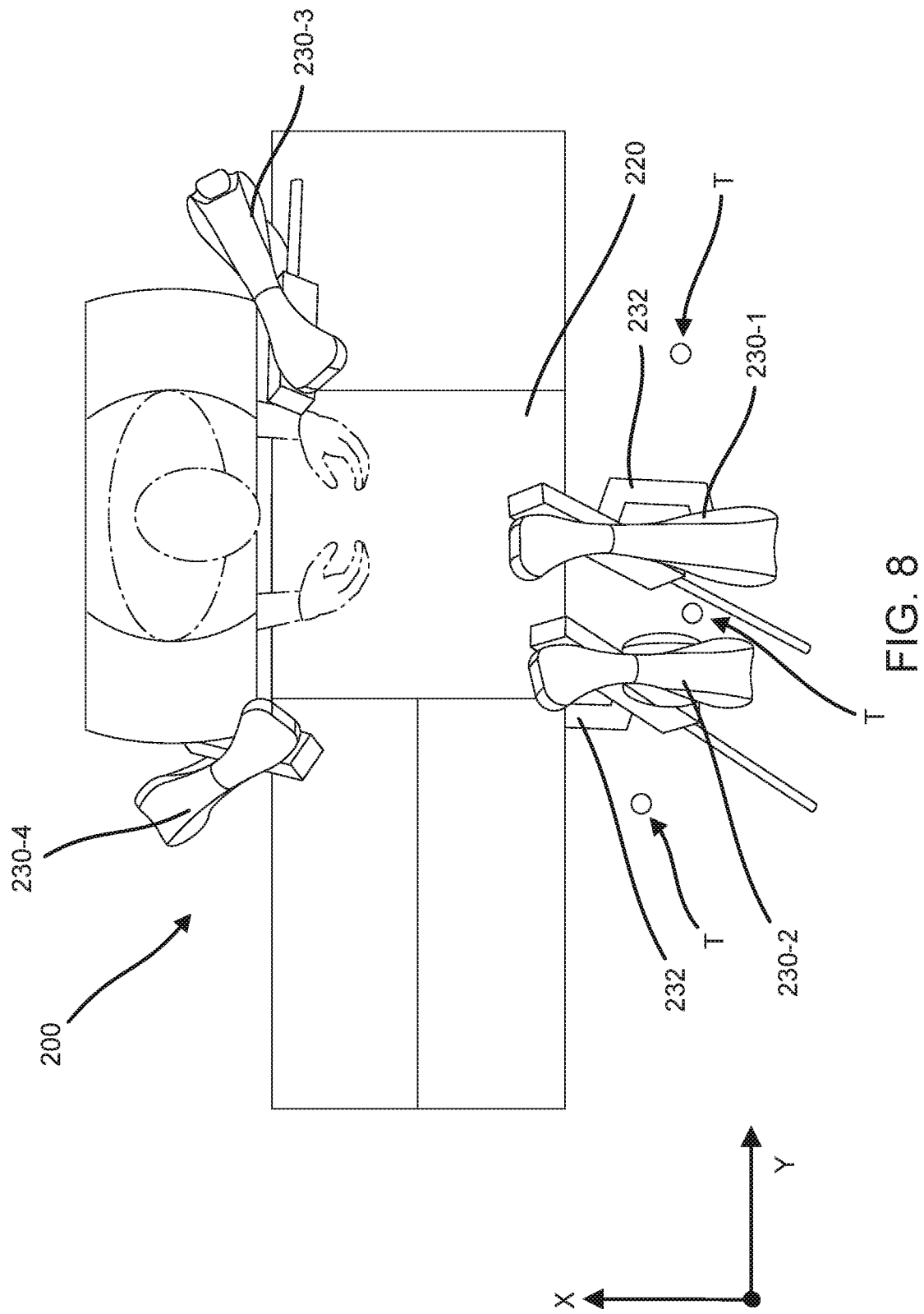

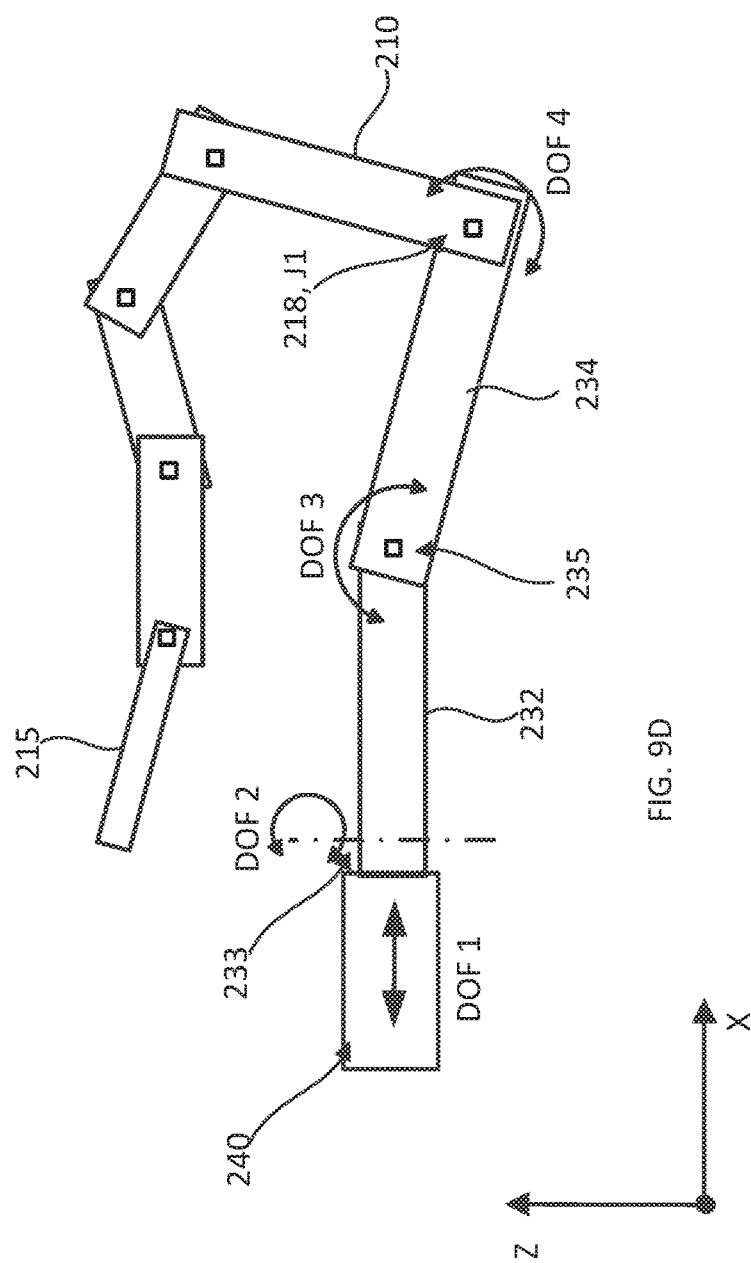

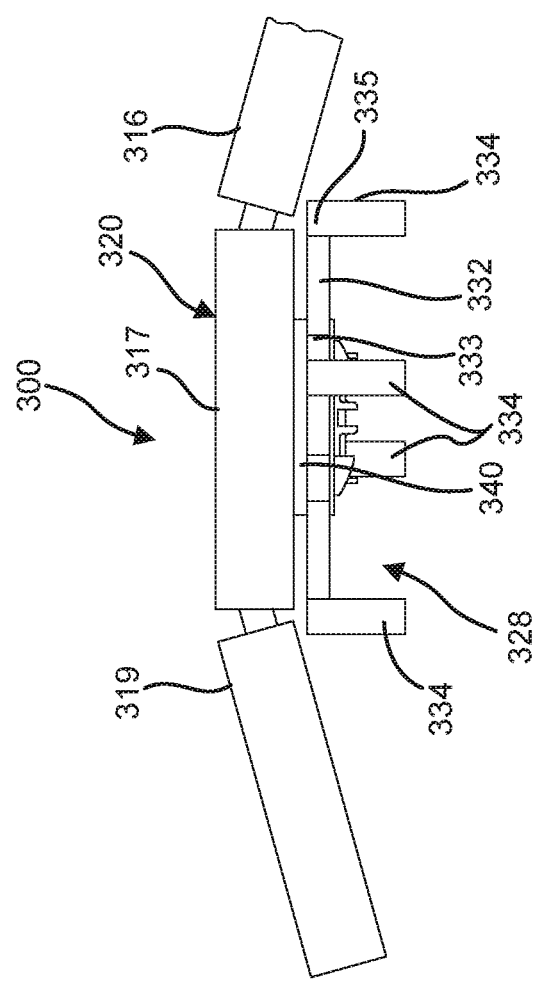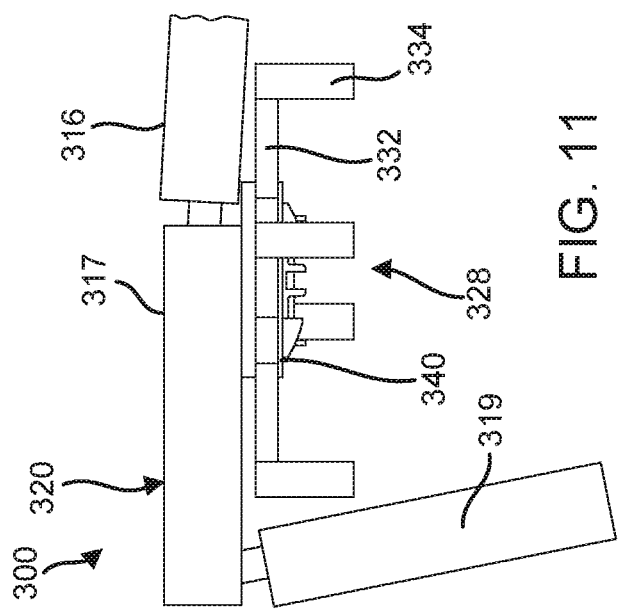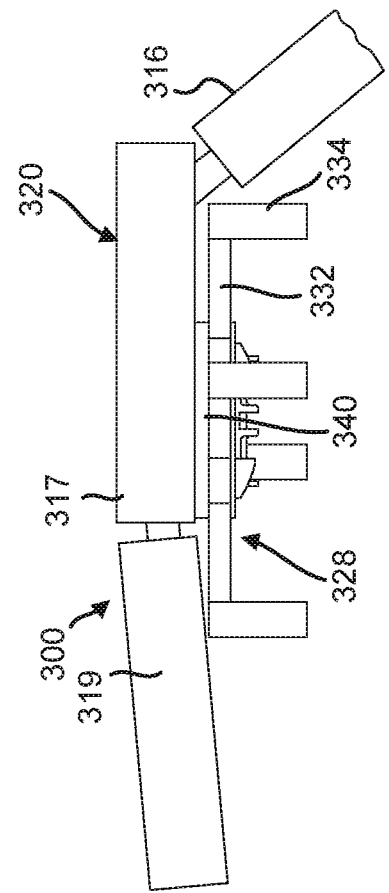
FIG. 10
FIG. 11
FIG. 12

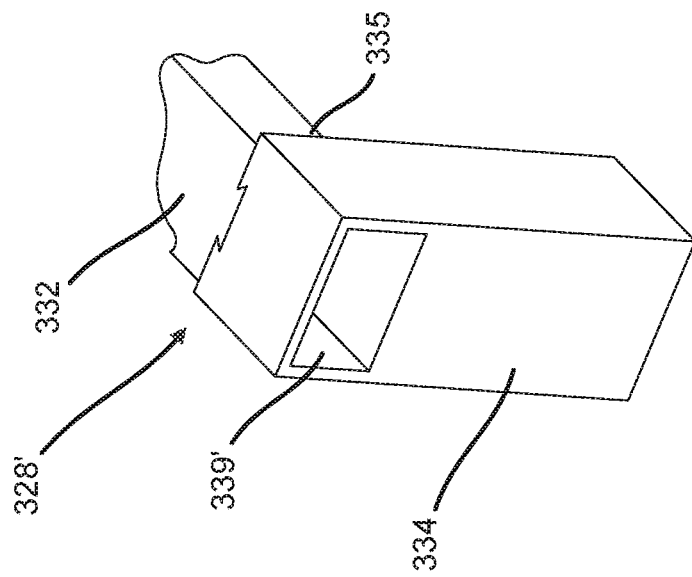
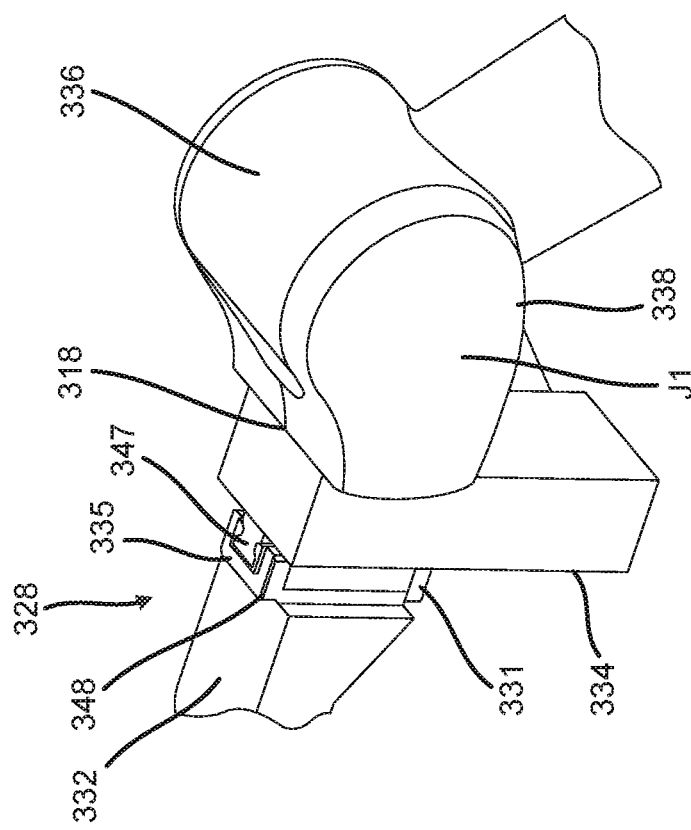
FIG. 14C
FIG. 14B

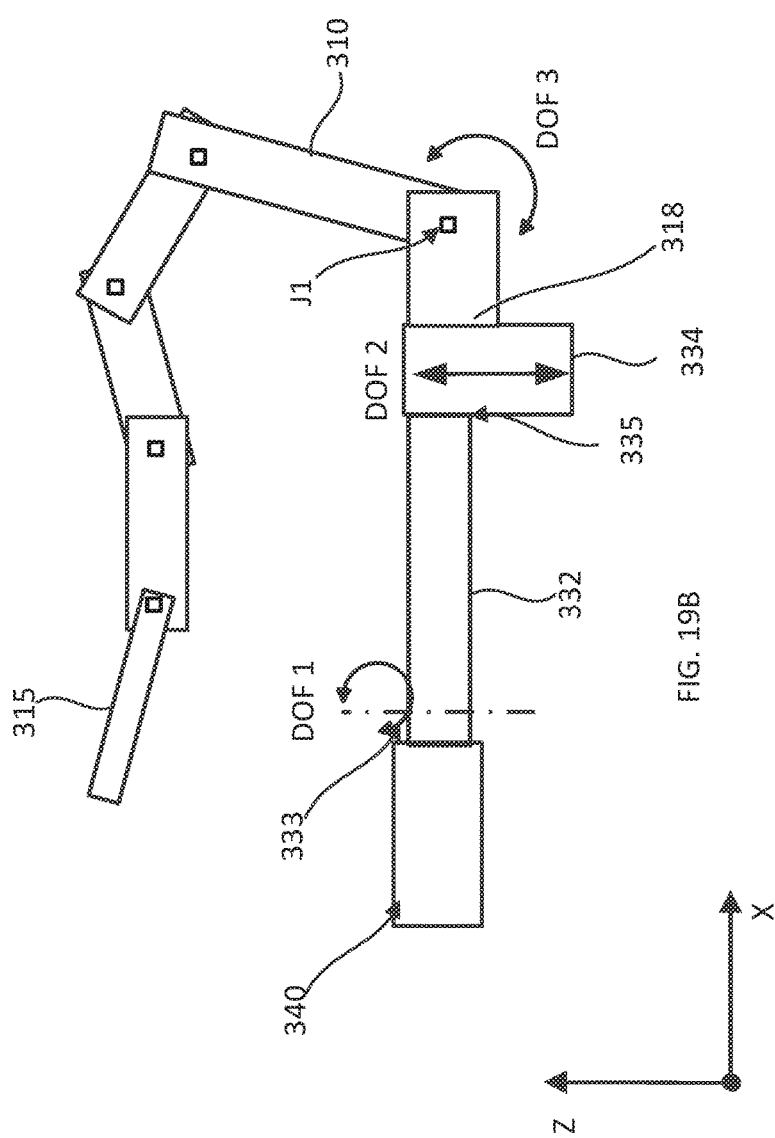

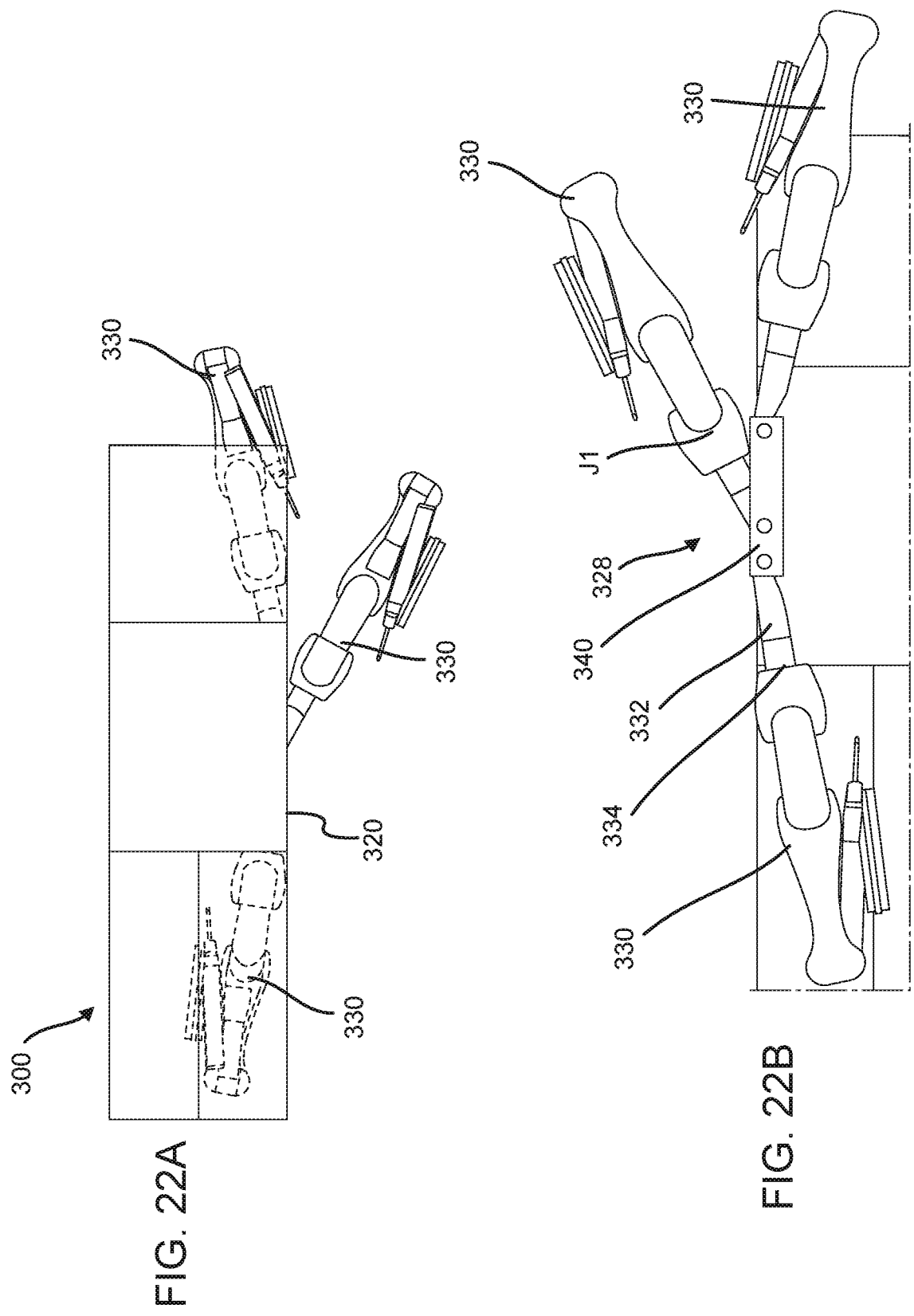

| DOF 1 | DOF 2 | DOF 3 |
|---|---|---|
| rotational | rotational | rotational |
| Z-axis rotation | X-Y plane rotation | X-Y plane rotation |

| DOF 1 | DOF 2 | DOF 3 |
|---|---|---|
| rotational | rotational | rotational |
| Z-axis rotation | X-Y plane rotation | X-Y plane rotation |

| DOF 1 | DOF 2 | DOF 3 | DOF 4 |
|---|---|---|---|
| rotational | rotational | rotational | rotational |
| Z-axis rotation | Z-axis rotation | X-Y plane rotation | X-Y plane rotation |

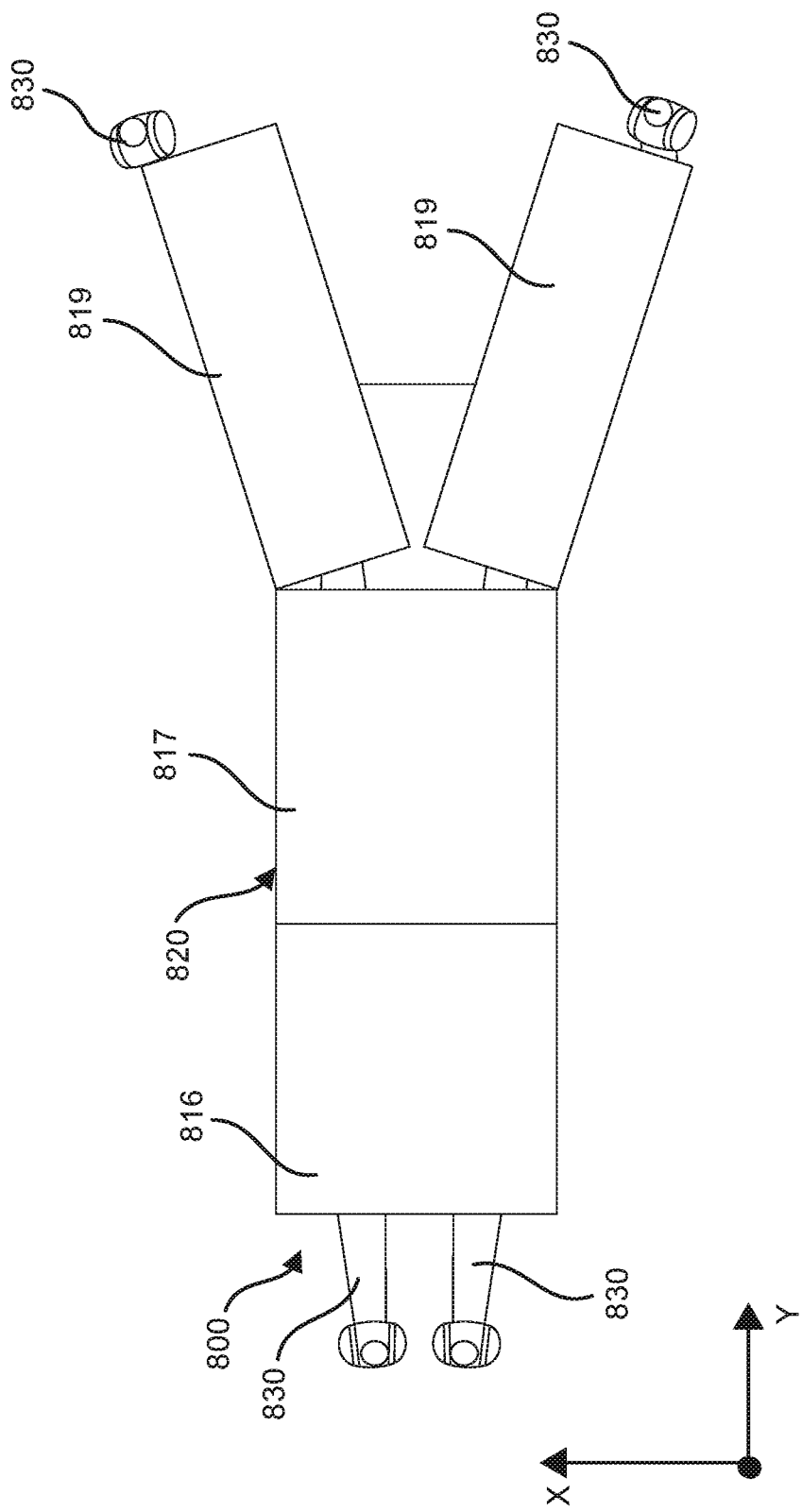

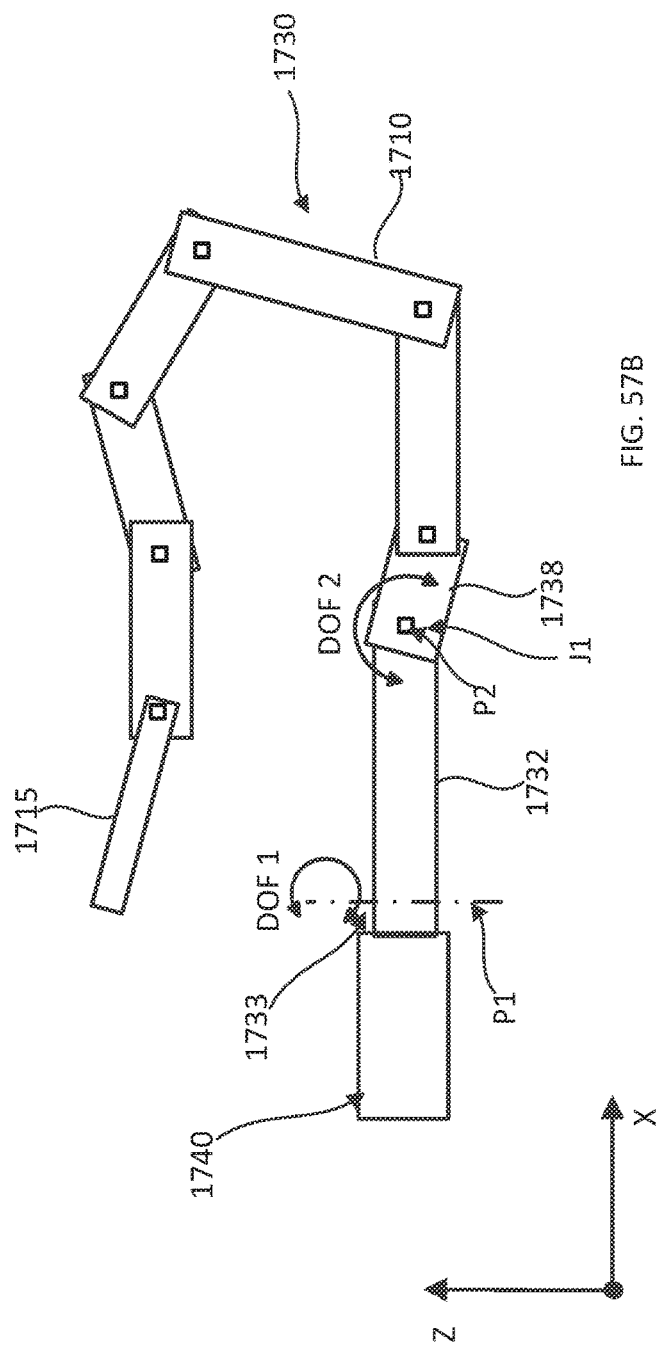

| DOF 1 | DOF 2 | DOF 3 |
|---|---|---|
| rotational | rotational | rotational |
| Z-axis rotation | X-Y plane rotation | X-Y plane rotation |

| DOF 1 | DOF 2 | DOF 3 |
|---|---|---|
| rotational | linear | rotational |
| Z-axis rotation | X-Y axis translation | X-Y axis rotation |

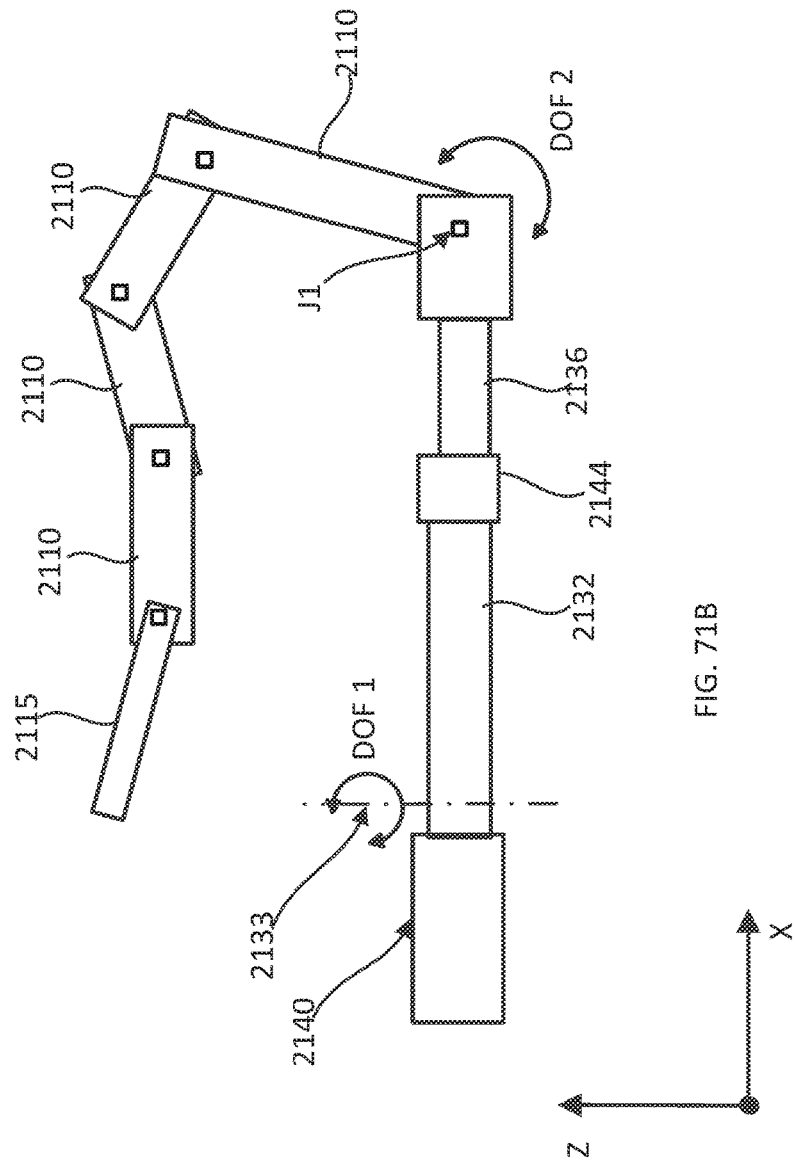

TABLE ADAPTERS FOR MOUNTING ROBOTIC ARMS TO A SURGICAL TABLE

CROSS-REFERENCE TO RELATED APPLICATIONS

This application claims priority to and the benefit of U.S. Provisional Patent Application Ser. No. 62/395,807, filed Sep. 16, 2016. This application also claims priority to and the benefit of U.S. Provisional Patent Application Ser. No. 62/417,211, filed Nov. 3, 2016, the disclosure of which is hereby incorporated herein by reference in its entirety.

BACKGROUND

Embodiments described herein relate to apparatus and methods for a surgical table with robotic arms that can be moved between multiple different positions relative to the surgical table, such as, for example, a stowed position, an operating position and a parked position.

SUMMARY

Apparatus and methods for providing a robotic surgical system including a surgical table having a table top on which a patient can be disposed are described herein. In some embodiments, an apparatus includes a surgical table and robotic arms coupled, or coupleable to, the surgical table, with each robotic arm supporting a medical instrument or tool, such as a surgical instrument, tool driver, and/or imaging device. The surgical table includes a base, a pedestal and a table top coupled to the pedestal. Each of the robotic arms may be coupled to at least one of the table top, the pedestal or the base. Each robotic arm provides two or more links between the proximal end of the arm (at which the arm is coupled to the table) and the distal end of the arm (at which the arm is coupled to the medical instrument). The links are coupled to each other, and may be coupled to the table and to the medical instrument, by a joint that provides one or more degrees of freedom of relative movement between the links coupled by the joint, and correspondingly one or more degrees of freedom of relative movement between the distal end of the robotic arm and the surgical table. In some embodiments, the robotic arm can be releasably coupled to the surgical table. In some embodiments, the robotic arm can include a releasable coupling at a location between its proximal end and its distal end, such that the proximal portion of the robotic arm can be coupled to the surgical table and the distal portion of the robotic arm can be removed from the proximal portion. In some embodiments, the proximal portion of the robotic arm can be implemented as an adapter, which may be fixedly coupled to the surgical table. The adapter can include a table interface structure, a first link member pivotally coupled to the table interface structure at a first joint, and coupled to a second link member of the adapter at a second joint. The second link member can also be coupled to a robotic arm via a coupling. The first joint is configured to allow the first link member to rotate about a first axis defined in a vertical direction relative to the table top, and the second joint is configured to allow the second link member and a robotic arm coupled thereto to move in a vertical direction relative to the table top. The first link member and the second link member collectively provide for movement of the robotic arm in at least one of a lateral, longitudinal or vertical direction relative to the table top.

BRIEF DESCRIPTION OF THE DRAWINGS

FIGS. 1A and 1B are a schematic side view and a schematic top view, respectively, of a surgical table, according to an embodiment.

FIG. 2F is a schematic illustration of a side view of the adapter and a robotic arm of FIG. 2E illustrating degrees of freedom associated with the joints of the adapter and the robotic arm.

FIGS. 2G and 2H are each a schematic illustration of a side view of the adapter and robotic arm of FIG. 2F illustrating degrees of freedom and an example releasable coupling location between a link of the adaptor and/or robotic arm.

FIG. 8 is a top view of the surgical table and adapter of FIGS. 3 and 4 with four robotic arms coupled to the adapter and shown in a parked position.

FIGS. 9C and 9D are a schematic top view and side view, respectively, of the adapter and a robotic arm of FIGS. 3-9B illustrating the degrees of freedom between the joints of the adapter and robotic arm; and FIG. 9E is a table listing the type of degree of freedom of each of the joints.

FIGS. 10-12 are each a side view of a surgical table with an adapter, according to an embodiment coupled thereto and positioned at different longitudinal locations relative to the table top.

FIG. 14B is an enlarged view of a portion of the adapter of FIG. 14A and a portion of a robotic arm coupled thereto.

FIG. 14C is an enlarged view of a portion of an alternative coupling for the adapter of FIG. 14A.

FIGS. 19A and 19B are a schematic top view and side view, respectively, of the adapter and a robotic arm of FIGS. 10-18 illustrating the degrees of freedom between the joints of the adapter and robotic arm; and FIG. 19C is a table listing the type of degree of freedom of each of the joints.

FIGS. 22A and 22B are a top view and a bottom view, respectively, of a portion of the surgical table, adapter and arms of FIGS. 20A and 20B shown in a stowed position.

FIG. 42B is a top view of the surgical table, adapter and four robotic arms of FIG. 39 shown in a stowed position.

FIGS. 57A and 57B are a schematic top view and side view, respectively, of the adapter and a robotic arm of FIGS. 52-56, illustrating the degrees of freedom between the joints of the adapter and robotic arm; and FIG. 57C is a table listing the type of degree of freedom of each of the joints.

FIGS. 71A and 71B are a schematic top view and side view, respectively, of the adapter and a robotic arm of FIGS. 64-70, illustrating the degrees of freedom between the joints of the adapter and robotic arm; and FIG. 71C is a table listing the type of degree of freedom of each of the joints.

DETAILED DESCRIPTION

Figure 1C:
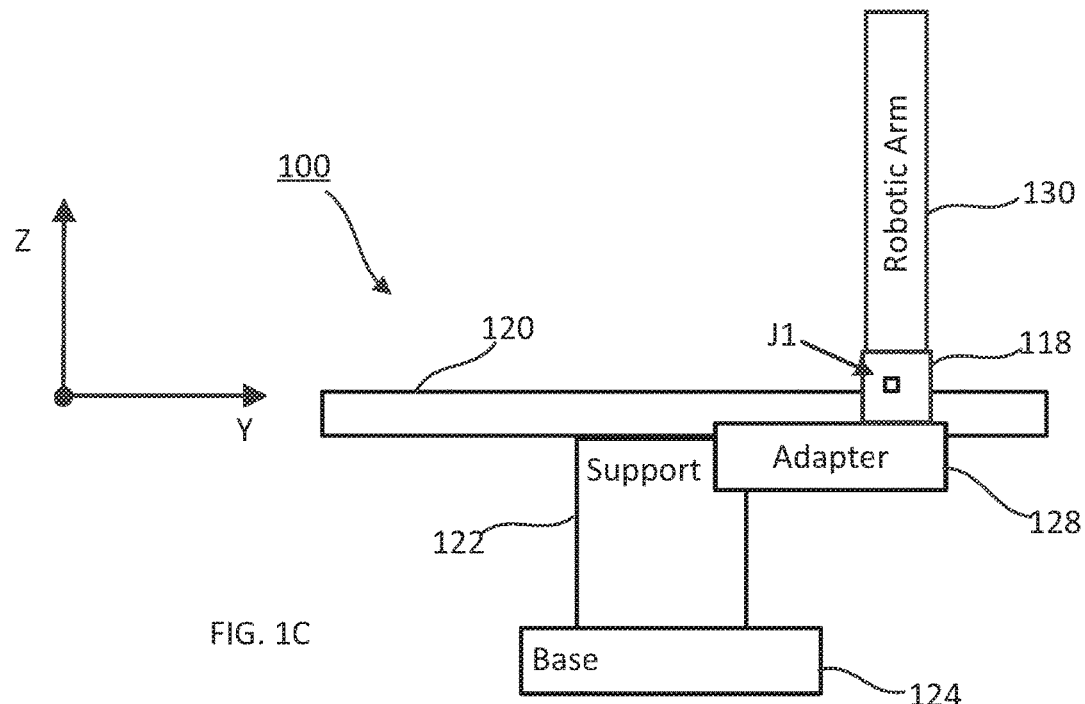
FIGS. 1C and 1D are a schematic side view and a schematic top view, respectively, of the surgical table of FIGS. 1A and 1B with an adapter and robotic arm coupled thereto.

Apparatus and methods for providing a robotic surgical system including a surgical table having a table top on which a patient can be disposed are described herein. In some embodiments, an apparatus includes a surgical table and robotic arms coupled, or coupleable to, the surgical table, with each robotic arm supporting a medical instrument, such as a surgical tool, tool driver, and/or imaging device. The surgical table includes a base, a pedestal and a table top coupled to the pedestal. Each of the robotic arms may be coupled to at least one of the table top, the pedestal or the base. Each robotic arm provides two or more links between the proximal end of the arm (at which the arm is coupled to the table) and the distal end of the arm (at which the arm is coupled to the medical instrument). The links are coupled to each other, and may be coupled to the table and to the medical instrument, by a joint that provides one or more degrees of freedom of relative movement between the links coupled by the joint, and correspondingly one or more degrees of freedom of relative movement between the distal end of the robotic arm and the surgical table. The links and corresponding degrees of freedom allow for movement of the distal end of the robotic arm about and/or along the X, Y, and/or Z axes, to a desired location relative to the table top and/or a patient disposed thereon and/or a desired target portion of the anatomy of a patient disposed thereon.

In some embodiments, an apparatus includes a surgical table having a patient table top, an adapter coupled to the surgical table, and one or more robotic arms coupled to the adapter. In some embodiments, an apparatus can include a surgical table having a patient table top and an adapter/robotic arm assembly coupled to the surgical table. For example, the adapter and robotic arm can be an integral mechanism or component. Each of the adapter and the robotic arms, or an adapter/robotic arm assembly, can include one or more links to allow for movement of the adapter and/or arms about and/or along the X, Y, and/or Z axes, to a desired location relative to the table top and/or a patient disposed thereon and/or a desired target portion of the anatomy of a patient disposed thereon.

In some embodiments, the robotic arm can be releasably coupled to the surgical table. In some embodiments, the robotic arm can include a releasable coupling between its proximal end and its distal end, such that the proximal portion of the robotic arm can be coupled to the surgical table and the distal portion of the robotic arm can be removed from the proximal portion. In some embodiments, the proximal portion of the robotic arm can be implemented as an adapter, which may be fixedly coupled to the surgical table. The adapter can include a table interface structure or mechanism, a first link member pivotally coupled to the interface structure at a first joint, and a second link member coupled to the first link member at a second joint. In some embodiments, the second link member can be pivotally coupled to the first link member at the second joint. In some embodiments, the second link member is slidably coupled to the first link member at the second joint. The second link member is also configured to be coupled to a robotic arm at a coupling that includes a coupling portion of the second link member and a coupling portion at a proximal or mounting end portion of the robotic arm. The robotic arm also includes a target joint at the mounting end portion of the robotic arm. In some embodiments, the target joint is included with the coupling portion at the mounting end portion of the robotic arm.

In some embodiments, an apparatus includes a surgical table and an adapter coupled to the surgical table. The adapter includes a table interface structure or mechanism, a first link member pivotally coupled to the interface structure at a first joint, and a second link member coupled to the first link member at a second joint. In some embodiments, the second link member can be pivotally coupled to the first link member at the second joint. In some embodiments, the second link member is slidably coupled to the first link member at the second joint. The second link member is also configured to be coupled to a robotic arm at a coupling that includes a coupling portion of the second link member and a coupling portion at a proximal or mounting end portion of the robotic arm. The robotic arm also includes a target joint at the mounting end portion of the robotic arm. In some embodiments, the target joint is included with the coupling portion at the mounting end portion of the robotic arm.

The robotic arm can be used to perform a surgical procedure on a patient disposed on the surgical table. The first joint can provide for rotational motion of the first link member about a vertical z-axis relative to a table top of the surgical table and movement of the first link member and the second link member in lateral and longitudinal directions (also referred to herein as x-direction and y-direction) relative to the table top of the surgical table. The second joint can provide a lift mechanism to allow for vertical movement (e.g. movement closer to, above, and/or further above, the table top of the surgical table) of the second link member and the mounting end portion of a robotic arm coupled thereto. The collective movement of the first link member and the second link member allows for the adapter and a robotic arm when coupled thereto move between a variety of different positions relative to the surgical table. For example, the adapter and robotic arm can be moved to a stowed position entirely beneath or substantially beneath the table top, and various operating positions where the target joint of the robotic arm can be placed at a target location to perform a particular surgical procedure on a patient disposed on the table top of the surgical table. The motion of the first link member and the second link member also provides for movement of the adapter and robotic arm to various parked or clearance positions in which the adapter and robotic arm are disposed such that access to the patient is not obstructed. For example, it may be desirable to move the adapter and robotic arm during a surgical procedure to provide clearance for equipment such as an imaging device and/or to provide clearance for additional medical personnel in, for example, an emergency during the procedure. In some cases, an operating position can also be a parked position.

As shown schematically in FIGS. 1A-1B, a surgical table 100 includes a table top 120, a table support 122 and a table base 124. The table top 120 has an upper surface on which a patient can be disposed during a surgical procedure, as shown schematically in FIG. 1A. The table top 120 is disposed on the support 122, which can be, for example, a pedestal, at a suitable height above the floor. The support 122 (also referred to herein as pedestal) may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axis. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, etc. The support 122 for the table top may be mounted to the base 124, which can be fixed to the floor of the operating room, or can be movable relative to the floor, e.g., by use of wheels on the base. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support pedestal 120. This also can allow robotic arms (arms 130 discussed below) coupled to the table 100 to reach a desired treatment target on a patient disposed on the table top 120.

As shown in FIG. 1B, the surgical table 100 may also include one or more rails 126 coupled to one or both sides or lateral edges of the table top 120, to which surgical accessories may be releasably mounted during the surgical procedure. The surgical table 100 may also include a radio-translucent window 127 that is without intrusion by radio-opaque components of the table 100 (e.g., an adapter or robotic arm both discussed below) during a surgical procedure to allow the ability to image (e.g., x-ray or another suitable imaging modality) a patient disposed on the table 100 through the window 127.

Figure 1D:
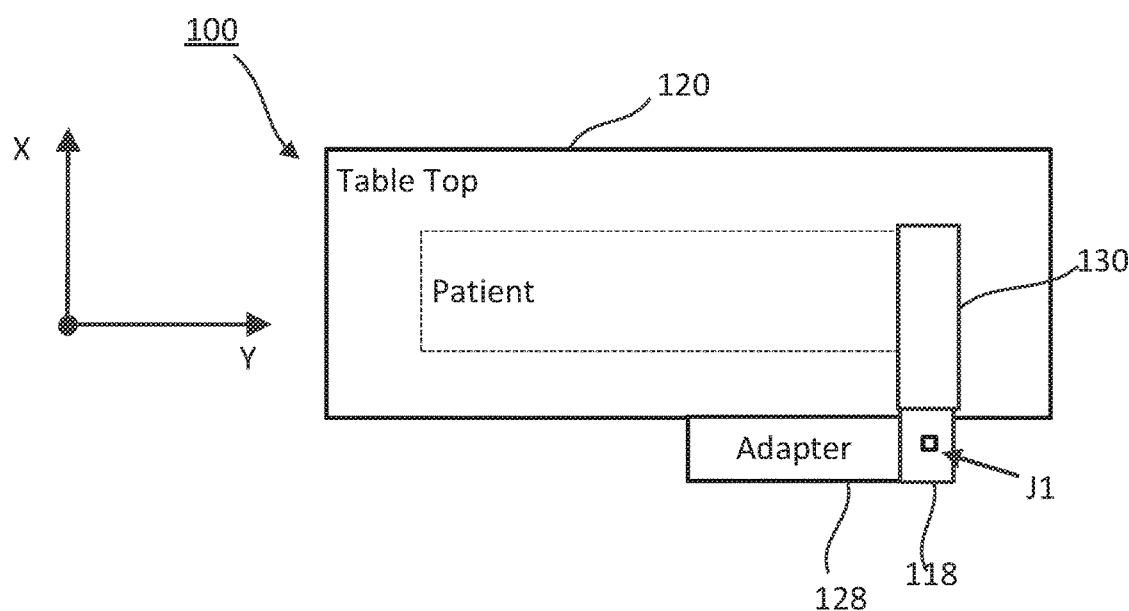

In a robotically assisted surgical procedure, one or more robotic arms 130 can be disposed in a desired operative position relative to a patient disposed on the table top 120 of the surgical table 100 (also referred to herein as "table"), as shown schematically in FIGS. 1C and 1D. The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function. The following description is for embodiments in which the connection between the surgical table and the distal end of the robotic arm (and thus the position and orientation of the medical instrument at the distal end of the robotic arm relative to the patient), is implemented with an adapter 128 and robotic arm(s) 130 coupled to the adapter 128. The adapter 128 can be separate from, but engageable with, or coupleable to, the surgical table 100, or can be fixedly attached to the surgical table 100. The adapter 128 can be coupled to, for example, the support 122, the table base 124 and/or the table top 120 of the table 100. However, as discussed in more detail below, the distinction between an adapter and robotic arm can be disregarded, and the connection between the surgical table and the distal end of the robotic arm can be conceptualized and implemented as a series of links and joints that provide the desired degrees of freedom for movement of the medical instrument, i.e. at the distal end of the connection. The connection may include a releasable coupling at any one or more link(s) or joint(s) or any location along the series of links and joints.

As described herein, the position and movement of the adapter 128, its constituent components and the robotic arms 130 are described in reference to X, Y and Z axes which can be defined relative to a top surface of the table top 120 of the surgical table 100 and in particular in reference to a top surface of the torso section of the table top 120. As used herein, the top surface refers to a top surface of the table top structure without any pads. Also as described herein, in some embodiments, the various sections of the table top 120 can move relative to each other (e.g., can be tilted or angled relative to each other) and/or the table top 120 can be moved (e.g., tilted, angled) relative to the support pedestal 122 and/or the base 124 of the surgical table 100. In some embodiments, it is contemplated that the adapter 128 and robotic arms 130 coupled thereto can move with the torso section of the table top 120 such that the frame of reference to the X, Y and Z axes for various embodiments remains relative to the top surface of the table top 120. In some embodiments, the adapter 128 and robotic arms 130 can be coupled to the support pedestal 122 of the table 100 and when the table top 120 is moved relative to the support 122, the positioning of the adapter 128 and arms 130 can be coordinated with the movement of the table top 120.

Figure 1E:
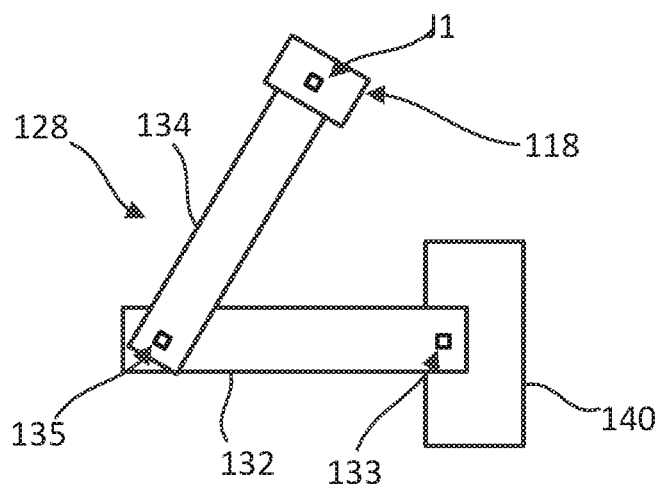
FIG. 1E is a schematic side view of an adapter, according to an embodiment, shown in an extended or use configuration.
Figure 1F:
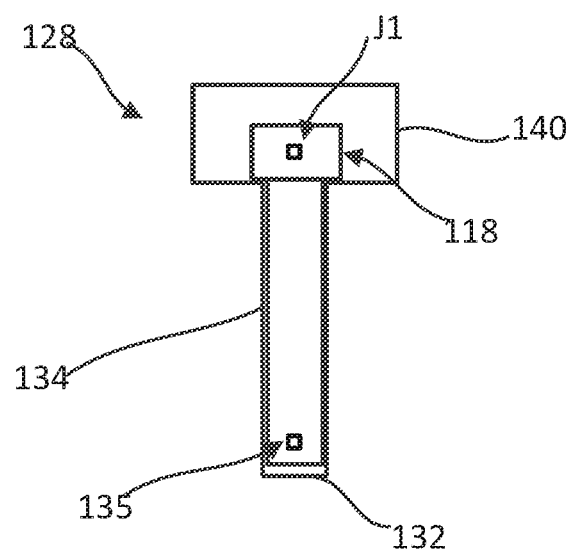
FIG. 1F is a schematic side view of the adapter of FIG. 1E, shown in a collapsed or folded configuration.

As shown schematically in FIGS. 1E and 1F, the adapter 128 can include a table interface structure or mechanism 140, and one or more link members. In this example embodiment, the adapter 128 includes a first link member 132 coupled to the interface structure 140 at a first joint 133, and a second link member 134 coupled to the first link member 132 at a second joint 135. In some embodiments, the first link member 132 can be pivotally coupled to the table interface structure 140 at the first joint 133. In some embodiments, the first link member 132 can be coupled to the table interface structure 140 with a joint that provides for linear motion. In some embodiments, the second link member 134 can be pivotally coupled to the first link member at the second joint and in some embodiments the second link member 134 can be, for example, linearly and/or or slidably coupled to the first link member at the second joint 135. Other types of coupling joints for the first joint 133 and the second joint 135 can alternatively be used. Thus, various different types of coupling joints (e.g., linear, rotational, slidable) can be used between the link members of the adapter to achieve a desired movement and reach of the adapter. The second link member 134 is also coupleable to a robotic arm 130 at a coupling 118 (also referred to herein as "coupling joint"). The adapter 128 can be moved between various extended configurations for use during a surgical procedure as shown in FIG. 1E, and various folded or collapsed configurations for storage when not in use, as shown in FIG. 1F.

In some embodiments, the adapter 128 can include more than two link members. For example, an adapter can include a third link member (not shown) coupled to the second link member 134 between the second link member 134 and the coupling 118 to the robotic arm 130. In some embodiments, the third link member can be configured to slide or telescope to provide a variable length of the third link member. This can provide a longer or shorter reach to extend the robotic arm 130 (e.g., the target joint J1 discussed below) further above the patient, for example, for larger patients. It can also be used to extend the position of the robotic arm 130 further under the table top 120 when the arm 130 is moved to a position on an opposite side of the table 100 as described in more detail below (e.g., the arm is moved to the opposite side to have three arms on one side of the table).

In accordance with various embodiments, each robotic arm 130 may be permanently, semi-permanently, or releasably coupled to the adapter 128 via the coupling 118. The coupling 118 can include a variety of different coupling mechanisms, including a coupling portion (not shown) on the adapter 128 that can be matingly coupled to a coupling portion (not shown) on the robotic arm. Each robotic arm 130 can be coupled at a fixed location on the table 100 or can be coupled such that the robotic arm 130 can be movable to multiple locations relative to the table top 120 and/or a patient disposed on the table top 120 as described in more detail herein. For example, the robotic arm 130 can be moved relative to the table top 120 and/or a specific target treatment location on the patient. In some embodiments, the axial motion (e.g., in the Y-axis direction) of the table top 120 can assist in allowing the arms 130 (and therefore, the medical instrument or tool coupled to the distal end of the arm) to reach the desired anatomy on the patient or provide clearance for access to the patient as needed. In some embodiments, the combination of vertical movement of the support pedestal 122, axial movement of the table top 120 and movement of, for example, the first link member 132 and the second link member 134, allows for placement of the robotic arms 130 in a position where it can reach the anatomy of the patient at the required height over the floor.

Some structural requirements for the adapter 128 can include providing a rigid support of the robotic arm 130 while maintaining adjustability for pre-operative and intra-operative position changes of the robotic arm 130. In some embodiments, the table adapter 128 can include a means of holding or locking the adapter 128 at a fixed position to withstand, for example, the effects of gravity, inertial effects due to robotic arm motion, and/or to withstand accidental bumps from a user or another part of the robotic system (including other robotic arms or table motion). The table adapter 128 can also include one or more sensors for measuring the spatial position of the adapter 128 and/or angles and displacements of various joints and coupling points of the adapter 128.

In some embodiments, the table adapter 128 can have a bending stiffness, for example, greater than 180 kN/m, with a range, for example, of 18 kN/m to 1800 kN/m. In some embodiments, the table adapter 128 can have a torsional stiffness greater than 800 N-m/deg, with a range of 80 N-m/deg to 8000 N-m/deg. The table adapter 128 can also include actuators to move the joints, such as motors, gearboxes, harmonic drives, pneumatic or hydraulic pistons and linkages. For example, the table adapter 128 can include force or torque sensors at the joints to detect loads applied, for example, by the user, by inertia, gravity, or accidental collision of the arms.

Structural elements of the table adapter 128 may be formed with various materials such as, for example, steel, stainless steel, aluminum, titanium, carbon fiber, or other strong and rigid materials that are resistant to chemicals. Structural elements of the table adapter 128 may also include materials to provide damping, such as, for example, rubber or viscoelastic coatings of the links. Structural stiffness of the adapter 128 can be important to minimize errors in controlling the position of the robotic arm(s), and also to reduce amplitude of unwanted vibrations.

Figure 1G:
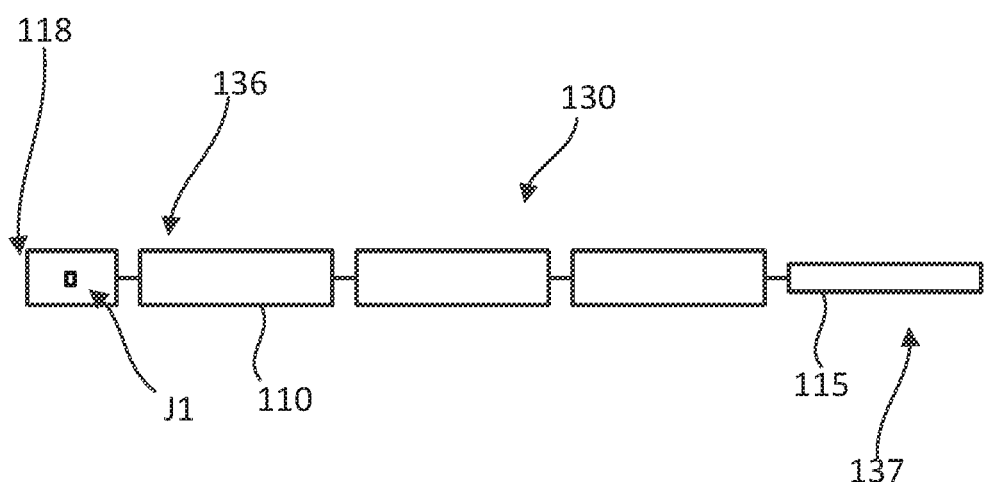
FIG. 1G is a schematic side view of a robotic arm, according to an embodiment, shown in an extended or use configuration.
Figure 1H:
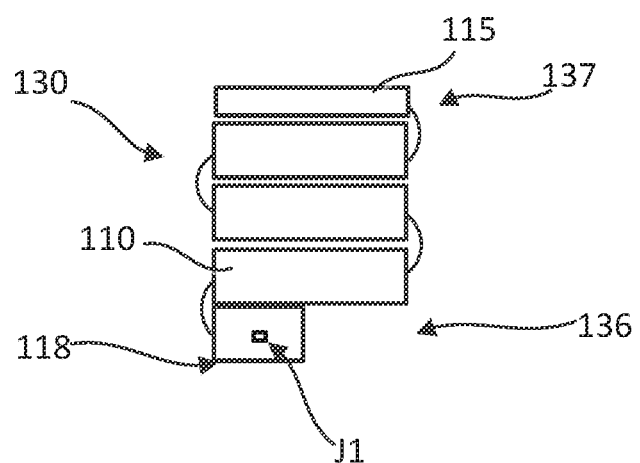
FIG. 1H is a schematic side view of the robotic arm of FIG. 1G, shown in a collapsed or folded configuration.

As shown schematically in FIGS. 1G and 1H, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the adapter 128 of the table 100. The robotic arm 130 can include two or more link members or segments 110 coupled together at joints that can provide for translation along and/or rotation about one or more of the X, Y and/or Z axes (shown, for example, in FIGS. 1A-1D). The coupling portion of the robotic arm 130 to couple the robotic arm 130 to the coupling portion of the adapter 128 at the coupling 118 can be disposed at the distal or mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling portion of the coupling 118 or disposed on a link or segment 110 of the robotic arm 130 coupled to the coupling portion. The target joint J1 can provide a pivot joint to allow a distal segment of the robotic arm 130 to pivot relative to the adapter 128. The robotic arm 130 can be moved between various extended configurations for use during a surgical procedure, as shown in FIG. 1G, and various folded or collapsed configurations for storage when not in use, as shown in FIG. 1H. As described in more detail below, the first joint 133 and the second joint 135 of the adapter 128 can provide for movement of the robotic arm 130 along and/or about the X, Y, and/or Z axes.

More specifically, in some embodiments, the first joint 133 can provide for rotational motion of the first link member 132 relative to the interface structure 140 about a vertical z-axis (shown in FIGS. 1C and 1D) relative to the table top 120, and thus for movement of the first link member 132 and second link member 134 in lateral and longitudinal directions (also referred to herein as x-direction and y-direction) relative to the table top 120 of the surgical table 100. The second joint 135 can provide a lift mechanism to allow for vertical movement of the second link member 134 and therefore, movement of the coupling 118 between the second link member 134 and the robotic arm 130 coupled thereto. The second joint 135 can be, for example, a pivotal coupling, a sliding mechanism or other type of coupling that provides for vertical movement of the second joint and therefore a robotic arm coupled thereto. Such vertical movement, whether produced by rotational and/or translational movement of the second link member 134 relative to the first link member 132, can produce movement of the coupling 118 closer to and/or further above, the table top 120 of the surgical table 100. In some embodiments, in which the lift mechanism includes a pivotal or rotary joint, the joint can provide for vertical motion as well as reach capabilities of the adapter 128. For example, the links coupled at the pivotal joint can be extended to a substantially linear position relative to each other to extend a length of the adapter 128 (i.e., the link members). This allows for additional reach capability to extend the adapter 128 and robotic arm 130 to a desired location relative to a patient disposed on the table top 120, including reaching to the opposite side of the table top 120. In addition, if the links are disposed about the pivotal joint at a substantial angle, up to 90 degrees, the height (Z-axis) of the arm can be maximized.

The collective motion of the first link member 132 and the second link member 134 of the adapter 128 can provide for movement of the coupling 118, and therefore, movement of a robotic arm 130 coupled thereto along and/or about the X, Y, and/or Z axes. For example, the target joint J1 of the robotic arm 130 can be moved to various target treatment locations relative to the table 100 to perform a variety of different surgical procedures on a patient disposed thereon. The collective motion of the first link member 132 and the second link member 134 also allows the adapter 128 and robotic arm 130 to move between a variety of different positions relative to the surgical table 100 including stowed positions, operating positions and parked or clearance positions.

Figure 2A:
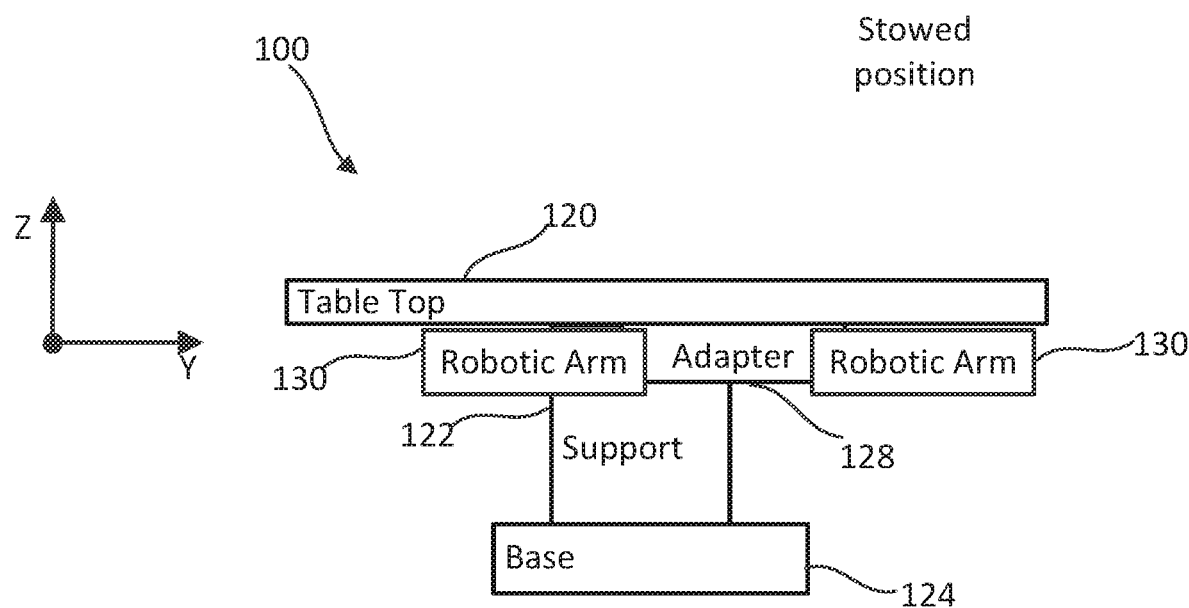
FIG. 2A is a schematic illustration of the surgical table, adapter and three robotic arms of FIGS. 1A-1H, shown in a stowed position.
Figure 2B:
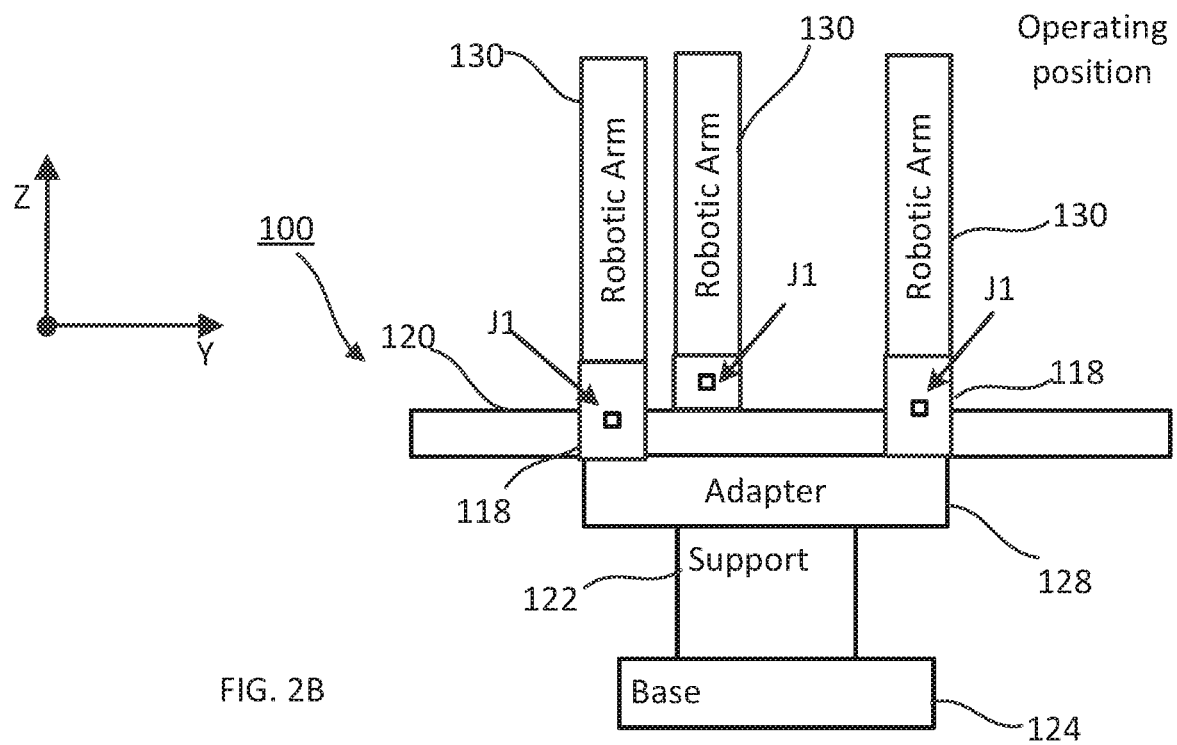
FIG. 2B is a schematic illustration of the surgical table, adapter and three arms of FIG. 2A shown in an operating position with the robotic arms in a ready configuration.
Figure 2C:
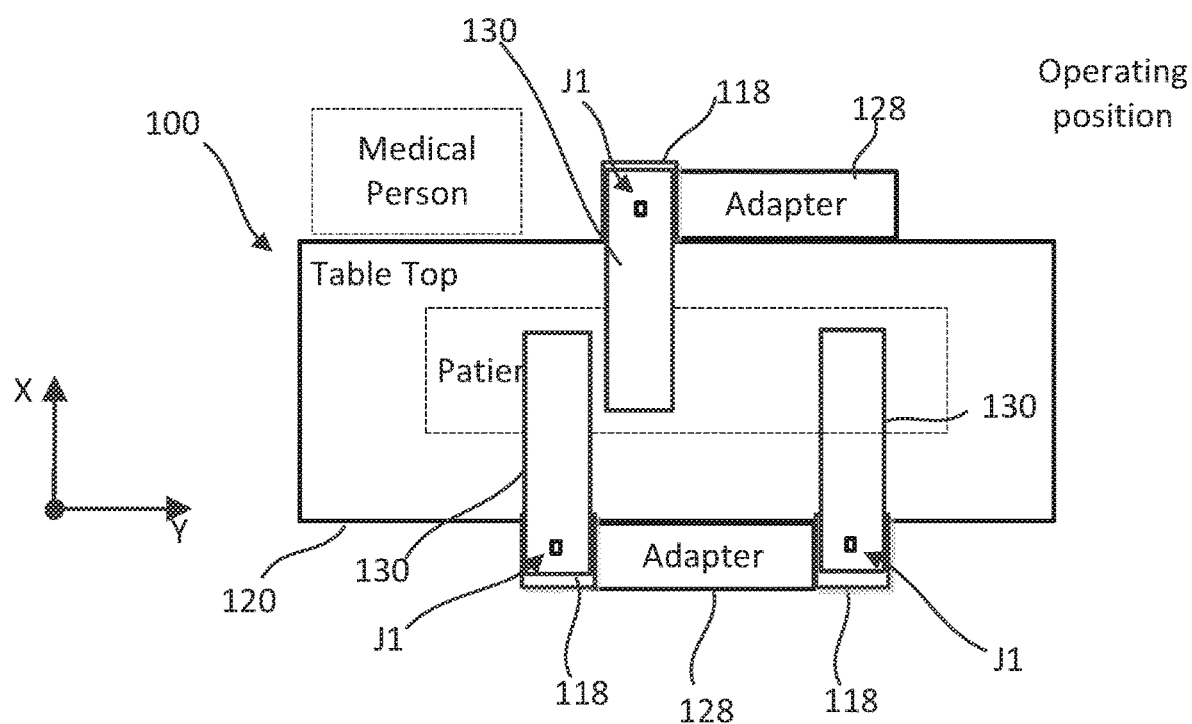
FIG. 2C is a schematic illustration of the surgical table, adapter and three arms of FIG. 2A shown in an operating position with the robotic arms in a treatment configuration.

For example, adapter 128 and robotic arm 130 can be moved to a stowed position entirely beneath or substantially beneath the table top 120 as shown in FIG. 2A, and various operating positions as shown in FIGS. 2B and 2C, in which the target joint J1 is disposed at a target location to perform a particular surgical procedure. In some embodiments, it may be desirable to dispose the target joint J1 above the table top 120 and above a sterile plane for the surgical procedure. The sterile plane can be defined, for example, by the table top 120. For example, the sterile plane can be defined at a bottom surface of the table top 120 or at a top surface of the table top 120 (e.g., a top surface of the torso section of the table top 120). The adapter 128 can provide for movement and positioning of the robotic arms 130 to operating positions, while also leaving space for medical personnel such as a surgical assistant to stand near the patient on the table top 120 during a surgical procedure, such as for example, near the patient's torso or head as shown in FIGS. 2C and 2D.

The location of the robotic arms 130 and medical personnel will depend on the particular surgical procedure to be performed.

To secure the table adapter 128 at various locations used during pre-operative setup and/or during surgery, the various joints and/or coupling locations may utilize braking or locking mechanisms. For example, braking mechanisms may provide the ability to hold position at any point in the range of motion of the joint. Braking mechanisms may include, for example, disc-caliper-style, drum-roller-style, or other friction-based mechanisms. Locking mechanisms may provide the ability to hold position at any number of discrete positions, but may not allow for continuous adjustment. Locking mechanisms can include, for example, disengaging-toothed, disengaging-pinned, or ball-detent, or other discrete position style locking mechanisms. In some embodiments, braking or locking mechanisms can prevent motion in an unpowered state and be biased towards a stopped or locked position via a spring or other mechanism. In some embodiments, in a powered state, braking or locking mechanisms may optionally release or engage depending on the desired state of the system.

Figure 2D:
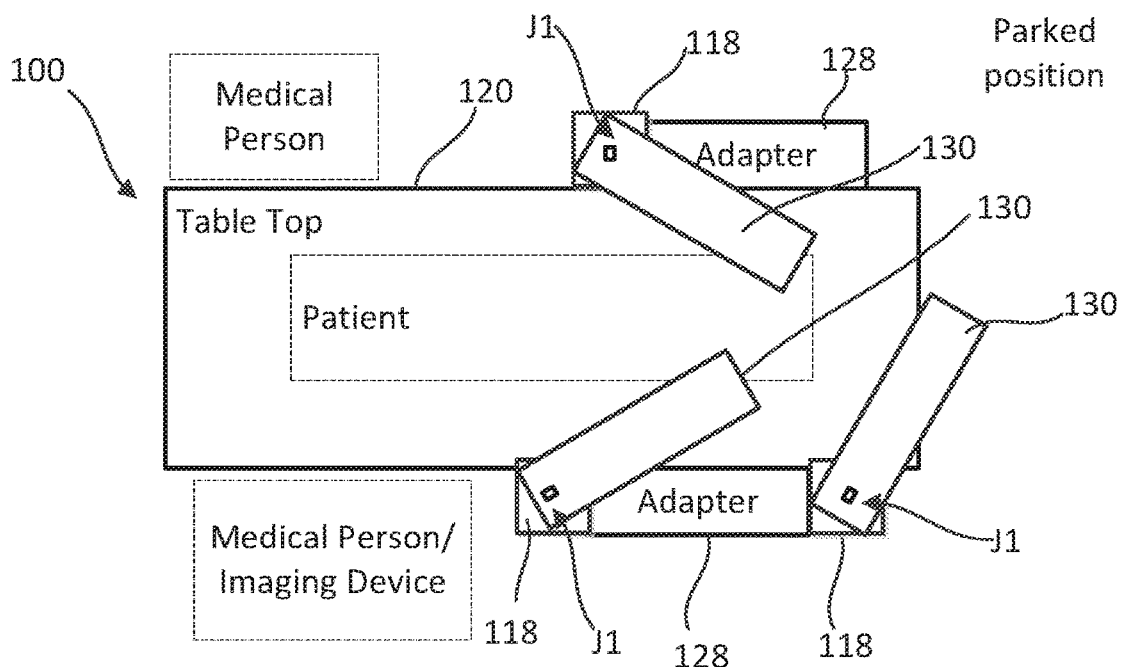
FIG. 2D is a schematic illustration of the surgical table, adapter and three arms of FIG. 2A, shown in a parked position.

The motion of the first link member 132 and the motion of the second link member 134 also provides for movement of the adapter 128 and robotic arm 130 to various parked or clearance positions in which the adapter 128 and robotic arm 130 are disposed such that access to the patient is not obstructed, as shown in FIG. 2D. For example, it may be desirable to move the robotic arm 130 during a surgical procedure to provide clearance for equipment such as an imaging device and/or to provide clearance for additional medical personnel in, for example, an emergency during the procedure. The robotic arm 130 can then be moved back to the operating position to continue the surgical procedure.

As described above for FIGS. 2A-2D, during the course of a surgical procedure it may be desirable to move the robotic arms 130 relative to the table top 120 and patient, i.e. move the robotic arm 130 along and/or about the X, Y, and/or Z axes, between two or more positions. For example, the robotic arms 130 can be moved from a stowed position to various operating positions and various parked positions relative to the table top 120 as described above. In the stowed positions, as shown, for example, in FIG. 2A, the robotic arms 130 are disposed entirely or substantially beneath the table top 120, i.e., entirely or substantially within an outer perimeter defined by the table top 120. This can allow for clearance to move a patient to the table top 120 from, for example, a gurney. In some instances, it may only be necessary to provide clearance on one side of the table top 120 (e.g., along the torso portion of the table top). Thus, one or more of the robotic arms 130 on one side of the table top 120 can be moved to an operating position, leaving one side clear for moving the patient to the table top 120. In other cases, it may be desirable to provide clearance on both sides of the table top 120. For example, in some cases, medical personnel may need to use straps to pull the patient from a gurney onto the table top 120. In such a case, both sides of the table top 120 should be clear of obstructions. In addition, it may be desirable to provide clearance at the head rest section of the table top 120, to provide clearance for anesthesia to be administered to the patient (e.g., clearance for anesthesiologists, equipment, and/or nurse, etc.). For example, a clearance region can be defined at an angle of 35° from a bottom of the head rest outwardly and away from the torso portion of the table top on both the left and right side of the table top.

With the patient disposed on the table top 120, the adapter 128 and arms 130 can be moved from the stowed position to an operating position where the target joint J1 is disposed at a target treatment location relative to the table top 120. For example, as shown in FIG. 2B, the adapter 128 and arms 130 are disposed in an operating position with the target joint J1 at a target location and the arms 130 are in a ready configuration relative to the table top 120. As shown in FIG. 2C, the adapter 128 and robotic arms 130 are in the operating position and the robotic arms 130 are also in a treatment configuration with a distal end 137 of the arms 130 (e.g., with the tool 115 coupled thereto) disposed within a treatment region. During the surgical procedure, it may also be desirable to provide for access to the patient by at least one medical staff near or at the side of the patient as shown in FIG. 2B. In some instances, as shown in FIG. 2D, it may be desirable to move the arms 130 and adapter 128 from an operating position (e.g., as in FIGS. 2B and 2C) to a parked position. In the parked position, the adapter 128 and robotic arms 130 do not obstruct access to the patient disposed on the table top 120. This allows clearance to position other devices and/or medical personnel and/or to accommodate various sized patients. For example, it may be desirable to provide access for an imaging device and/or to provide access to medical staff in the operating room, for example, during a medical emergency. In one example, to facilitate surgery on obese patients, e.g., for bariatric surgical procedures, the robotic arm(s) 130 can be moved relative to the table 100 to a position spaced laterally further away from the longitudinal axis (y-axis) of the surgical table 100, thus accommodating a wider patient.

The various parked or clearance positions of the robotic arm(s) 130 may be enabled by moving the robotic arm(s) 130 about and/or along the X, Y, and/or Z axes, to a desired clearance location relative to the table top 120, with the robotic arm(s) 130 remaining attached to, and/or in some cases being separated from the surgical table 100. Thus, the arms 130 can be moved laterally away from the surgical table 100, longitudinally along the table top 120 and/or raised vertically relative to the table top 120, to provide access, for example, for an imaging device and/or medical staff. The robotic arms 130 can be moved in a variety of different manners depending on the particular configuration of the adapter 128 and/or the coupling 118 between the robotic arm 130 and the adapter 128.

As described above, the table 100 may include or have coupled thereto multiple robotic arms 130 via the adapter 128. The coupling 118 and adapter 128 provide the ability to move the robotic arms 130 to various positions relative to the table top 120 and to move the location of target joint J1 to various desired target treatment locations relative to the table top 120 depending on the particular surgical procedure to be performed. The adapter 128 can also provide for movement of the robotic arms 130 such that the window 127 is free of obstructions to allow for imaging of the patient through the window 127. In some embodiments, the adapter 128 and/or the robotic arm(s) 130 can be moved manually by a user of the surgical table between the various positions. In some embodiments the adapter 128 and/or the robotic arm(s) 130 can be coupled to a system to allow for automated controls. For example the adapter and/or robotic arms can be coupled to a drive motor(s) that can be controlled and operated by a user (e.g., medical professional).

As described above, the links (of the adapter 128 and/or the robotic arm 130) are coupled to each other, and may be coupled to the table 100 and to the medical instrument 115, by a joint that provides one or more degrees of freedom of relative movement between the links coupled by the joint, and correspondingly one or more degrees of freedom of relative movement between the distal end of the robotic arm 130 and the surgical table 100. The links and corresponding degrees of freedom allow for movement of the distal end of the robotic arm (and medical instrument 115) about and/or along the X, Y, and/or Z axes, to a desired location relative to the table top and/or a patient disposed thereon and/or a desired target portion of the anatomy of a patient disposed thereon.

Figure 2E:
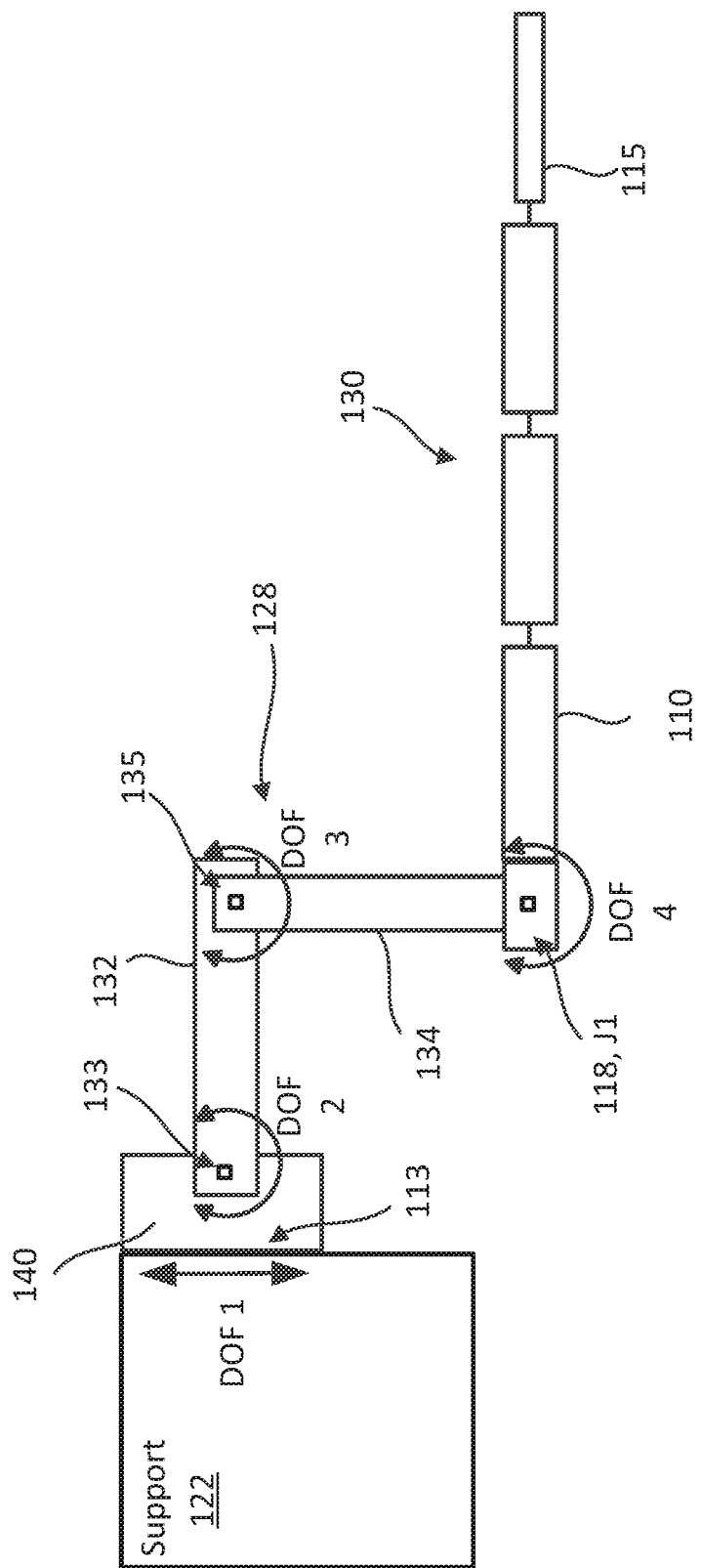
FIG. 2E is a schematic illustration of a top view of a portion of the surgical table, adapter and robotic arm of FIGS. 1A-1H, illustrating degrees of freedom associated with the joints of the adapter.

FIG. 2E is a top view of a portion of support 122, adapter 128 and a robotic arm 130 illustrating example degrees of freedom associated with the joints of the adapter 128 and/or robotic arm 130.

As shown in FIG. 2E, and as described above, the first link member 132 can be coupled to the interface mechanism 140 at a joint 133 and the second link member 134 can be coupled to the first link member 132 at a joint 135. The robotic arm 130 can be coupled to the second link member 134 at a coupling joint 118 and each of the links 110 of the robotic arm 130 can be coupled to each other at a joint. As shown in this example, the J1 joint of the robotic arm 130 coincides with the coupling joint 118. In some embodiments, the adapter 128, and more particularly, the interface mechanism 140 can be movably coupled to the surgical table (e.g., to the support 122) at a coupling joint 113 such that a first degree of freedom DOF 1 is provided at the coupling joint 113. In the example of FIG. 2E, the coupling joint 113 provides for linear movement between the interface mechanism 140 and the surgical table, i.e. translation parallel to the X axis. In other embodiments, the coupling joint can provide pivotal or rotational movement of the interface mechanism 140 relative to the surgical table. In other embodiments, the interface mechanism 140 is fixedly coupled to the surgical table, and thus, does not move relative to the surgical table.

As also shown in FIG. 2E, a second degree of freedom DOF 2 is provided at the joint 133 between the first link member 132 and the interface mechanism, and a third degree of freedom DOF 3 is provided at the joint 135 between the first link member 132 and the second link member 134. A fourth degree of freedom DOF 4 is provided at the joint 118, J1 between the second link member 134 and a link 110 of the robotic arm 130. In this example, each of DOF 2, DOF 3, and DOF 4 are shown as rotation about the Z axis.

FIG. 2F is another example schematic illustration of the adapter 128 and robotic arm 130 demonstrating the degrees of freedom associated with various joints. FIG. 2f also illustrates various joints J2, J3, J4 between links 110 of the robotic arm 130 and a joint J5 between a link 110 and the medical instrument 115. In this example, a first degree of freedom DOF 1 is provided at joint 133 between the first link member 132 and the interface mechanism (not shown) of the adapter 128, a second degree of freedom DOF 2 is provided at joint 135 between the first link member 132 and the second link member 134, and a third degree of freedom DOF3 is provided between the second link member 134 and the robotic arm 130 at the J1 joint.

As described above, the robotic arm 130 or a portion thereof can be releasably coupled to the adapter 128 and/or portions (e.g., links) of the robotic arm 130 can be incorporated into the adapter 128. Thus, the connection between the surgical table and the distal end of the robotic arm 130 can be conceptualized and implemented as a series of links and joints that provide the desired degrees of freedom for movement of the medical instrument 115 at the distal end of the connection. The connection may include a releasable coupling at any one or more link(s) or joint(s) or any location along the series of links and joints.

FIGS. 2G and 2H illustrate two different example locations for the releasable coupling described above. It should be understood that FIGS. 2G and 2H illustrate only two examples, and that the releasable coupling can be provided at various different locations along the series of links and joints that are illustrated in this example as including an adapter and a robotic arm 130, though as noted above this distinction can be considered as arbitrary. As shown in FIG. 2G, a releasable coupling can be provided at an interface location INT between a portion of the robotic arm 130 (e.g., at a link 110) and the second link member 134. The example of FIG. 2H illustrates the releasable coupling at an interface INT between the joint J2 and the joint J3 of the robotic arm 130. Thus, in the example of FIG. 2H, a portion of the links 110 of the robotic arm 130 are incorporated with the adapter 128.

The various degrees of freedom of the links of the adapter 128 and/or robotic arm 130 provide for movement of the robotic arm 130 and therefore, a medical instrument 115 disposed at a distal end thereof to be moved to a variety of different positions and orientations relative to the table top 120 to perform various different procedures on a patient disposed thereon. The adapters 128 described herein can also provide for variations on the number of robotic arms 130 that are coupled to the table to use for a particular procedure, and to position robotic arms 130 on one or both sides of the table top 120. For example, in some procedures, it may be desirable to position two robotic arms 130 on one side of the table top 120 and two robotic arms 130 on an opposite side of the table top 120. In other procedures, it may be desirable to position three robotic arms 130 on one side of the table top 120 and one robotic arm 130 on an opposite side of the table top 120. Although many of the embodiments described herein describe the use of four robotic arms 130, it should be understood that the number of robotic arms 130 to be used for a particular surgery can vary and more or less than four robotic arms 130 can be used. Various specific example embodiments are described herein demonstrating the movement and location of the robotic arms relative to the table top 120 within a treatment area or treatment "cloud" for various different procedures.

Each of the embodiments described herein can include the same or similar features as the surgical table, adapter, and robotic arms described with respect to FIGS. 1A-2H.

Figure 3:
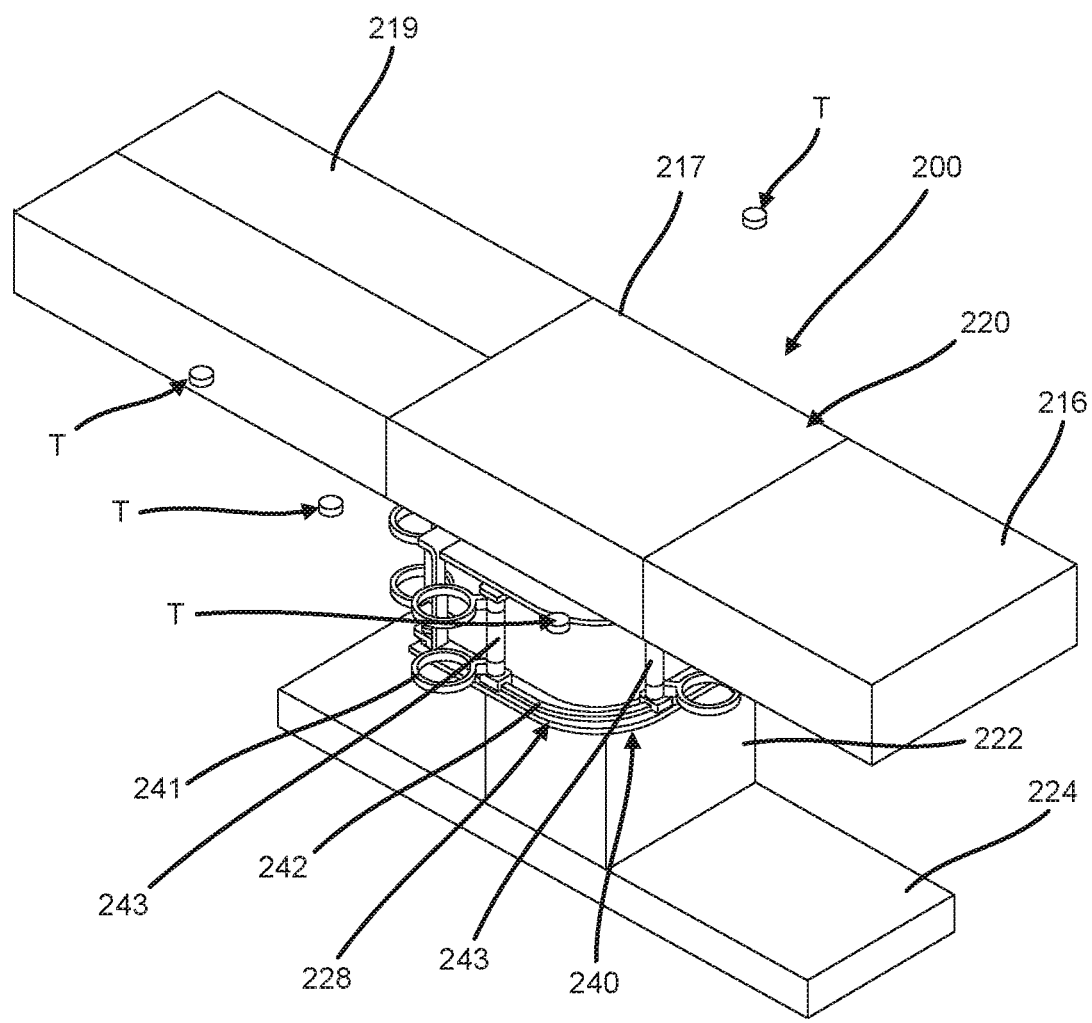
FIG. 3 is a perspective view of a surgical table with a portion of an adapter according to an embodiment attached thereto.

FIGS. 3-9B illustrate a surgical table and adapter according to another embodiment. As shown in FIG. 3, a surgical table 200 includes a table top 220, a support 222 (also referred to herein as pedestal) and a base 224. As described above, the support 222 for the table top 220 may be mounted to the base 224, which can be fixed to the floor of an operating room, or can be movable relative to the floor, e.g., by use of wheels on the base. The table top 220 includes a head section 216, a torso section 217 and a leg section 219 (including the feet). The table top 220 can also include an arm section(s) (not shown). The table top 220 has a top surface on which a patient can be disposed. The support 222 may provide for movement of the table top 220 in a desired number of degrees of freedom, such as translation in the Z axis (height above the floor), Y axis (along the longitudinal axis of the table), and/or X axis (along the lateral axis of the table), and/or rotation about the Z, Y, and/or X axis. The head section 216, torso section 217 and leg section 219 (and arm section if included) can be movable relative to each other along/about any suitable axes. As described above movement of the table top 220 and/or its constituent sections may be performed manually, driven by motors, controlled remotely, etc. The surgical table 200 can also include a radio-translucent window (not shown) that is without intrusion by other components of the table 200 (e.g., an adapter or robotic arm both discussed below) during a surgical procedure to allow the ability to image (e.g., x-ray) a patient disposed on the table 200 through the window.

Figure 4:
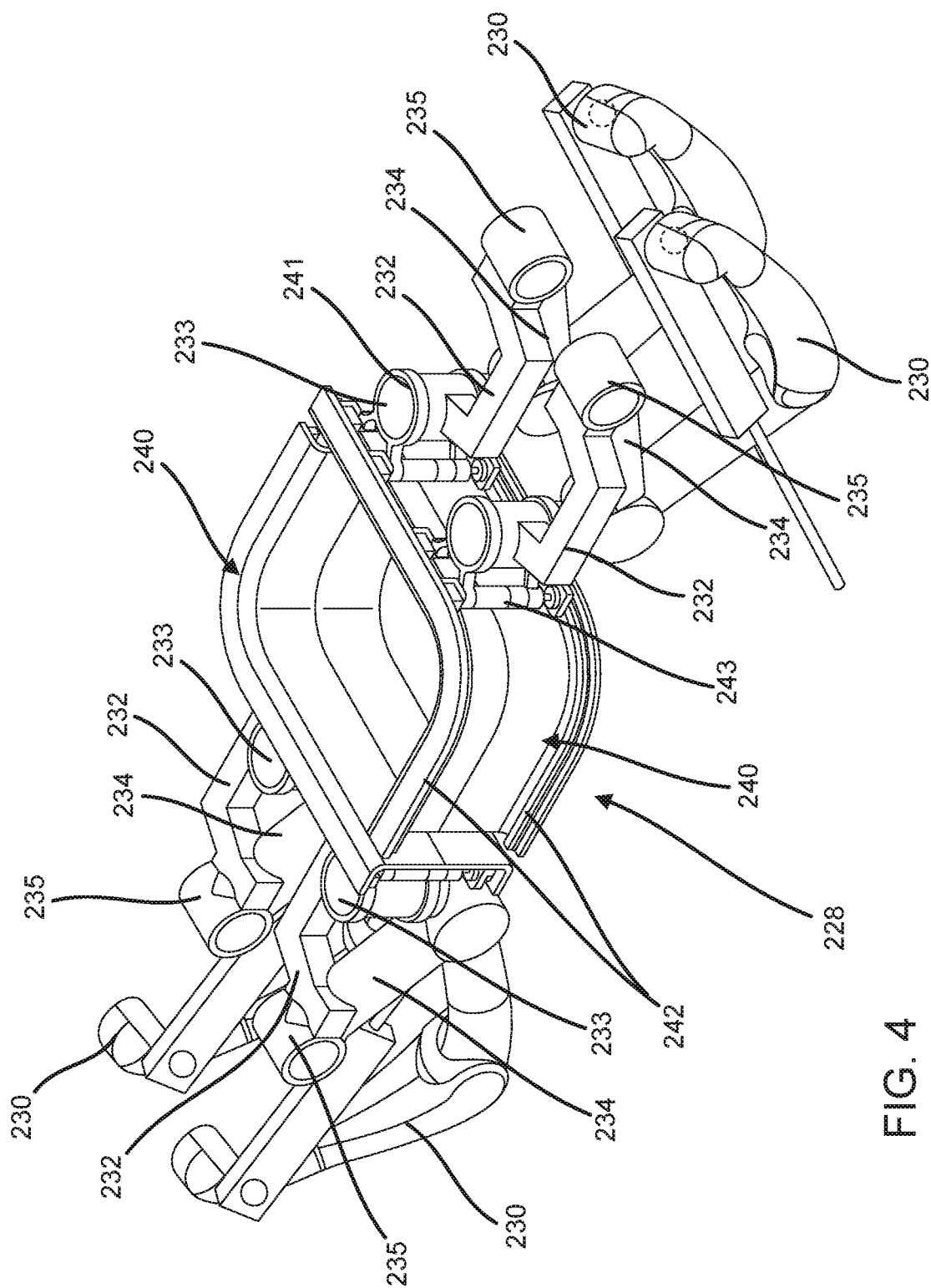
FIG. 4 is a perspective view of an adapter, according to an embodiment, with four robotic arms coupled thereto.
Figure 5:
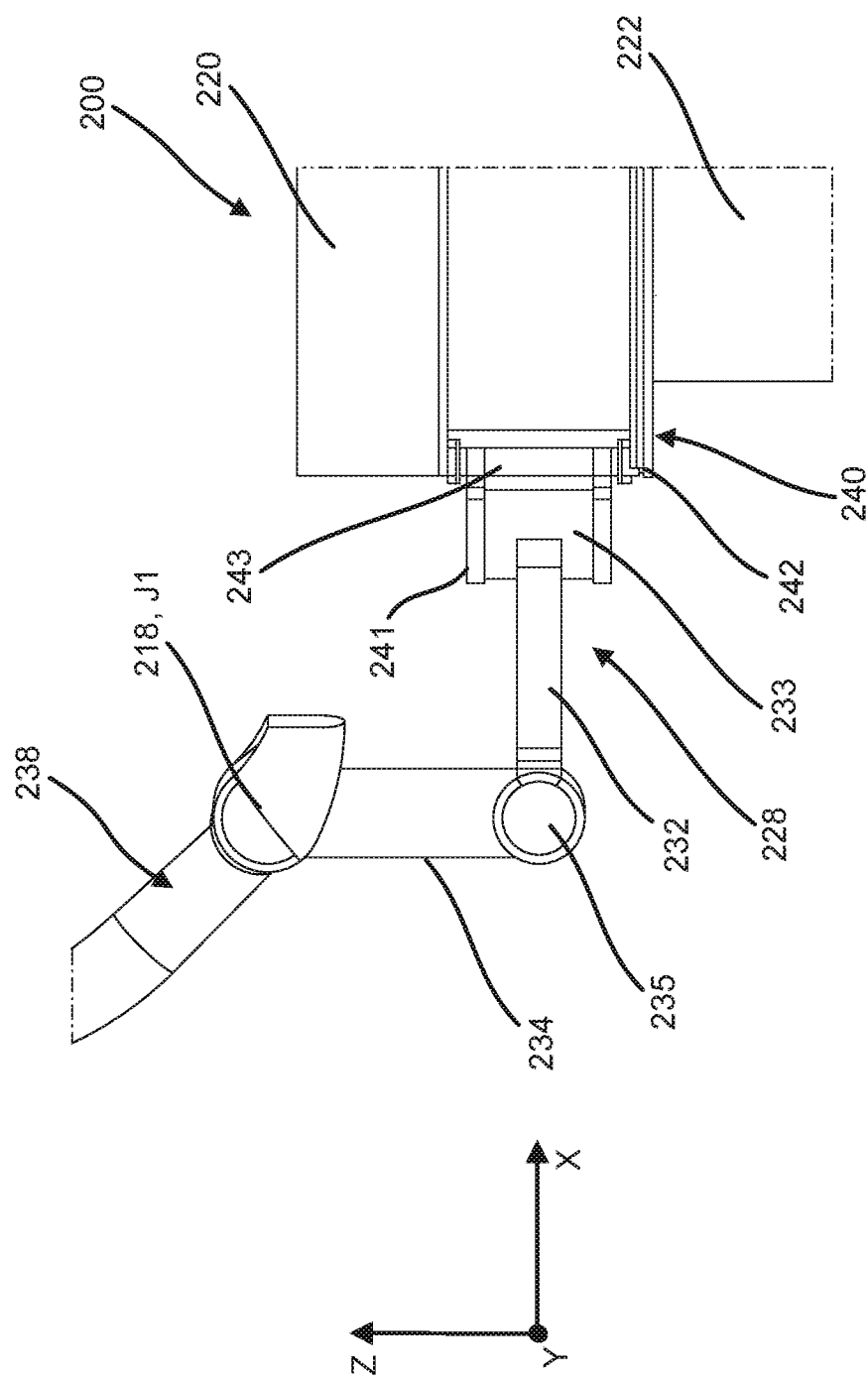
FIG. 5 is a side view of a portion of the surgical table and adapter of FIGS. 3 and 4 shown coupled to a robotic arm.
Figure 9A:
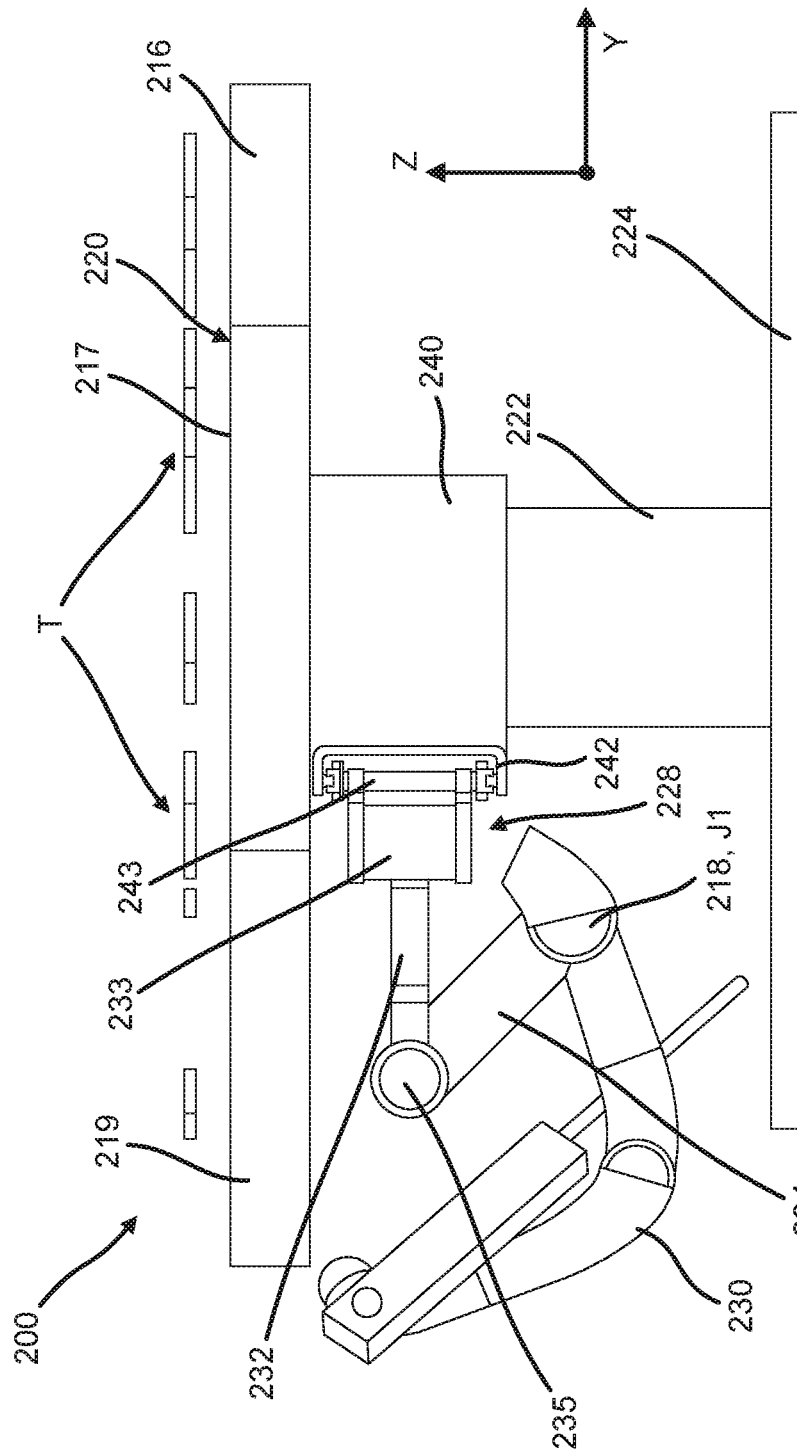
FIGS. 9A and 9B are each a side view of a portion of the surgical table and adapter of FIGS. 3 and 4 with one arm attached to the adapter and shown in a stowed position.

A portion of a table adapter 228 (also referred to herein as "adapter") is shown coupled to the surgical table of FIG. 3. As best shown in FIGS. 4 and 5, the adapter 228 includes two table interface mechanisms 240 coupled to the support 222. Each of the two table interface mechanisms 240 includes a pair of L-shaped rails 242 vertically spaced from each other, multiple vertical posts 243 and mounting members 241. Each of the interface mechanisms 240 can wrap around an opposite corner of the support pedestal 222. In this embodiment, each of the interface mechanisms 240 can support two robotic arms 230 and can have the same components and function in the same manner. FIG. 9A illustrates an interface mechanism 240 attached at a corner of the support 222 near the head section of the table 200, and FIG. 9A illustrates an interface mechanism 240 attached to the support 222 at an opposite corner near the leg section 219 of the table 200.

The posts 243 of the interface mechanisms 240 are slidably received within the vertically spaced tracks of the rails 242. Two first link members 232 are each pivotally coupled to a mounting member 241 at a first joint 233, and two second link members 234 are each pivotally coupled to one of the first link members 232 at a second joint 235. Each of the second link members 234 can also be coupled to a robotic arm 230 at a coupling 218. In this embodiment, the coupling 218 is a pivotal coupling joint between a coupling portion (not shown) on the adapter 228 and a coupling portion (not shown) on the robotic arm 230 that includes the target joint J1. Four robotic arms 230-1, 230-2, 230-3 and 230-4 (collectively referred to as robotic arms 230) are coupled to the adapter 228. More specifically, two robotic arms 230 (230-1 and 230-2) are coupled to one of the interface mechanisms 240 and two robotic arms 230 (230-3 and 230-4) are coupled to the other interface mechanism 240 as shown, for example, in FIG. 6. The first joint 233 and the second joint 235 of the adapter 228 allow the adapter 228 to be moved between an extended configuration for use during a surgical procedure as shown, for example, in FIGS. 5 and 6, and a folded or collapsed configuration for storage when not in use, as shown, for example, in FIGS. 7, 9A and 9B.

As described above, the robotic arm(s) 230 can be used to perform a surgical procedure on a patient disposed on the surgical table 200. Each robotic arm 230 can be configured the same as or similar to, and function the same as or similar to, the robotic arms 130 described above and thus, specific details regarding the robotic arms are not discussed with respect to this embodiment. For example, as described above for robotic arms 130, the robotic arms 230 can include multiple links or segments and can be moved between an extended configuration for use during a surgical procedure, and a folded or collapsed configuration for storage when not in use. The first joint 233, the second joint 235 and the coupling 218 can provide for movement of the robotic arm 230 along and/or about the X, Y, and/or Z axes as described in more detail below.

Figure 7:
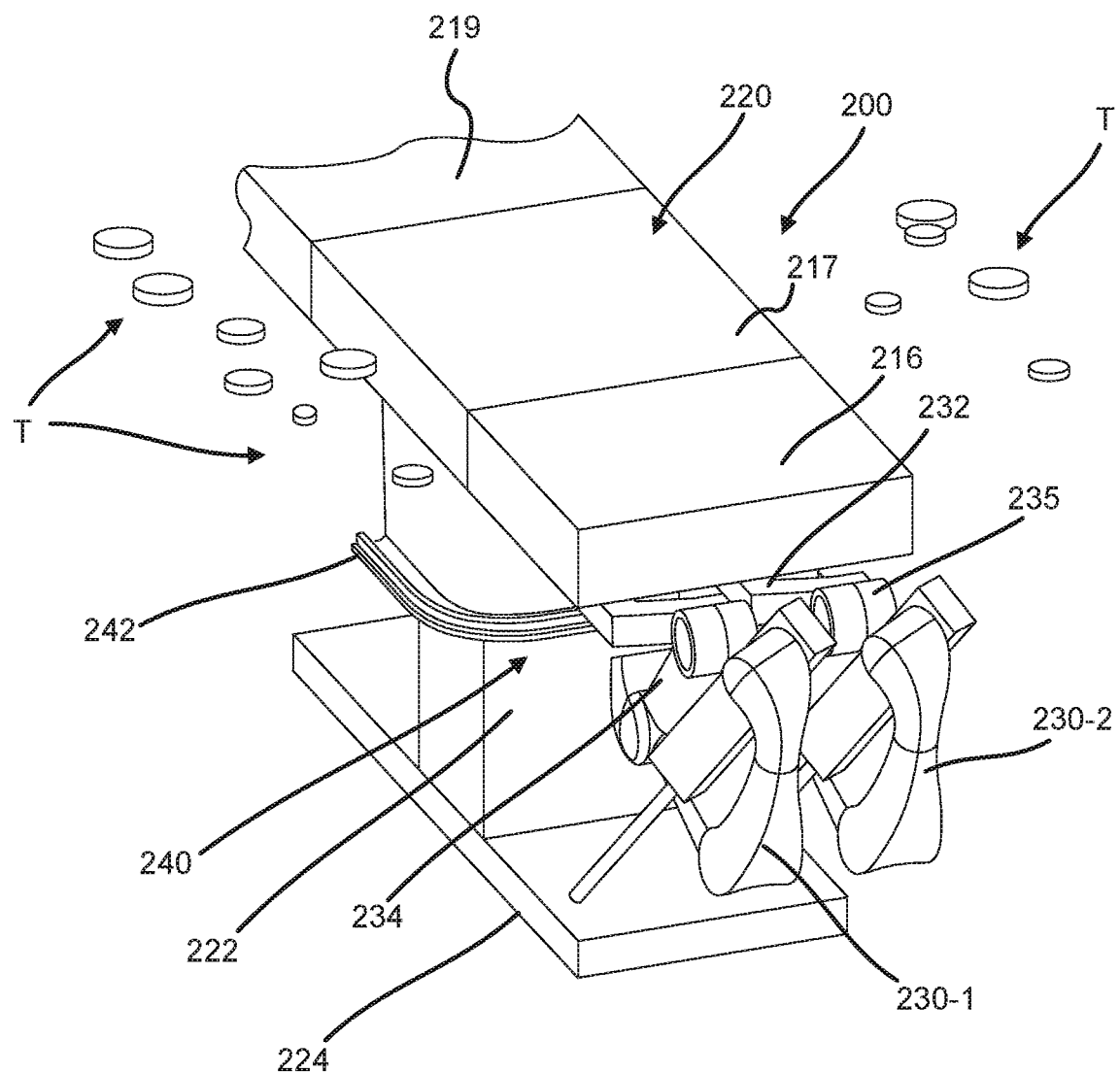
FIG. 7 is an end perspective view of a portion of the surgical table, adapter and two robotic arms of FIG. 5 with the adapter and arms shown in a stowed position.
Figure 9B:
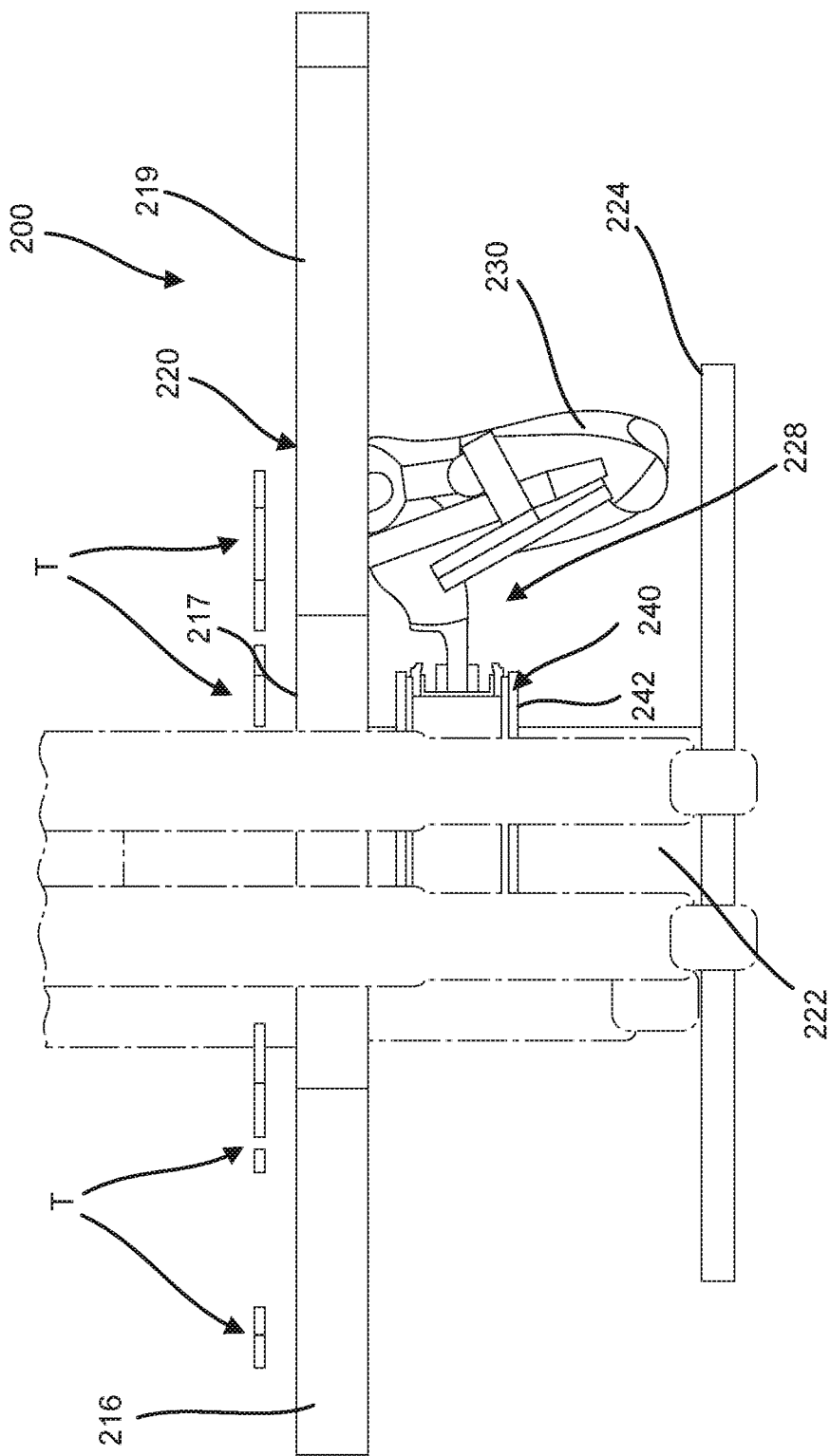

More specifically, the first joint 233 includes a pivotal coupling that can provide for rotational motion of the first link member 232 relative to the interface structure 240 (and table 200) about a vertical z-axis (shown in FIGS. 5 and 9A) relative to the top surface of the table top 220 (e.g., the top surface of the torso section 217), and movement of the first link member 232 and second link member 234 in lateral and longitudinal directions (also referred to herein as x-direction and y-direction) relative to the table top 220 of the surgical table 200. The second joint 235 can provide a lift mechanism to allow for vertical movement of the second link member 234 and the coupling 218 between the second link member 234 and the robotic arm 230 coupled thereto. In this embodiment, the second joint 235 includes a pivotal coupling that provides for the second link member 234 to rotate about an axis within, or parallel to, the x-y plane (see X and Y axes in FIGS. 5 and 8) parallel to a plane of the top surface of the table 200 (e.g., a top surface of the torso section 217) Thus, the motion of the first link member 232 and the second link member 234 of the adapter 228 can provide for movement of the coupling 218 and therefore, movement of a robotic arm 230 coupled thereto along and/or about the X, Y, and/or Z axes to position the target joint J1 at a desired treatment location relative to the top surface of the table top 220. For example, the target discs labeled T in FIGS. 3, 7, 8, 9A and 9B represent target treatment locations for placement of the target joint J1 for various procedures. More specifically, as shown in FIGS. 3 and 8 four target discs T are illustrated (only three target discs T are visible in the top view of FIG. 8) and represent the target locations for the target joint J1 on four robotic arms 230 when positioned in an operating position to perform a particular surgical procedure. FIGS. 7, 9A and 9B, illustrate multiple different sets of target discs T and each set represents the target positions for the target joint J1 of a set of robotic arms 230 to perform a particular surgical procedure.

The collective motion of the first link member 232 and the second link member 234 allows the adapter 228 and robotic arms 230 to move between a variety of different positions relative to the surgical table 200 during a surgical procedure. For example, adapter 228 and robotic arms 230 can be moved to a stowed position substantially beneath the table top 220 as shown, for example, in FIGS. 7 and 9 (FIG. 8 shows only a single arm coupled to the adapter for illustrative purposes). In this embodiment, in the stowed position, the arms 230 extend slightly beyond the head section 216 of the table top 220 (best seen in FIG. 9). The arms 230 and adapter 228 are each in a folded or collapsed configuration in the stowed position disposed beneath the table top 220 within an outer perimeter defined by the table top 220. In this embodiment, the adapter 228 can accommodate movement of the arms 230 about the table top 220 by slidably moving the arms 230 along the rails 242 via the vertical posts 243. As shown in FIG. 7, the arms 230-1 and 230-2 have been moved (i.e., traveled along the rails 242) of the interface mechanism 240 to a position at an end of the table 200 substantially beneath the head section 216, which provides clearance along the sides of the table 200 to, for example, move a patient from a gurney onto the table top 220 as described above. Although not shown, the other two arms 230-2 and 230-4 can similarly be moved along the rails 242 to a position at the opposite end of the table 200 (beneath the leg section 219).

Figure 6:
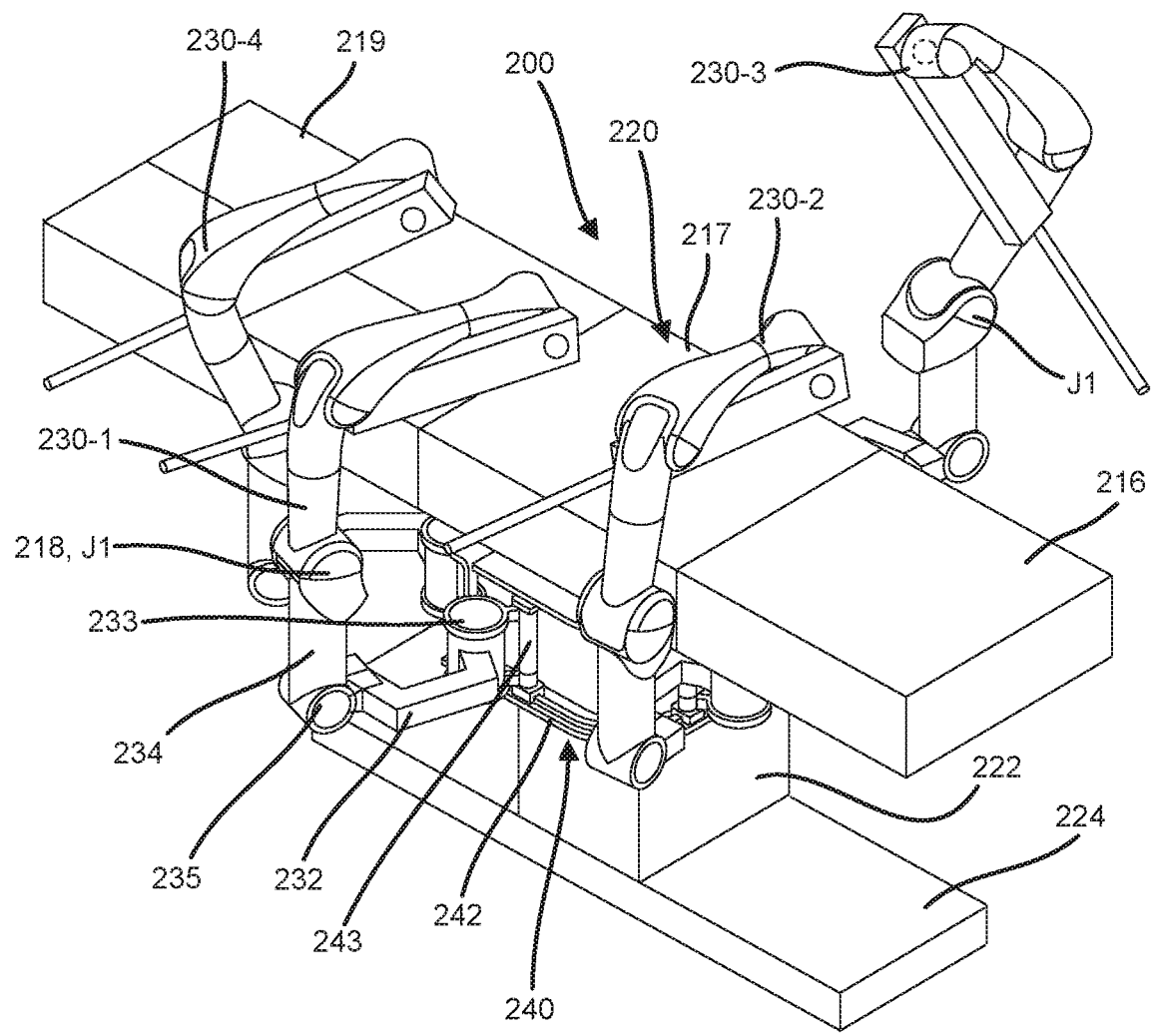
FIG. 6 is a perspective view of the surgical table of FIG. 3 and the adapter of FIG. 4 attached thereto with four robotic arms attached to the adapter, and the adapter and arms shown in an operating position.

The adapter 228 and arms 230 can also be moved to various operating positions as shown for example, in FIGS. 6 and 8. In this embodiment, the positioning of the arms about the table top 220 can be varied to accommodate various different procedures. For example, in some procedures it may be desirable to have an operating position in which three robotic arms 230 are disposed on one side of the table top 220 and one arm 230 is disposed on an opposite side of the table top 220 as shown in FIG. 6. Such a positioning of the arms 230 may be desirable for performing, for example, a prostatectomy procedure on a patient disposed on the table top 220. The adapter 228 can accommodate movement of the arms relative to the table top 220 by slidably moving one of the arms 230-4 around the support 222 via the rails 242 of the second interface mechanism 240 on the opposite corner of the support 222 (not shown) as described above. As shown in FIG. 6, the robotic arms 230 are also disposed in a treatment configuration in which a distal end of the arms 230 (and instrument coupled thereto) is disposed in a treatment zone.

In some embodiments, it may be desirable to position two robotic arms 230 on each side of the table 200 as shown in FIG. 8. Such positioning of the arms 230 may be desirable to perform, for example, a lower anterior resection ("LAR") procedure on a patient disposed on the table top 220. FIG. 8 also illustrates the arms 230 disposed in a parked position. As described above, the parked position is used when access to the patient is needed, and the robotic arms 230 are moved to a clearance position relative to the table top 220. As shown in FIG. 8, in this example, the robotic arms 230-3 and 230-4 have been moved longitudinally along the side of the table top 220 and out of the treatment zone to provide space for a medical professional to tend to the patient. The arms 230-1 and 230-2 have also been moved out of the treatment zone. When the need for the clearance has passed, the arms 230 can then be placed back into the operating position with the target joints J1 disposed at the target treatment locations relative to the table top 220.

Figure 9C:
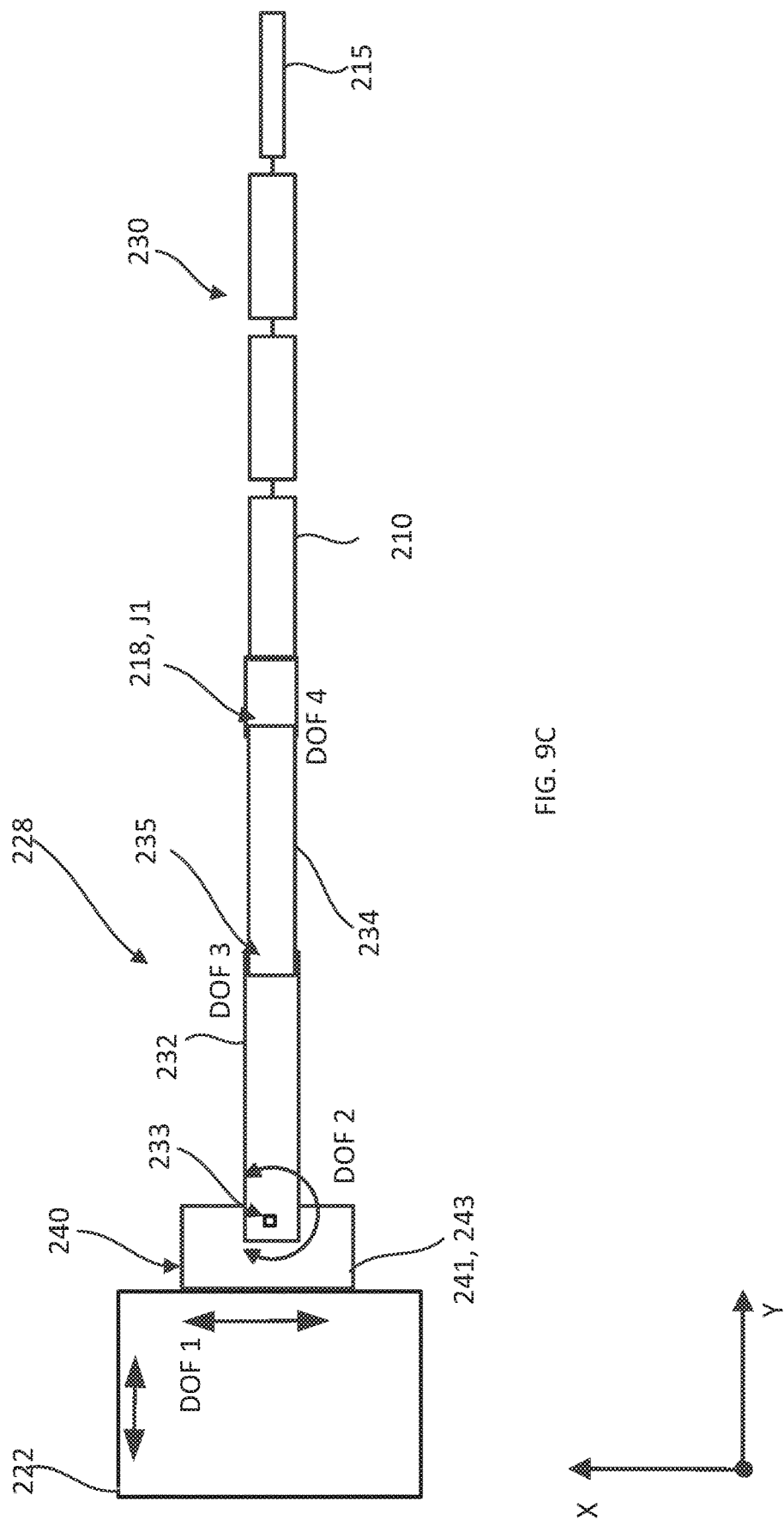

FIGS. 9C and 9D are schematic illustrations of the various degrees of freedom provided by the joints of the adapter 228 and robotic arm 230, and FIG. 9E is a table listing the type of degree of freedom (e.g., rotational, linear) associated therewith. As shown in FIGS. 9C and 9D, and as described above, the interface mechanism 240 is coupled to the support 222 of the table 200 and includes a pair of L-shaped rails 242 vertically spaced from each other, multiple vertical posts 243 that slide within the rails 242 about the support 222, and mounting members 241 coupled to the posts 243 and to which the link members 232 are coupled. The movement of the vertical posts 243 within the rails 242 allows the first link members 232 to translate in the x-direction and the y-direction, providing a first degree of freedom DOF 1 that includes X-axis translation and Y-axis translation (i.e., translation about along the side and end of the table 200). The first link members 232 are also pivotally coupled to the mounting members 232 such that the first link members 232 can rotate about the z-axis and provide a second degree of freedom DOF 2 at joint 233, i.e. Z-axis rotation. The joint 235 between the first link member 232 and the second link member 234 is also a rotational or pivotal joint that can pivot about a horizontal axis, i.e. an axis lying in the X-Y plane and thus provide a third degree of freedom DOF 3 (best shown in the side view illustration of FIG. 9D) that is X-Y plane rotation. Similarly, the joint J1 at the coupling 218 is also a pivotal joint that can pivot about a horizontal axis and provide a fourth degree of freedom DOF 4 (best shown in the side view illustration of FIG. 9D) that is X-Y plane rotation. Although not labeled in FIGS. 9C and 9D, the various joints between links 210 of the arm 230 and a medical instrument 215 disposed on the distal end of the robotic arm 230 can provide additional motion of the arm relative to a patient (e.g., a target treatment location on the patient) disposed on the table 200, and therefore, additional degrees of freedom.

FIGS. 10-22C illustrate another embodiment of a surgical table and adapter. As shown in FIGS. 10-12 a surgical table 300 includes a table top 320, a support 322 (see FIG. 15 and exploded view of FIG. 17) (also referred to herein as pedestal) and a base 324 (see, e.g., FIGS. 15 and 17). As described above for previous embodiments, the support 322 can be mounted to the base 324, which can be fixed to the floor of an operating room, or can be movable relative to the floor. The table top 320 includes a head section 316, a torso section 317 and a leg section 319. The table top 320 can also include an arm section(s) (not shown). The table top 320 has a top surface on which a patient can be disposed. The support 322 can provide for movement of the table top 320 in a desired number of degrees of freedom as described above. In this embodiment, the head section 316 is pivotally coupled to a first end of the torso section 317 and the leg section 319 is pivotally coupled to a second end of the torso section 317 such that the head section 316 and leg section 319 can be rotated about an x-axis extending in a lateral direction relative to the table top 320, as shown in FIGS. 10-12. As described above, movement of the table top 320 and/or its constituent sections may be performed manually, driven by motors, controlled remotely, etc. The surgical table 300 can also include a radio-translucent window (not shown) as described for previous embodiments.

Figure 13:
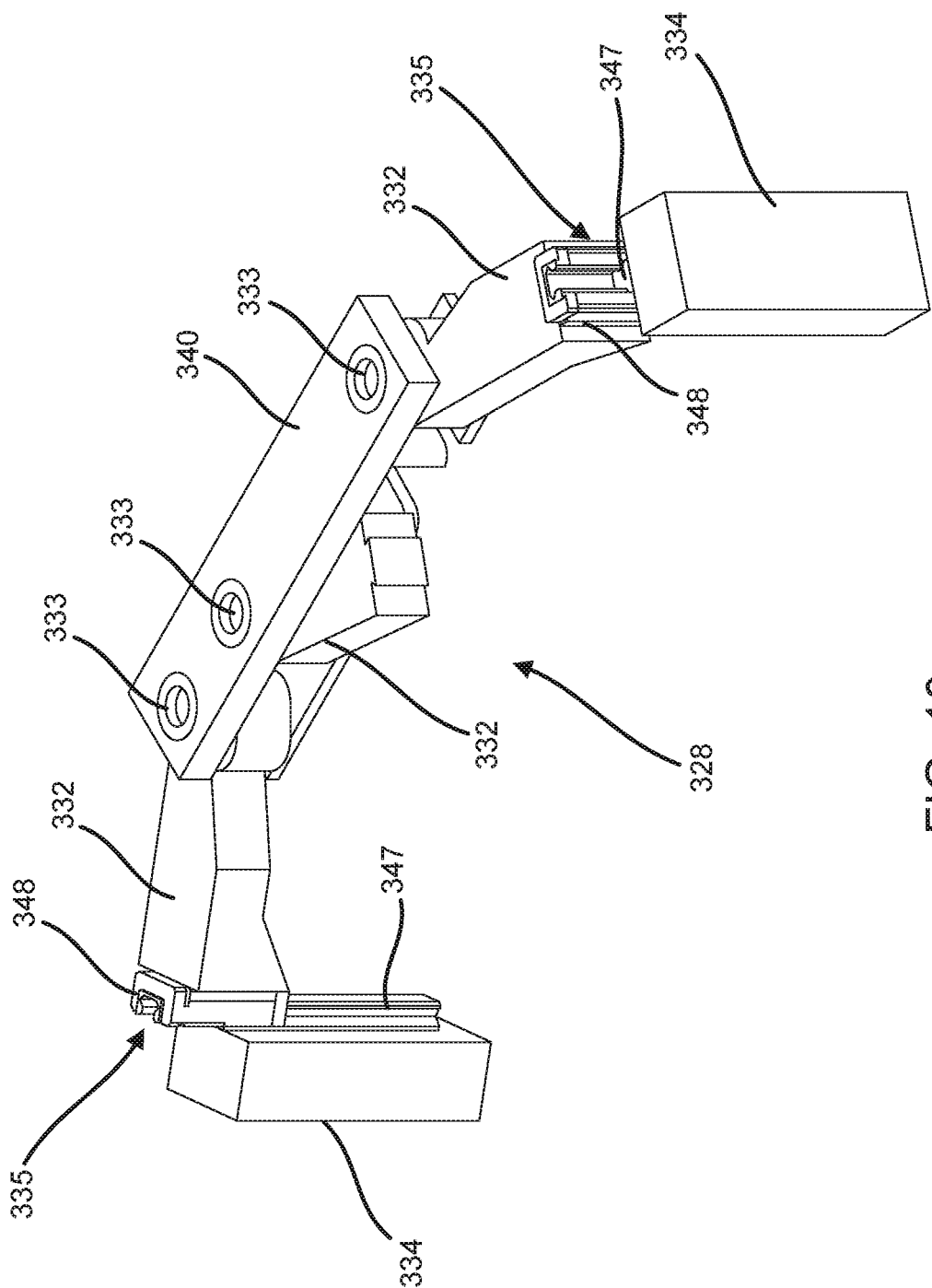
FIG. 13 is a perspective view of the adapter of FIGS. 10-12.
Figure 14A:
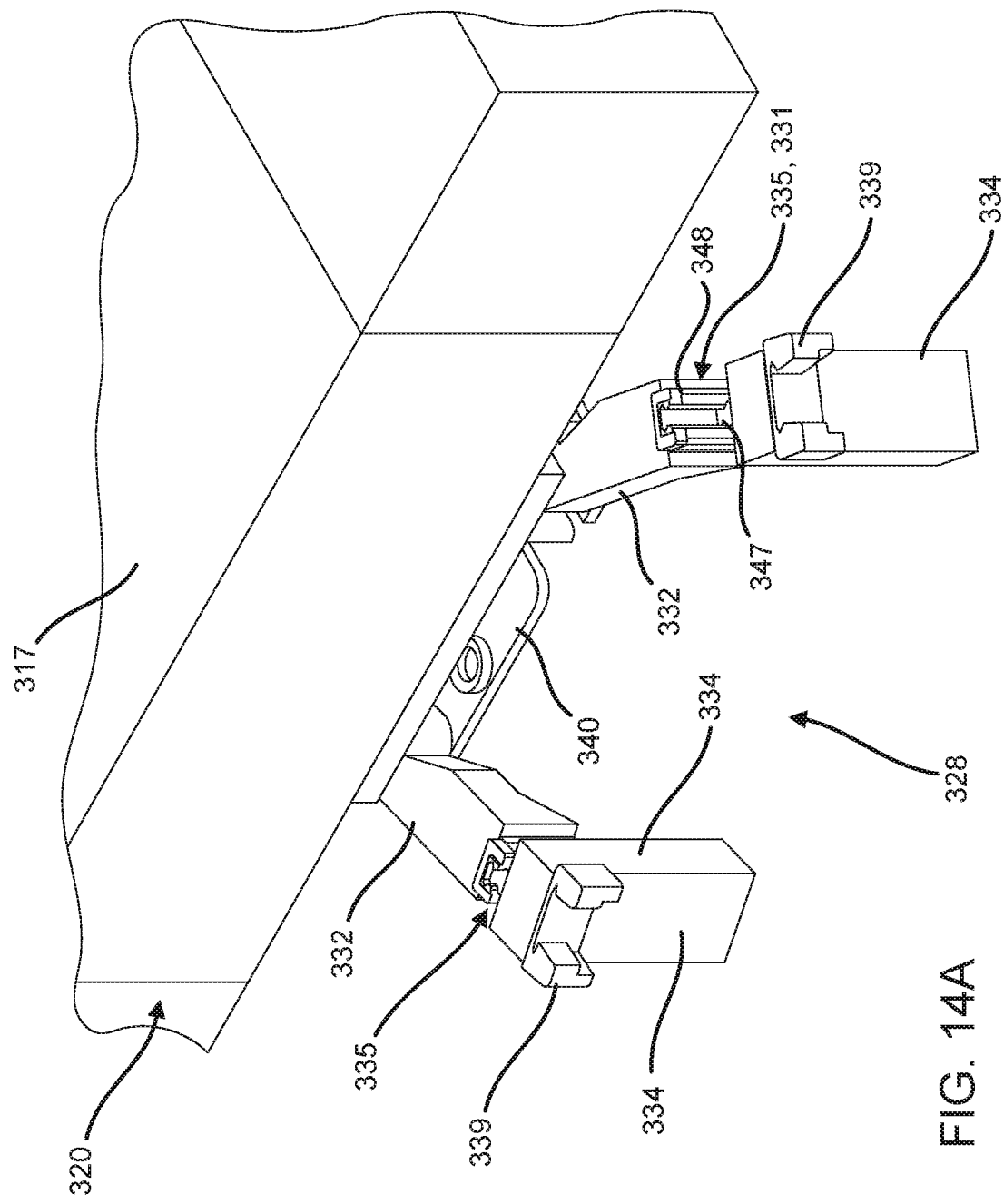
FIG. 14A is a side perspective view of a portion of the surgical table and adapter of FIGS. 10-12.
Figure 15:
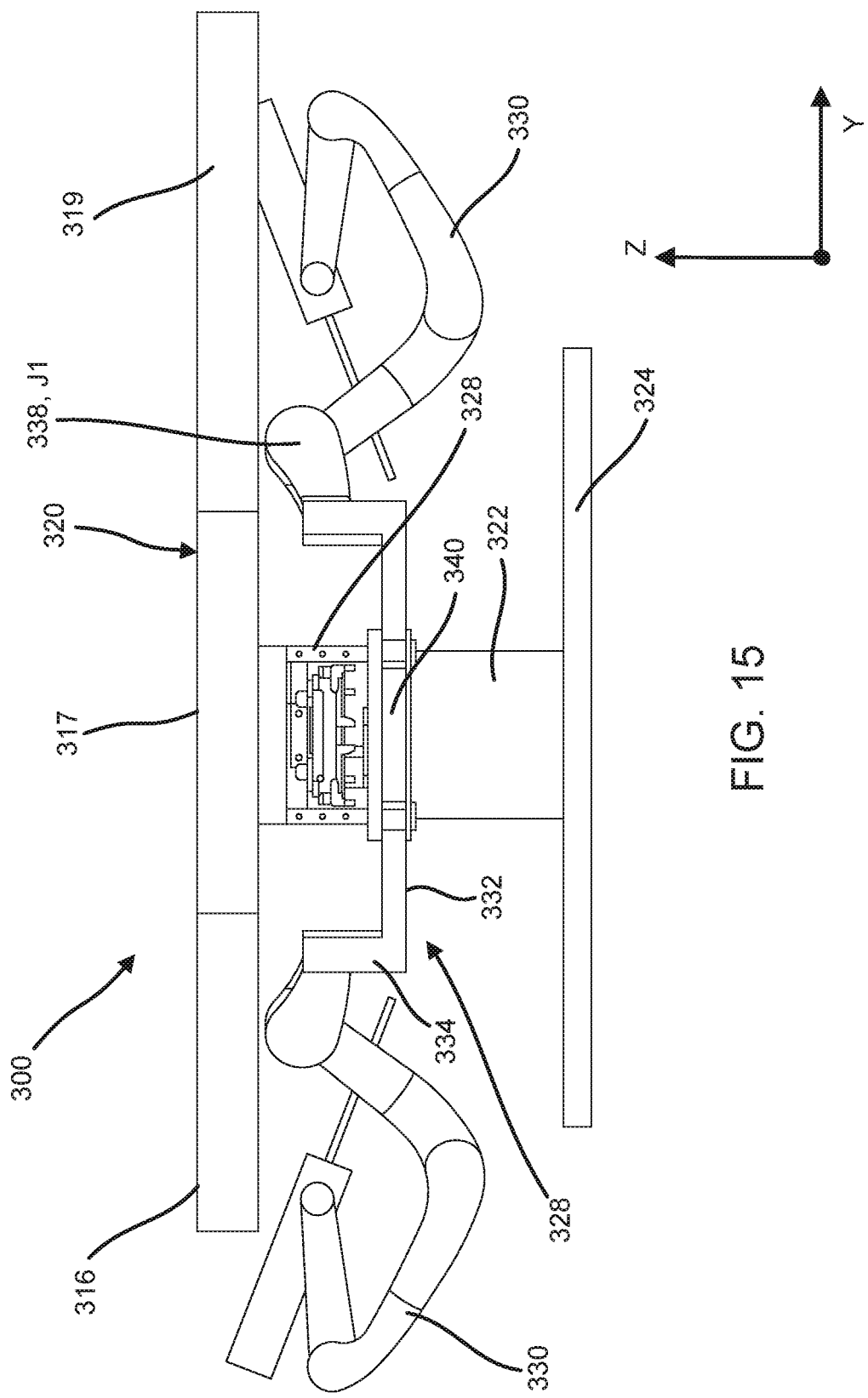
FIG. 15 is a side table of the surgical table and adapter of FIGS. 10-12 with two robotic arms coupled to the adapter and in a stowed position.
Figure 16:
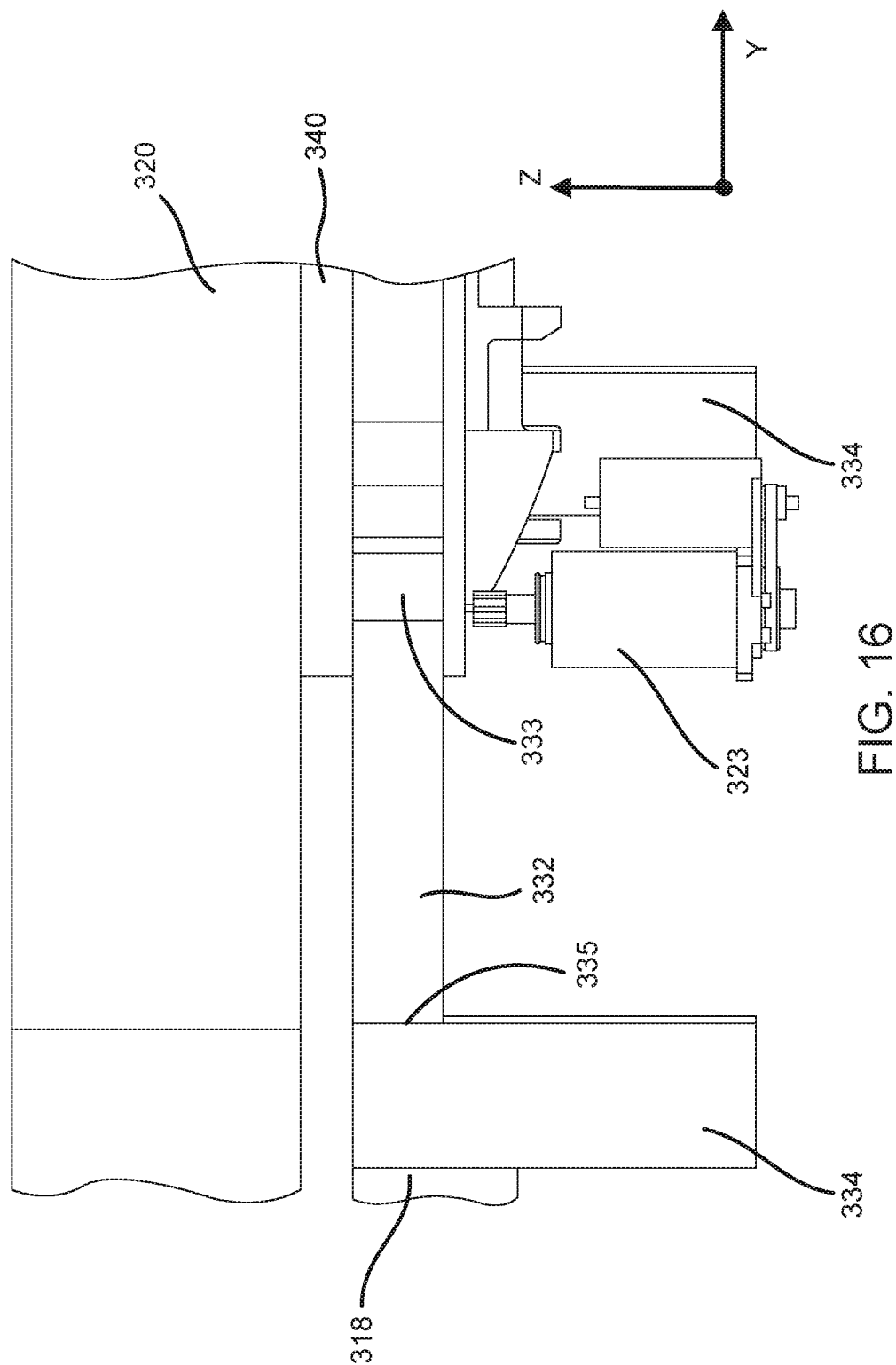
FIG. 16 is an enlarged view of a portion of the surgical table and adapter of FIGS. 13-15 and a motor (shown detached from the table) that can optionally be operatively coupled to the adapter.

A table adapter 328 (also referred to herein as "adapter") is shown coupled to the surgical table 300 without robotic arms attached thereto in FIGS. 10-12. As best shown in FIGS. 13-15, the adapter 328 includes a table interface structure 340 coupled to the support 322. The table interface structure 340 includes a support plate that can be coupled to the support 322 and/or the table top 320. In some embodiments, the interface structure 340 can be a single structure that supports up to six robotic arms 330 (described below). In some embodiments, the adapter 328 can include two interface mechanisms 340, each being coupleable to the table 300 on an opposite side of the table top 320. In some embodiments, the adapter 328 can be coupled to the support 322 such that the adapter 328 can move vertically up and down relative to the support 322 as shown in FIG. 15. For example, the table interface structure 340 can be motor driven to ride along rails 329. In some embodiments, the table top 320 can be moved longitudinally (in the Y-axis direction) relative to the adapter 328, or the adapter 328 can be moved relative to the table top 320. For example, the adapter 328 can be coupled to the support 322 and when the table top 320 moves relative to the support 322, the table top 320 will move relative to the adapter 328. For example, FIG. 10 illustrates the table top 320 substantially centered with the adapter 328. FIG. 11 illustrates the table top 320 offset to the left relative to the adapter 328 (so that the adapter 328 is partially beneath head section 316), and FIG. 12 illustrates the table top 320 offset to the right relative to the adapter 328 (so that the adapter 328 is partially beneath leg section 319).

The adapter 328 further includes multiple first link members 332 that are each pivotally coupled to the table interface structure at a first joint 333, and multiple second link members 334 that are each coupled to one of the first link members 332 at a second joint 335. The second joint 335 provides the lift mechanism for moving the second link member 334 vertically. In this embodiment, the second joint 335 includes a linear motion mechanism 331 that allows the second link member 334 to translate vertically, i.e. parallel to the z-axis, relative to the first link member 332. As shown in FIGS. 13, 14A and 14B, the linear motion guide mechanism 331 includes first component 347 coupled to the second link member 334 that includes an elongate protrusion that can be slidably received within a track or recess of a second component 348 coupled to the first link member 332.

In an alternative embodiment, the vertical linear motion of the second link member 334 relative the first link member 332 can be provided by a slide feature that can include, for example, a slot in the second link member 334 that receives a mating protrusion on the first link member 332 as shown in FIG. 14C. In some embodiments, the lift mechanism can provide for at least 6.5 inches of vertical travel. In another alternative embodiment, the second joint 335 that provides the lift mechanism can be a pivotal joint as described herein for other embodiments. As with previous embodiments, the first joint 333 and the second joint 335 of the adapter 328 allow the adapter 328 to be moved between an extended configuration for use during a surgical procedure as shown, for example, in FIGS. 20A, 20B, 21A and 21B, and a folded or collapsed configuration for storage when not in use, as shown, for example, in FIGS. 17 and 18.

In this embodiment, the adapter 328 supports three sets of first link member 332 and second link members 334. For example, three first link members 332 and three second link members 334 can be coupled to the adapter 328 and disposed on one side of the table 300, and three first link members 332 and three second link members 334 can be coupled to the adapter 328 and disposed on an opposite side of the table 300. In some embodiments, each of the first link members 332 and/or each of the second link members 334 can have varying lengths. For example, as best shown in FIG. 13, on one side of the adapter 328, a middle first link member 332 (shown without a second link member coupled thereto) is shorter than the other two first link members 332.

Each of the second link members 334 can also be coupled to a robotic arm 330 at a coupling 318. In this embodiment, the coupling 318 includes a coupling portion 339 on the second link member 334 (see FIG. 14A) includes a u-shaped connector (shown in FIG. 14A) that can be matingly coupled to a connector (not shown) at the mounting end 336 of the robotic arm 330. In an alternative embodiment, the coupling 318 can include a coupling portion 339' in the form of an opening configured to receive a post (not shown) of a coupling portion 338 at a mounting end 336 of a robotic arm 330. In this embodiment the coupling portion 338 includes the target joint J1 as shown in FIG. 14B.

In this embodiment, the adapter 328 can accommodate six robotic arms 330 (i.e., the adapter 328 can include six first link members 332 and six second link members 334 as described above). Each robotic arm 330 can be releasably coupled to the adapter 328 via the coupling 318. Each robotic arm 330 can be configured the same as or similar to, and function the same as or similar to, the robotic arms 130 described above and thus, specific details regarding the robotic arms are not discussed with respect to this embodiment. For example, as described above for robotic arms 130, the robotic arms 330 can include multiple links or segments coupled together to allow for movement of the arms 330 between an extended configuration for use during a surgical procedure, and a folded or collapsed configuration for storage when not in use. The movement of the first link member 332 and the second link member 334 can provide for movement of the robotic arm 330 (and the target joint J1) along and/or about the X, Y, and/or Z axes as described in more detail below.

Figure 17:
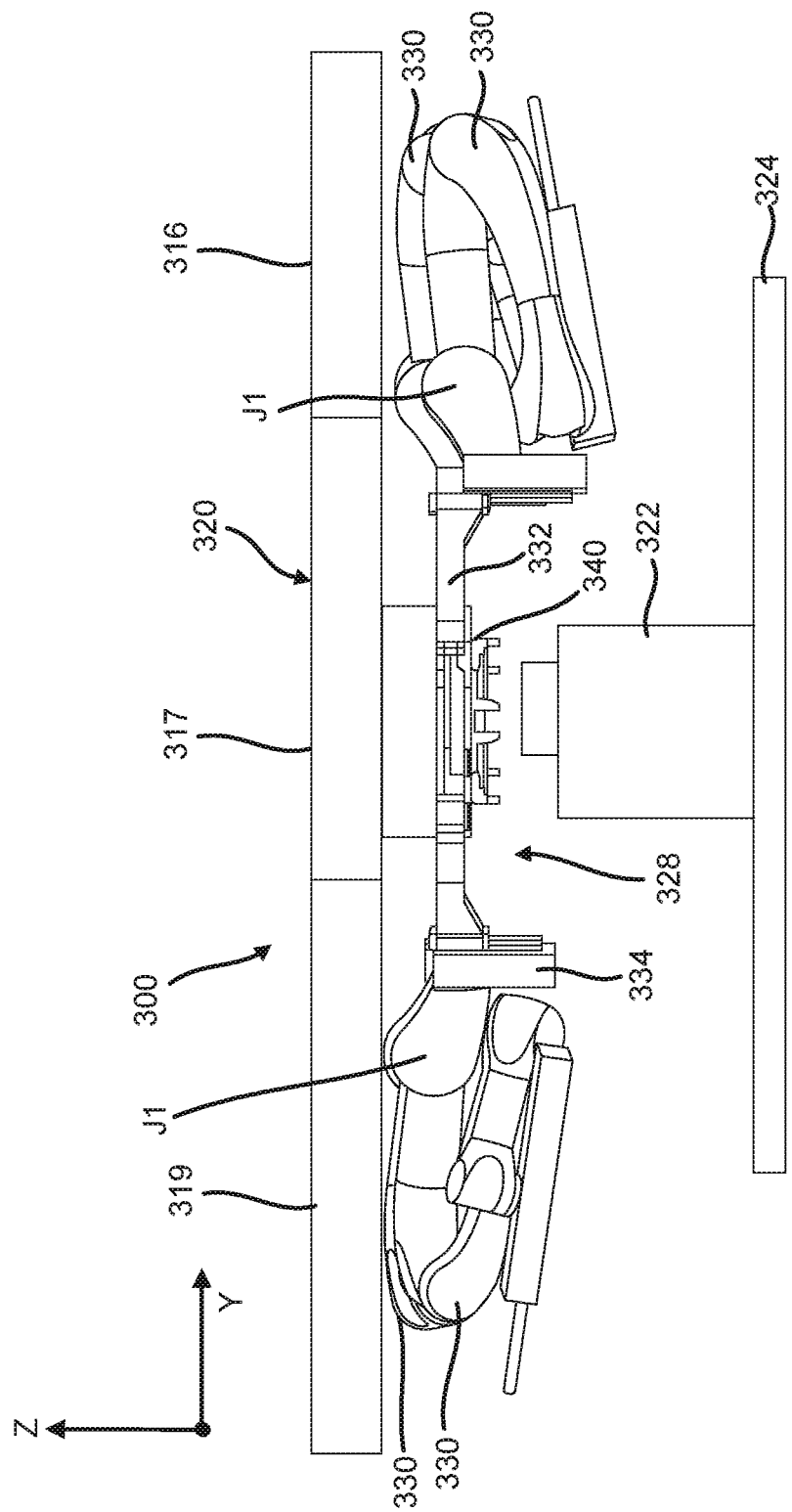
FIGS. 17 and 18 are a partial exploded side view and top view, respectively, of the surgical table and adapter of FIGS. 10-15 with four robotic arms coupled to the adapter and the adapter and arms shown in a stowed position.
Figure 18:
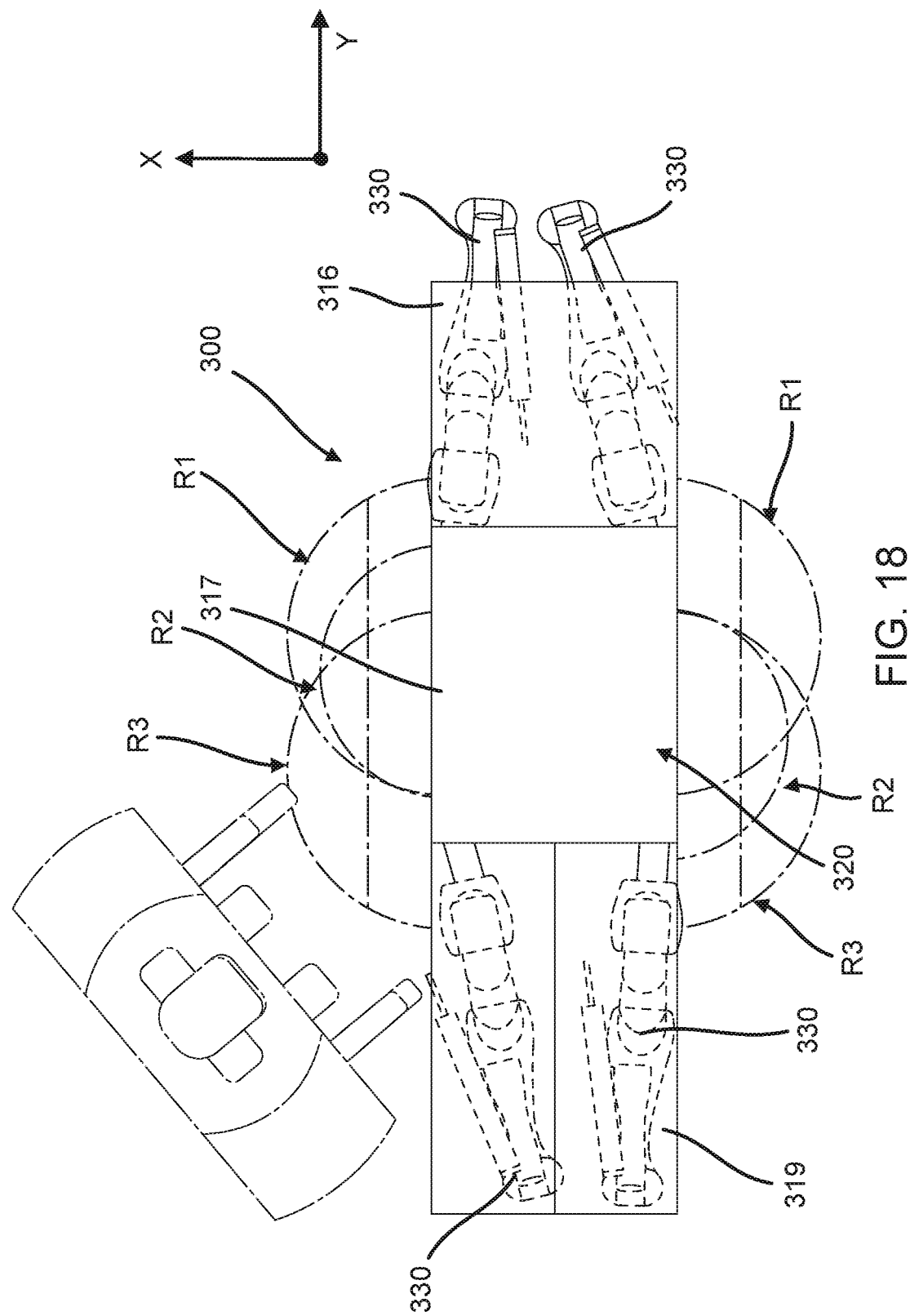
Figure 19A:
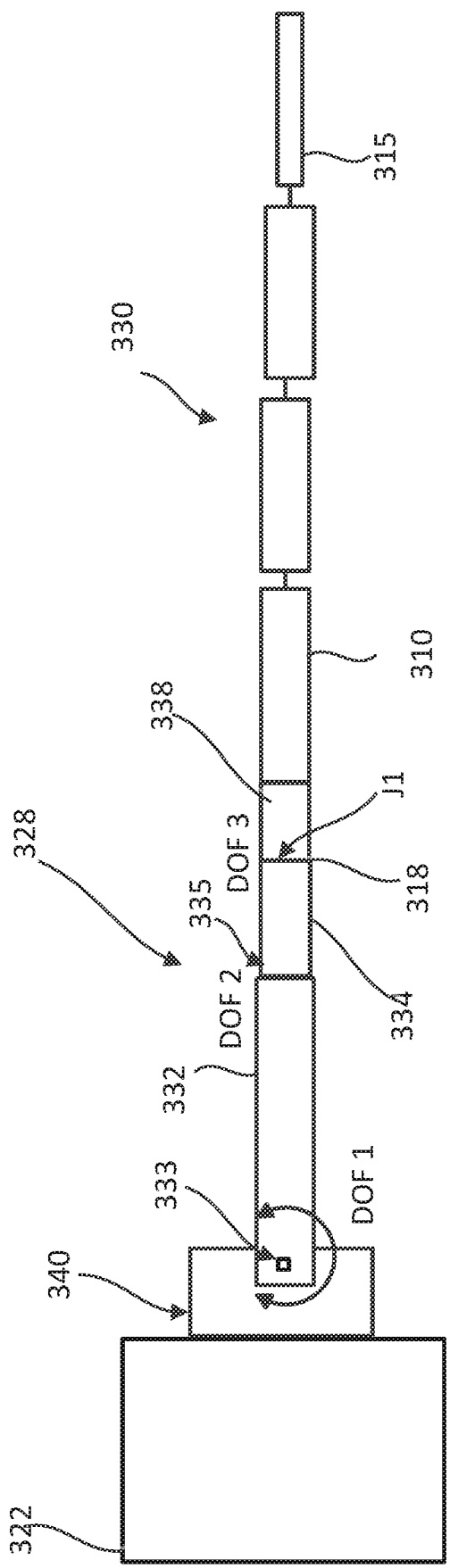

More specifically, as with the previous embodiments, the first joint 333 can provide for rotational motion of the first link member 333 relative to the table interface structure 340 (and table 300) about a vertical z-axis (shown in FIGS. 15-17) relative to a top surface of the table top 320 (e.g., the top surface of the torso section 317), and movement of the first link member 332 and second link member 334 in lateral and longitudinal directions (also referred to herein as x-direction and y-direction) parallel to the top surface of the table top 320 of the surgical table 300 (see, e.g., X-Y axes in FIGS. 18, 19A and 19B). As described above, the second joint 335 can provide the lift mechanism to allow for vertical movement of the second link member 334 and the coupling 318 between the second link member 334 and the robotic arm 330. Thus, the motion of the first link member 332 and the second link member 334 of the adapter 328 can provide for movement of the robotic arm 330 coupled thereto along and/or about the X, Y, and/or Z axes to position the target joint J1 at a desired treatment location relative to the table top 320. For example, as shown in FIG. 18 an example range of motion or travel arc for the target joints J1 are illustrated and labeled R1, R1, and R3. The three travel arcs R1, R2 and R3 are shown on each side of the table 300 and represent an example range of motion of the target joint J1 for three robotic arms 330 when coupled to the adapter 328 on one side of the table. As shown in FIG. 18, in some embodiments, the travel arc for target joint J1 for one robotic arm can be smaller than for another robotic arm. For example, one of the first link members 332 and/or second link members 334 may be shorter than the other first link members 332 and/or second link members 334 as described above. Thus, various different travel arcs can be defined by different robotic arms. The range of motion is shown extending in the X-Y directions and also extends within a Z-axis direction (coming out of the page) via the lift mechanism of the second joint 335 and the movement capability of the robotic arms 330.

The collective motion of the first link member 332 and the second link member 334 allows the adapter 328 and robotic arms 330 to move between a variety of different positions relative to the surgical table 300 during a surgical procedure. For example, adapter 328 and robotic arms 330 can be moved to a stowed position substantially beneath the table top 320 as shown, for example, in FIGS. 17 and 18. FIGS. 17 and 18 illustrate a stowed position with four robotic arms 330 coupled to the adapter 328. Thus, if more than four robotic arms 330 are used, two of the arms 330 may be removed in this stowed position. For example, the releasable coupling 318 of the arms 330 to the second link member 334 allows for removal and recoupling of the arms 330 at different locations on the adapter 328 as needed. In this embodiment, the arms 330 and the link members 332 and 334 can be moved to the stowed position via the first joint 333 and the second joint 335. For example, the arms 330 and the second links 334 can be lowered via the second joint 335. The first links 332, second links 334 and arms 330 can then be pivoted to the ends via the first joint 333. The arms 330 can be further folded via the joints between the links/segments of the arms 330. Similarly, the first link member 332 and the second link member 334 can be further folded or collapsed. The arms 330 and adapter 328 are thus in a folded or collapsed configuration in the stowed position and the arms 330 extend slightly beyond the head section 316 of the table top 320 as shown in FIGS. 17 and 18.

FIGS. 19A and 19B are schematic illustrations of the various degrees of freedom provided by the joints of the adapter 328 and robotic arm 330, and FIG. 19C is a table listing the type of degree of freedom (e.g., rotational, linear) associated therewith. As shown in FIGS. 19A and 19B, and as described above, the interface mechanism 340 is coupled to the support 322 of the table 300 and the first link members 332 are pivotally coupled to the interface mechanism 340 at joint 333. The pivotal joint 333 of the first link members 332 to the interface mechanism 340 allows the first link members 332 to rotate about the z-axis and provide a first degree of freedom DOF 1. The second link members 334 are coupled to the first link members 332 at joint 335 such that the second link members 334 can translate in the Z-axis direction (i.e., linear motion in the Z-axis) and provide a second degree of freedom DOF 2 (as best shown in the side view of FIG. 19B). The second link member 334 is coupled to the coupling portion 338 of the robotic arm 330 at the coupling 318. The coupling portion 338 of the robotic arm 330 includes the J1 joint. The J1 joint is a pivotal joint that provides for rotational motion of the robotic arm 330 to pivot about a horizontal axis, i.e. an axis lying in the X-Y plane and thus provide a third degree of freedom DOF 3 (best shown in the side view illustration of FIG. 19B) that is X-Y plane rotation. Although not labeled in FIGS. 19A and 19B, the various joints between links 310 of the arm 330 and a medical instrument 315 disposed on the distal end of the robotic arm 330 can provide additional degrees of freedom relative to a patient (e.g., a target treatment location on the patient) disposed on the table 300.

Figure 21B:
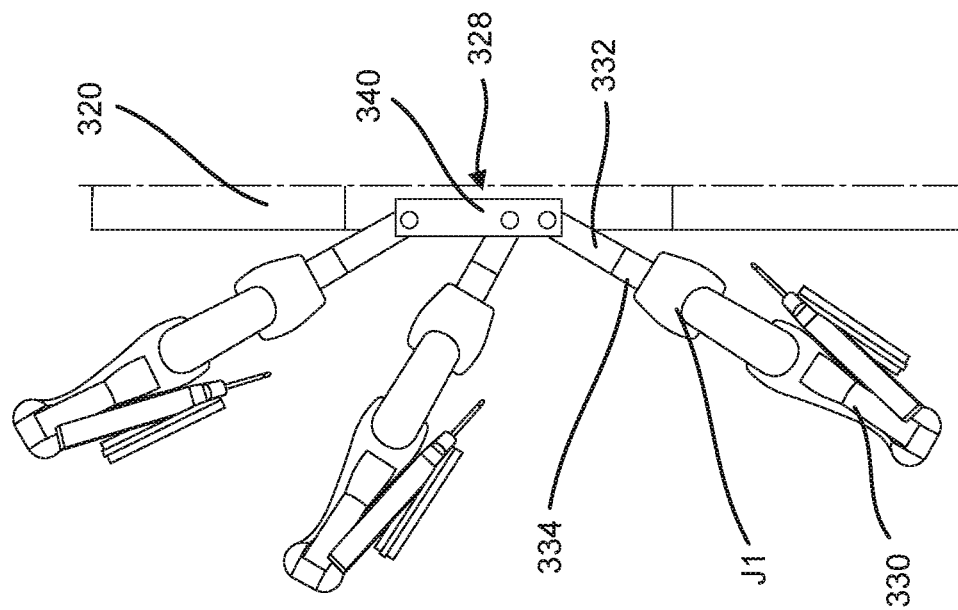
FIG. 21B is bottom view of one side portion of the surgical table, adapter and robotic arms of FIG. 21A shown in an operating position and the robotic arms in a ready configuration.
Figure 21A:
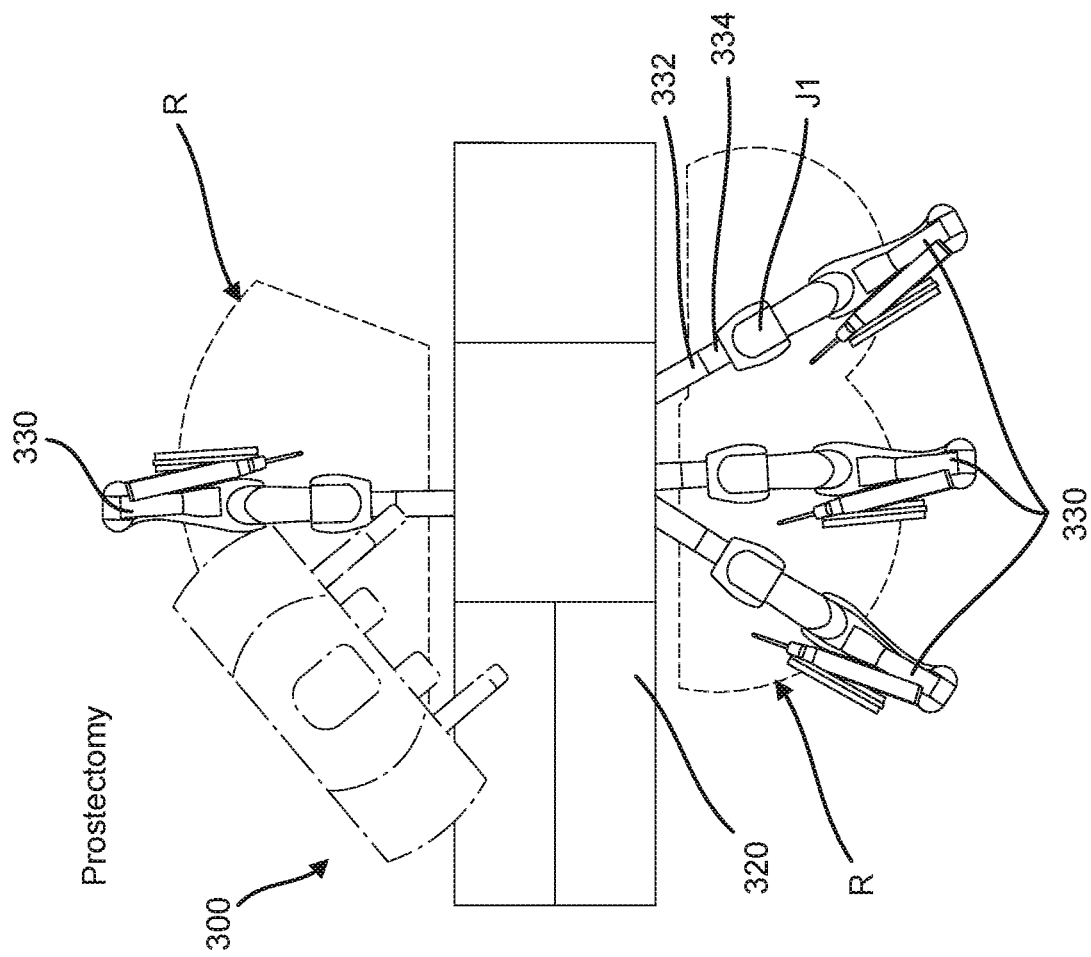
FIG. 21A is a top view of the surgical table of FIGS. 17 and 18 with four robotic arms coupled to the adapter and shown with three arms on one side of the table and one arm on the opposite side of the table and shown in an operating position and the robotic arms in a ready configuration.

FIGS. 22A and 22B illustrate an example stowed position for when three arms 330 are coupled to the adapter 328 on one side of the table 300 such as in FIG. 21A. Only one side of the table 300 is shown in FIGS. 22A and 22B for illustrative purposes. In this alternative stowed position, with three arms 330 disposed on one side of the table, one of the arms 330 is not stowed beneath the table top 320. This same configuration could be done on the opposite side of the table 300, for example, if six arms 330 are attached to the adapter 328.

Figure 20B:
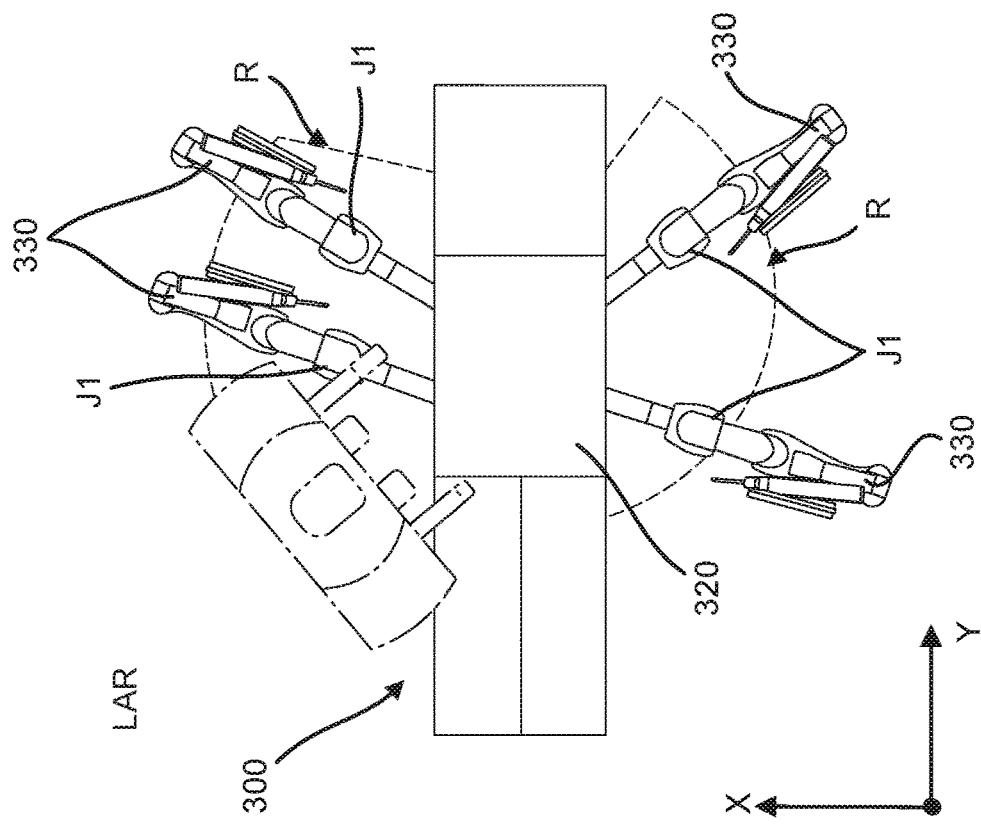
FIG. 20B is a top view of the surgical table of FIGS. 17 and 18 with four robotic arms coupled to the adapter and shown with two arms on each side of the table in an operating position and the robotic arms in a ready configuration.
Figure 20A:
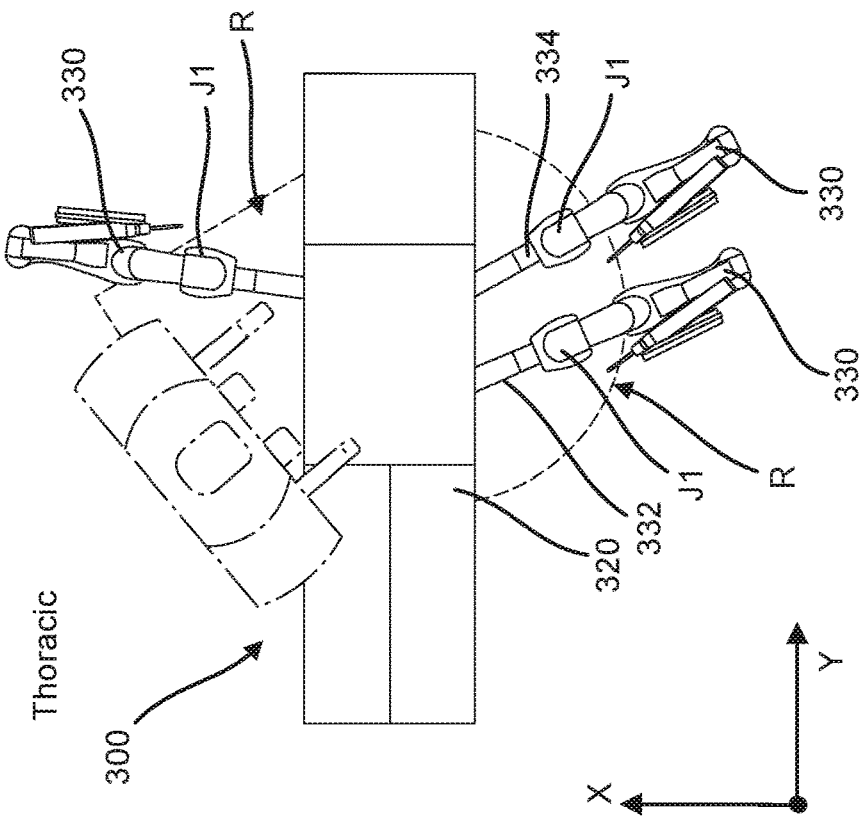
FIG. 20A is a top view of the surgical table of FIGS. 17 and 18 with three robotic arms coupled to the adapter and shown in an operating position and the arms shown in a ready configuration.

The adapter 328 and arms 330 can also be moved from the stowed position to various operating positions in a similar manner using the first joints 333 and the second joints 335. Further, if more than two arms 330 are needed on one side of the table 300, a third arm 330 can be coupled to the adapter 328 as needed. FIGS. 20A, 20B, 21A and 21B illustrate the robotic arms 330 and adapter 328 in various different operating positions for particular surgical procedures. FIG. 20A illustrates an example operating position for a thoracic procedure that includes two arms 330 on one side of the table top 320 and one arm 330 on an opposite side of the table top 320. FIG. 20B illustrates an example operating position for a lower anterior resection procedure that includes two arms 330 on each side of the table top 320. FIG. 21A illustrates an example operating position for a prostatectomy procedure in which three arms 330 are disposed on one side of the table top 320 and one arm 330 is on the opposite side of the table top 320. To achieve this configuration, a third arm 330 can be coupled to the adapter 328 as discussed above or one of the arms 330 on one side of the table 300 can be moved to the opposite side of the table 300. For example, if two arms 330 are coupled to the adapter 328 on each side of the table 300, one arm 330 can be moved (e.g., via movement of the first and second link members 332 and 334) to the opposite side of the table 300 to accommodate a procedure that requires three arms 330 positioned on one side of the table 300. In the operating positions, the target joint J1 for each arm 330 is positioned at a target location relative to the table top 320 such that a distal end of the arm 330 (e.g., with medical instrument thereon) can be disposed in a desired treatment zone. As described above for FIG. 18, a range of motion or travel arc can be defined for each of the arms 330 used for various different surgical procedures as illustrated in FIGS. 20A, 20B and 21A. The individual travel arcs for each robotic arm 330 are shown collectively as a range of motion R in FIGS. 20A, 20B and 21A. As described for FIG. 18, the range of motion extends in the X-Y direction and also within a Z-axis direction (coming out of the page in FIGS. 20A, 20B and 21A) via the lift mechanism of the second joint 335 and the movement capability of the robotic arms 330.

Figure 22C:
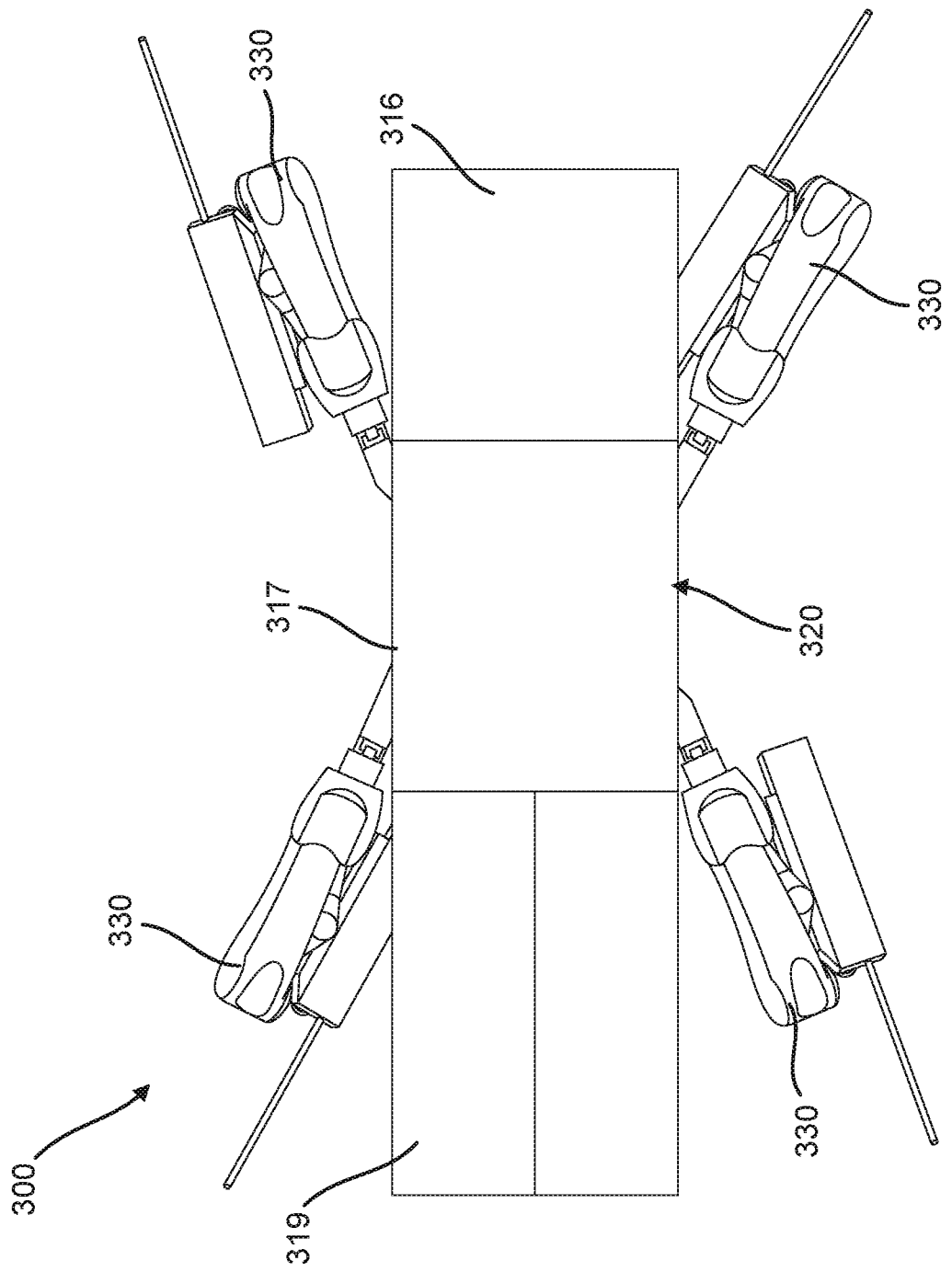
FIG. 22C is a top view of a portion of the surgical table, adapter and arms of FIG. 19B shown in a parked position.

As described above, during a surgical procedure, the adapter 328 and arms 330 can also be moved to various parked positions to provide clearance for medical staff to access the patient or to provide clearance for other devices such as an imaging device. The arms 330 and adapter 328 can be moved to the parked position via the first joint 333 and the second joint 335 as described above. When the need for the clearance has passed, the arms 330 can then be placed back into the operating position with the target joints J1 disposed at the target treatment locations relative to the table top 320. FIG. 22C illustrates the surgical table 300 and robotic arms 330 shown in a parked position. As shown in FIG. 22C, a medical professional (e.g., surgical staff) can be disposed in a clearance region between the arms 330 to have access to a patient (not shown) disposed on the table top 320.

FIGS. 23A-29B illustrate a surgical table and an adapter according to another embodiment. A surgical table 400 includes a table top 420 (see FIGS. 25-29), a support 422 (also referred to herein as pedestal) and a base 424. As described above for previous embodiments, the support 422 can be mounted to the base 424, which can be fixed to the floor of an operating room, or can be movable relative to the floor. The table top 420 includes a head section 416, a torso section 417 and a leg section 419. The table top 420 can also include an arm section(s) (not shown). The table top 420 has a top surface on which a patient can be disposed. The support 422 can provide for movement of the table top 420 in a desired number of degrees of freedom as described above for previous embodiments. Also as described above, movement of the table top 420 and/or its constituent sections may be performed manually, driven by motors, controlled remotely, etc. The surgical table 400 can also include a radio-translucent window (not shown) as described for previous embodiments.

Figure 23A:
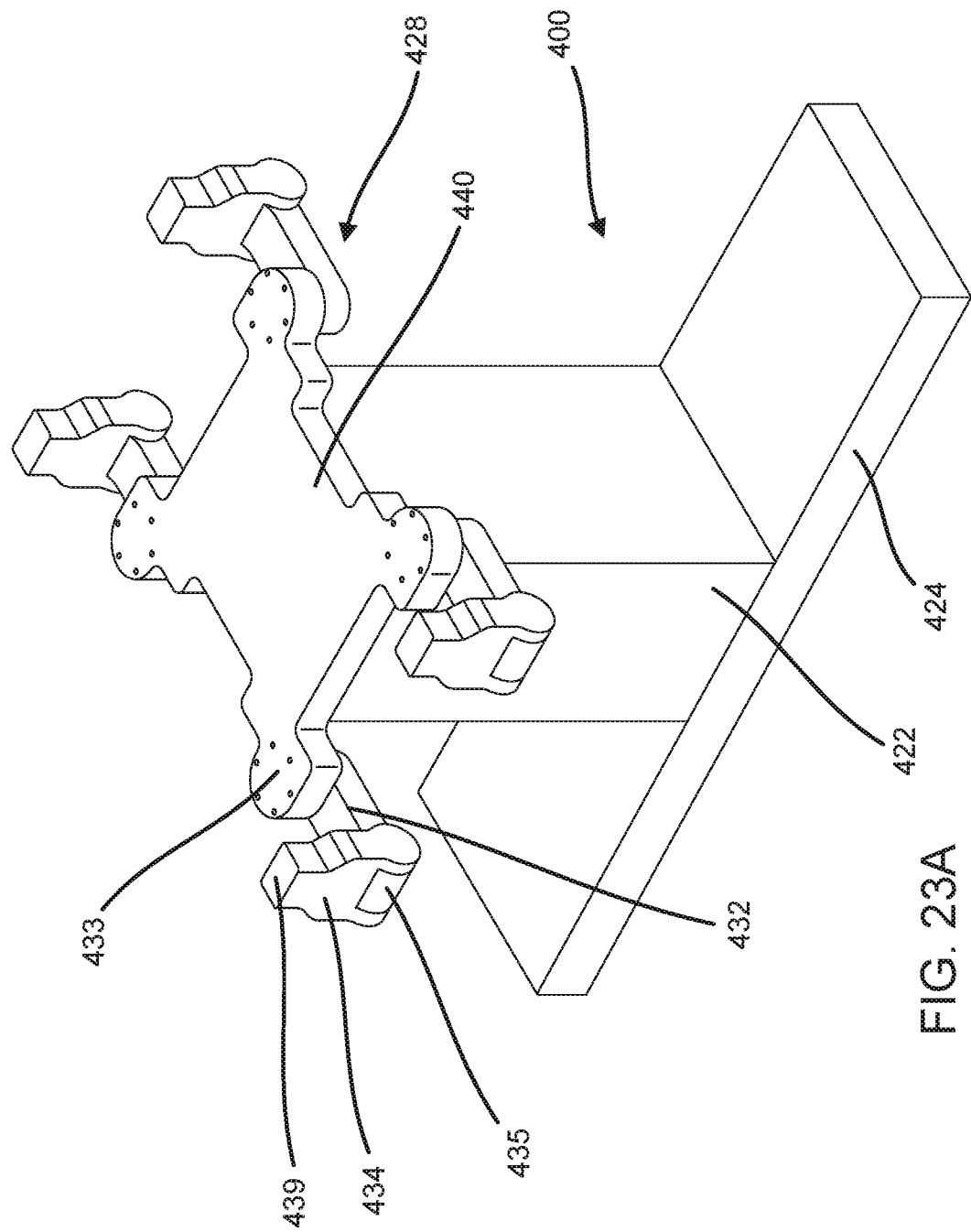
FIG. 23A is a perspective view of an adapter according to another embodiment shown coupled to a pedestal of a surgical table and in an operating position.
Figure 23B:
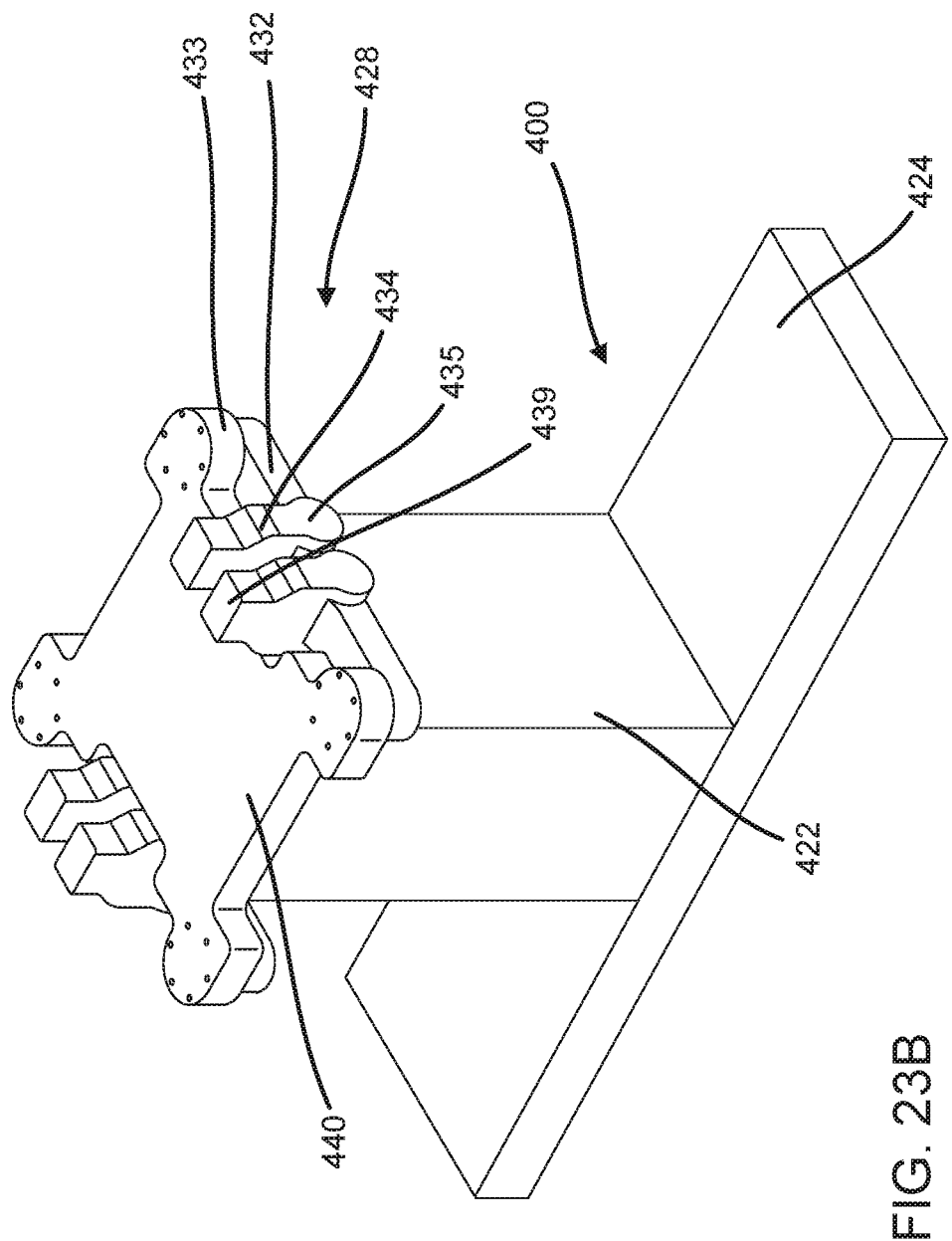
FIG. 23B is a perspective view of the surgical table and adapter of FIG. 23A shown in a stowed position.
Figure 24:
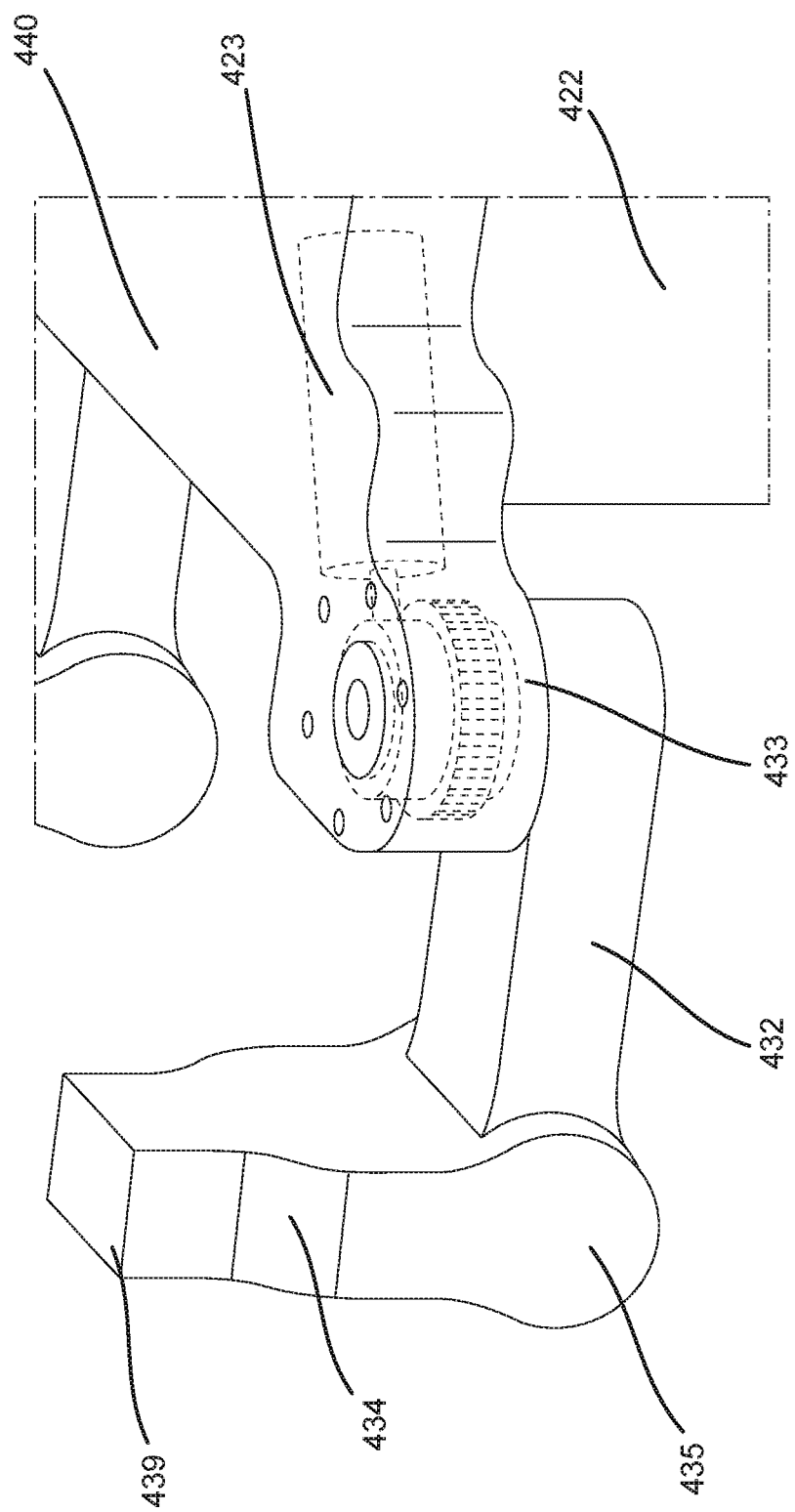
FIG. 24 is an enlarged view of the adapter of FIGS. 20 and 21 with an optional motor that can be operatively coupled to the adapter.

A table adapter 428 (also referred to herein as "adapter") is shown coupled to the surgical table 400 without robotic arms attached thereto and with the table top 420 removed in FIGS. 23A and 23B. The adapter 428 includes a table interface structure 440 coupled to the support 422. In this embodiment, the table interface structure 440 is a support plate that can be coupled to the support 422 and/or the table top 420 (not shown in FIGS. 23A and 23B). FIG. 23A illustrates the adapter 428 in an extended configuration such as in an operating position and FIG. 23B illustrates the adapter 428 in a stowed position. Such a stowed position can be achieved, for example, when no robotic arms are coupled to the adapter 428.

The adapter 428 further includes multiple first link members 432 that are each pivotally coupled to the table interface structure 440 at a first joint 433, and multiple second link members 434 that are each coupled to one of the first link members 432 at a second joint 435. The second joint 435 provides the lift mechanism for moving the second link member 434 vertically. In this embodiment, the second joint 435 includes a pivotal coupling between the first link member 432 and the second link member 434. The first link member 432 and the second link member 434 can be moved between an extended configuration for use during a surgical procedure as shown, for example, in FIGS. 25-27 and 29B, and a folded or collapsed configuration for storage when not in use, as shown, for example, in FIG. 29A.

Each of the second link members 434 can also be coupled to a robotic arm 430 at a coupling 418. In this embodiment, the coupling 418 includes a coupling portion 439 on the second link member 434 (see, e.g., FIGS. 23-24) in the form of a post (shown schematically) configured to be received within an opening (not shown) defined in a coupling portion 438 at a mounting end 436 of a robotic arm 430. As with the previous embodiment, in this embodiment, the coupling portion 438 includes the target joint J1. In this embodiment, the robotic arms 430 are releasably coupled to the adapter 428 and as such the robotic arms 430 can be removed and attached as needed for a particular surgical procedure. In this embodiment, the adapter 428 can accommodate four arms 430 (i.e., the adapter 428 can include four first link members 432 and four second link members 434). Each robotic arm 430 can be releasably coupled to the adapter 428 via the coupling 418. Each robotic arm 430 can be configured the same as or similar to, and function the same as or similar to, the robotic arms 130 described above and thus, specific details regarding the robotic arms are not discussed with respect to this embodiment. For example, as described above for robotic arms 130, the robotic arms 430 can include multiple links or segments and can be moved between an extended configuration for use during a surgical procedure, and a folded or collapsed configuration for storage when not in use. The movement of the first link member 432 and the second link member 434 can provide for movement of the robotic arm 430 (and the target joint J1) along and/or about the X, Y, and/or Z axes as described in more detail below.

Figure 25:
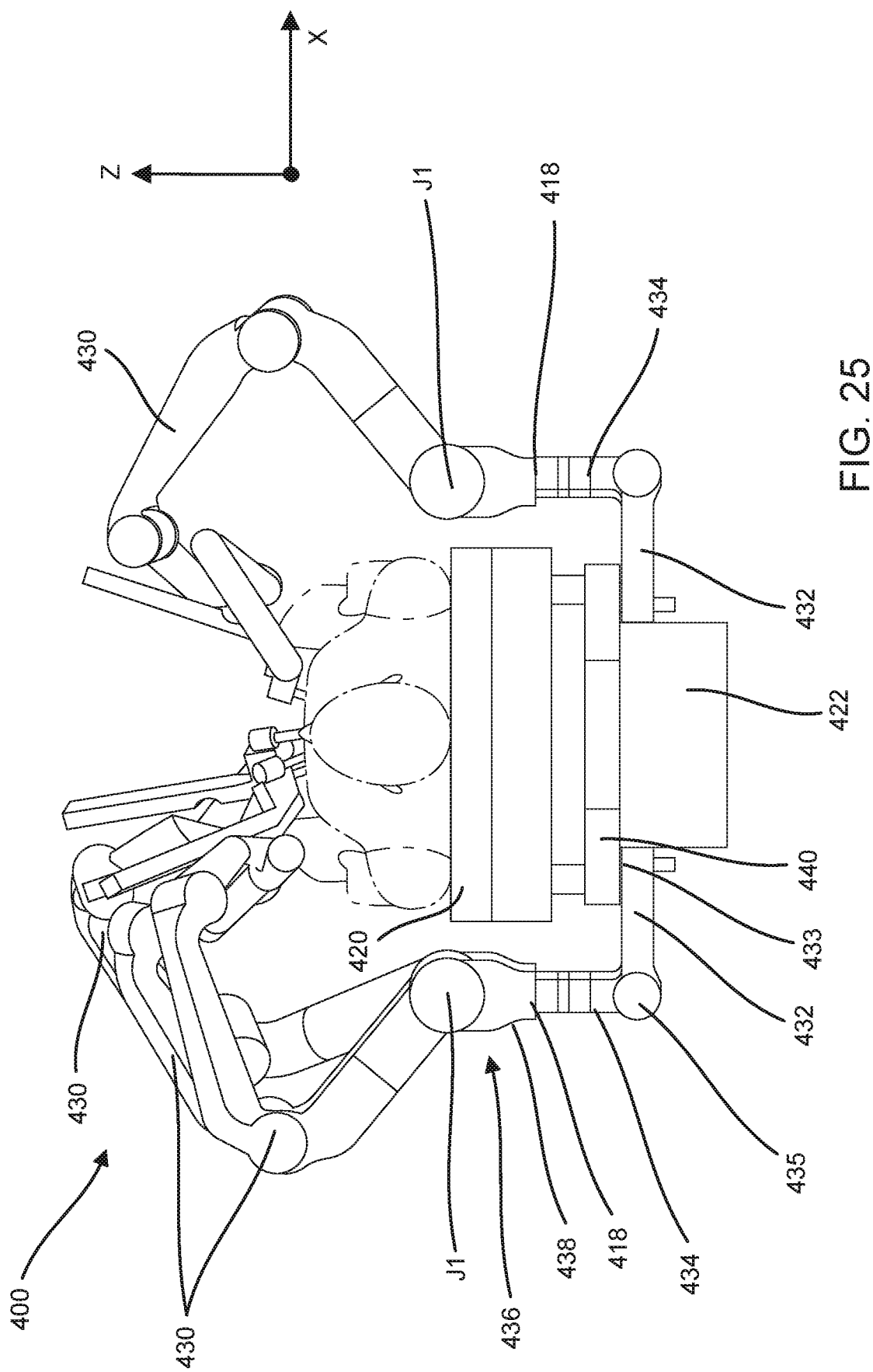
FIG. 25 is an end view of the surgical table and adapter of FIGS. 20 and 21 with four robotic arms coupled to the adapter, with three arms on one side of the table and one arm on the opposite side of the table and in an operating position.
Figure 26:
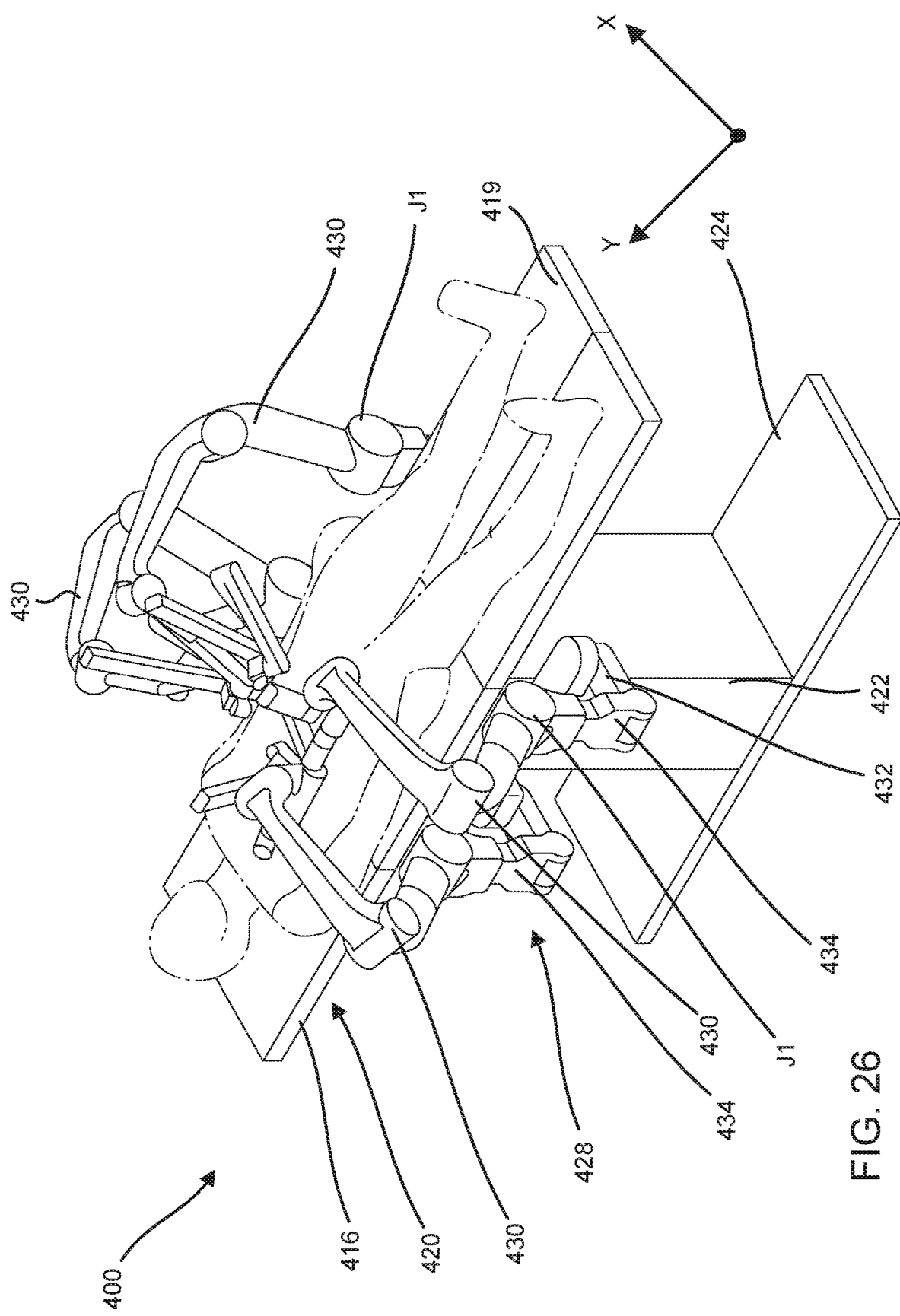
FIGS. 26 and 27 are each a perspective view of the surgical table and adapter of FIGS. 20 and 21 with four robotic arms coupled to the adapter, with two arms on each side of the table and in an operating position.

More specifically, as with the previous embodiments, the first joint 433 can provide for rotational motion of the first link member 432 relative to the table interface structure 440 (and table 400) about a vertical z-axis (shown in FIG. 25) relative to a top surface of the table top 420 (e.g., the top surface of the torso section 417), and movement of the first link member 432 and second link member 434 in lateral and longitudinal directions (also referred to herein as x-direction and y-direction) relative to a top surface of the table top 420 of the surgical table 300 (see, e.g., X-Y axes in FIG. 26). As described above, the second joint 435 can provide the lift mechanism to allow for vertical movement of the second link member 434 and the coupling 418 between the second link member 434 and the robotic arm 430. Thus, the motion of the first link member 432 and the second link member 434 of the adapter 428 can provide for movement of a robotic arm 430 coupled thereto along and/or about the X, Y, and/or Z axes to position the target joint J1 at a desired treatment location relative to the table top 420.

Figure 28A:
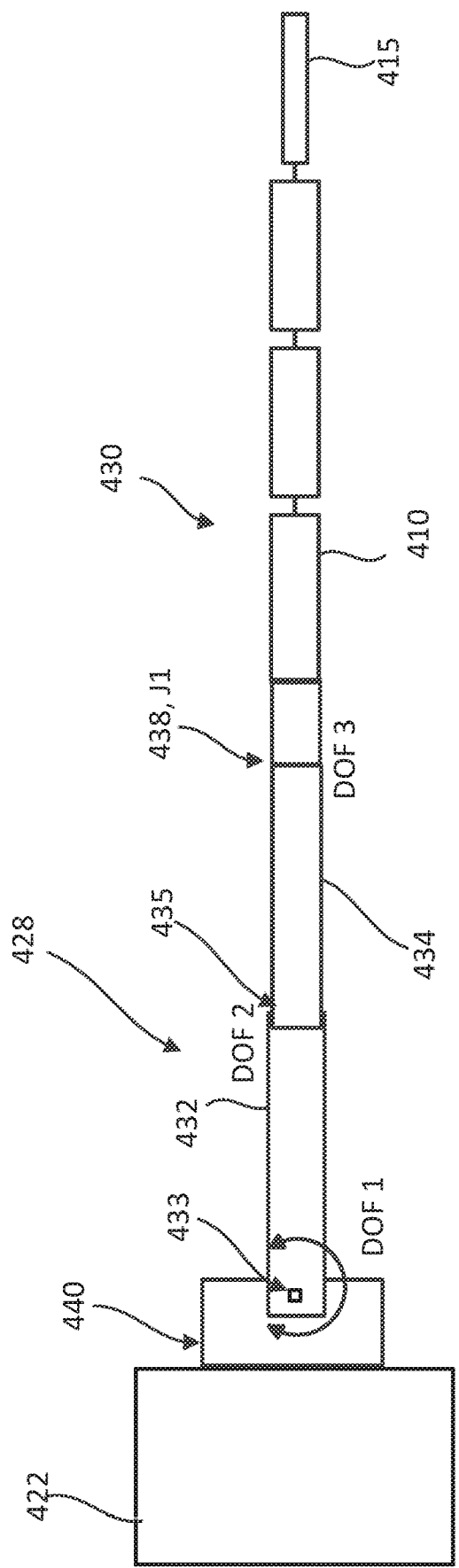
FIGS. 28A and 28B are a schematic top view and side view, respectively, of the adapter and a robotic arm of FIGS. 23A-27 illustrating the degrees of freedom between the joints of the adapter and robotic arm.
Figures 28B, 28C:
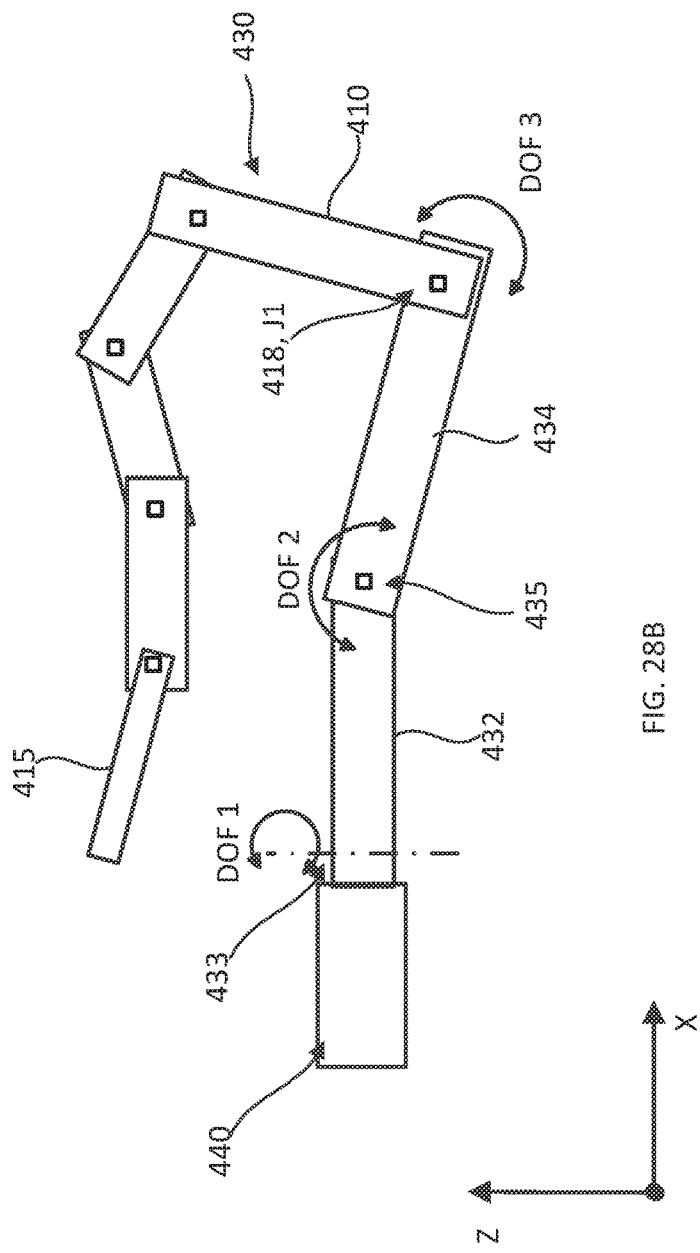
FIG. 28C is a table listing the type of degree of freedom of each of the joints.

FIGS. 28A and 28B are schematic illustrations of the various degrees of freedom provided by the joints of the adapter 428 and robotic arm 430, and FIG. 28C is a table listing the type of degree of freedom (e.g., rotational, linear) associated therewith. As shown in FIGS. 28A and 28B, and as described above, the interface mechanism 440 is coupled to the support 422 of the table 400 and the first link members 432 are pivotally coupled to the interface mechanism 440 at joint 433. The pivotal joint 433 of the first link members 432 to the interface mechanism 440 allows the first link members 432 to rotate about the z-axis and provide a first degree of freedom DOF 1 at joint 433, i.e., Z-axis rotation. The joint 435 between the first link member 432 and the second link member 434 is also a rotational or pivotal joint that can pivot about a horizontal axis, i.e. an axis lying in the X-Y plane and thus provide a second degree of freedom DOF 2 (best shown in the side view illustration of FIG. 28B) that is X-Y plane rotation. Similarly, the joint J1 at the coupling 418 is also a pivotal joint that can pivot about a horizontal axis and provide a third degree of freedom DOF 3 (best shown in the side view illustration of FIG. 28B) that is X-Y plane rotation. Although not labeled in FIGS. 28A and 28B, the various joints between links 410 of the arm 430 and a medical instrument 415 disposed on the distal end of the robotic arm 430 can provide additional motion of the arm relative to a patient (e.g., a target treatment location on the patient) disposed on the table 400, and therefore, additional degrees of freedom.

Figure 29A:
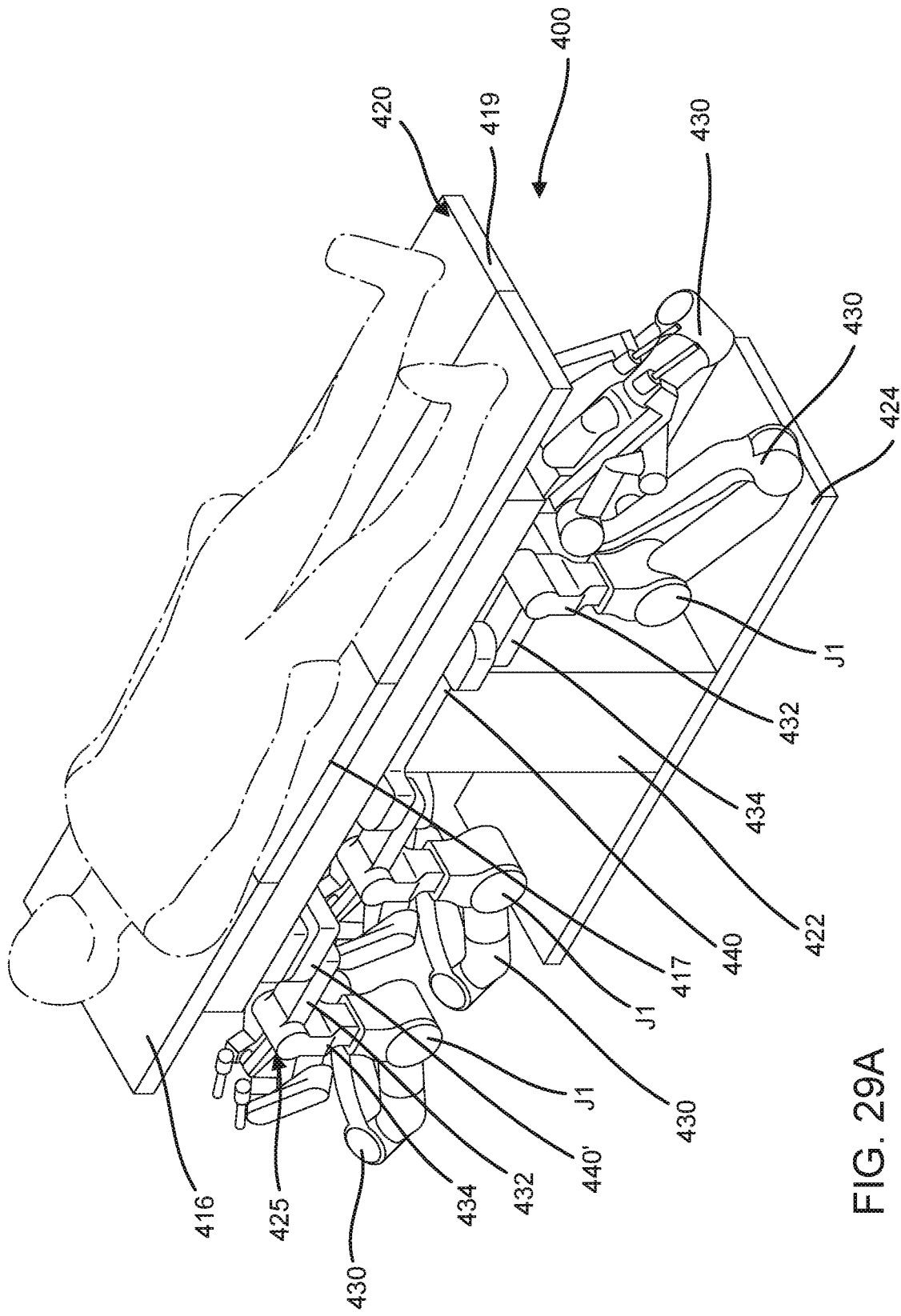
FIG. 29A is a side perspective view of the surgical table, adapter and robotic arms of FIG. 22 shown in a stowed position, and an auxiliary adapter coupled to the table, with robotic arms coupled thereto and shown in a stowed position.

The collective motion of the first link member 432 and the second link member 434 allows the adapter 428 and robotic arms 430 to move between a variety of different positions relative to the surgical table 400 during a surgical procedure. For example, adapter 428 and robotic arms 430 can be moved to a stowed position substantially beneath the table top 320 as shown, for example, in FIG. 29A. FIG. 29A illustrates a stowed position of the adapter 428 with four robotic arms 430 coupled thereto and also a second auxiliary adapter 425 with two robotic arms 430 coupled thereto. The auxiliary adapter 425 can be configured the same as or similar to the adapter 428 except it includes a table interface structure 440' that is half the size of the structure 440 and includes only two locations, one on each side of the table 400 to attach robotic arms 430. The table interface structure 440' can be attached to the head section 416 of the table top 420. The auxiliary adapter 435 can include first and second link members configured the same as or similar to the first and second link members 432 and 434. The auxiliary adapter 425 allows for additional configurations of the robotic arms 430 and for three robotic arms 430 to be coupled to the adapter(s) 428, 425 on one side of the table 400.

As with the previous embodiments, the arms 430 and the link members 432 and 434 can be moved to the stowed position via the first joint 433 and the second joint 435. For example, the arms 430 and the second links 434 can be lowered via the second joint 435. The first links 432, second links 434 and the arms 430 can then be pivoted to the ends via the first joint 433. The arms 430 can be further folded via the joints between the links/segments of the arms 430. Similarly, the first link member 432 and the second link member 434 can be further folded or collapsed. The arms 430 and adapter 428 are thus in a folded or collapsed configuration in the stowed position and disposed substantially beneath the table top 420 within an outer perimeter defined by the table top 420.

Figure 27:
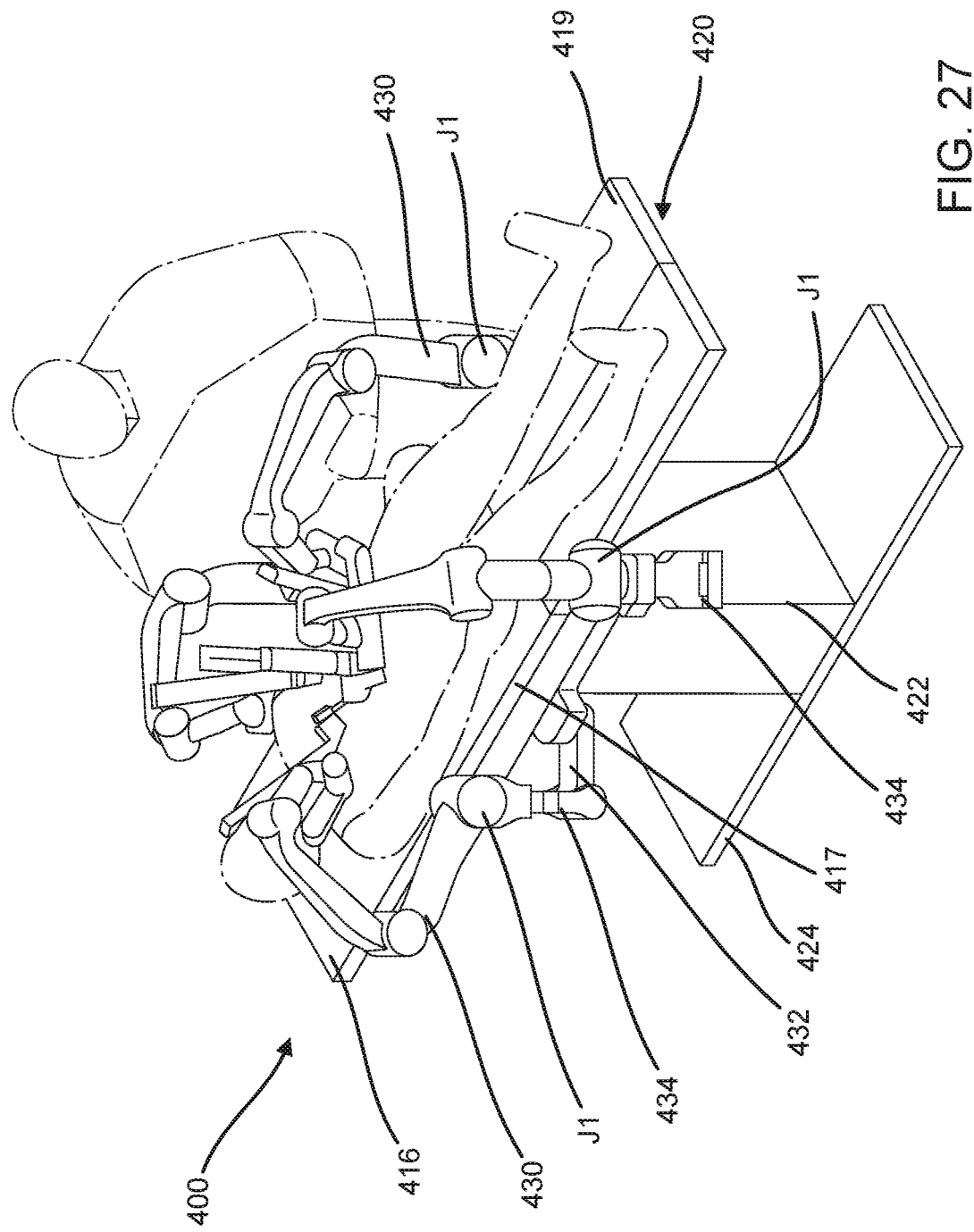
Figure 29B:
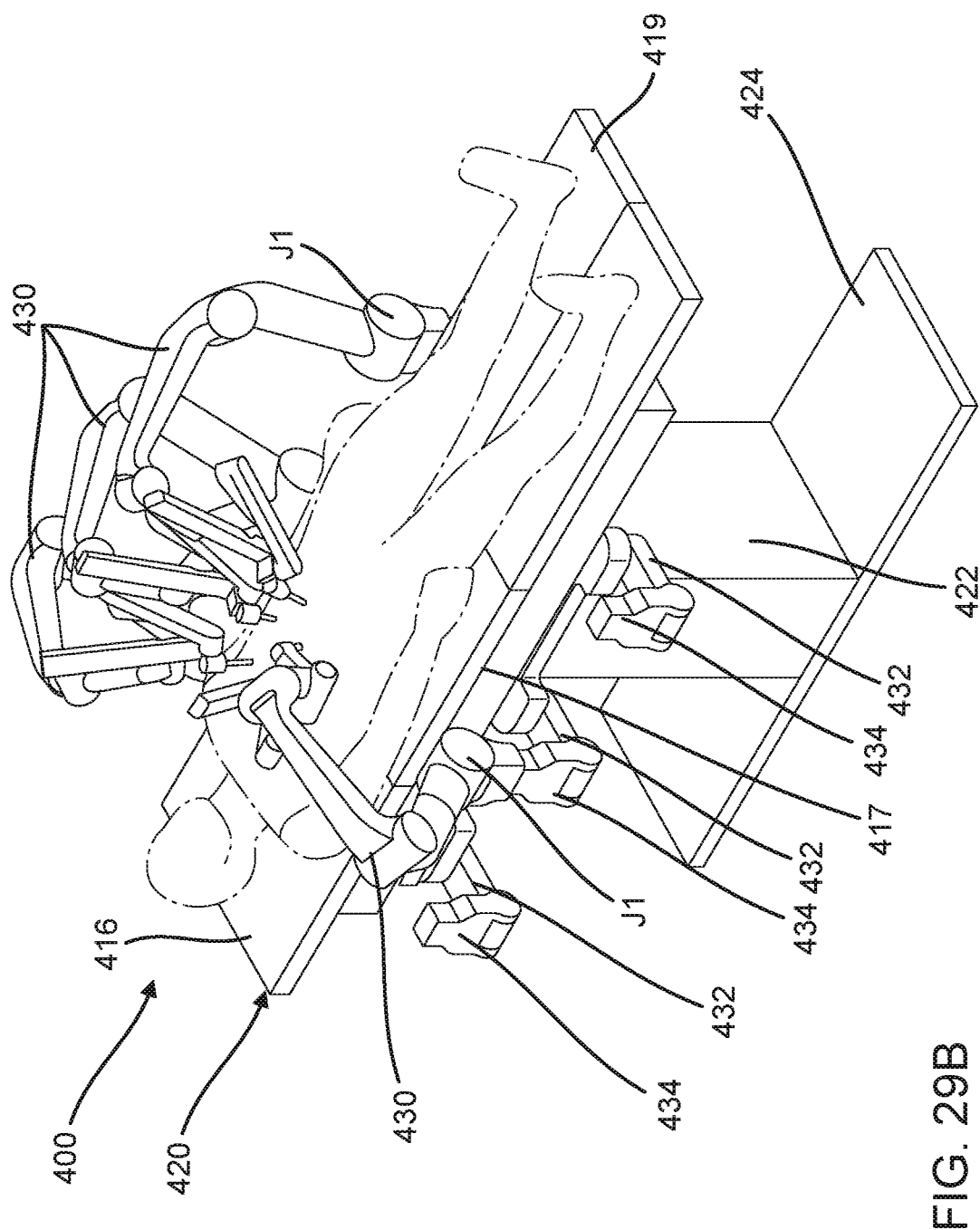
FIG. 29B is a side perspective view of the surgical table, adapter and auxiliary adapter of FIG. 26 and four robotic arms coupled to the adapter with three arms on one side of the table and one arm on the opposite side of the table in an operating position.

The adapter 428 and arms 430 can also be moved from the stowed position to various operating positions in a similar manner by moving the arms 430 via the first joints 433 and the second joints 435. Further, as described above, if more than two arms 430 are needed on one side of the table 400, an auxiliary adapter 425 can be used and an arm 430 can be coupled thereto. FIGS. 25-27 and 29B illustrate the robotic arms 430 and adapter 428 in various different operating positions for particular surgical procedures. FIGS. 25 and 29 illustrate an example operating position that includes three arms 430 on one side of the table 400 and one arm 430 on the opposite side of the table 430. Thus, an auxiliary adapter 425 is used in these examples. Such a configuration may be used to perform, for example, prostatectomy procedure. As best shown in FIG. 29B, in this configuration, only one of the three available coupling locations on the adapters 428 and 425 are used on one side of the table 400. FIGS. 26 and 27 illustrate an example operating position that includes two arms 430 on each side of the table 400. Such an operating position may be used to perform, for example, a LAR procedure. FIG. 27 illustrates a medical person disposed next to the table top 420. As described above, it may be desirable to have space for a medical person (e.g., a surgical assistant, physician) to be located near the patient. In each of the operating positions, the target joint J1 for each arm 430 is positioned at a target location relative to the table top 420 such that a distal end of the arm 430 (e.g., with medical instrument thereon) can be disposed in a desired treatment zone and can be maneuvered within a range of motion in a treatment region or zone.

As described above, during a surgical procedure, the adapter 428 and arms 430 can also be moved to a parked position (not shown) to provide clearance, for example, for medical staff to access the patient or to provide clearance for other devices such as an imaging device. The arms 430 and adapter 429 can be moved to the parked position via the first joint 433 and the second joint 435 as described above. When the need for the clearance has passed, the arms 430 can then be placed back into the operating position with the target joints J1 disposed at the target treatment locations relative to the table top 420.

FIGS. 30A-38 illustrate a surgical table and an adapter according to another embodiment. A surgical table 500 includes a table top 520, a support 522 (also referred to herein as pedestal) and a base 524 (see FIGS. 31 and 33). As described above for previous embodiments, the support 522 can be mounted to the base 524, which can be fixed to the floor of an operating room, or can be movable relative to the floor. The table top 520 includes a head section 516, a torso section 517 and a leg section 519. The table top 520 can also include an arm section(s) (not shown). The table top 520 has a top surface on which a patient can be disposed. The support 522 can provide for movement of the table top 520 in a desired number of degrees of freedom as described above for previous embodiments. Also as described above, movement of the table top 520 and/or its constituent sections may be performed manually, driven by motors, controlled remotely, etc. The surgical table 500 can also include a radio-translucent window (not shown) as described for previous embodiments.

A table adapter 528 (also referred to herein as "adapter") can be coupled to the surgical table 500 and is shown in FIG. 30 with four robotic arms 530 attached thereto. The adapter 528 includes a table interface mechanism 540 (a portion of which is shown in FIG. 30) that can be coupled to the support 522 and/or the table top 520. In some embodiments, the adapter 528 can be coupled to the support 522 such that the adapter 528 can move vertically up and down relative to the support 522 as described above.

The adapter 528 further includes multiple first link members 532 that are each pivotally coupled to the table interface mechanism 540. In this embodiment, two first link members 532 are coupled to the interface mechanism at a single shared first joint 533 on each side of the interface mechanism 540. Multiple second link members 534 are each coupled to one of the first link members 532 at a second joint 535. The second joint 535 provides the lift mechanism for moving the second link member 534 vertically. In this embodiment, the second joint 535 includes a pivotal coupling between the first link member 532 and the second link member 534. The first link member 532 and the second link member 534 can be moved between an extended configuration for use during a surgical procedure as shown, for example, in FIGS. 33-36, and a folded or collapsed configuration for storage when not in use, as shown, for example, in FIGS. 31 and 32.

Each of the second link members 534 can also be coupled to a robotic arm 530 at a coupling 518. The coupling 518 includes a coupling portion (not shown) on the second link member 534 that can be coupled to a coupling portion 538 at a mounting end of a robotic arm 530. As with the previous embodiment, in this embodiment, the coupling portion 538 includes the target joint J1. In this embodiment, the robotic arms 530 are fixedly or semi-fixedly coupled to the adapter 528. In this embodiment, the adapter 528 can accommodate four arms 530 (i.e., the adapter 528 can include four first link members 532 and four second link members 534). Each robotic arm 530 can be configured the same as or similar to, and function the same as or similar to, the robotic arms 130 described above and thus, specific details regarding the robotic arms are not discussed with respect to this embodiment. For example, as described above for robotic arms 130, the robotic arms 530 can include multiple links or segments coupled together to allow the robotic arm 530 to move between an extended configuration for use during a surgical procedure, and a folded or collapsed configuration for storage when not in use. The movement of the first link member 532 and the second link member 534 can provide for movement of the robotic arm 530 (and the target joint J1) along and/or about the X, Y, and/or Z axes as described in more detail below.

Figure 31:
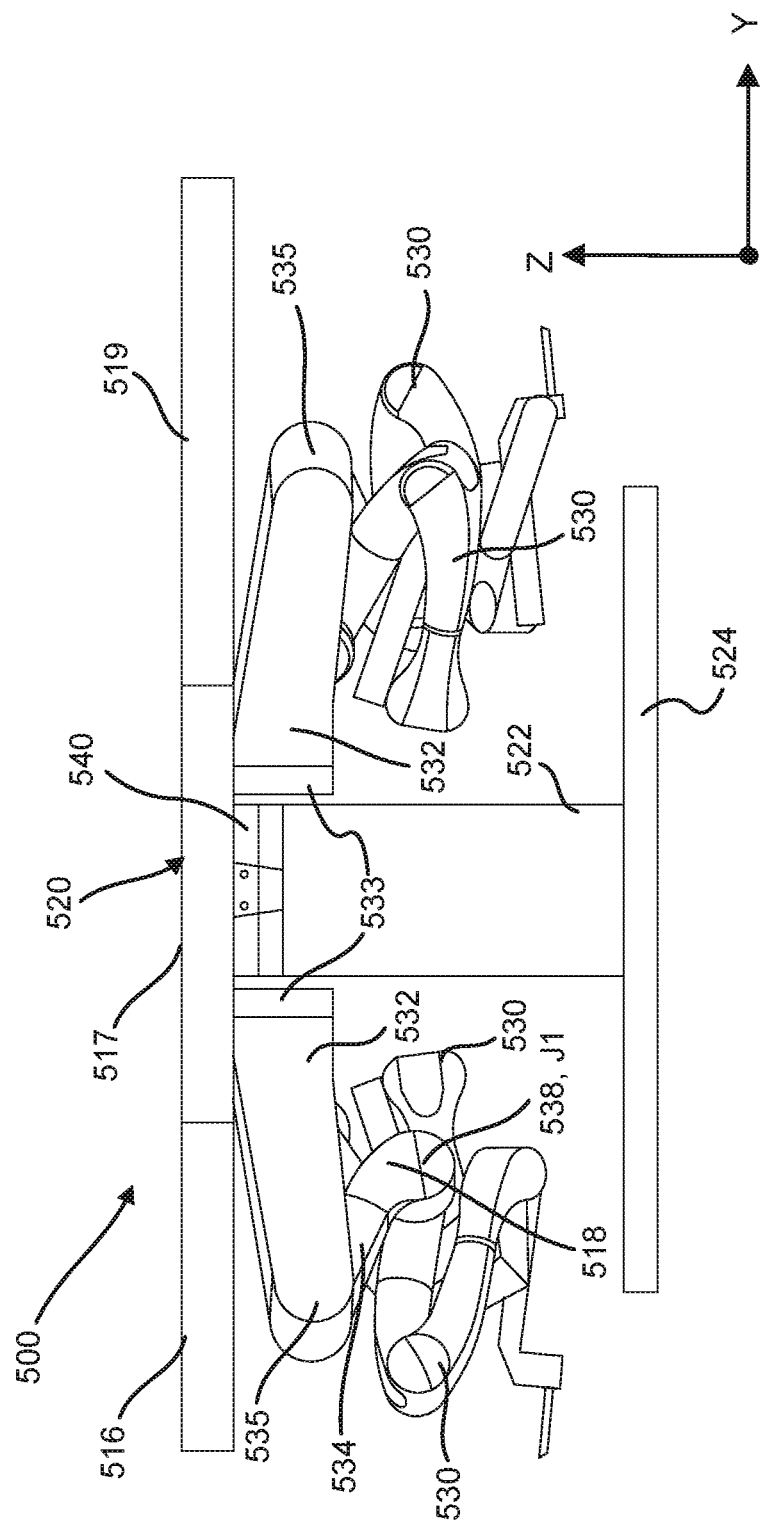
FIG. 31 is a side view of a surgical table and the adapter and robotic arms of FIG. 30 shown in a stowed position.
Figure 32:
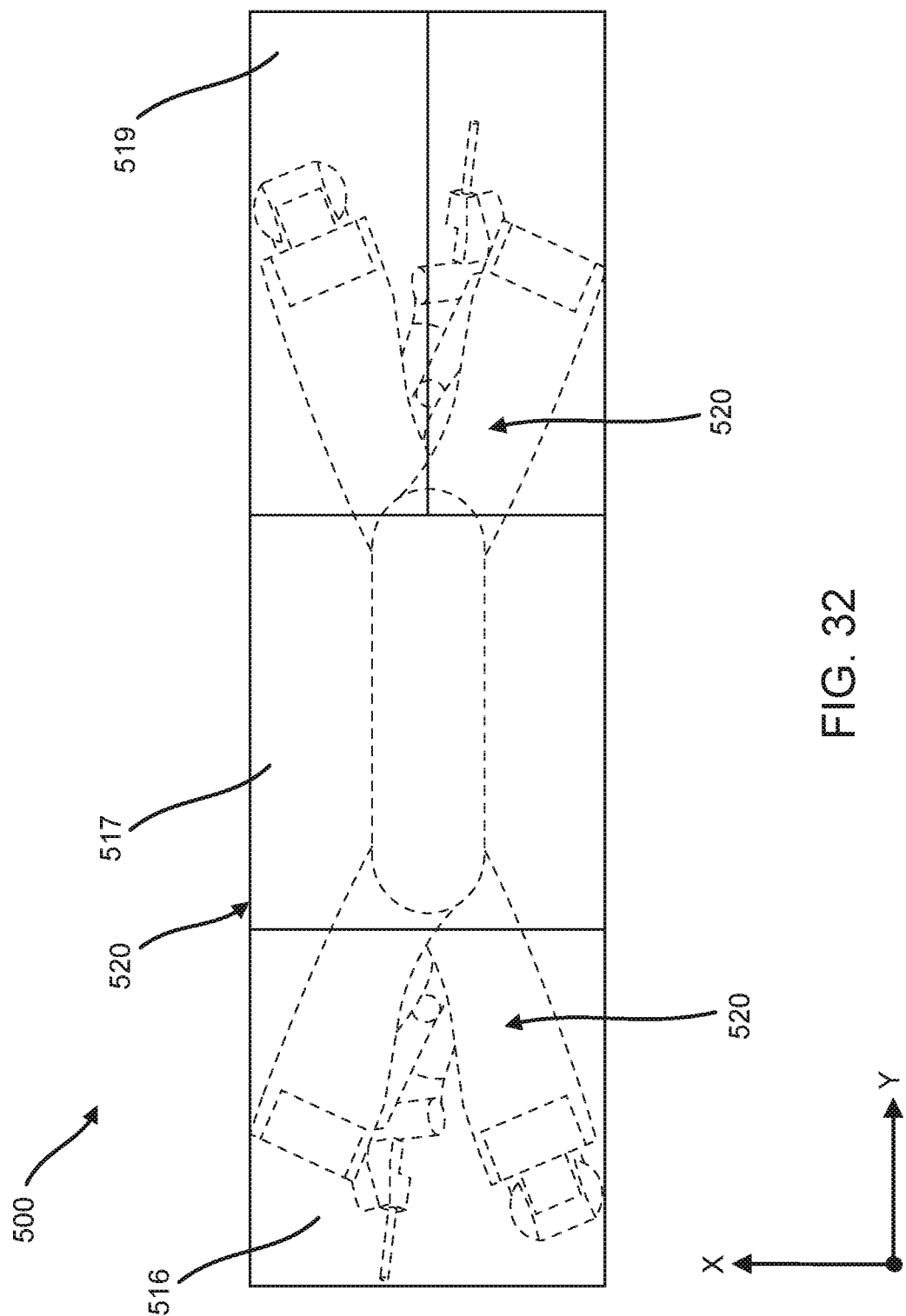
FIG. 32 is top view of the surgical table with the table top shown partially transparent and the adapter of FIG. 31 shown in the stowed position.

More specifically, as with the previous embodiments, the first joint 533 can provide for rotational motion of the two first link members 532 coupled thereto relative to the table interface structure 540 (and table 500) about a vertical z-axis (shown in FIG. 31) relative to a top surface of the table top 520 (e.g., a top surface of the torso section 517), and movement of the first link members 532 and second link members 534 in lateral and longitudinal directions (also referred to herein as x-direction and y-direction) relative to a top surface of the table top 520 of the surgical table 500 (see, e.g., X-Y axes in FIG. 32). As described above, the second joint 535 can provide the lift mechanism to allow for vertical movement of the second link member 534 and the coupling 518 between the second link member 534 and the robotic arm 530. Thus, the motion of the first link member 532 and the second link member 534 of the adapter 528 can provide for movement of a robotic arm 530 coupled thereto along and/or about the X, Y, and/or Z axes to position the target joint J1 at a desired treatment location relative to the table top 520.

Figure 30A:
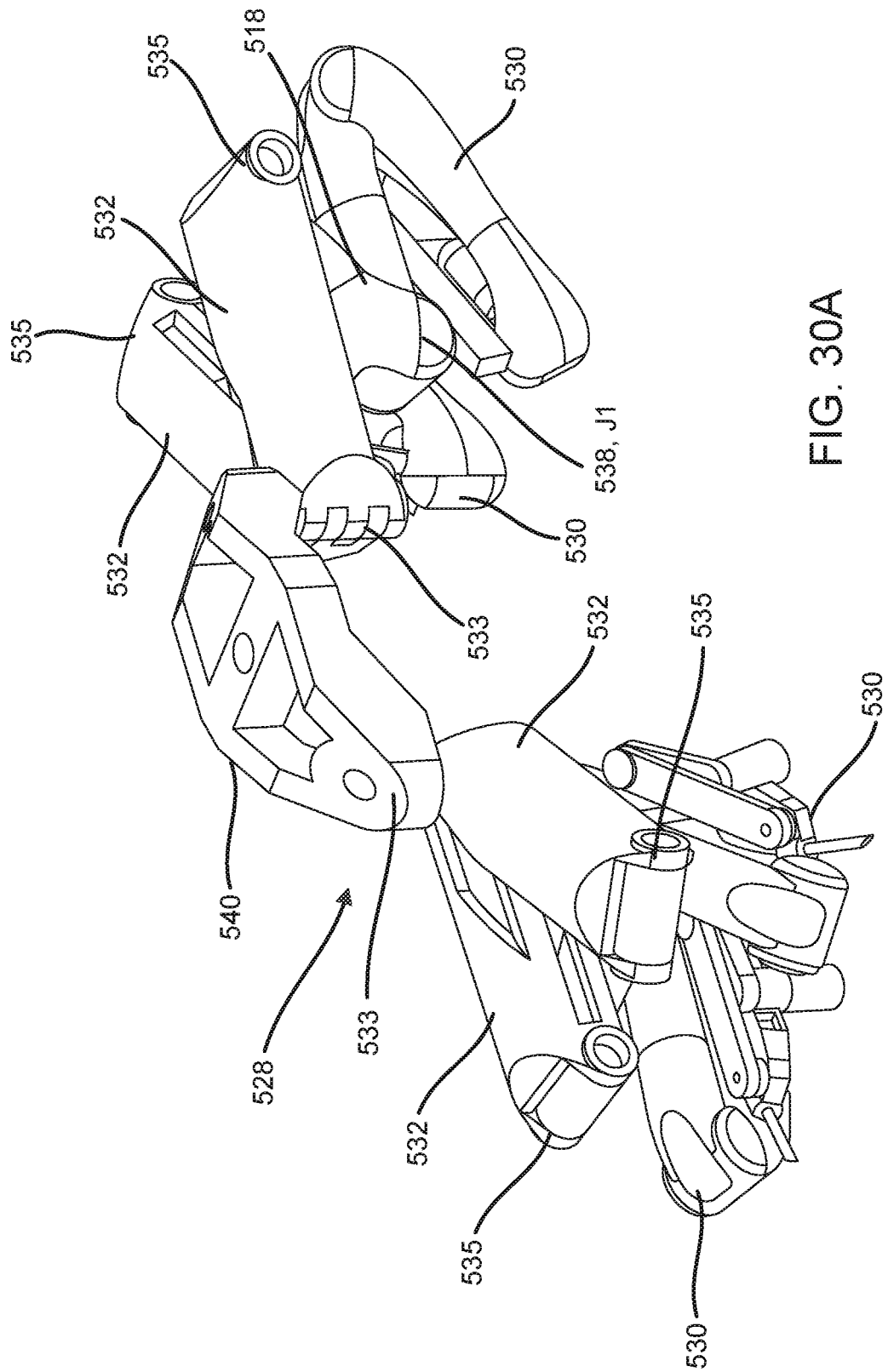
FIG. 30A is a perspective view of an adapter, according to another embodiment, with four robotic arms coupled thereto.
Figure 30B:
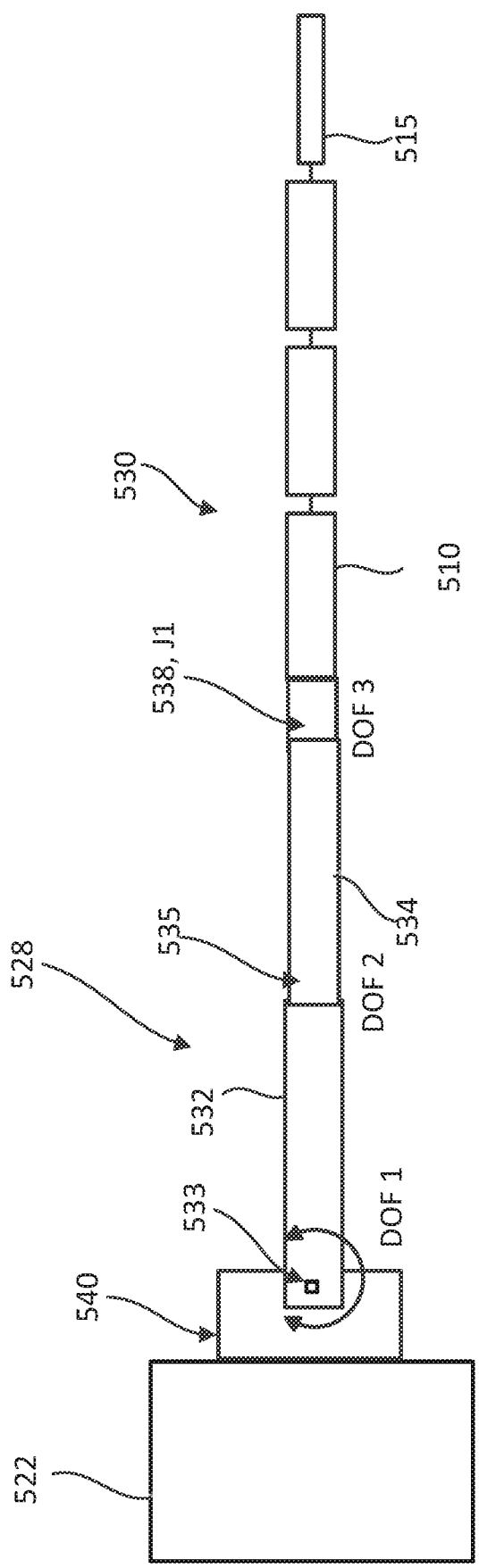
FIGS. 30B and 30C are a schematic top view and side view, respectively, of the adapter and a robotic arm of FIG. 30A illustrating the degrees of freedom between the joints of the adapter and robotic arm.
Figures 30C, 30D:
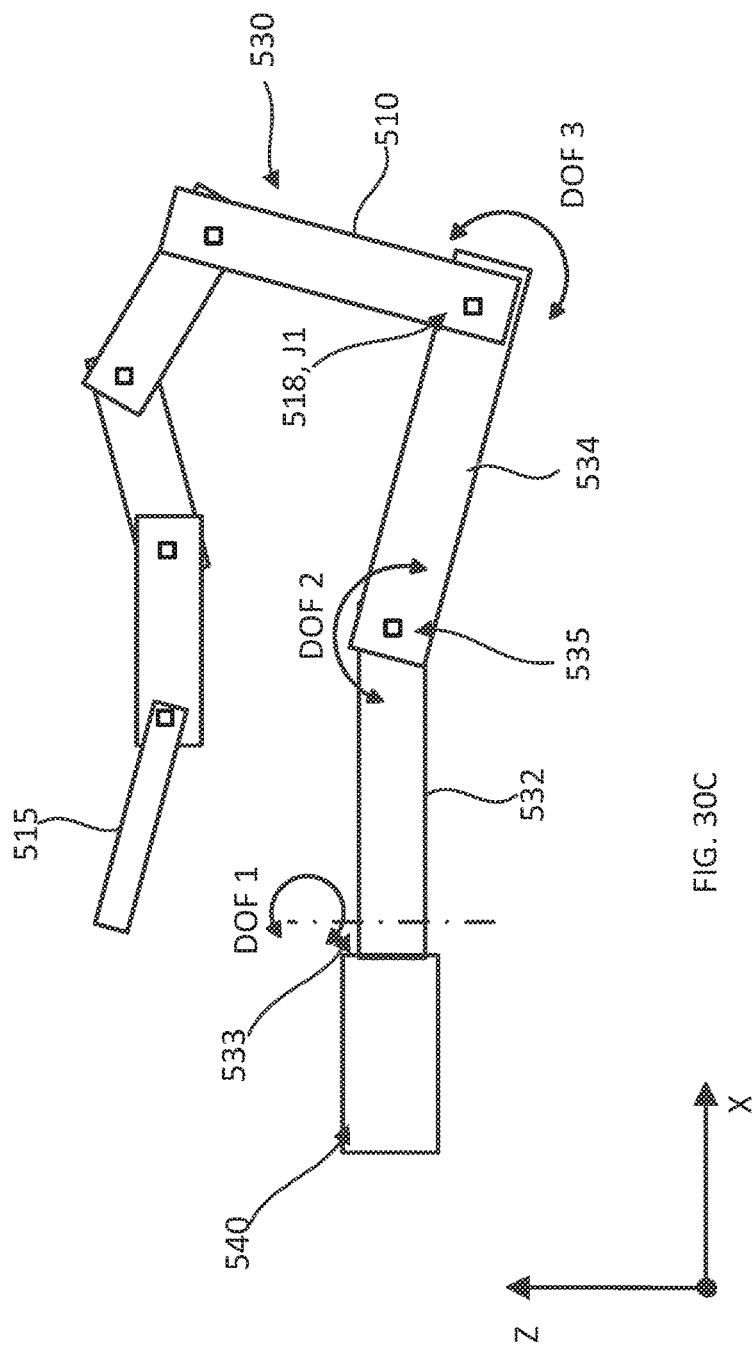
FIG. 30D is a table listing the type of degree of freedom of each of the joints.

FIGS. 30B and 30C are schematic illustrations of the various degrees of freedom provided by the joints of the adapter 528 and robotic arm 530, and FIG. 30D is a table listing the type of degree of freedom (e.g., rotational, linear) associated therewith. As shown in FIGS. 30B and 30C, and as described above, the interface mechanism 540 is coupled to the support 522 of the table 500 and the first link members 532 are pivotally coupled to the interface mechanism 540 at joint 533. The pivotal joint 533 of the first link members 532 to the interface mechanism 540 allows the first link members 532 to rotate about the z-axis and provide a first degree of freedom DOF 1 at joint 533, i.e., Z-axis rotation. The joint 535 between the first link member 532 and the second link member 534 is also a rotational or pivotal joint that can pivot about a horizontal axis, i.e. an axis lying in the X-Y plane and thus provide a second degree of freedom DOF 2 (best shown in the side view illustration of FIG. 30C) that is X-Y plane rotation. Similarly, the joint J1 at the coupling 518 is also a pivotal joint that can pivot about a horizontal axis and provide a third degree of freedom DOF 3 (best shown in the side view illustration of FIG. 30C) that is X-Y plane rotation. Although not labeled in FIGS. 30B and 30C, the various joints between links 510 of the arm 530 and a medical instrument 515 disposed on the distal end of the robotic arm 530 can provide additional motion of the arm relative to a patient (e.g., a target treatment location on the patient) disposed on the table 500, and therefore, additional degrees of freedom.

The collective motion of the first link members 532 and the second link members 534 allows the adapter 528 and robotic arms 530 to move between a variety of different positions relative to the surgical table 500 during a surgical procedure. For example, adapter 528 and robotic arms 530 can be moved to a stowed position substantially beneath the table top 520 as shown, for example, in FIGS. 31 and 32). As shown in FIG. 31, two arms 530 are disposed beneath the head section 516 and two arms 530 are disposed beneath the leg section 519 of the table top 520.

As with the previous embodiment, the arms 530 and the link members 532 and 534 can be moved to the stowed position via the first joint 533 and the second joint 535. For example, the arms 530 and the second links 534 can be lowered via the second joint 535. The first links 532, second links 534 and the arms 530 can then be pivoted to the ends via the first joints 533. The arms 530 can be further folded via the joints between the links/segments of the arms 530. Similarly, the first link member 532 and the second link member 534 can be further folded or collapsed. The arms 530 and adapter 528 are thus in a folded or collapsed configuration in the stowed position and disposed substantially beneath the table top 520 within an outer perimeter defined by the table top 520.

Figure 33:
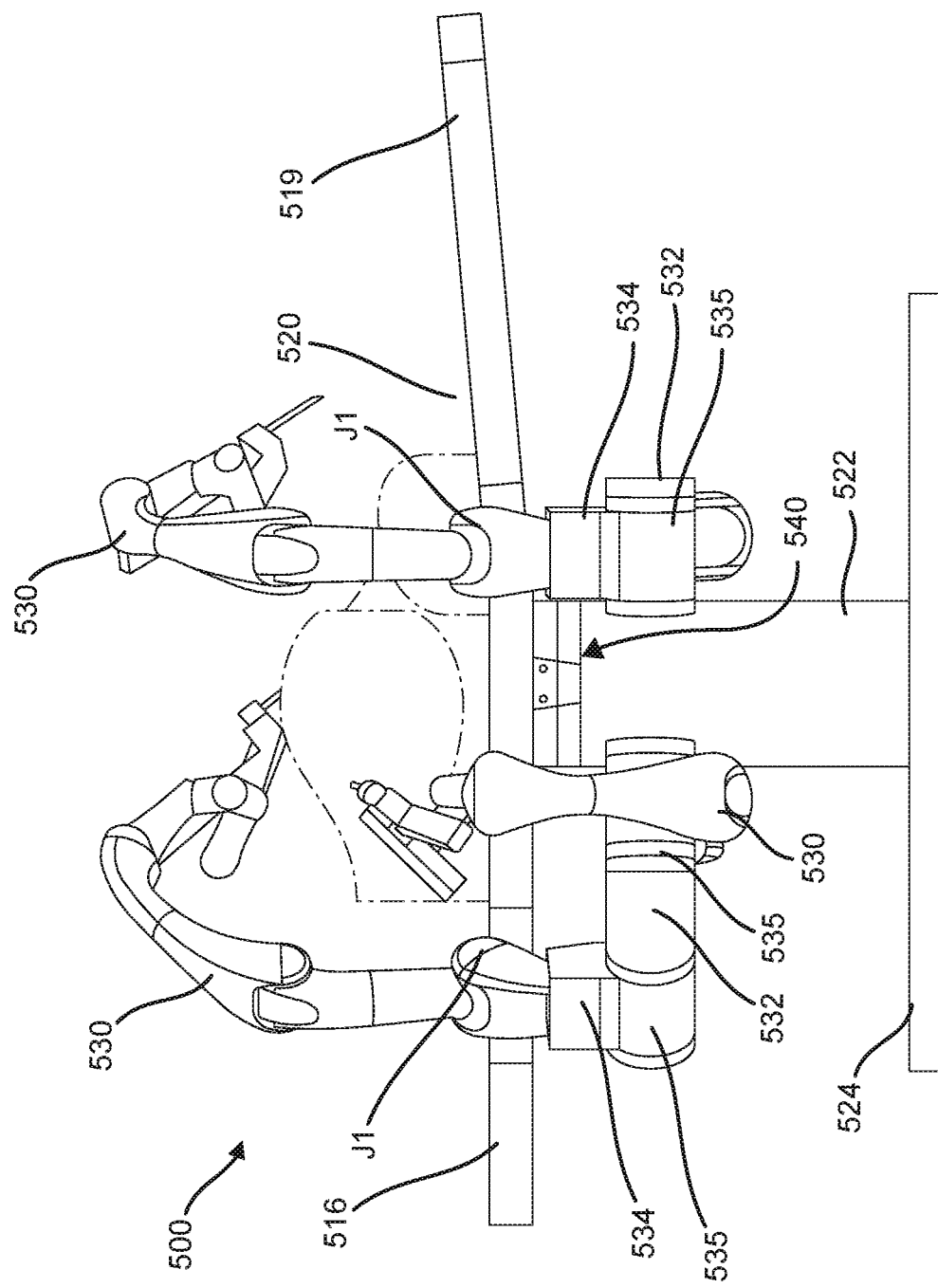
FIG. 33 is a side view of the surgical table, adapter and arms of FIG. 31 shown in an operating position with three arms on one side of the table and one arm on the opposite side of the table.
Figure 34:
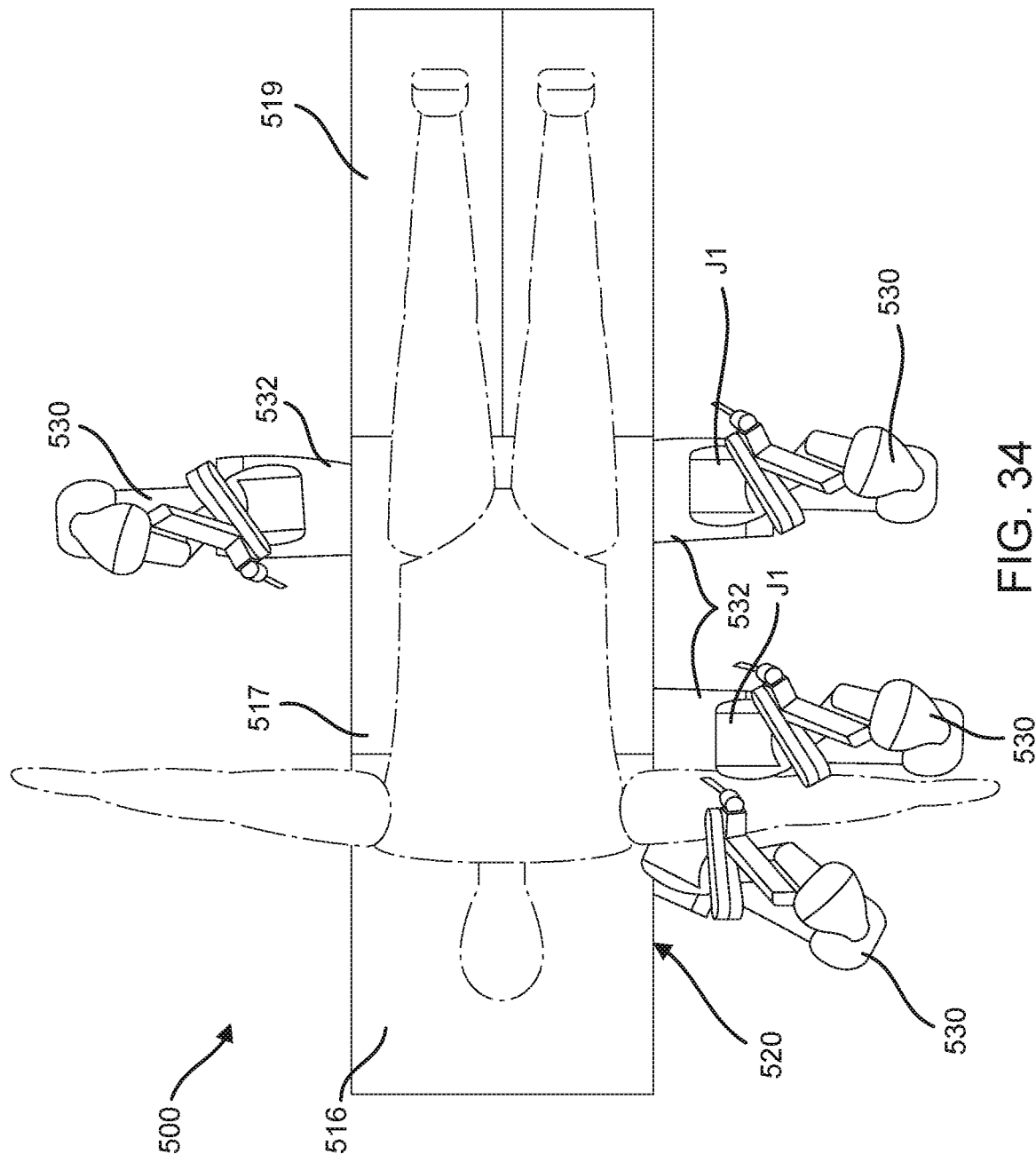
FIG. 34 is a top view of the surgical table, adapter and arms of FIG. 33 shown in an operating position with three arms on one side of the table and one arm on the opposite side of the table.

The adapter 528 and arms 530 can also be moved from the stowed position to various operating positions in a similar manner by moving the arms 530 via the first joints 533 and the second joints 535. FIGS. 33-36 illustrate the robotic arms 530 and adapter 528 in various different operating positions for particular surgical procedures. FIGS. 33 and 34 illustrate an example operating position that includes three arms 530 on one side of the table 500 and one arm 530 on the opposite side of the table 530. To achieve this configuration, one arm from the pair of arms 530 coupled to the adapter 528 on one side of the table 500 can be pivoted via the first joint 533 to the other side of the table. For example, from the stowed configuration, the arms can be pivoted out from under the table top 520 and then upward using the second pivot joint 535. Such a configuration may be used to perform, for example, a prostatectomy procedure.

Figure 35:
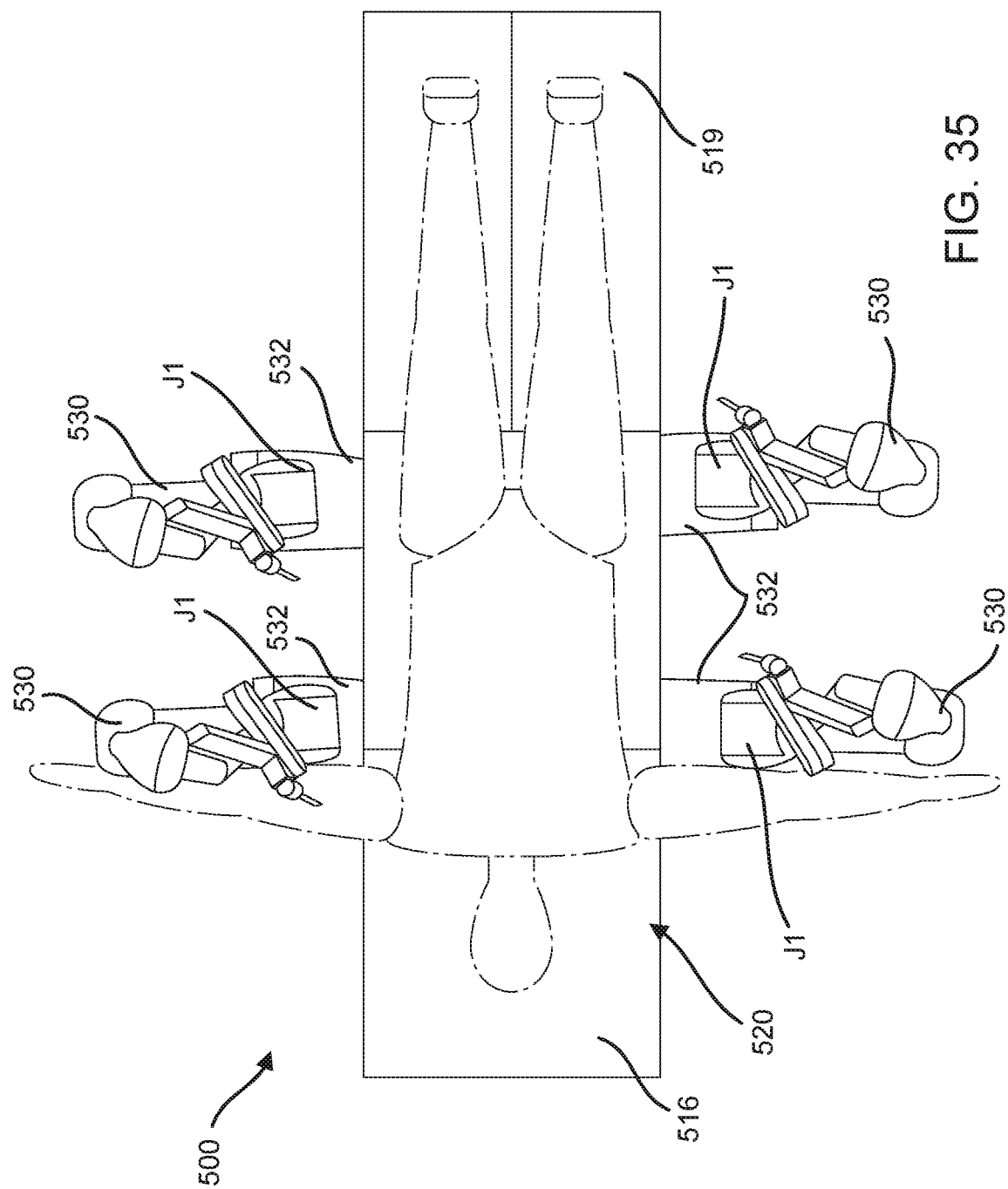
FIG. 35 is a top view of the surgical table, adapter and arms of FIG. 33 shown in an operating position with two arms on each side of the table.
Figure 36:
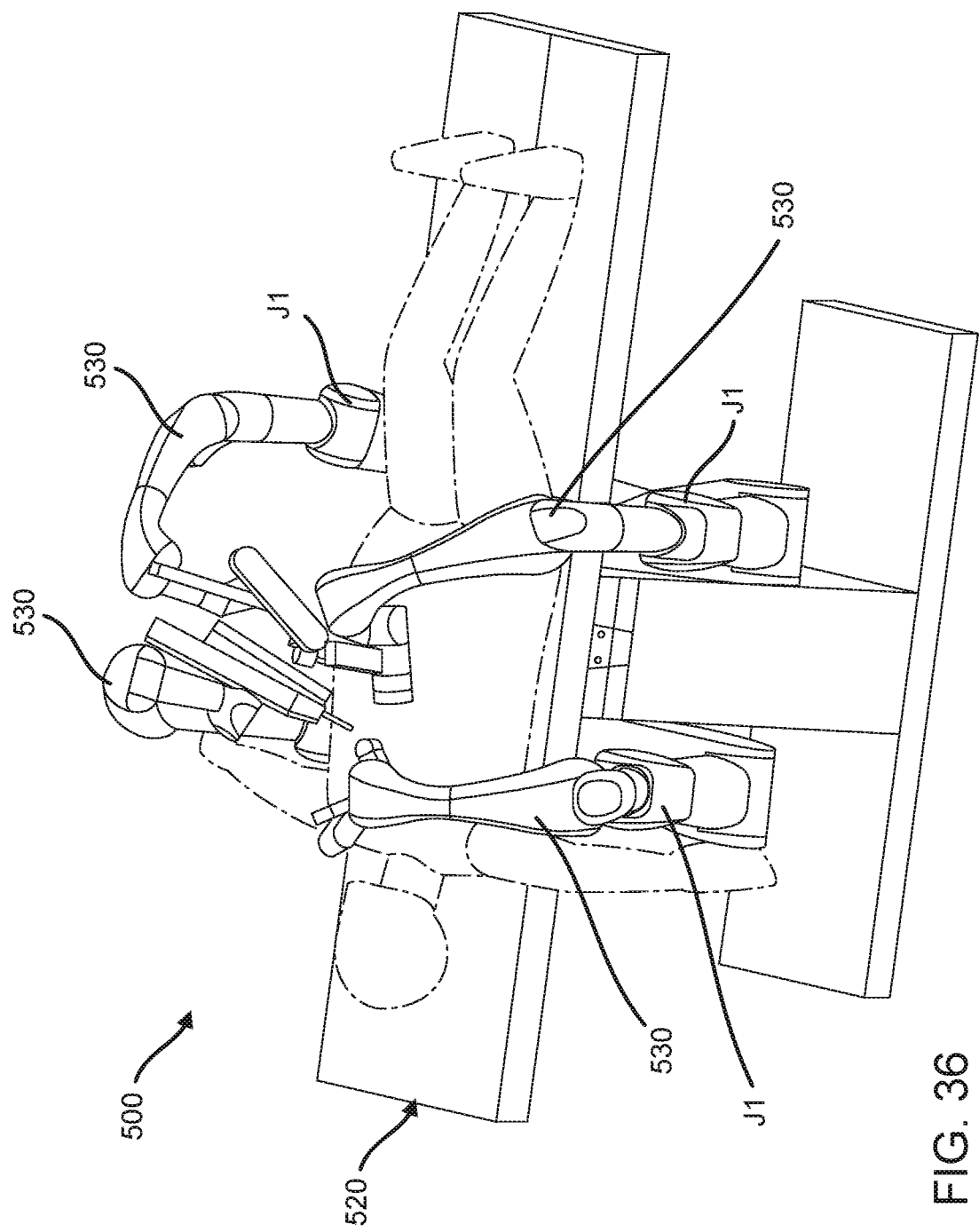
FIG. 36 is a side perspective view of the surgical table, adapter and arms of FIG. 35 shown in an operating position with two arms on each side of the table.

FIGS. 35 and 36 illustrate an example operating position that includes two arms 530 on each side of the table 500. Such an operating position may be used to perform, for example, a LAR procedure. FIG. 35 illustrates the arms 530 in a ready configuration on the sides of the table top 520, and FIG. 36 illustrates the arms 530 in a treatment configuration with the distal ends of the arms 530 (with medical instrument thereon) disposed in a treatment zone above the patient. Also, although not shown, as described above, in the operating positions it may be desirable to have space for a medical person (e.g., a surgical assistant, physician) to be located near the patient. Thus, the arms 530 can be positioned to accommodate such a situation. In each of the operating positions, the target joint J1 for each arm 530 is positioned at a target location relative to the table top 520 such that a distal end of the arm 530 (e.g., with medical instrument thereon) can be disposed in a desired treatment zone and can be maneuvered within a range of motion in a treatment region or zone.

Figure 37:
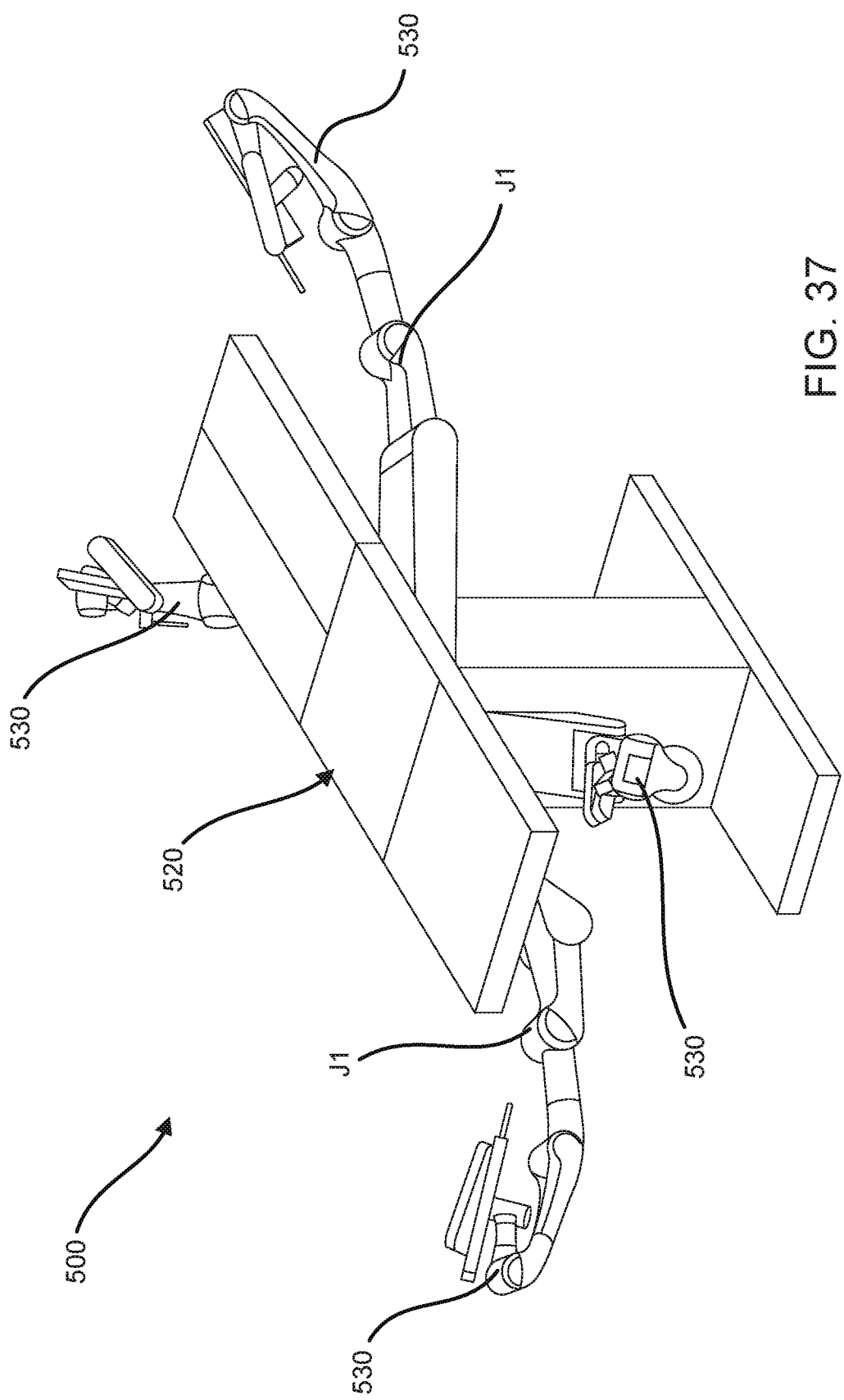
FIGS. 37 and 38 are a side perspective view and a top view, respectively, of the surgical table and arms of FIG. 35 shown in a parked position.
Figure 38:
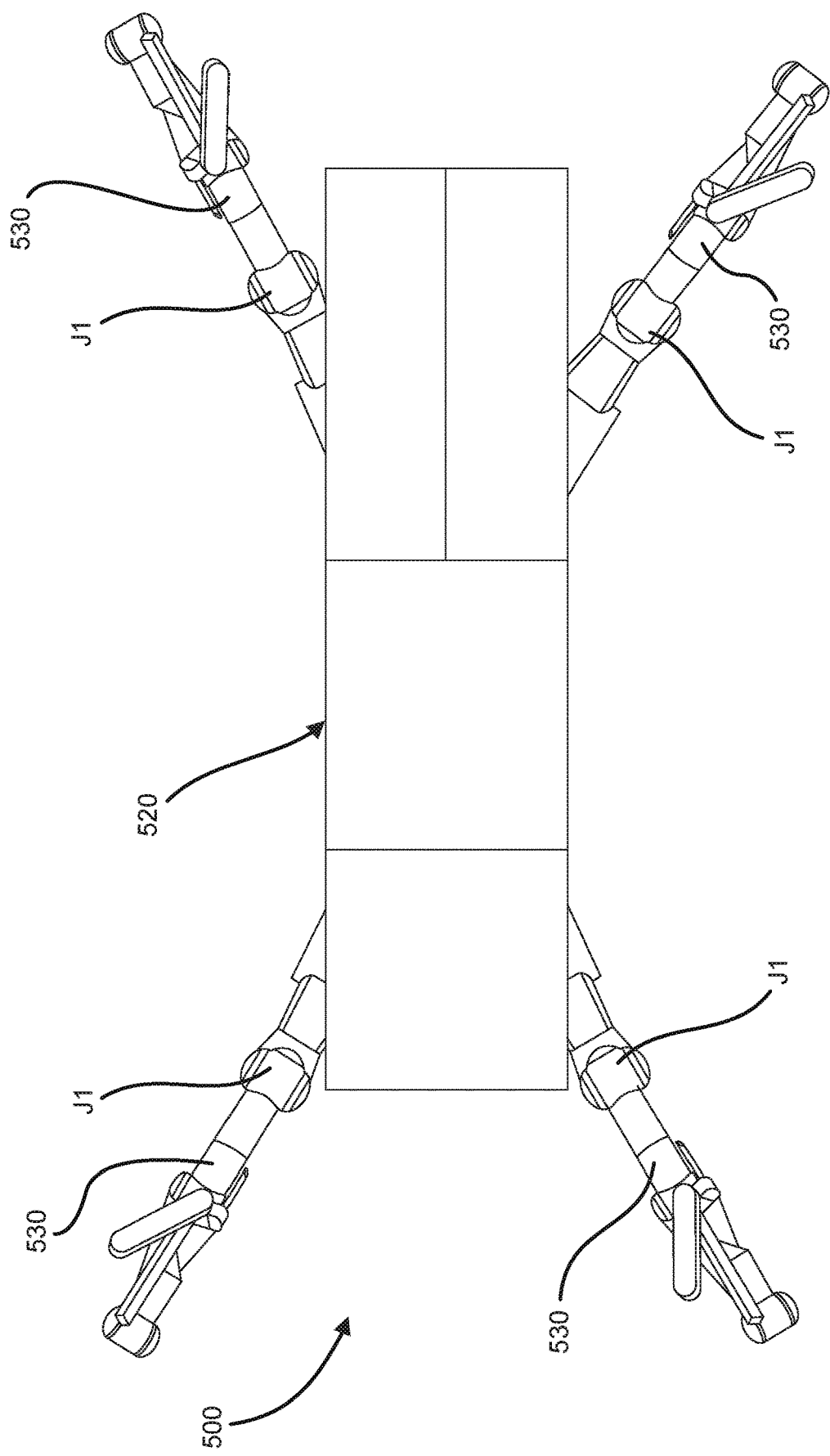

As described above, during a surgical procedure, the adapter 528 and arms 530 can also be moved to a parked position to provide clearance, for example, medical staff to access the patient or to provide clearance for other devices such as an imaging device. FIGS. 37 and 38 illustrate an example parked position in which the arms 530 are disposed out of the way of the sides of the table 500 to provide clearance for medical personnel or other equipment. When the need for the clearance has passed, the arms 530 can then be placed back into the operating position with the target joints J1 disposed at the target treatment locations relative to the table top 520.

Figure 39:
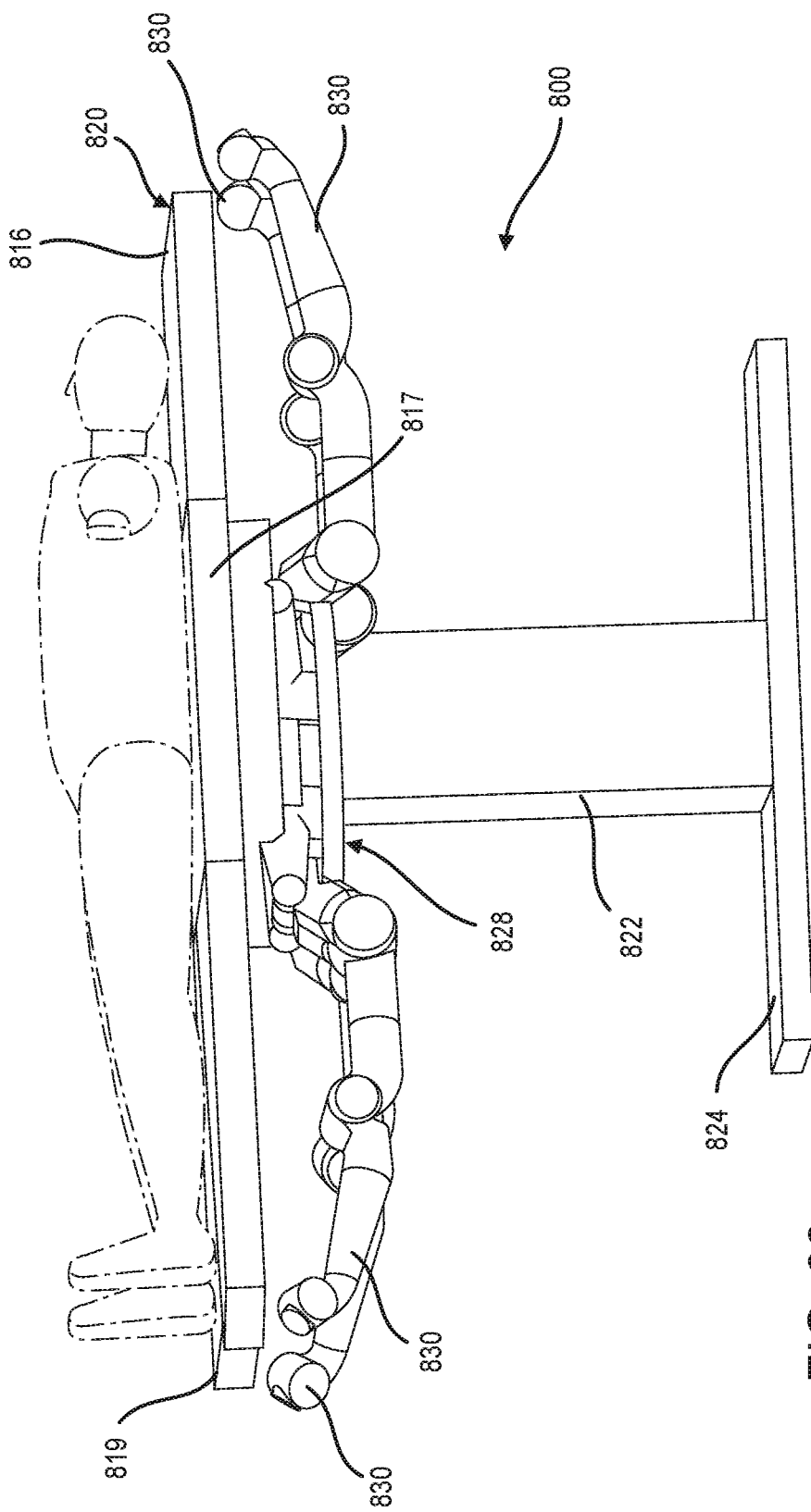
FIG. 39 is perspective view of a surgical table and an adapter, according to an embodiment, with four robotic arms coupled thereto and shown in a stowed position.
Figure 40:
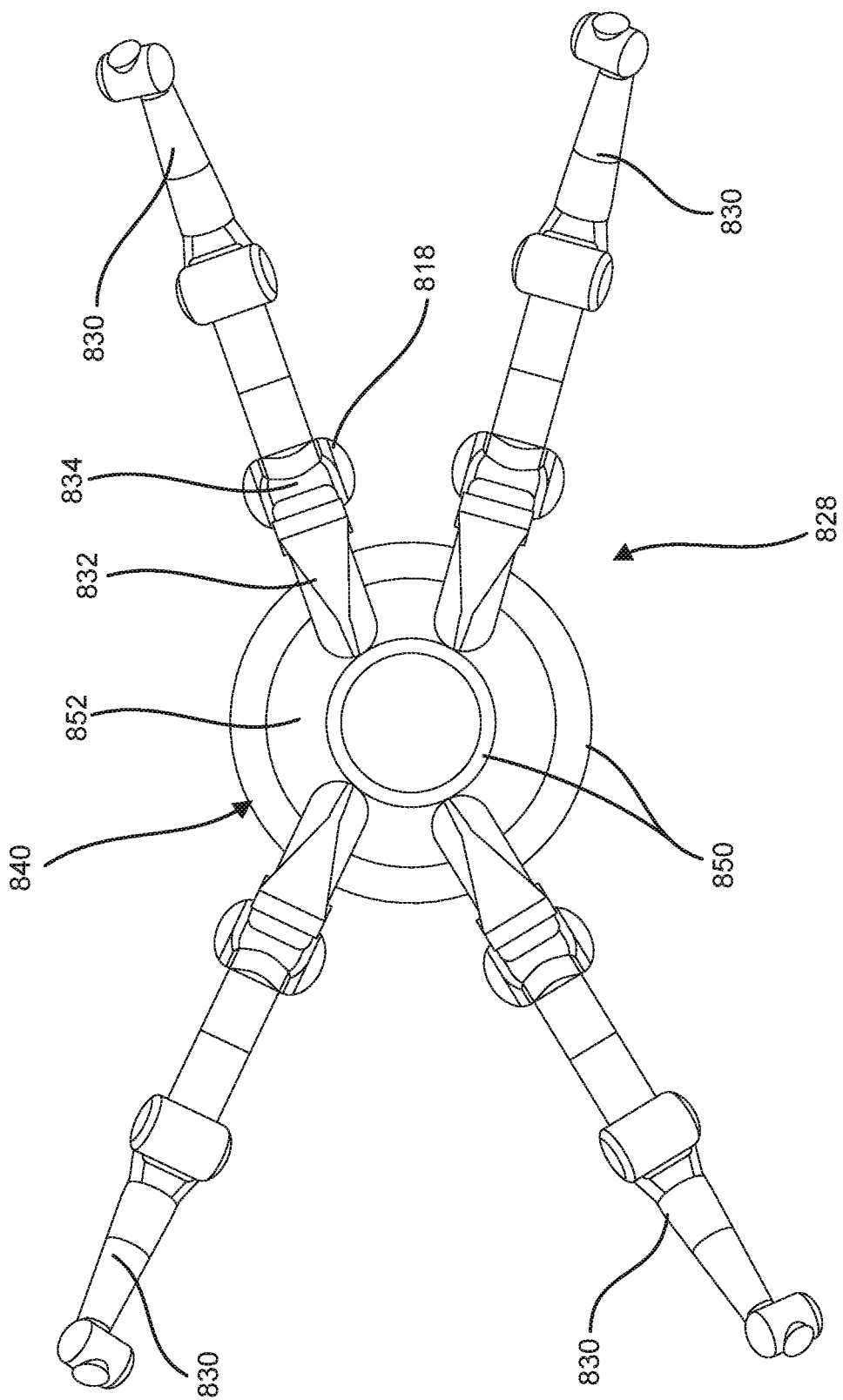
FIG. 40 is a top view of the adapter of FIG. 39, with four robotic arms coupled thereto.

FIGS. 39-51B illustrate a surgical table and adapter according to another embodiment. As shown in FIG. 39, a surgical table 800 includes a table top 820, a support 822 (also referred to herein as pedestal) and a base 824. As described above, the support 822 for the table top 820 may be mounted to the base 824, which can be fixed to the floor of an operating room, or can be movable relative to the floor, e.g., by use of wheels on the base. The table top 820 includes a head section 816, a torso section 817 and a leg section 819 (including the feet). The table top 820 can also include an arm section(s) (not shown). The table top 820 has a top surface on which a patient can be disposed. The support 822 may provide for movement of the table top 820 in a desired number of degrees of freedom, such as translation in the Z axis (height above the floor), Y axis (along the longitudinal axis of the table), and/or X axis (along the lateral axis of the table), and/or rotation about the Z, Y, and/or X axis. The head section 816, torso section 817 and leg section 819 (and arm section if included) can be movable relative to each other along/about any suitable axes. Further, the leg section 819 can have two portions that are movable relative to each other. As described above movement of the table top 820 and/or its constituent sections may be performed manually, driven by motors, controlled remotely, etc. The surgical table 800 can also include a radio-translucent window (not shown) that is without intrusion by other components of the table 800 (e.g., an adapter or robotic arm both discussed below) during a surgical procedure to allow the ability to image (e.g., x-ray) a patient disposed on the table 800 through the window.

Figure 41A:
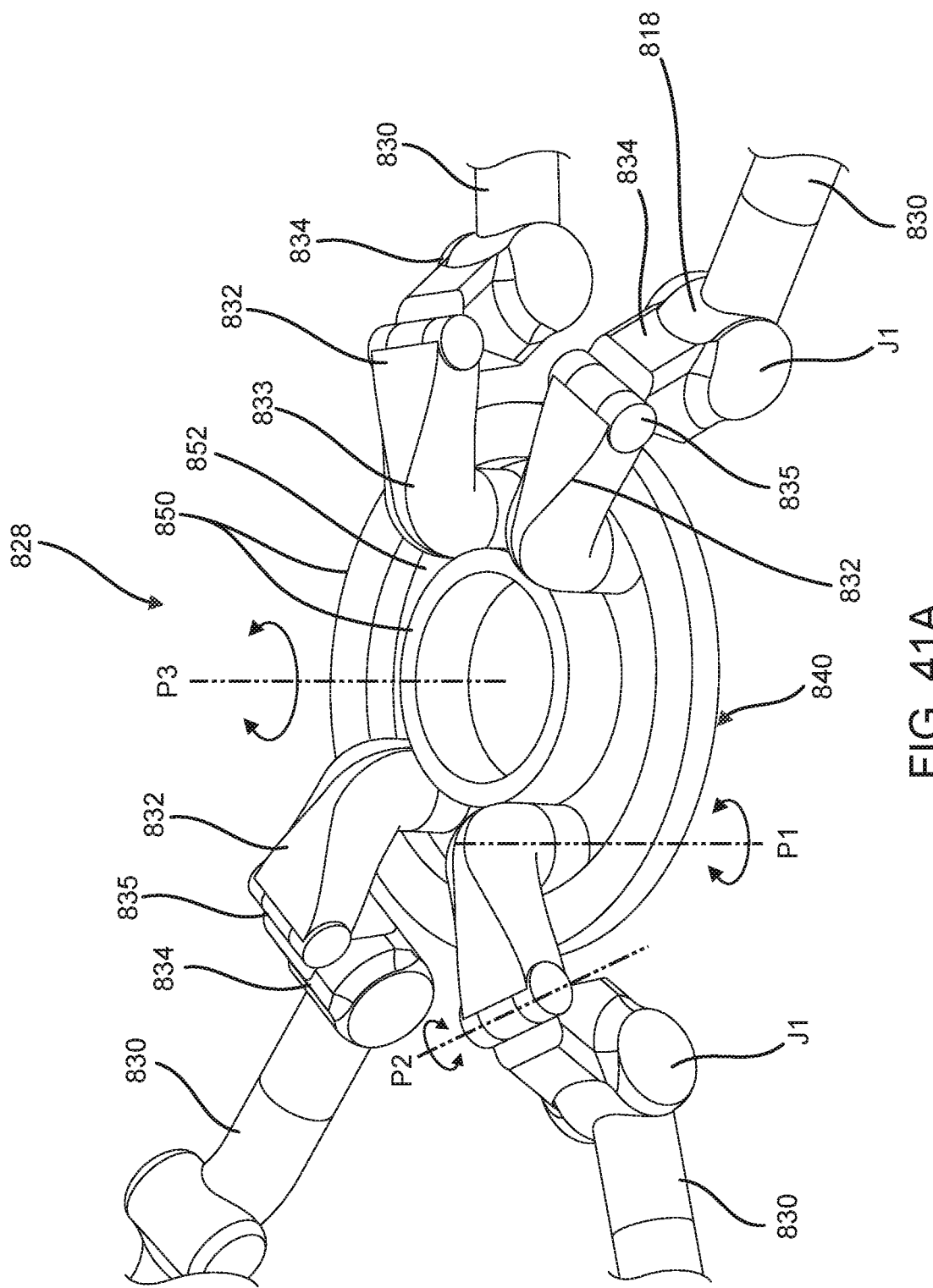
FIG. 41A is a perspective view of the adapter of FIG. 39, with four robotic arms coupled thereto.

A table adapter 828 (also referred to herein as "adapter") is coupled to the surgical table 800. As best shown in FIGS. 39 and 41A, the adapter 828 includes a table interface mechanism 840 coupleable to the support 822. The table interface mechanism 840 includes a pair of circular concentric rails 850 disposed horizontally spaced from each other defining a radial gap 852 therebetween. In this embodiment, the adapter 828 is shown supporting four robotic arms 830.

Four first link members 832 are each pivotally coupled to the interface mechanism 840 at a pivot joint 833 and can pivot about a pivot axis P1 as shown in FIG. 41A. The first link members 832 can also each travel within the gap 852 around the interface mechanism 840 about a central pivot axis P3 of the interface mechanism 840. Each of four second link members 834 are pivotally coupled to one of the first link members 832 at a second joint 835 and can pivot about a second pivot axis P2. Each of the second link members 834 can also be coupled to a robotic arm 830 at a coupling 818. In this embodiment, the coupling 818 is a pivotal coupling joint between a coupling portion (not shown) on the second link member 834 and a coupling portion (not shown) on the robotic arm 830 that includes the target joint J1. The target joint J1 is a pivotal joint that can allow the coupling portion of the robotic arm 830 to pivot about a fourth pivot axis P4 (shown in FIGS. 41B and 41C). The first joints 833 and the second joints 835 of the adapter 828 allow the adapter 828 to be moved between an extended configuration for use during a surgical procedure, and a folded or collapsed configuration for storage when not in use.

As described above, the robotic arm(s) 830 can be used to perform a surgical procedure on a patient disposed on the surgical table 800. Each robotic arm 830 can be configured the same as or similar to, and function the same as or similar to, the robotic arms 830 described above and thus, specific details regarding the robotic arms are not discussed with respect to this embodiment. For example, as described above for robotic arms 130, the robotic arms 830 can include multiple links or segments and can be moved between an extended configuration for use during a surgical procedure, and a folded or collapsed configuration for storage when not in use. The first joint 833, the second joint 835 and the coupling 818 (e.g., target joint J1) can provide for movement of the robotic arm 830 along and/or about the X, Y, and/or Z axes as described in more detail below.

Figure 42A:
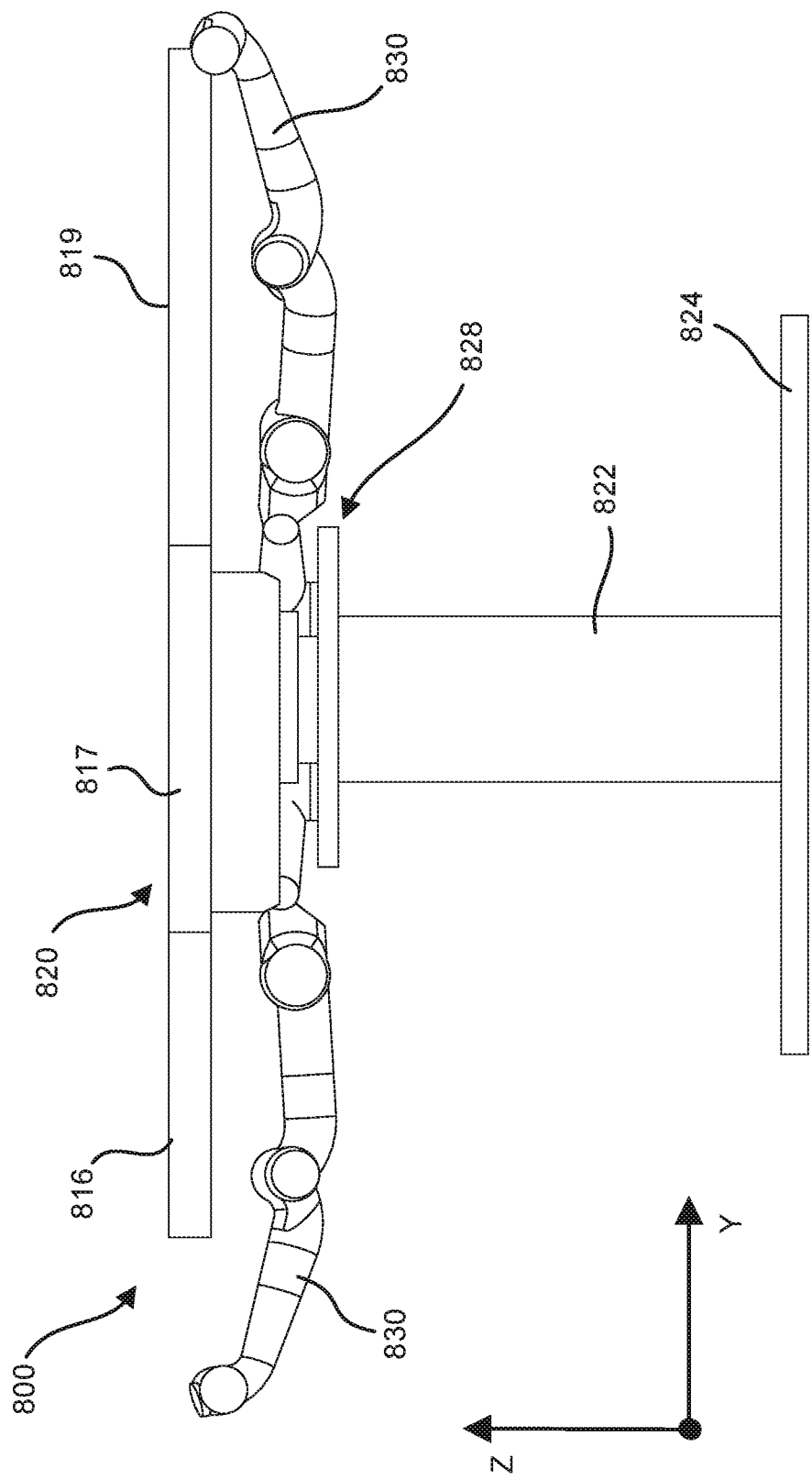
FIG. 42A is a side view of the surgical table, adapter and two of the robotic arms of FIG. 39 shown in a stowed position.

More specifically, the first joint 833 can provide for rotational motion of the first link member 832 relative to the interface structure 840 (and table 800) about a vertical z-axis (shown in FIG. 42A) (i.e., pivot axis P1 in FIG. 41A) relative to the top surface of the table top 820 (e.g., the top surface of the torso section 817), and movement of the first link member 832 and the second link member 834 in lateral and longitudinal directions (also referred to herein as x-direction and y-direction, see X-Y axes in, e.g., FIG. 42B) relative to the table top 820 of the surgical table 800. The second joint 835 can provide a lift mechanism to allow for vertical movement of the second link member 834 and the coupling 818 between the second link member 834 and the robotic arm 830 coupled thereto. In this embodiment, the second joint 835 includes a pivotal coupling that provides for the second link member 834 to rotate about an axis within, or parallel to, the x-y plane (see, e.g., X and Y axes in FIG. 42B) (i.e., pivot axis P2 in FIG. 41A) parallel to a plane of the top surface of the table 800 (e.g., a top surface of the torso section 817). Thus, the motion of the first link member 832 and the second link member 834 of the adapter 828 can provide for movement of the coupling 818 and therefore, movement of a robotic arm 830 coupled thereto along and/or about the X, Y, and/or Z axes to position the target joint J1 at a desired treatment location relative to the top surface of the table top 820. In addition, as described above, the first link members 832 can move or travel within the gap 852 defined by tracks 850 of the interface mechanism 840 such that the arms 830 can be moved about the table support 822 360 degrees about a pivot axis P3.

Figure 41B:
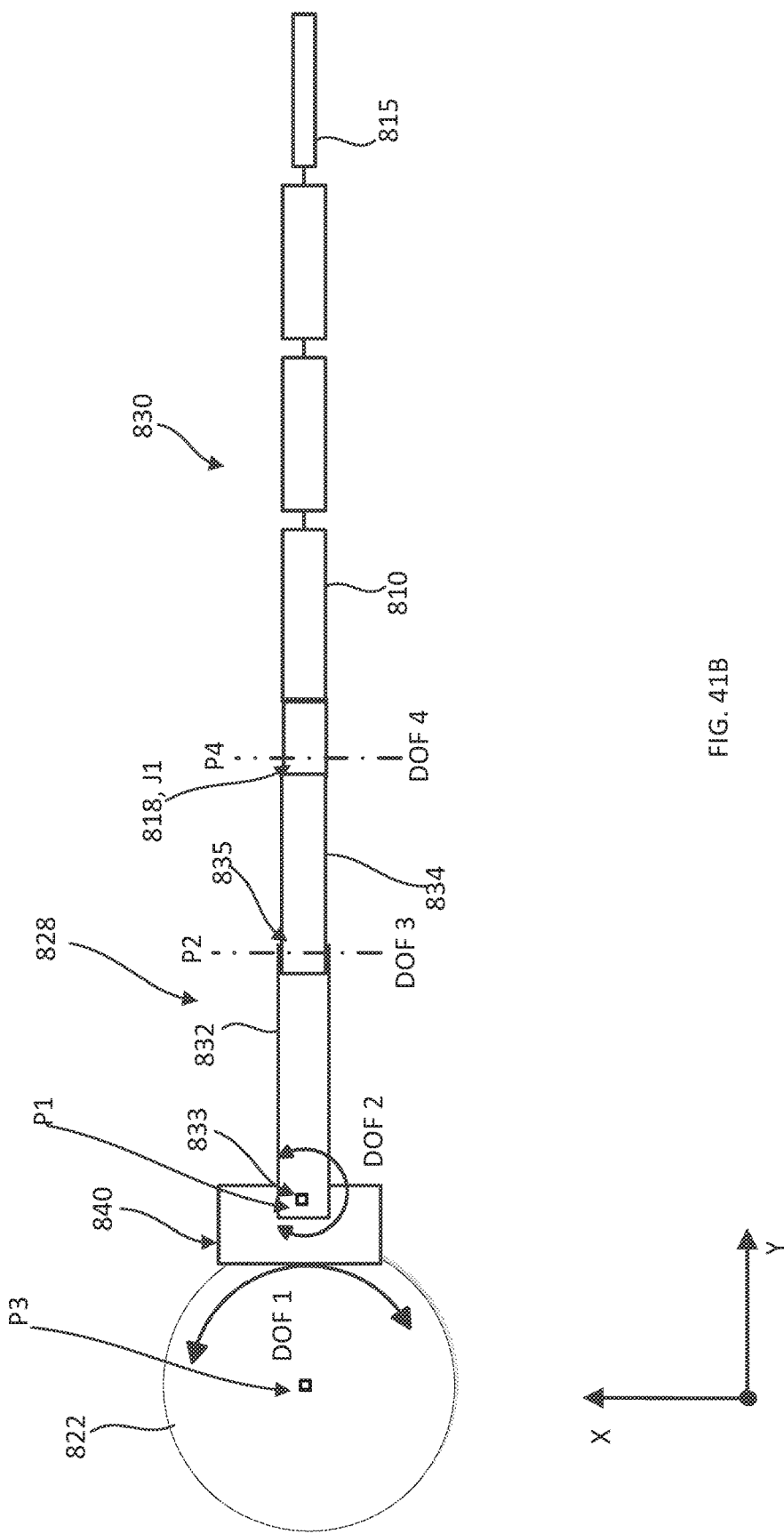
FIGS. 41B and 41C are a schematic top view and side view, respectively, of the adapter and a robotic arm of FIGS. 39-41A illustrating the degrees of freedom between the joints of the adapter and robotic arm.
Figures 41C, 41D:
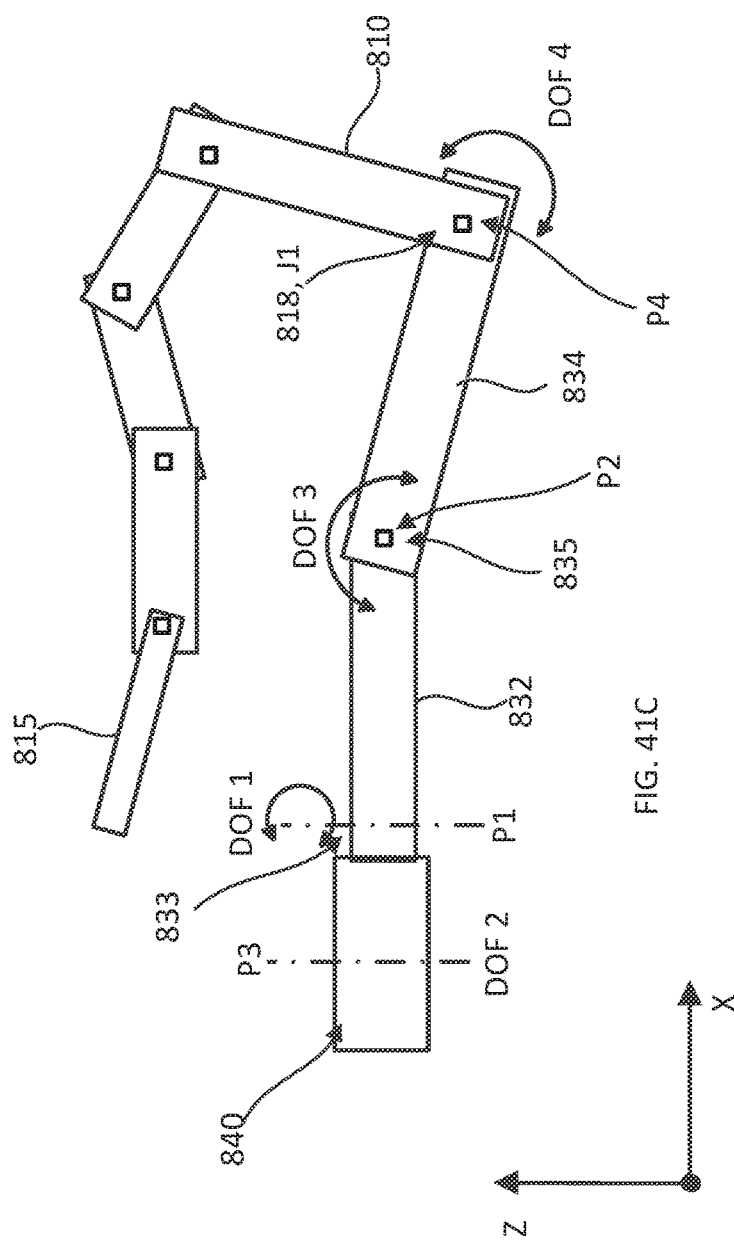
FIG. 41D is a table listing the type of degree of freedom of each of the joints.

FIGS. 41B and 41C are schematic illustrations of the various degrees of freedom provided by the joints of the adapter 828 and robotic arm 830, and FIG. 41D is a table listing the type of degree of freedom (e.g., rotational, linear) associated therewith. As shown in FIGS. 41B and 41C, and as described above, the interface mechanism 840 is coupleable to the support 822 of the table 800 and the first link members 832 are pivotally coupled to the interface mechanism 840 at joint 833 about a pivot axis P1 labeled in FIGS. 41A-41C. The pivotal joint 833 of the first link members 832 to the interface mechanism 840 allows the first link members 832 to rotate about the z-axis and provide a first degree of freedom DOF 1 at joint 833, i.e., Z-axis rotation. In this embodiment, the first link members 832 can also rotate within the gap 852 of tracks 850 around the table support 822 about a z-axis labeled P3 in FIGS. 41A-41C.

The joint 835 between the first link member 832 and the second link member 834 is also a rotational or pivotal joint that can pivot about a horizontal axis (i.e., pivot axis P2 in FIGS. 41A-41C) and provide a third degree of freedom DOF 3 (best shown in the side view illustration of FIG. 41C) that is X-Y plane rotation. Similarly, the joint J1 between the coupling portion of the adapter 828 and the coupling portion of the robotic arm 830 is also a pivotal joint that can pivot about a horizontal axis and provide a fourth degree of freedom DOF 4 (best shown in the side view illustration of FIG. 41C) that is X-Y plane rotation. Although not labeled in FIGS. 41B and 41C, the various joints between links 810 of the arm 830 and a medical instrument 815 disposed on the distal end of the robotic arm 830 can provide additional motion of the arm relative to a patient (e.g., a target treatment location on the patient) disposed on the table 800, and therefore, additional degrees of freedom.

Figure 43:
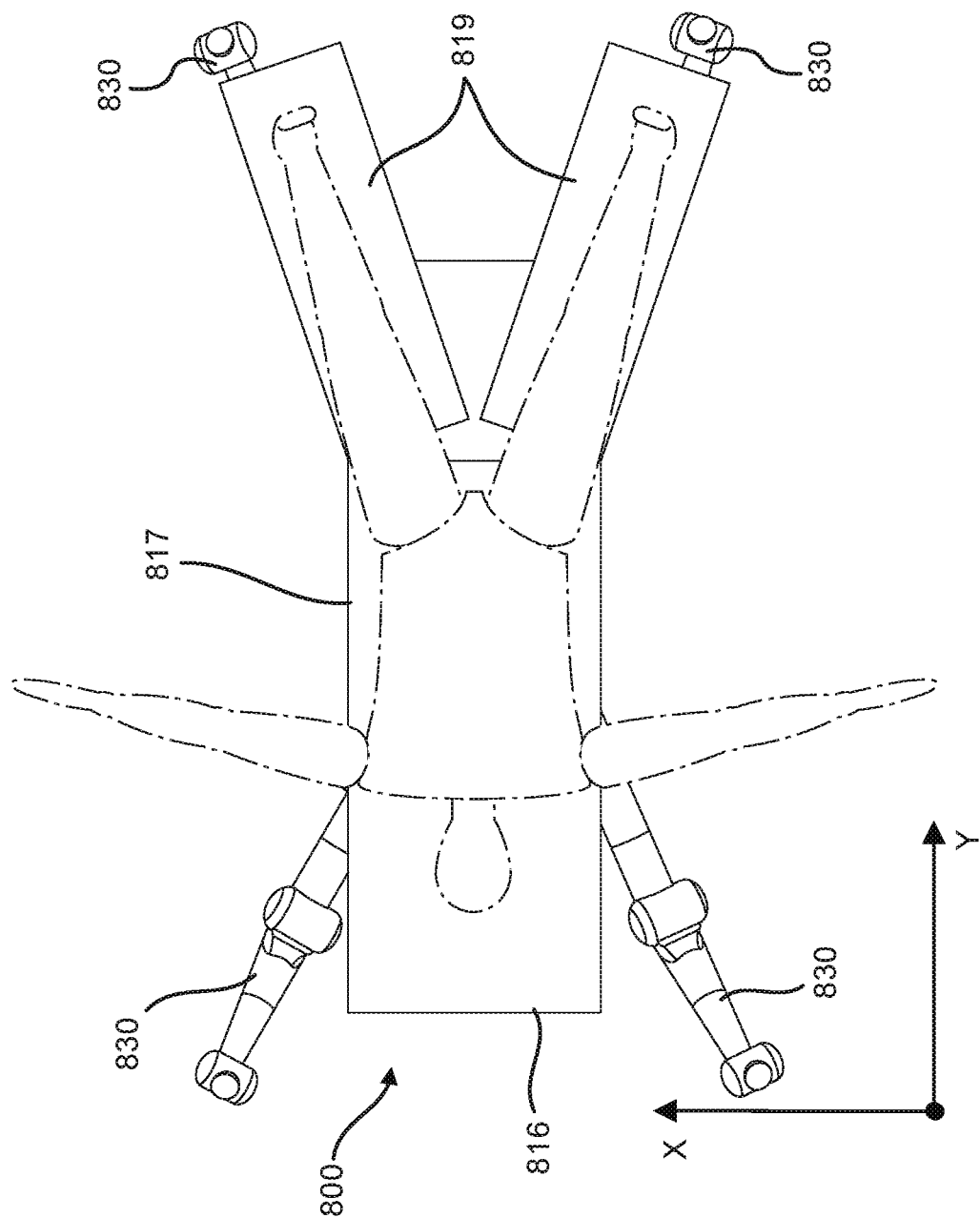
FIG. 43 is a top view of the surgical table, adapter and four robotic arms of FIG. 39 shown with two of the arms in a stowed position and two of the arms in a parked position.

The collective motion of the first link members 832 and the second link members 834 allows the adapter 828 and robotic arms 830 to move between a variety of different positions relative to the surgical table 800 during a surgical procedure. For example, adapter 828 and robotic arms 830 can be moved to a stowed position substantially beneath the table top 820 as shown, for example, in FIGS. 42A and 42B. In this example embodiment, in the stowed position, the arms 830 are shown extending slightly beyond the head section 816 of the table top 820 (FIG. 42A illustrates two arms 830 and FIG. 42B illustrates four arms 830). In the stowed position, the arms 830 and adapter 828 are each in a folded or collapsed configuration disposed beneath the table top 820 within an outer perimeter defined by the table top 820. To move the adapter 828 and arms 830 to the stowed position, the arms 830 can be slidably moved within the gap 852 of rails 850 via the first link members 832 until two of the first link members 832, second link members 834 and arms 830 are disposed beneath the table top 820 at a foot end of the table 800 beneath the leg section 819 (e.g., one arm beneath each of the leg portions of the leg section 819), and two first link members 832, second link members 834 and arms 830 are disposed beneath the table top 820 at the head end of the table 800 beneath the head section 816. In the stowed position of FIGS. 42A and 42B, the adapter 828 and arms 830 are in a position which provides clearance along the sides of the table 800 to, for example, move a patient from a gurney onto the table top 820, or for anesthetic to be administered, as described above for previous embodiments. FIG. 43 illustrates the two arms 830 previously disposed under the head section 816, moved outwardly in the x-direction, but still providing side access clearance to the table top 820.

Figure 44:
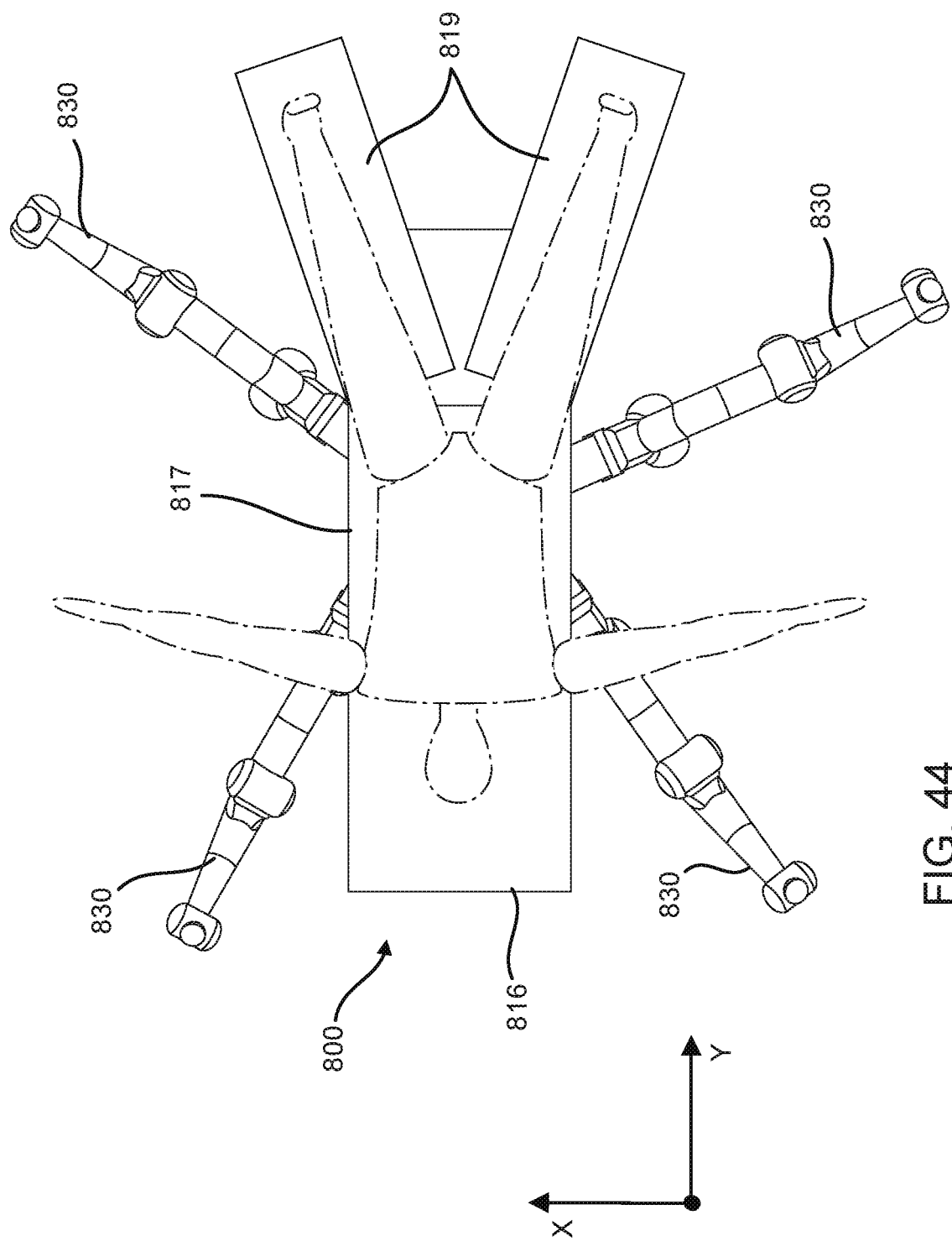
FIG. 44 is a top view of the surgical table, adapter and four robotic arms of FIG. 39 shown in a parked position.

FIG. 44 illustrates the arms 830 disposed in a parked position. As described above, the parked position is used when access to the patient is needed, and the robotic arms 830 are moved to a clearance position relative to the table top 820. As shown in FIG. 44, in this example, the robotic arms 830 have been moved longitudinally along the side of the table top 820 (i.e., via the movement of first link member 832 with the gap 852 of the interface mechanism 840) and out of a treatment zone to provide space for a medical professional to tend to the patient. When the need for the clearance has passed, the arms 830 can then be placed back into an operating position (described in more detail below) with the target joints J1 disposed at the desired target treatment locations relative to the table top 820.

Figure 45A:
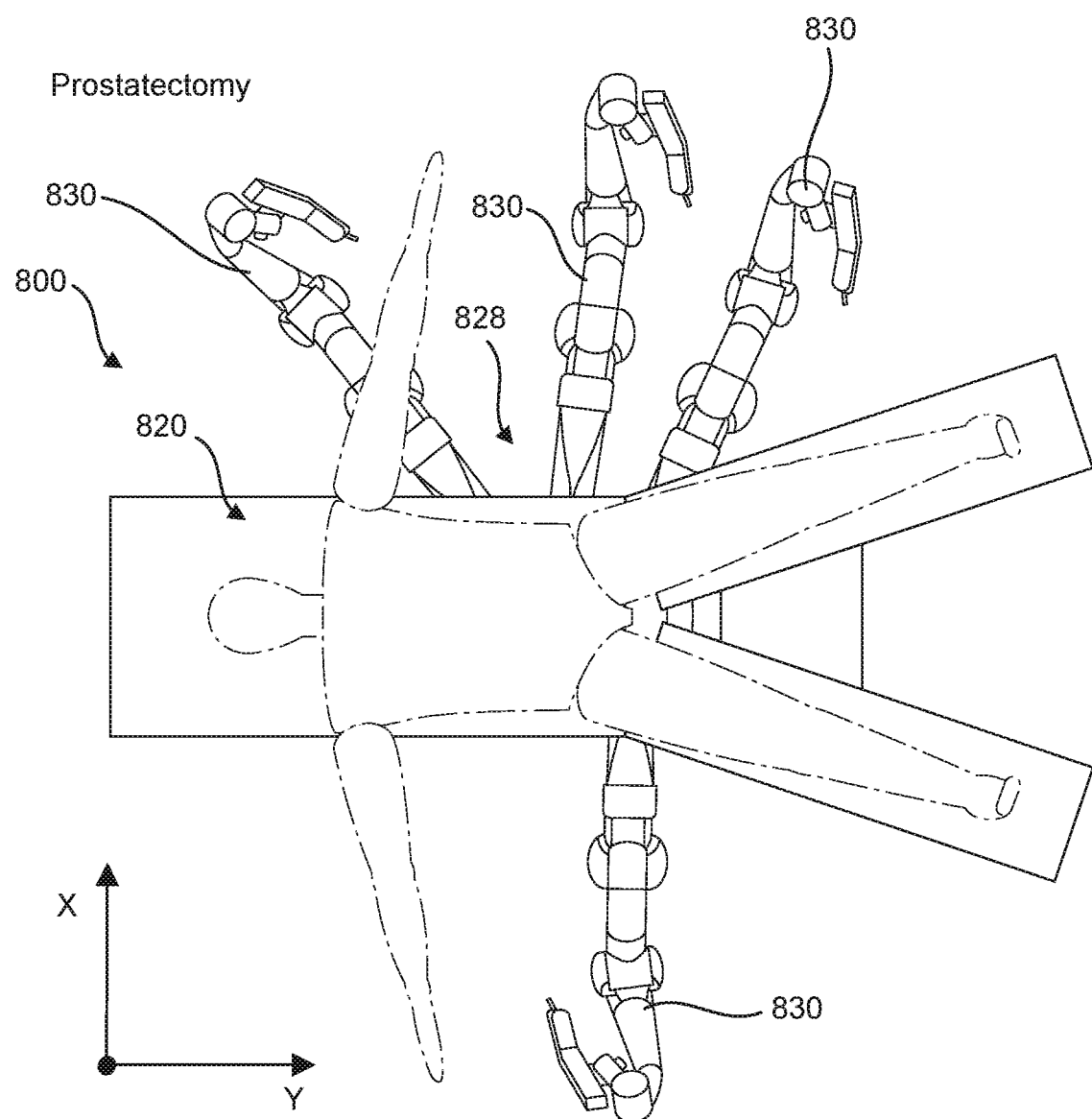
FIG. 45A is a top view of the surgical table, adapter and four robotic arms of FIG. 39 shown in an operating position.
Figure 45B:
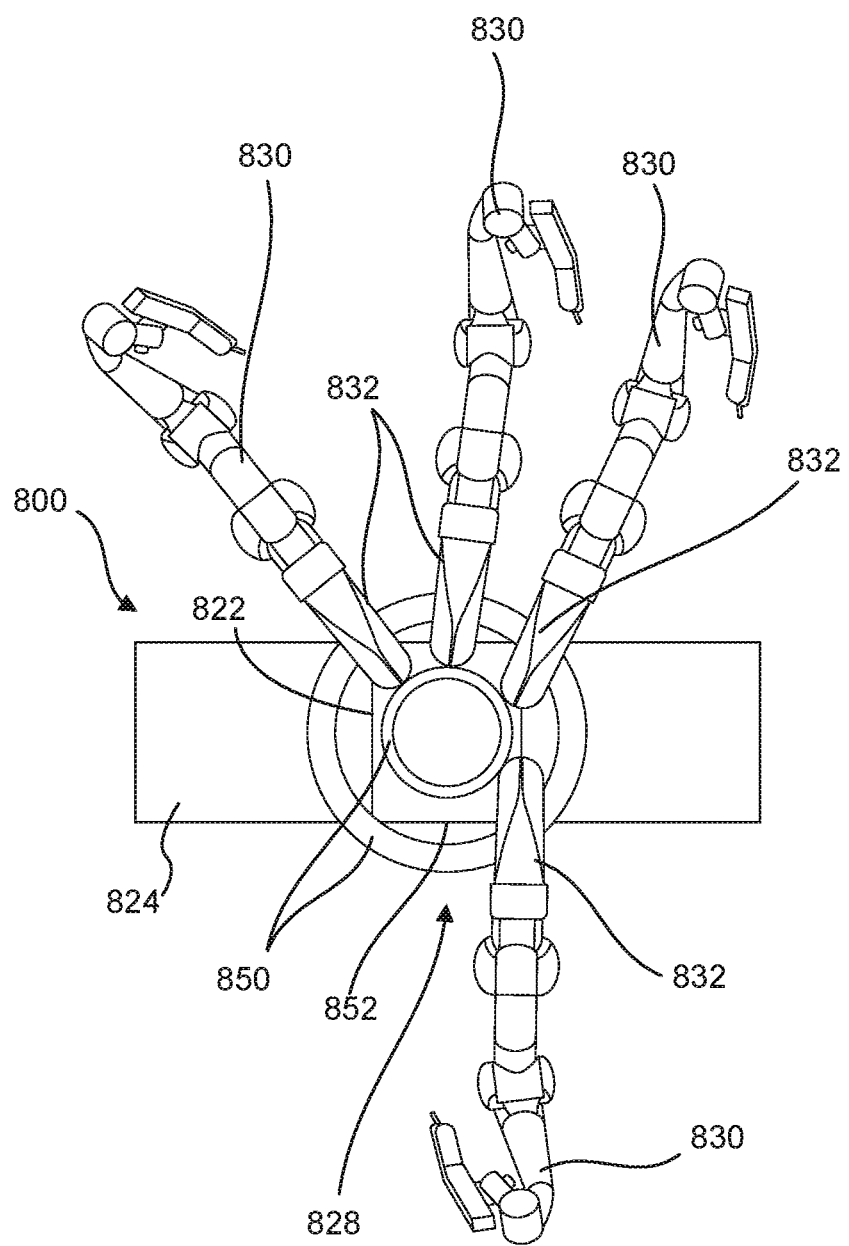
FIG. 45B is a top view of the surgical table without the table top for illustrative purposes, the adapter and four robotic arms of FIG. 45A shown in an operating position.

The adapter 828 and arms 830 can also be moved to various operating positions in which the target joints J1 of the arms 830 are each positioned at a target treatment location relative to the table top 820 for a particular procedure to be performed. Example operating positions for various procedures are shown in FIGS. 45A-51B. As with previous embodiments, the positioning of the arms 830 about the table top 820 can be varied to accommodate the various different procedures. For example, in some procedures it may be desirable to have an operating position in which three robotic arms 830 are disposed on one side of the table top 820 and one arm 830 is disposed on an opposite side of the table top 820 as shown in FIGS. 45A and 45B, which is an example operating position to perform a prostatectomy. The adapter 828 can accommodate movement of the arms 830 relative to the table top 820 by slidably moving the arms 830 under the table top 820 about the support 822 via the first link members 832, which are movably coupled to the interface mechanism 840, as described above. As shown in FIG. 45A, the robotic arms 830 are shown in a ready configuration in which a distal end of the arms 830 (and instrument coupled thereto) are disposed outside of a treatment zone.

Figure 46A:
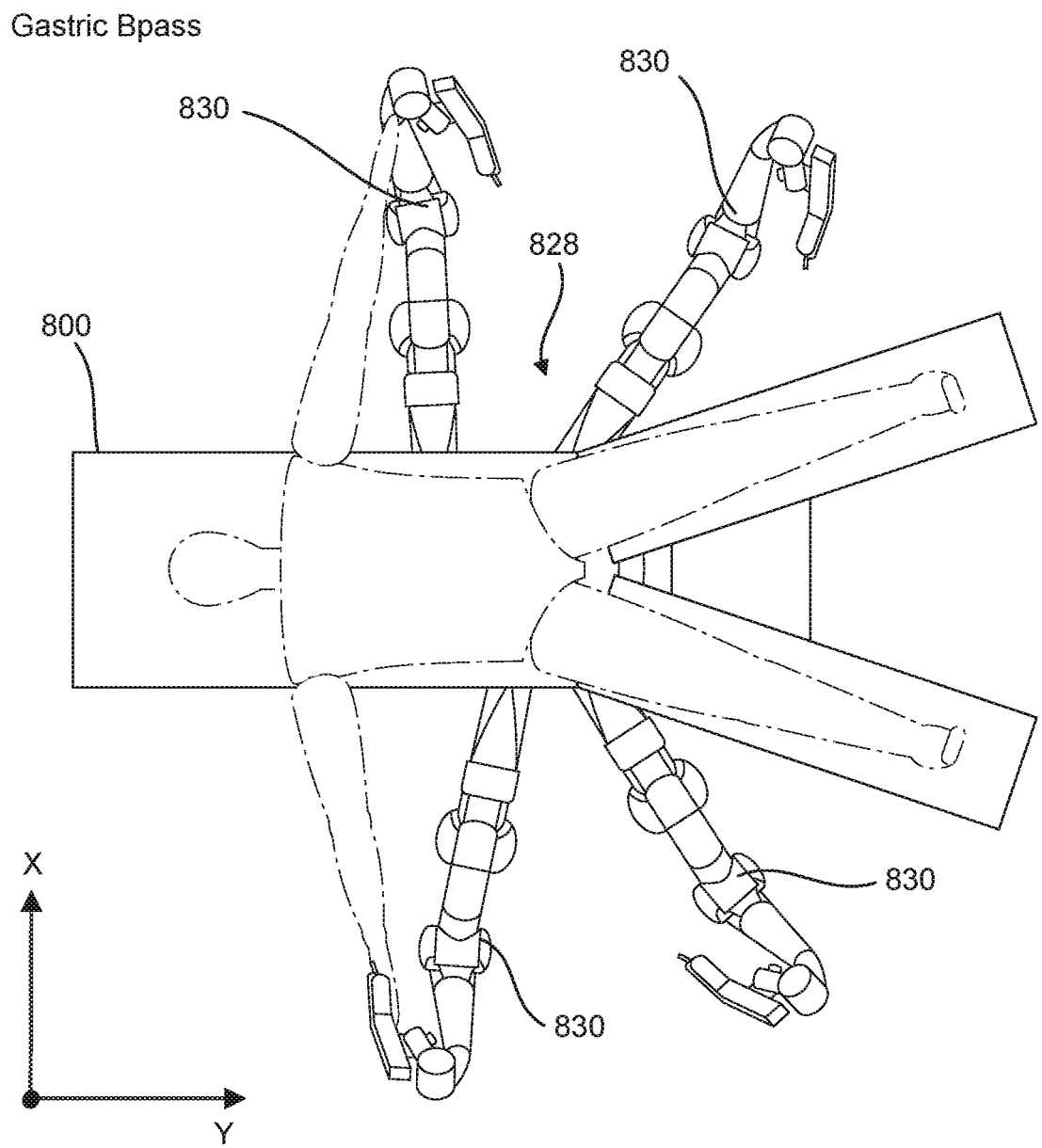
FIG. 46A is a top view of the surgical table, adapter and four robotic arms of FIG. 39 shown in an operating position.
Figure 46B:
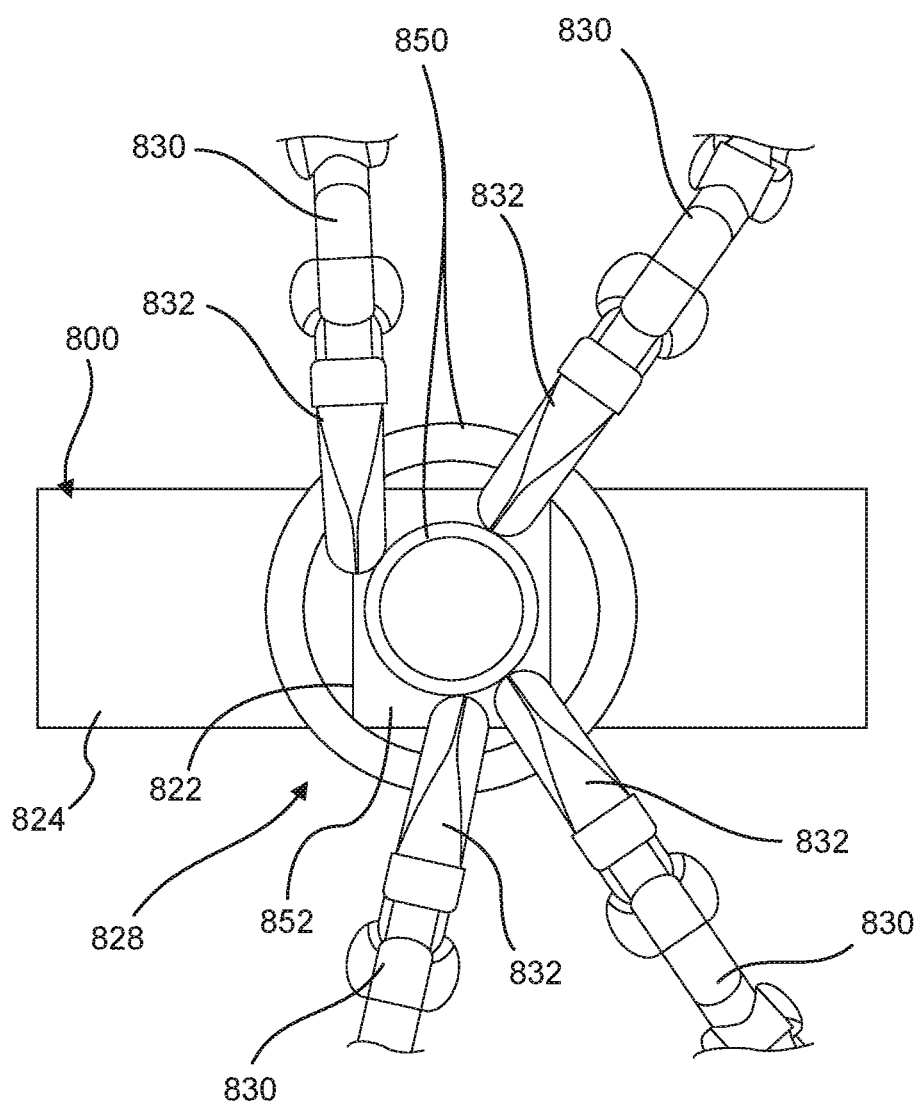
FIG. 46B is a top view of the surgical table without the table top for illustrative purposes, the adapter and four robotic arms of FIG. 46A shown in an operating position.
Figure 47:
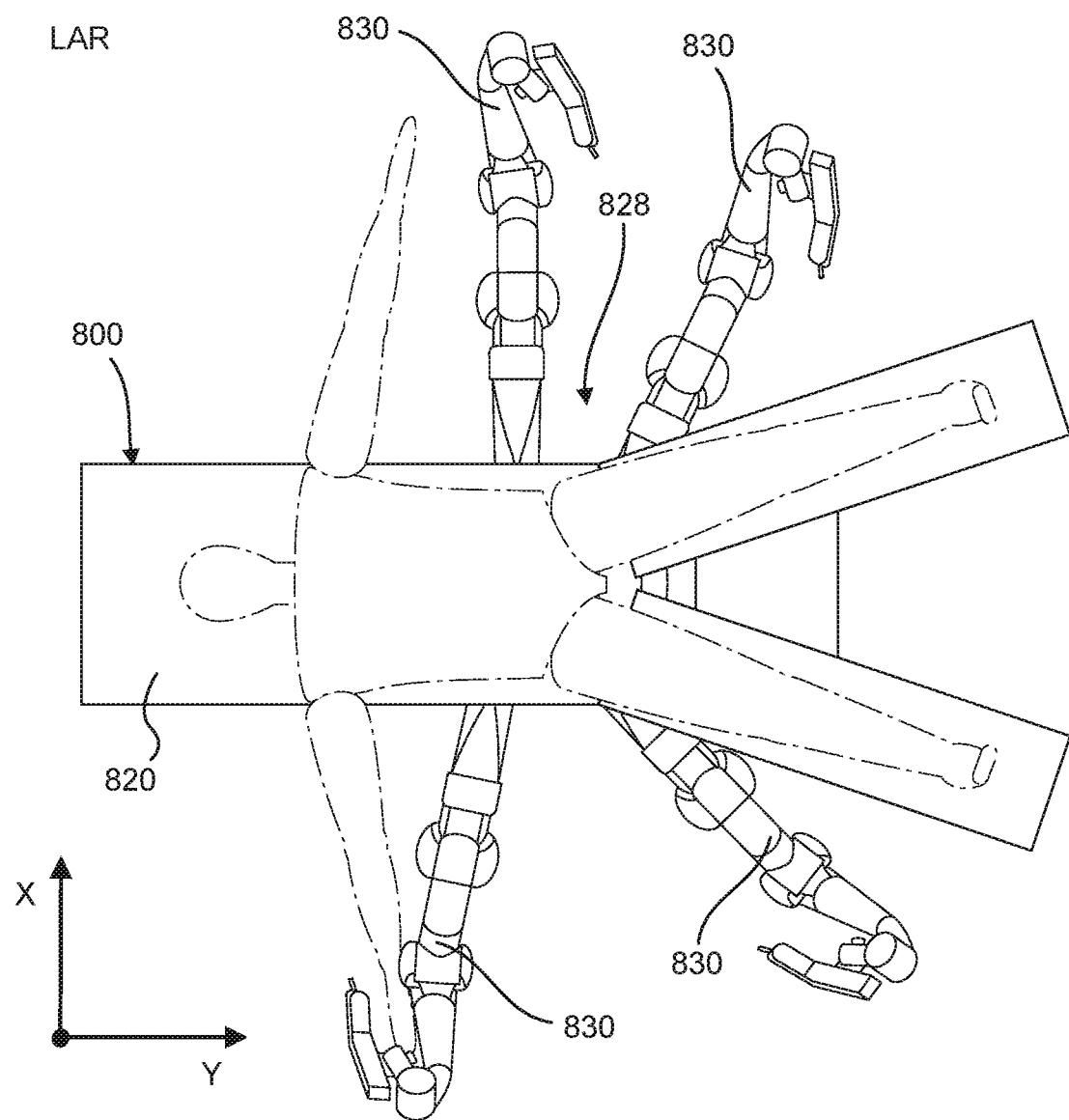
FIG. 47 is a top view of the surgical table, adapter and four robotic arms of FIG. 58 shown in an operating position.

In some embodiments, it may be desirable to position two robotic arms 830 on each side of the table 800 as shown, for example, in FIGS. 46A, 46B and 47. FIG. 46A is a top view of an example operating position for performing a gastric bypass procedure on a patient disposed on the table top 820. FIG. 47 is a top view of an example operating position for performing a LAR procedure on a patient disposed on the table top 820.

Figure 48A:
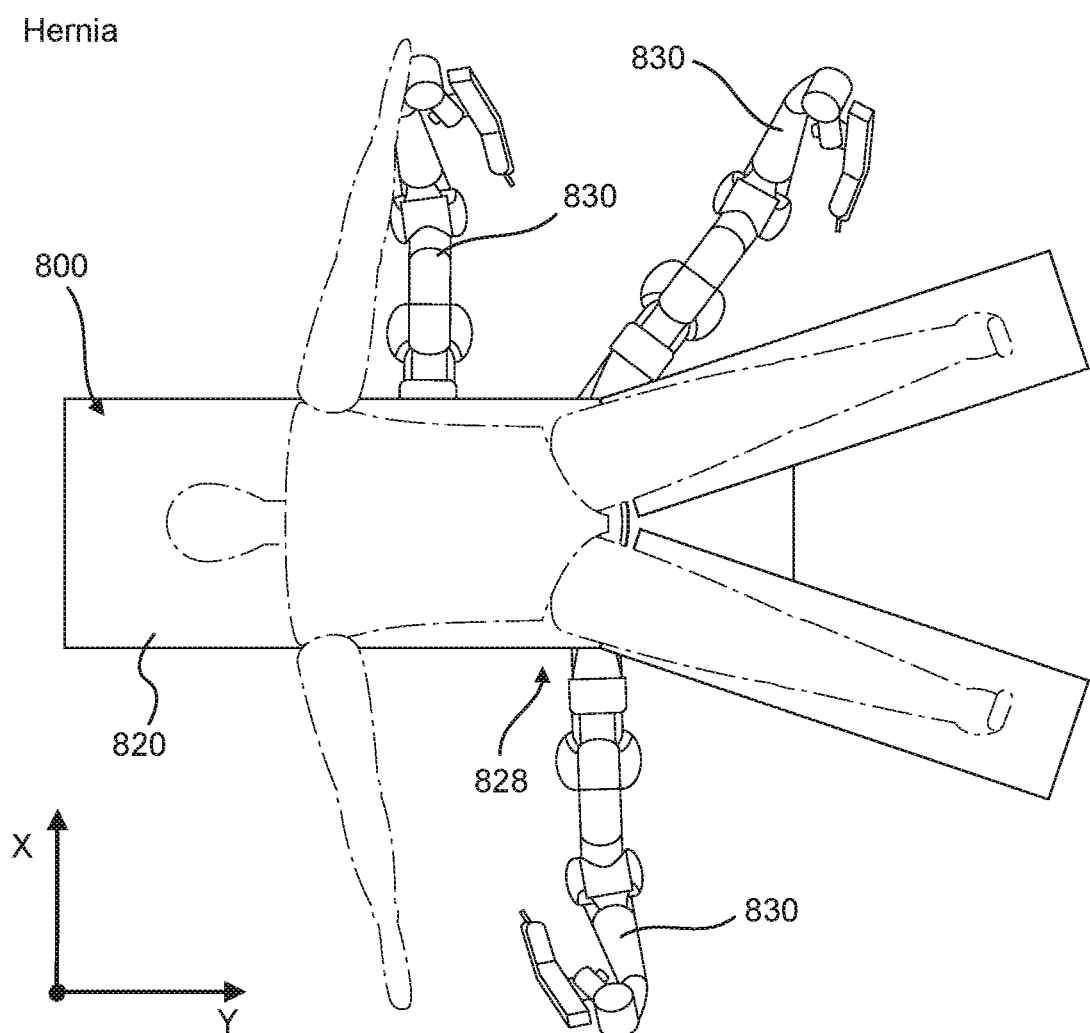
FIG. 48A is a top view of the surgical table, adapter and three of the robotic arms of FIG. 39 shown in an operating position.
Figure 48B:
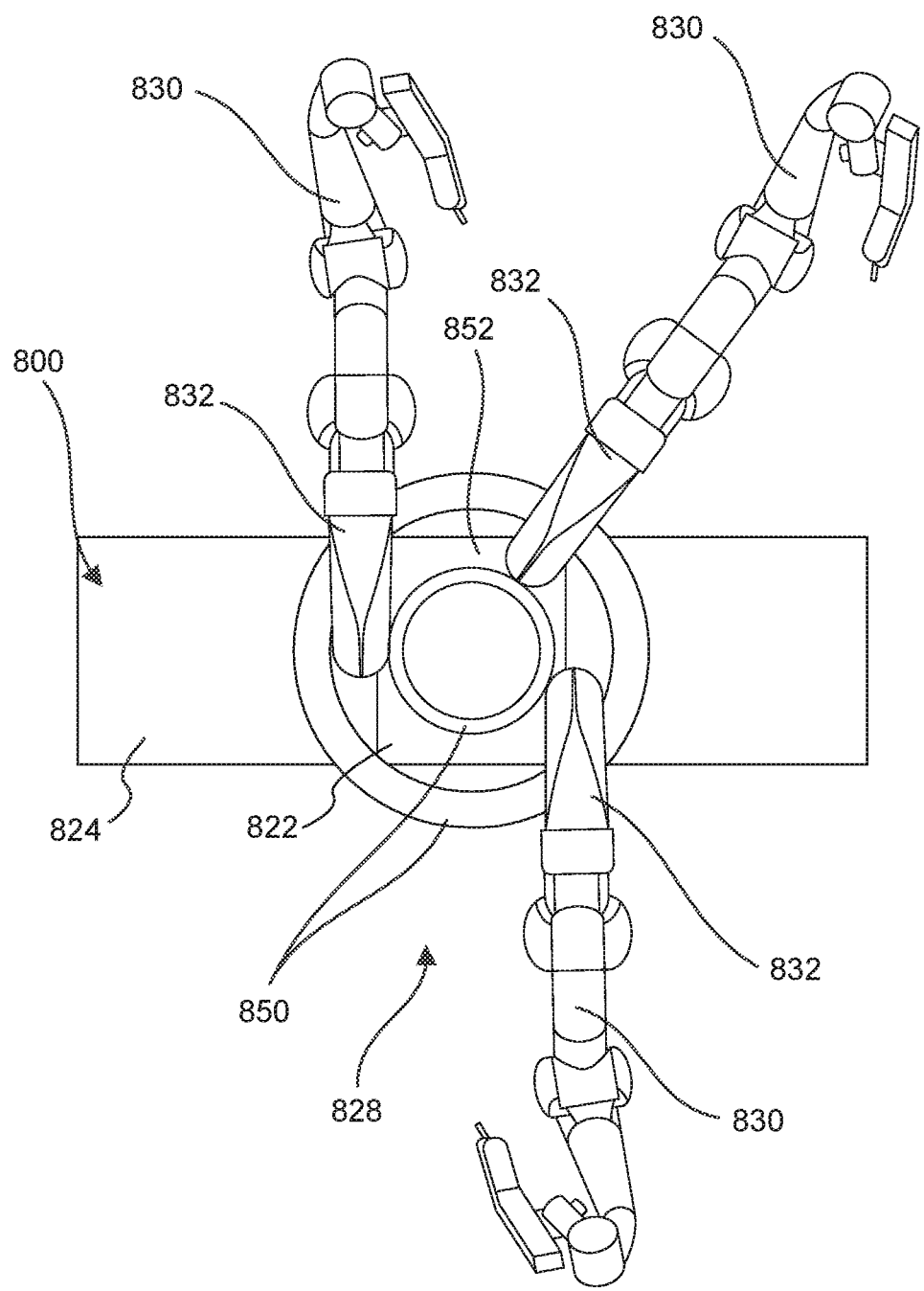
FIG. 48B is a top view of the surgical table without the table top for illustrative purposes, the adapter and four robotic arms of FIG. 48A shown in an operating position.
Figure 49A:
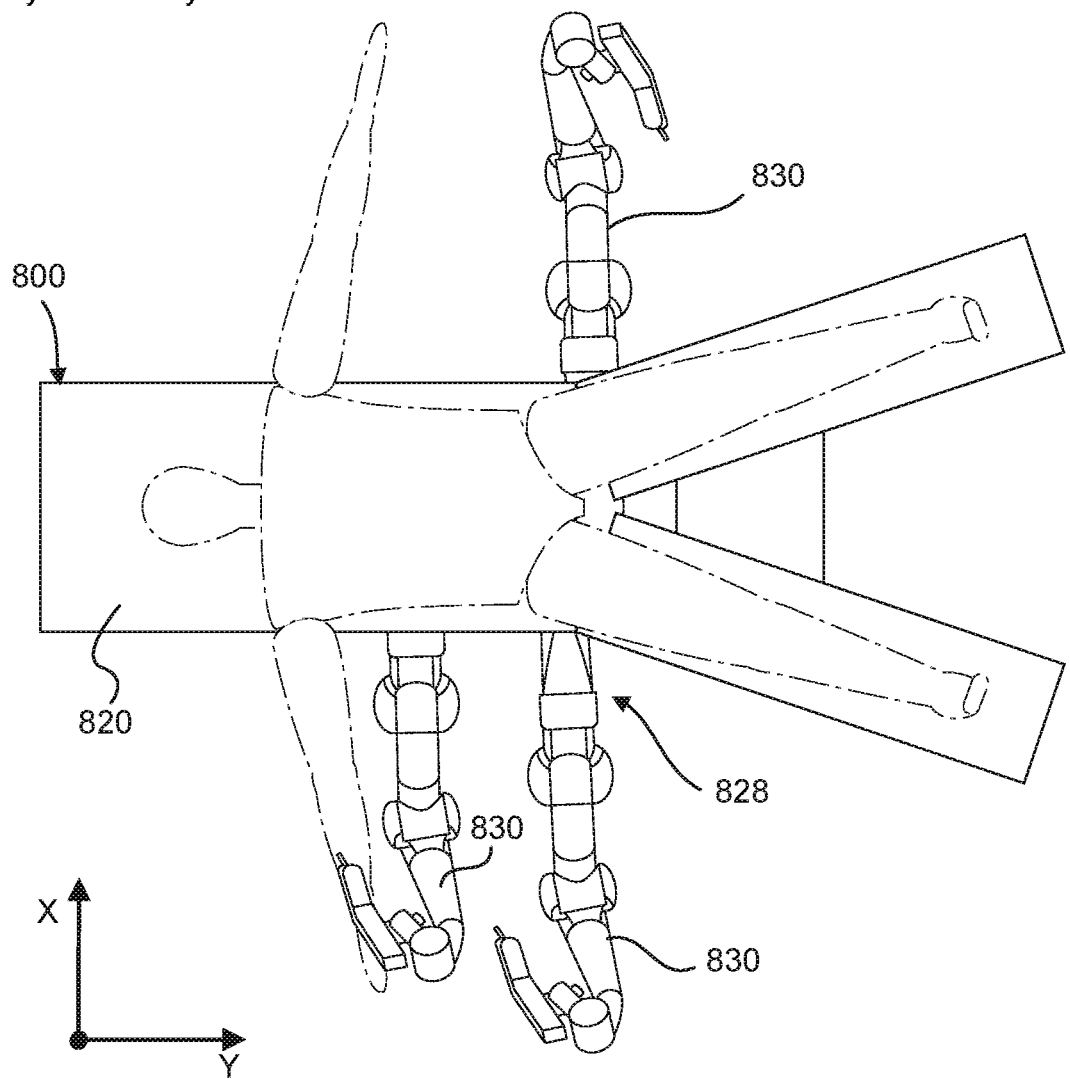
FIG. 49A is a top view of the surgical table, adapter and three of the robotic arms of FIG. 39 shown in an operating position.
Figure 49B:
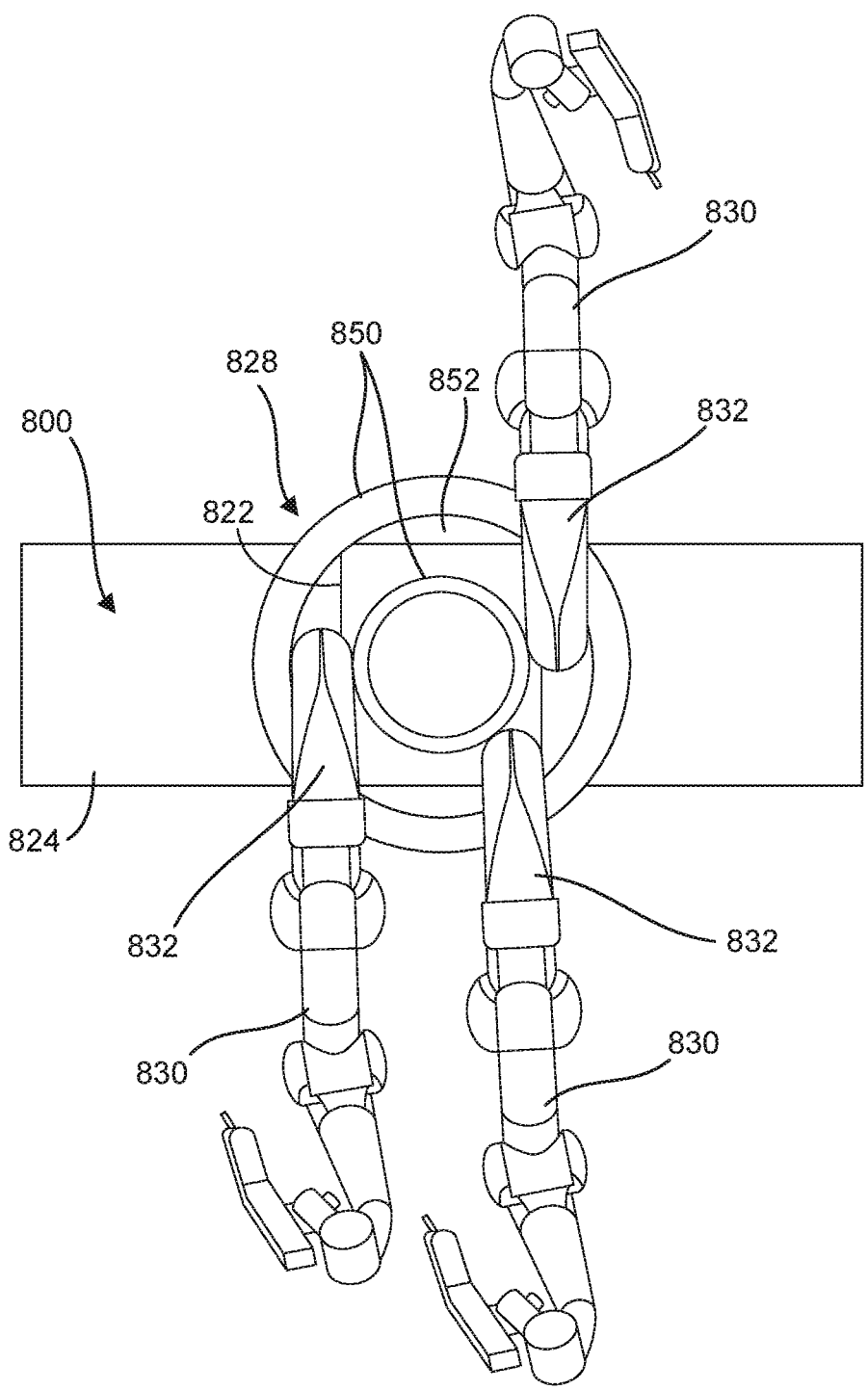
FIG. 49B is a top view of the surgical table without the table top for illustrative purposes, the adapter and four robotic arms of FIG. 49A shown in an operating position.
Figure 50A:
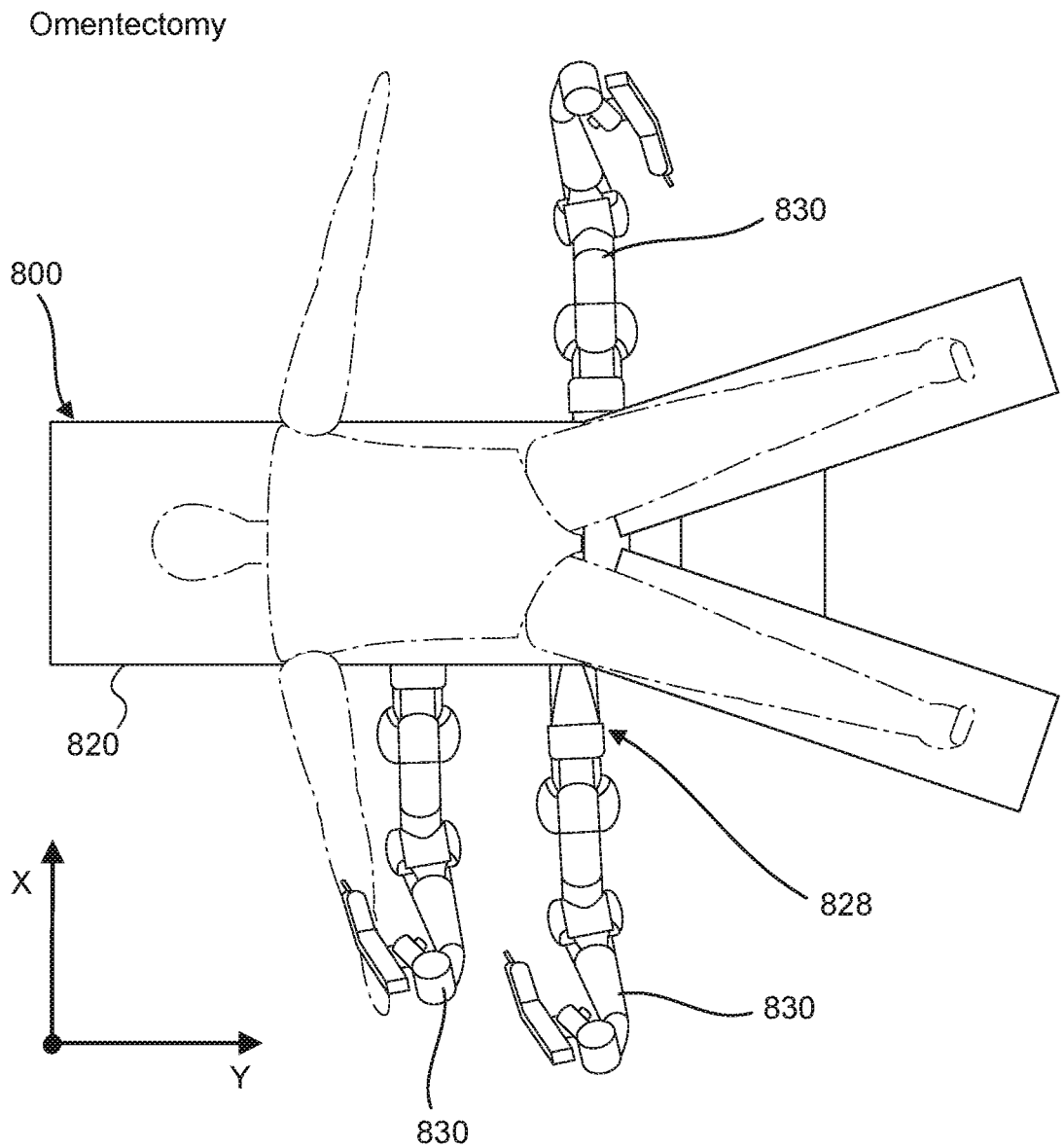
FIG. 50A is a top view of the surgical table, adapter and three of the robotic arms of FIG. 39 shown in an operating position.
Figure 50B:
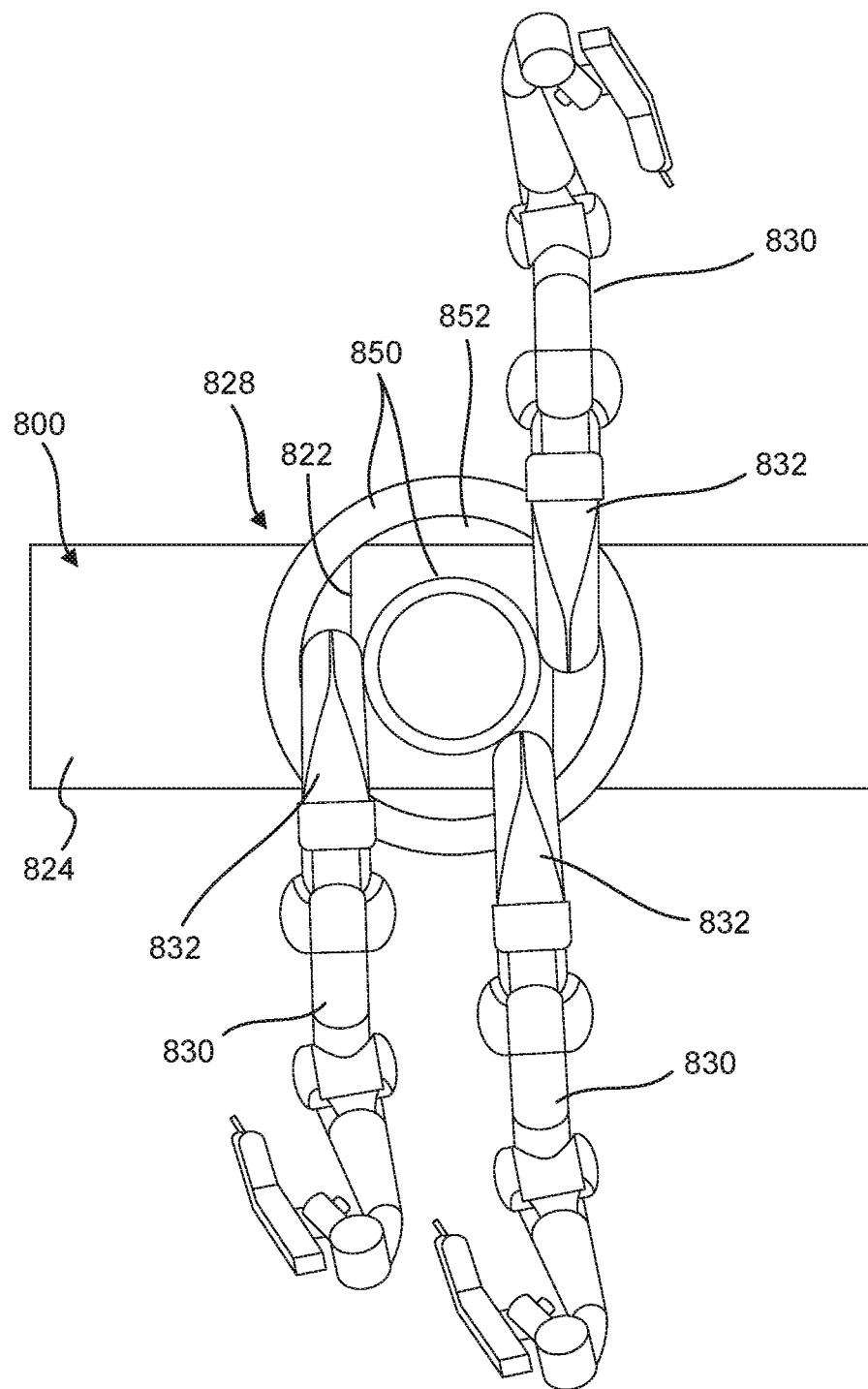
FIG. 50B is a top view of the surgical table without the table top for illustrative purposes, the adapter and four robotic arms of FIG. 50A shown in an operating position.
Figure 51A:
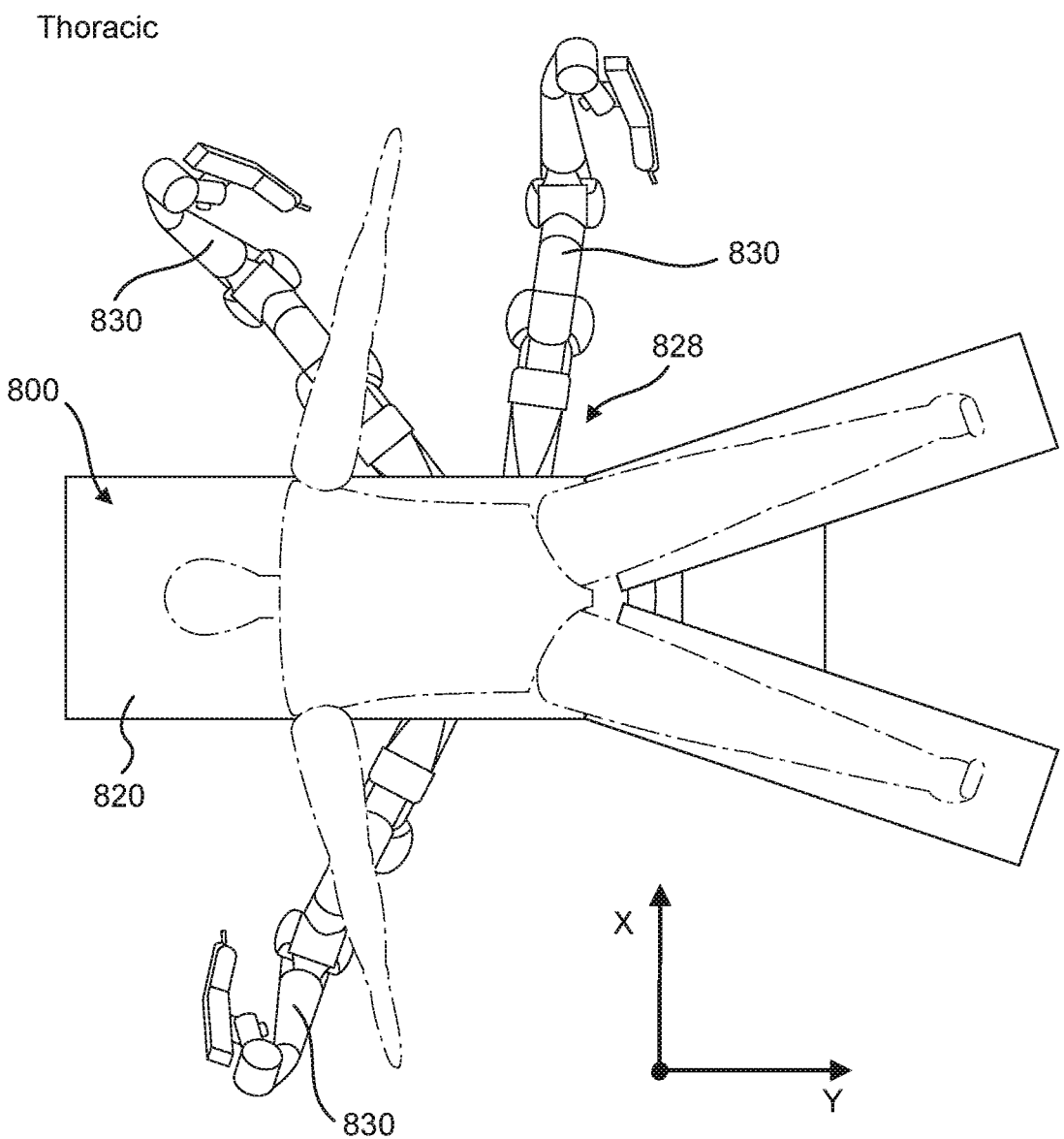
FIG. 51A is a top view of the surgical table, adapter and three of the robotic arms of FIG. 39 shown in an operating position.
Figure 51B:
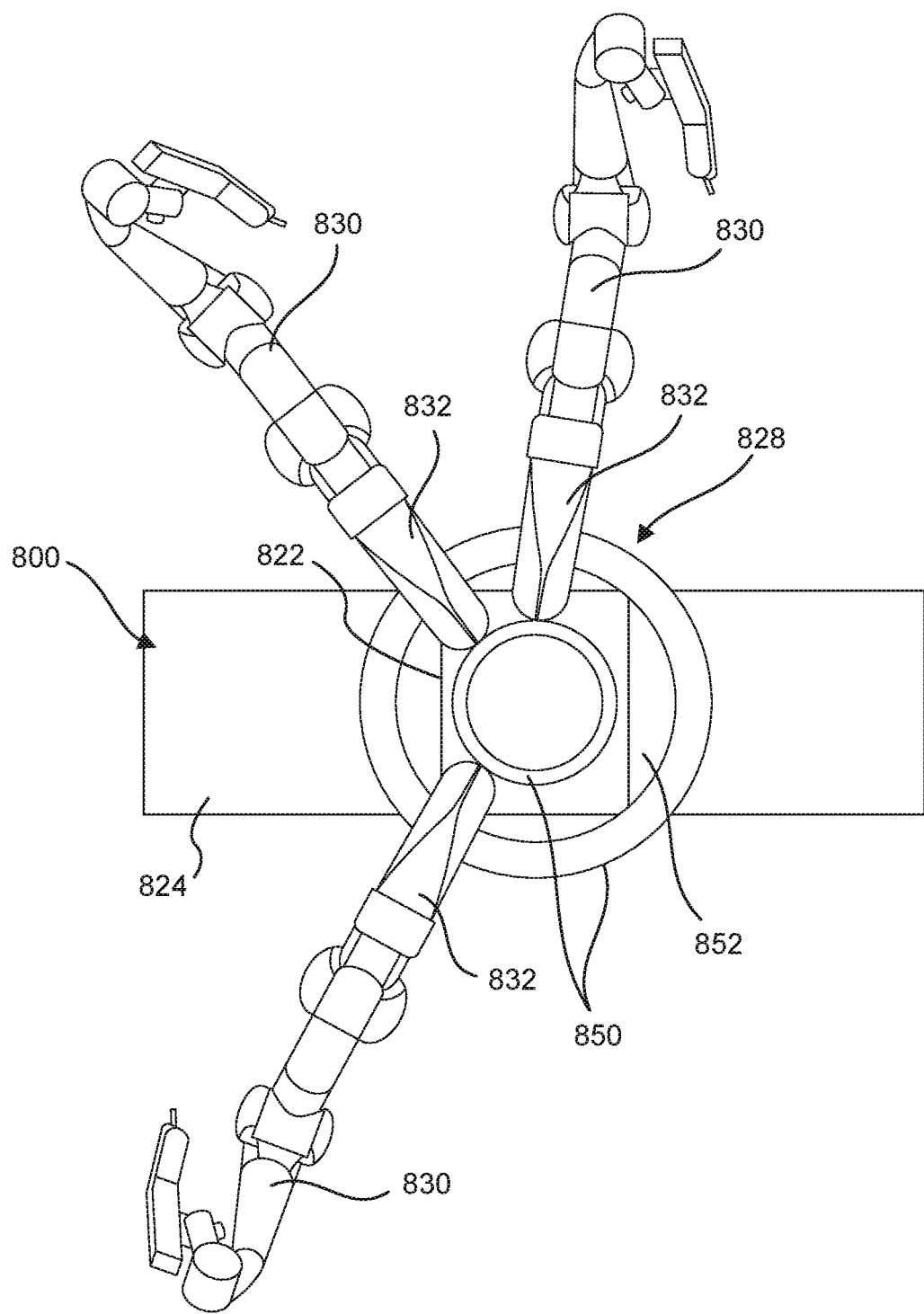
FIG. 51B is a top view of the surgical table without the table top for illustrative purposes, the adapter and four robotic arms of FIG. 51A shown in an operating position.

In some embodiments, it may be desirable to position two robotic arms 830 on one side of the table 800 and one arm on the opposite side of the table 800 as shown, for example, in FIGS. 48A-51B. FIGS. 48A and 48B illustrate an example operating position for a hernia procedure. FIGS. 49A-49B illustrate an example operating position for a hysterectomy procedure. FIGS. 50A-50B illustrate an example operating position for an omentectomy procedure, and FIGS. 51A-51B illustrate an example operating position for a thoracic procedure.

FIGS. 52-57C illustrate another embodiment of an adapter 1728 that can be coupled to a surgical table (not shown) that can include the same or similar components and function in the same or similar manner as the surgical tables described above, and therefore, is not described in detail with respect to this embodiment.

Figure 52:
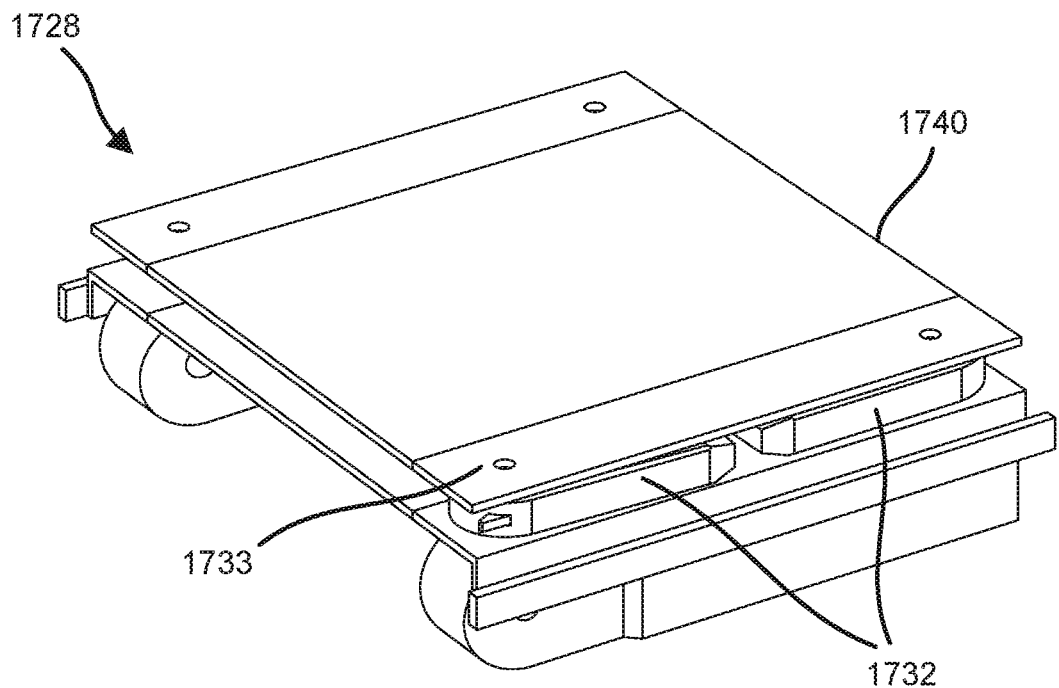
FIG. 52 is a top perspective view of an adapter according to another embodiment.
Figure 53:
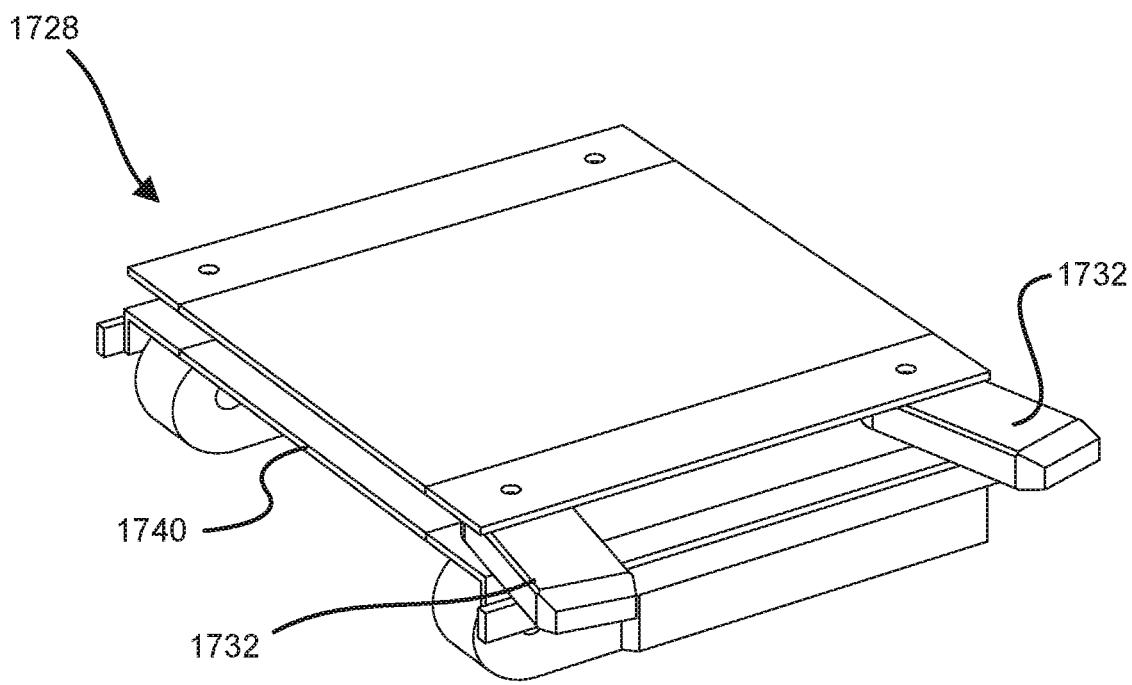
FIG. 53 is a top perspective view of the adapter of FIG. 52 with two link members in a rotated position.
Figure 54:
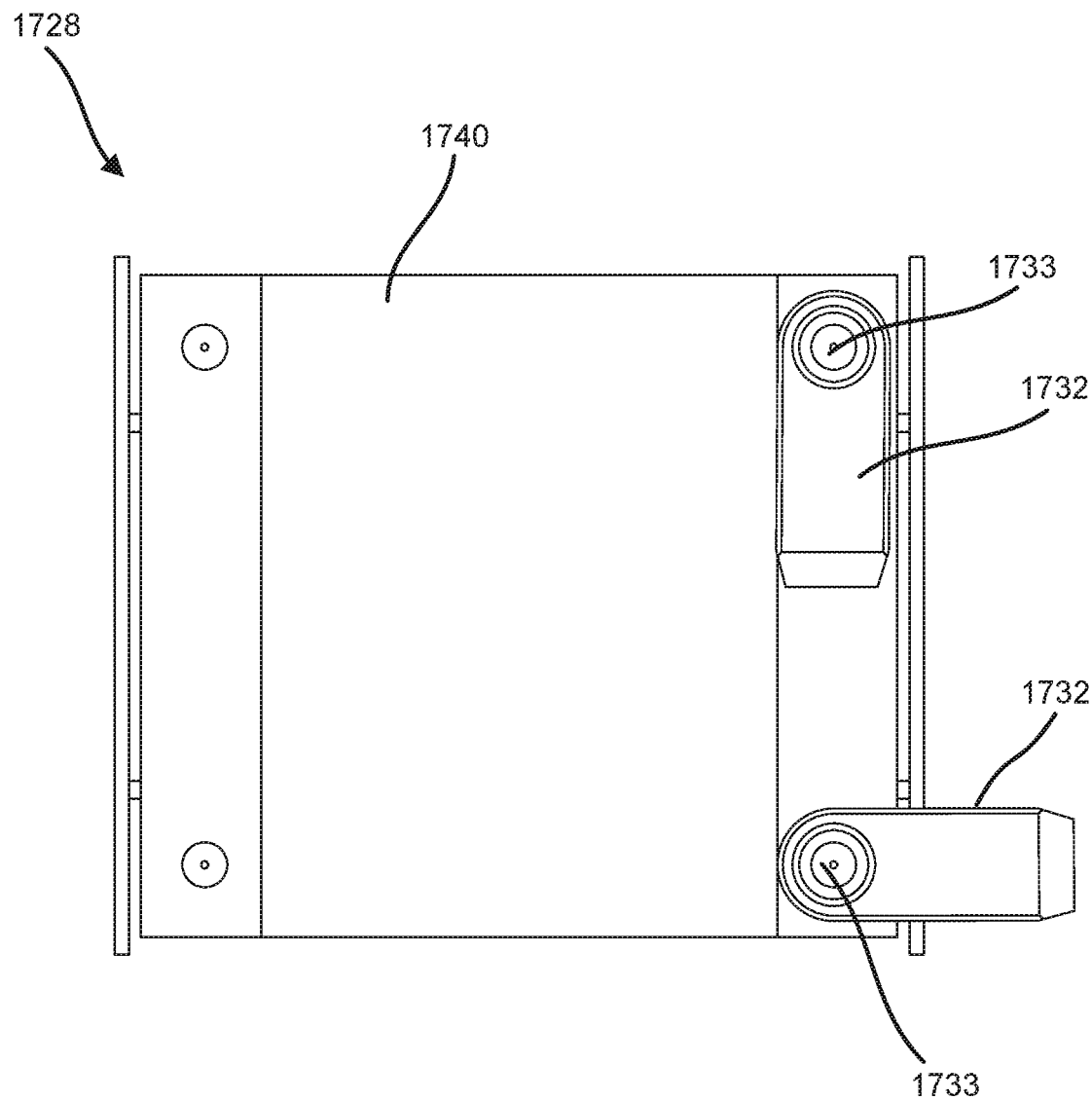
FIG. 54 is a top perspective view of the adapter of FIG. 52 with a top plate removed and with one link member in a rotated position.
Figure 55:
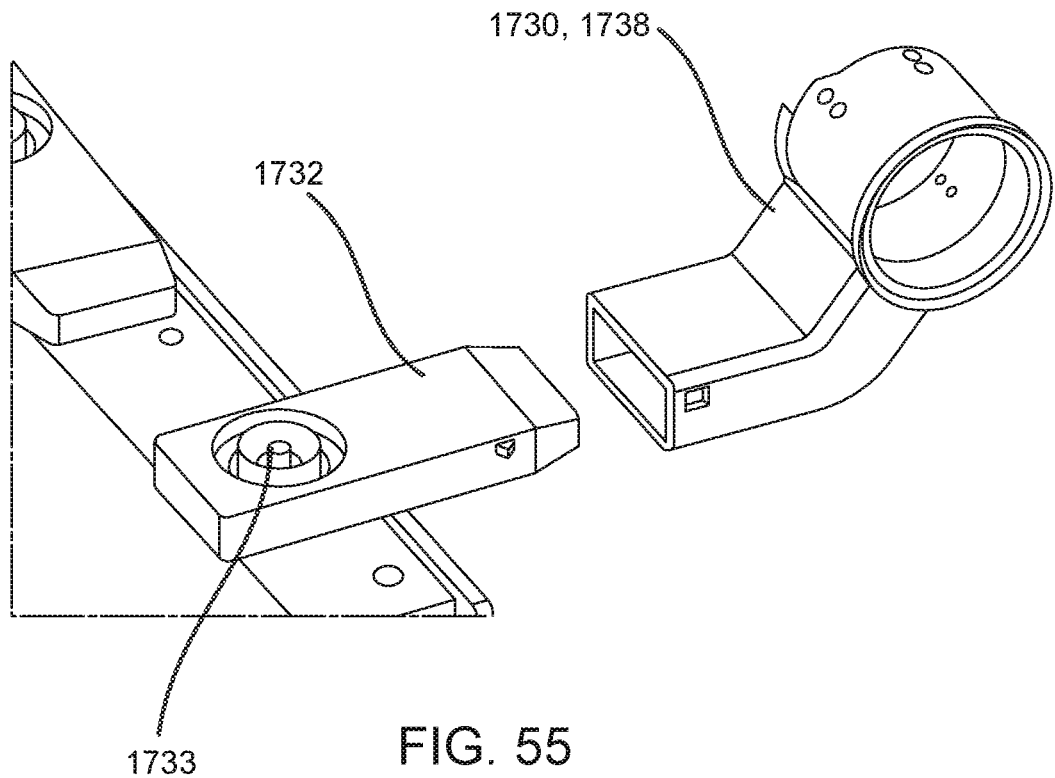
FIG. 55 is a top perspective view of a portion of the adapter of FIG. 52 and a portion of a robotic arm.
Figure 56:
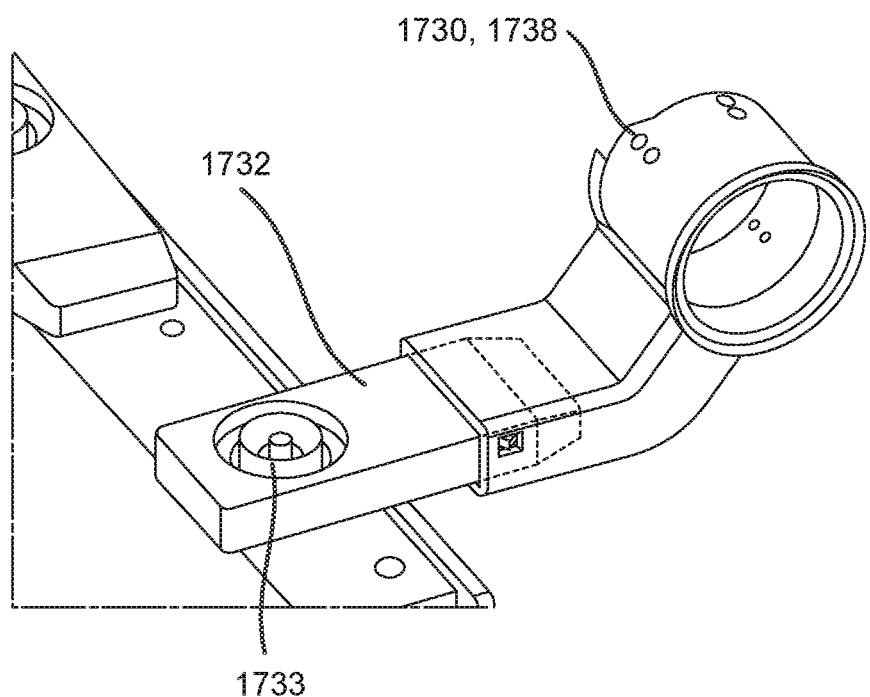
FIG. 56 is a top perspective view of the portion of the adapter of FIG. 55 with the portion of the robotic arm coupled to the adapter.
Figure 57A:
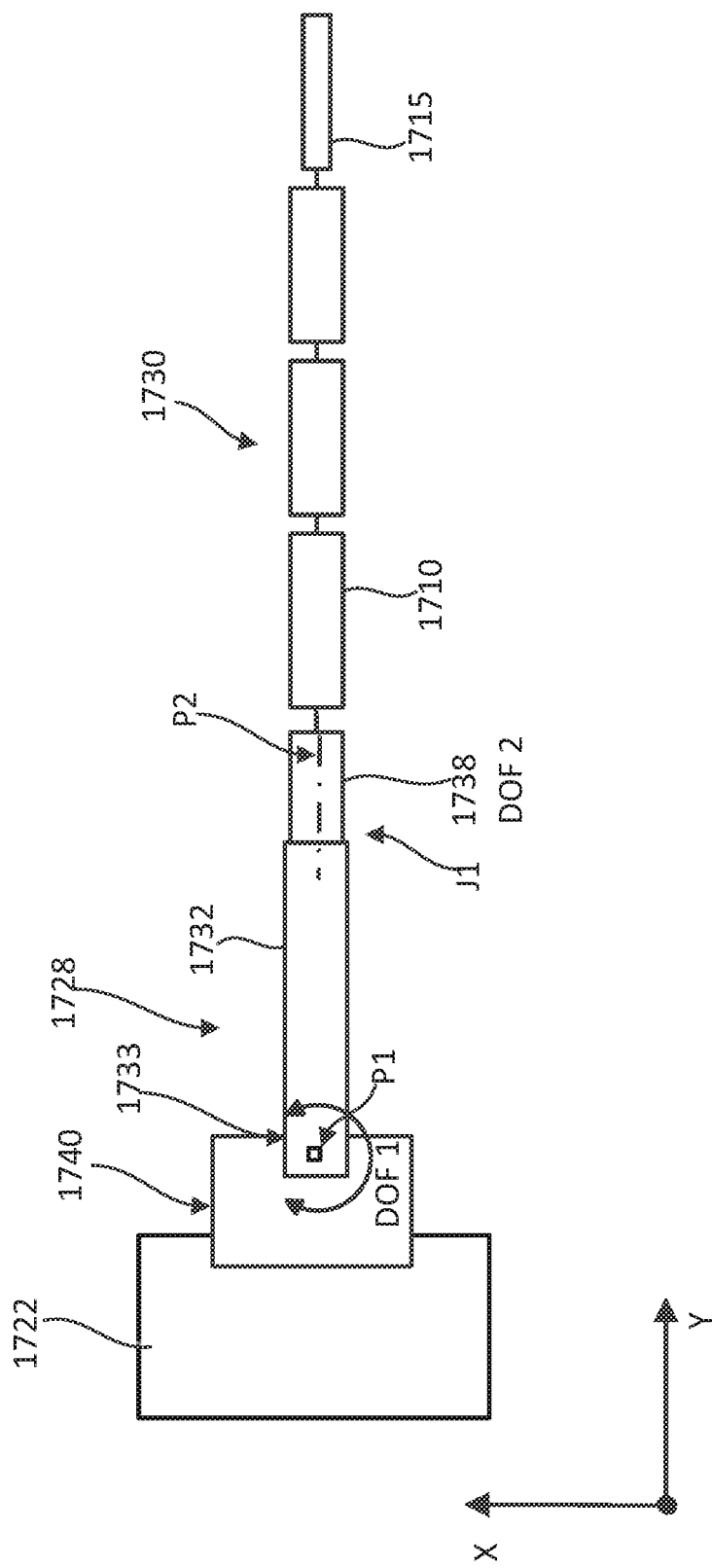
Figure 58:
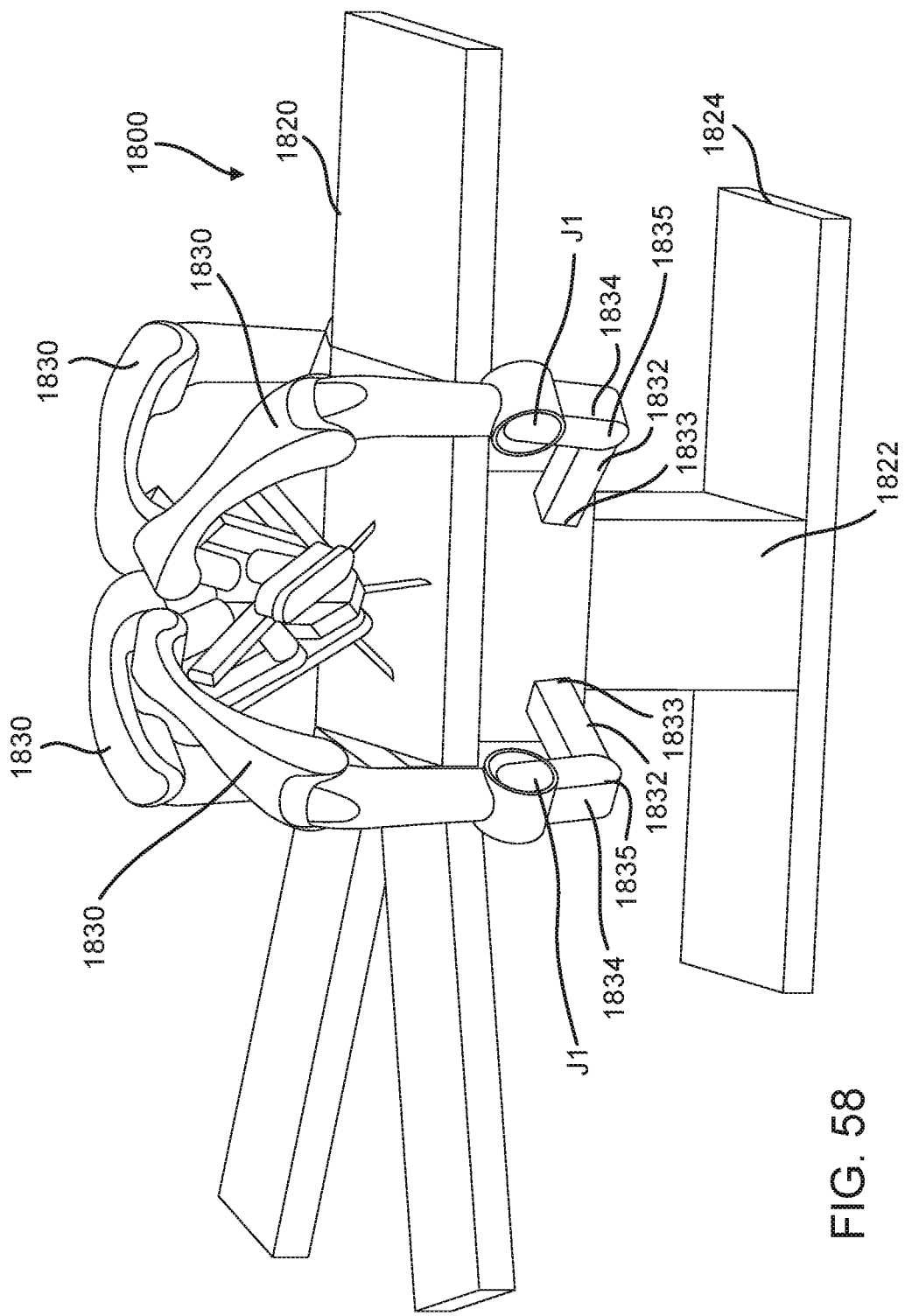
FIG. 58 is a side perspective view of an adapter according to another embodiment coupled to a surgical table and four robotic arms coupled to the adapter and in an operating position.
Figure 59A:
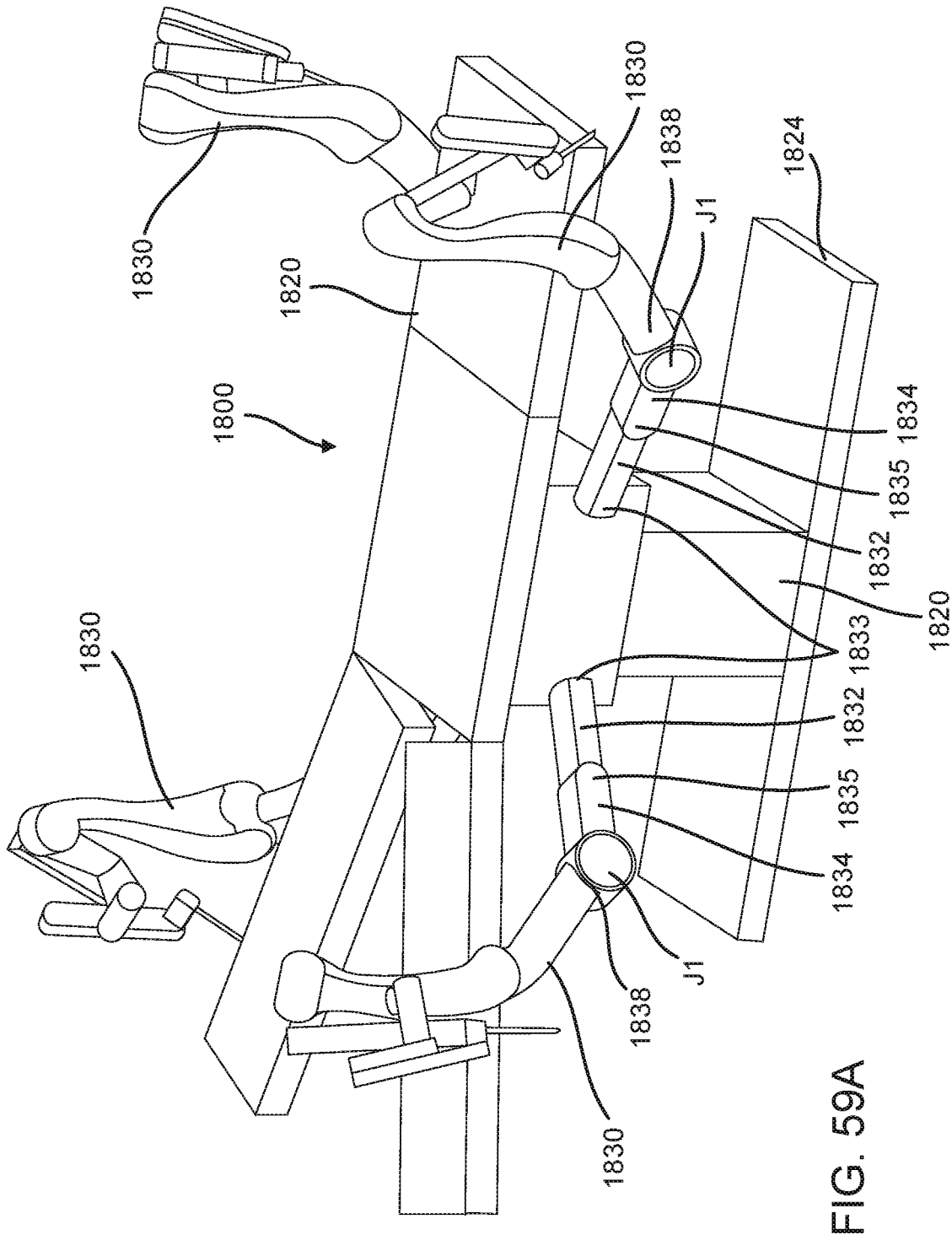
FIG. 59A is a side perspective view of the adapter, robotic arms and surgical table of FIG. 58 with the robotic arms in a stowed position.
Figure 59B:
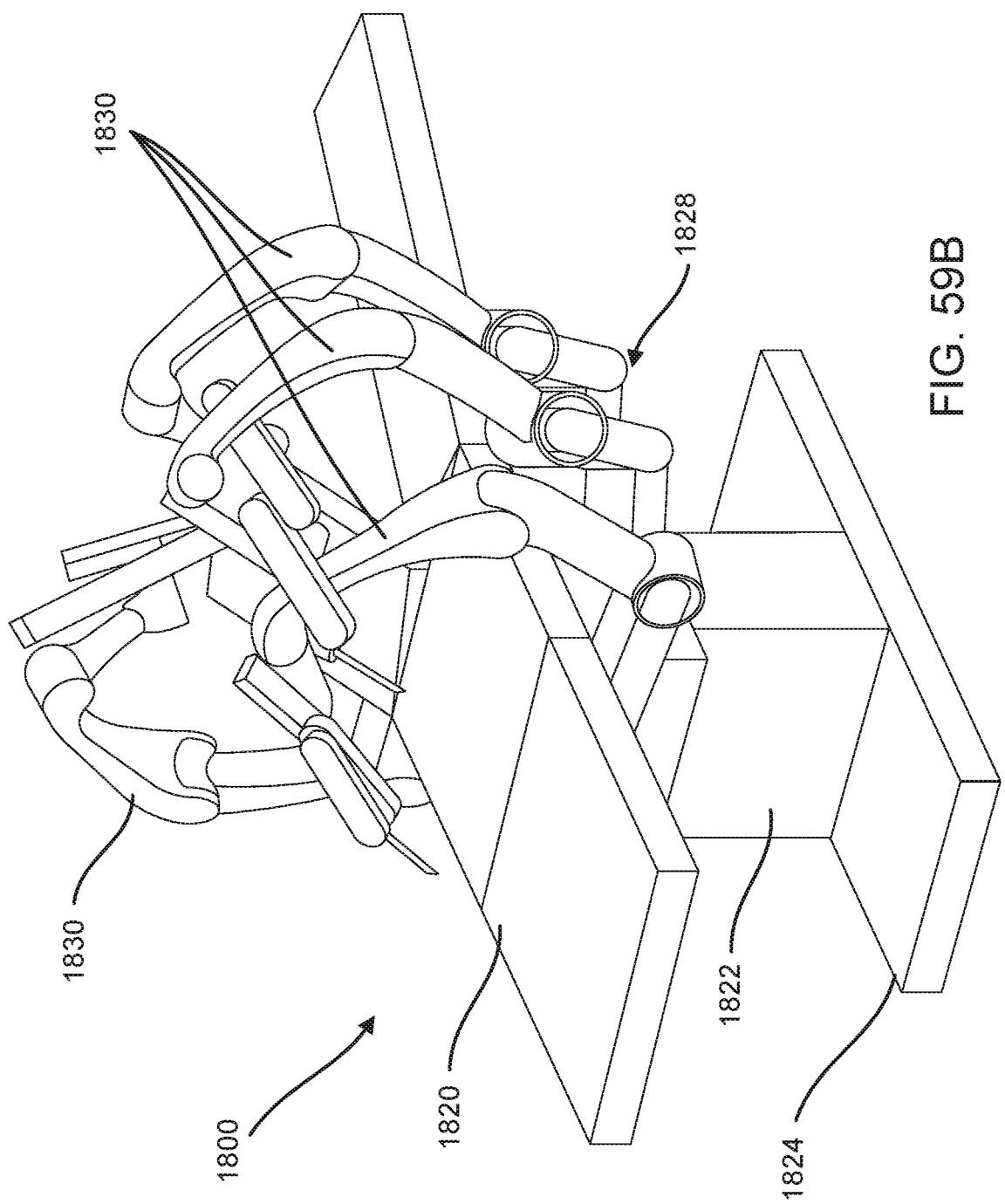
FIG. 59B is a side perspective view of the adapter, robotic arms and surgical table of FIG. 58 with the robotic arms in an operating position.

The table adapter 1728 (also referred to herein as "adapter") includes a table interface mechanism 1740 that can be coupled to the support (not shown) of the surgical table and multiple link members 1732 coupled to the interface mechanism 1740. In this embodiment, the link members 1732 re pivotally coupled to the interface mechanism 1740 at a joint 1733 such that the link members 1732 can pivot about a pivot axis P1. For example, the link members 1732 can be moved between a stowed position, pivoted inward within the interface mechanism 1740 (as shown, for example, in FIG. 52), and an extended, use positon (as shown, for example, in FIG. 53). FIG. 54 illustrates one of the link members 1732 in the extended position and one in the folded, stowed position. The link members 1732 also include a coupling portion that can be releasably coupled to a coupling portion 1738 of a robotic arm 1730 (see FIGS. 55 and 56). The coupling portion 1738 can include the target joint J1, which can provide for rotation about a pivot axis P2 (as shown in FIGS. 57A and 57B). Although FIGS. 52-54 show only two link members 1732, two additional link members 1732 can be coupled to an opposite side of the interface mechanism 1740 (e.g., at a pivot joint 1733). Thus, when the interface mechanism 1740 is coupled to a surgical table, two link members 1728 can be on each side of the surgical table to accommodate four robotic arms 1730. In some embodiments, a third link member 1728 can be coupled on one or both sides of the interface mechanism 1740 to accommodate three robotic arms 1730 on one or both sides of the surgical table. For example, a middle link member 1732 can be coupled to the interface mechanism 1740 between the two link members 1728 that are disposed at or near the corners of the interface mechanism 1740.

As described above for previous embodiments, the robotic arm(s) 1730 can be used to perform a surgical procedure on a patient disposed on the surgical table. Each robotic arm 1730 can be configured the same as or similar to, and function the same as or similar to, the robotic arms described above and thus, specific details regarding the robotic arms are not discussed with respect to this embodiment. For example, as described above for robotic arms 130, the robotic arms 1730 can include multiple links or segments and can be moved between an extended configuration for use during a surgical procedure, and a folded or collapsed configuration for storage when not in use. The motion provided by the various coupling joints can provide for movement of the robotic arm 1730 along and/or about the X, Y, and/or Z axes as described in more detail below.

More specifically, as shown in FIGS. 57A and 57B, the joint 1733 can provide for rotational motion of the first link members 1732 relative to the interface structure 1740 (and table) about a vertical z-axis (i.e., pivot axis P1) relative to the top surface of the table top (e.g., the top surface of the torso section of the table top) and provide a first degree of freedom DOF 1. The target joint J1 can provide rotation about the axis P2 which rotates within the X-Y plane, and provides a second degree of freedom DOF 2. The J1 joint can provide a lift mechanism to allow for vertical movement of the robotic arm 1730. The pivotal motion of the first link member 1732 together with the target joint J1 can provide for movement of the robotic arm 1730 along and/or about the X, Y, and/or Z axes to position the target joint J1 at a desired treatment location relative to the top surface of the table top. Although not labeled in FIGS. 57A and 57B, the various joints between links 1710 of the arm 1730 and a medical instrument 1715 disposed on the distal end of the robotic arm 1730 can provide additional motion of the arm 1730 relative to a patient (e.g., a target treatment location on the patient) disposed on the table and therefore, additional degrees of freedom.

The adapter 1728 and robotic arms 1730 can be moved between a variety of different positions relative to the surgical table during a surgical procedure. For example, the robotic arms 1730 can be removed from the adapter 1728 and the adapter 1728 can be moved to a stowed or folded position (see, e.g., FIG. 52) substantially beneath the table top (not shown). The adapter 1728 and arms 1730 can also be disposed in a parked position (not shown) and various operating positions (not shown). In an operating position, the target joints J1 are disposed at a desired target treatment location relative to the table top to accommodate a particular surgical procedure to be performed as described above for previous embodiments.

FIGS. 58-60C illustrate another embodiment of an adapter 1828 that can be coupled to a surgical table 1800 that includes a table top 1820, a support 1822 and a base 1824. The surgical table 1800 can include the same or similar components and function in the same or similar manner as the surgical tables described above, and therefore, is not described in detail with respect to this embodiment.

The table adapter 1828 (also referred to herein as "adapter") includes a table interface mechanism 1840 (shown schematically in FIGS. 60A and 60B) that can be coupled to the support 1822 of the surgical table 1800. The adapter 1828 also includes multiple first link members 1832 that are pivotally coupled to the interface mechanism 1840 at a first joint 1833 and can rotate about a pivot axis P1 (see FIGS. 60A and 60B). Multiple second link members 1834 are each pivotally coupled to a first link member 1832 at a joint 1835 and can rotate within a horizontal plane about a pivot axis P2. The second link members 1834 are also pivotally coupleable to a coupling portion 1838 of a robotic arm 1830. The coupling portion 1838 can include the target joint J1, which can provide for rotation about a pivot axis P3.

As described above for previous embodiments, the robotic arm(s) 1830 can be used to perform a surgical procedure on a patient disposed on the surgical table. Each robotic arm 1830 can be configured the same as or similar to, and function the same as or similar to, the robotic arms described above and thus, specific details regarding the robotic arms are not discussed with respect to this embodiment. For example, as described above for robotic arms 130, the robotic arms 1830 can include multiple links or segments and can be moved between an extended configuration for use during a surgical procedure, and a folded or collapsed configuration for storage when not in use. The motion provided by the various coupling joints can provide for movement of the robotic arm 1830 along and/or about the X, Y, and/or Z axes as described in more detail below.

Figure 60A:
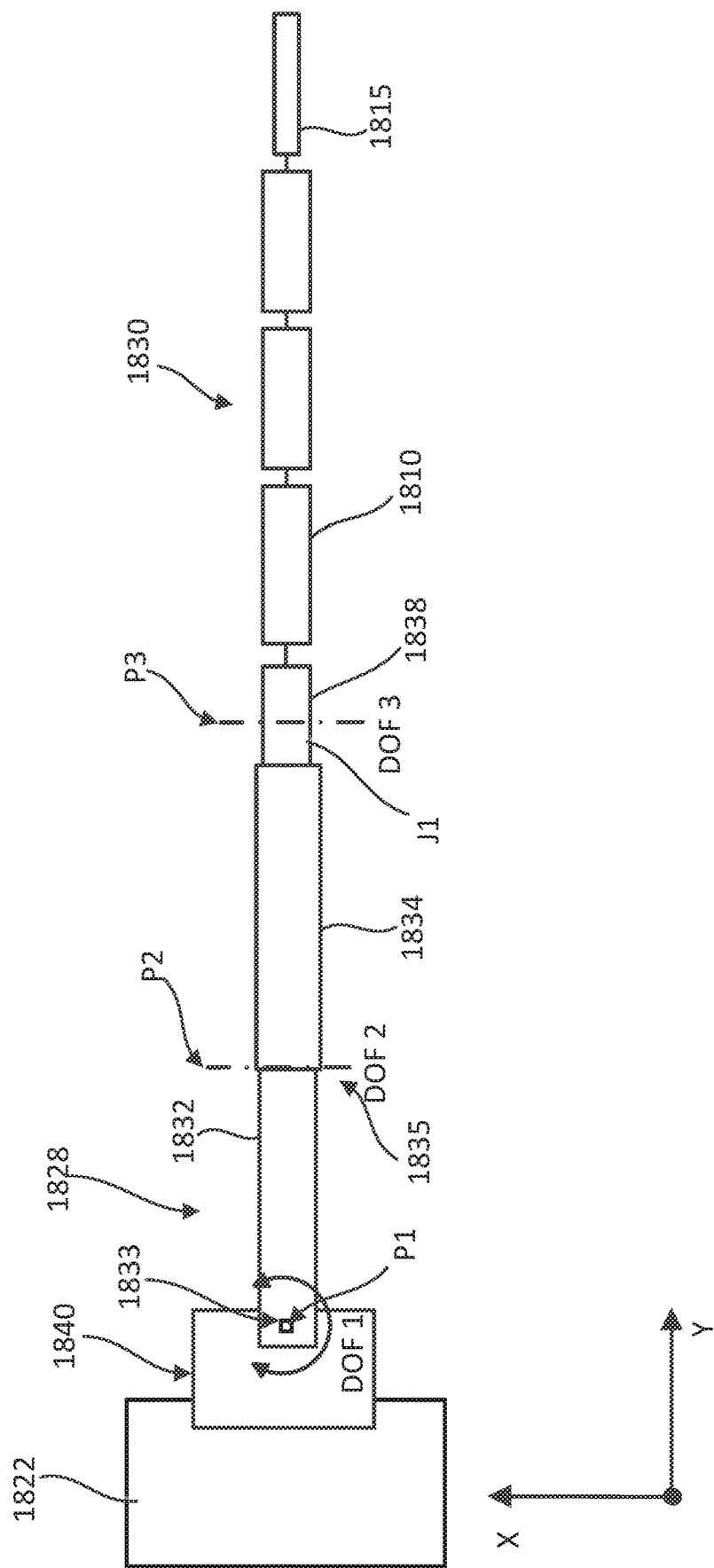
FIGS. 60A and 60B are a schematic top view and side view, respectively, of the adapter and a robotic arm of FIGS. 58-120B, illustrating the degrees of freedom between the joints of the adapter and robotic arm.
Figures 60B, 60C:
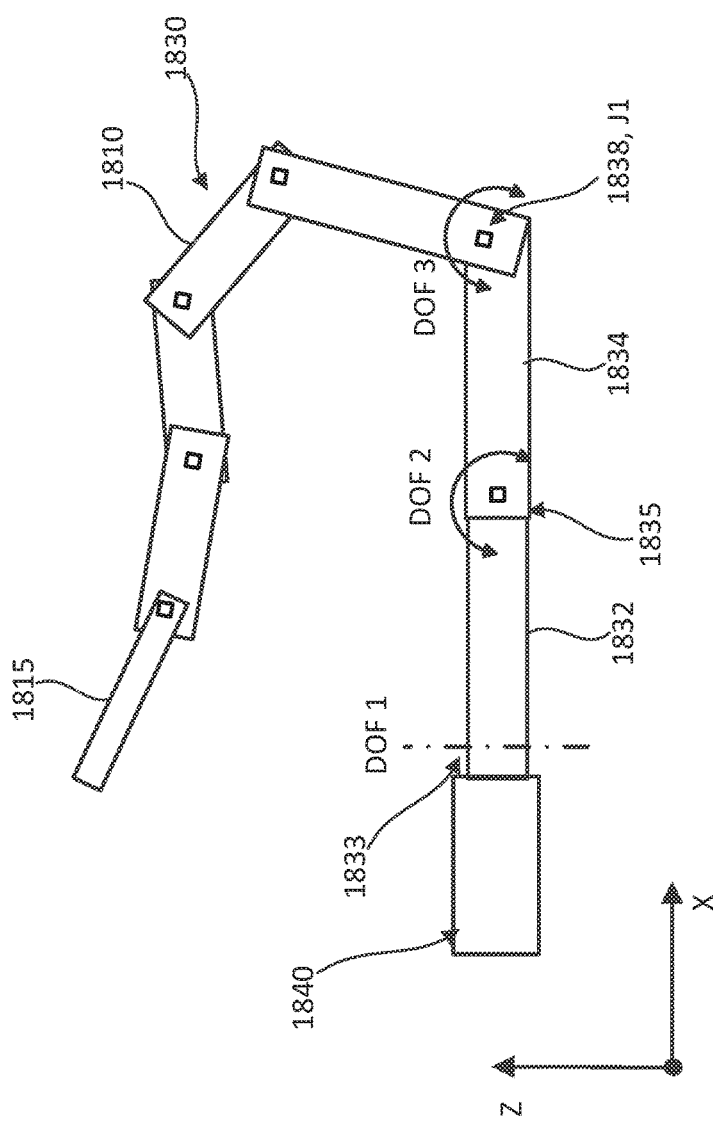
FIG. 60C is a table listing the type of degree of freedom of each of the joints.
Figure 61:
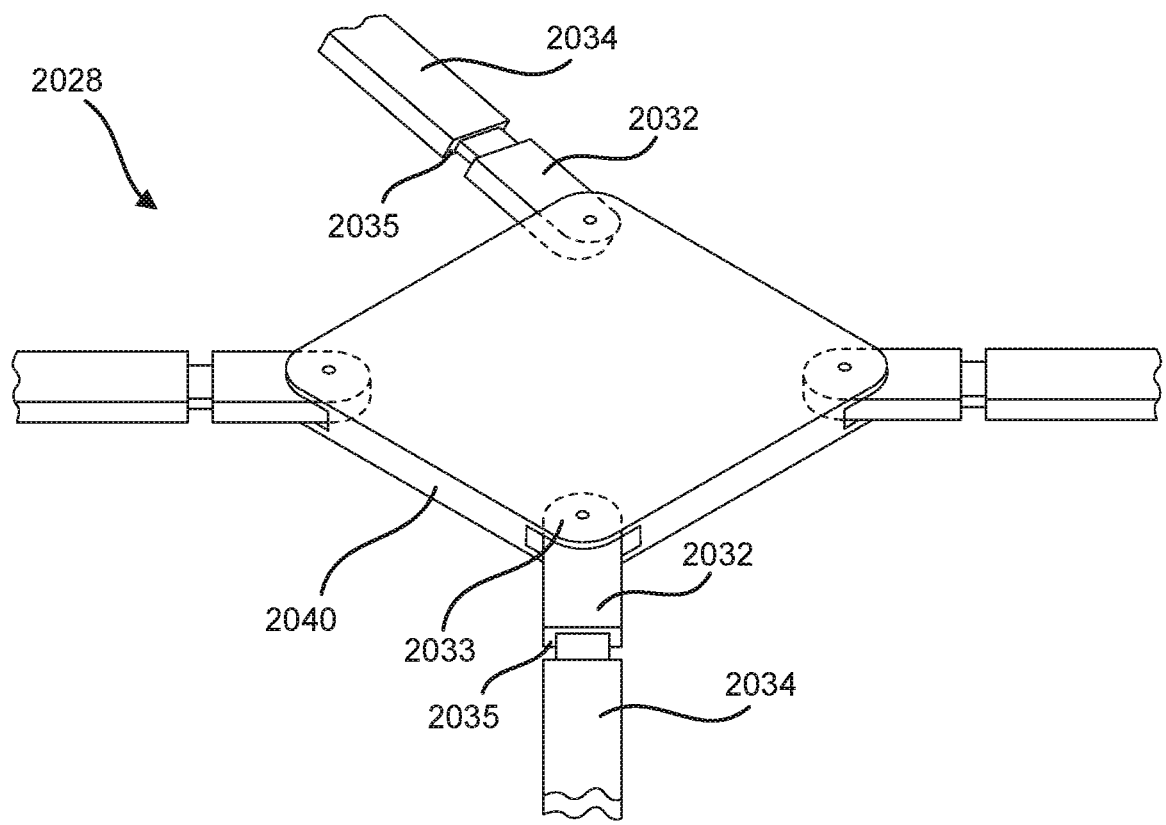
FIG. 61 is a top perspective view of a portion of an adapter according to another embodiment.
Figure 62:
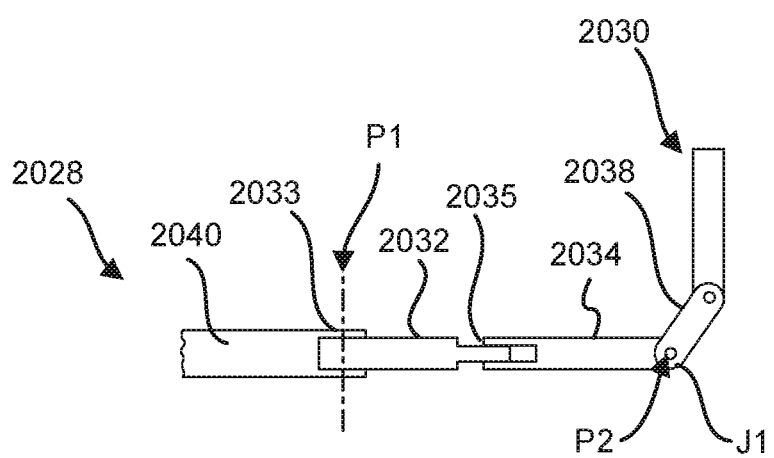
FIG. 62 is a side view of the adapter of FIG. 61 and a portion of a robotic arm coupled thereto.

More specifically, as shown in FIGS. 60A and 60B, the joint 1833 can provide for rotational motion of the first link members 1832 relative to the interface structure 1840 (and table 1800) about a vertical z-axis (i.e., pivot axis P1) relative to the top surface of the table top (e.g., the top surface of the torso section of the table top) and provide a first degree of freedom DOF 1. The joint 1835 can provide for rotational motion of the second link members 1834 relative to the first link members 1832 about a vertical z-axis (i.e., pivot axis P2) and provide a third degree of freedom DOF 2. The target joint J1 provides rotation about the axis P3 which rotates within the X-Y plane, and provides a fourth degree of freedom DOF 3. The joint 1833 and the J1 joint collectively provide a lift mechanism to allow for vertical movement of the robotic arm 1830. The various motions provided by the motion of the first link members 1832 and second link members 1834, together with the rotation provided at the joint J1 can provide for movement of the robotic arm 1830 along and/or about the X, Y, and/or Z axes to position the target joint J1 at a desired treatment location relative to the top surface of the table top. Although not labeled in FIGS. 60A and 60B, the various joints between links 1810 of the arm 1830 and a medical instrument 1815 disposed on the distal end of the robotic arm 1830 can provide additional motion of the arm 1830 relative to a patient (e.g., a target treatment location on the patient) disposed on the table and therefore, additional degrees of freedom.

As described above for previous embodiments, the collective motion of the various components of the adapter 1828 allow the robotic arms 1830 to move between a variety of different positions relative to the surgical table 1800 during a surgical procedure. For example, adapter 1828 and robotic arms 1830 can be moved to a stowed or folded position substantially beneath the table top (not shown). In the stowed position, the arms 1830 and adapter 1828 are each in a folded or collapsed configuration disposed beneath the table top within an outer perimeter defined by the table top. The adapter 1828 and arms 1830 can also be disposed in a parked position (see FIG. 59A) and various operating positions (see FIGS. 58 and 59B). In an operating position, the target joints J1 are disposed at a desired target treatment location relative to the table top to accommodate a particular surgical procedure to be performed.

FIGS. 61-63C illustrate another embodiment of an adapter 2028 that can be coupled to a surgical table (not shown) that includes a table top (not shown), a support 2022 (see FIG. 63A) and a base (not shown). The surgical table can include the same or similar components and function in the same or similar manner as the surgical tables described above, and therefore, is not described in detail with respect to this embodiment.

The table adapter 2028 (also referred to herein as "adapter") includes a table interface mechanism 2040 that can be coupled to the support 2022 of the surgical table. The adapter 2028 also includes multiple first link members 2032 that are pivotally coupled to the interface mechanism 2040 at a first joint 2033 and can rotate about a pivot axis P1 (see FIGS. 62, 63A and 63B). Multiple second link members 2034 are each slidably coupled to a first link member 2032 a coupling location 2035. For example, the second link members 204 can be telescopically coupled to the first link members 2032. The second link members 2034 are also pivotally coupleable to a coupling portion 2038 of a robotic arm 2030. The coupling portion 2038 can include the target joint J1, which can provide for rotation about a pivot axis P2.

As described above for previous embodiments, the robotic arm(s) 2030 can be used to perform a surgical procedure on a patient disposed on the surgical table. Each robotic arm 2030 can be configured the same as or similar to, and function the same as or similar to, the robotic arms described above and thus, specific details regarding the robotic arms are not discussed with respect to this embodiment. For example, as described above for robotic arms 130, the robotic arms 2030 can include multiple links or segments and can be moved between an extended configuration for use during a surgical procedure, and a folded or collapsed configuration for storage when not in use. The motion provided by the various coupling joints can provide for movement of the robotic arm 2030 along and/or about the X, Y, and/or Z axes as described in more detail below.

Figure 63A:
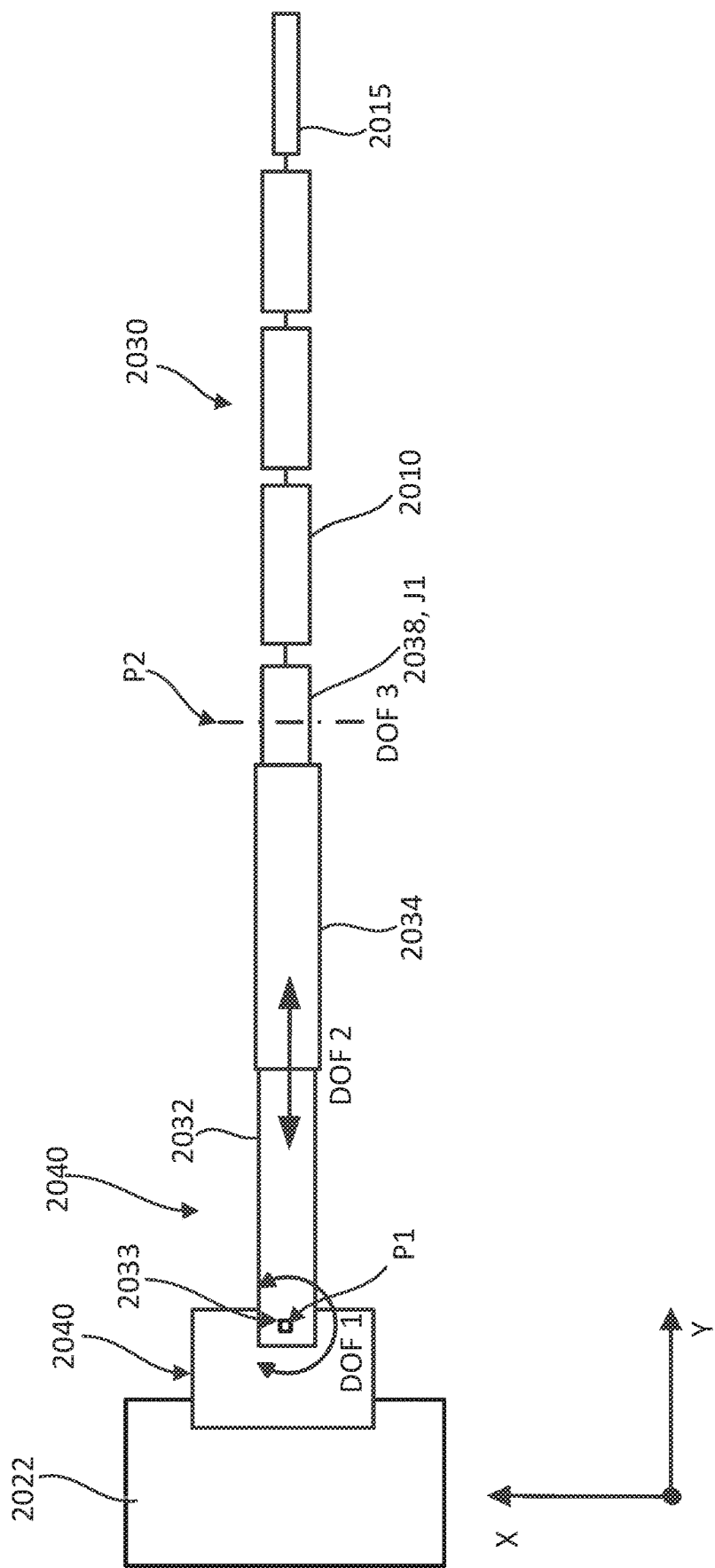
FIGS. 63A and 63B are a schematic top view and side view, respectively, of the adapter and robotic arm of FIGS. 61-62, illustrating the degrees of freedom between the joints of the adapter and robotic arm.
Figures 63B, 63C:
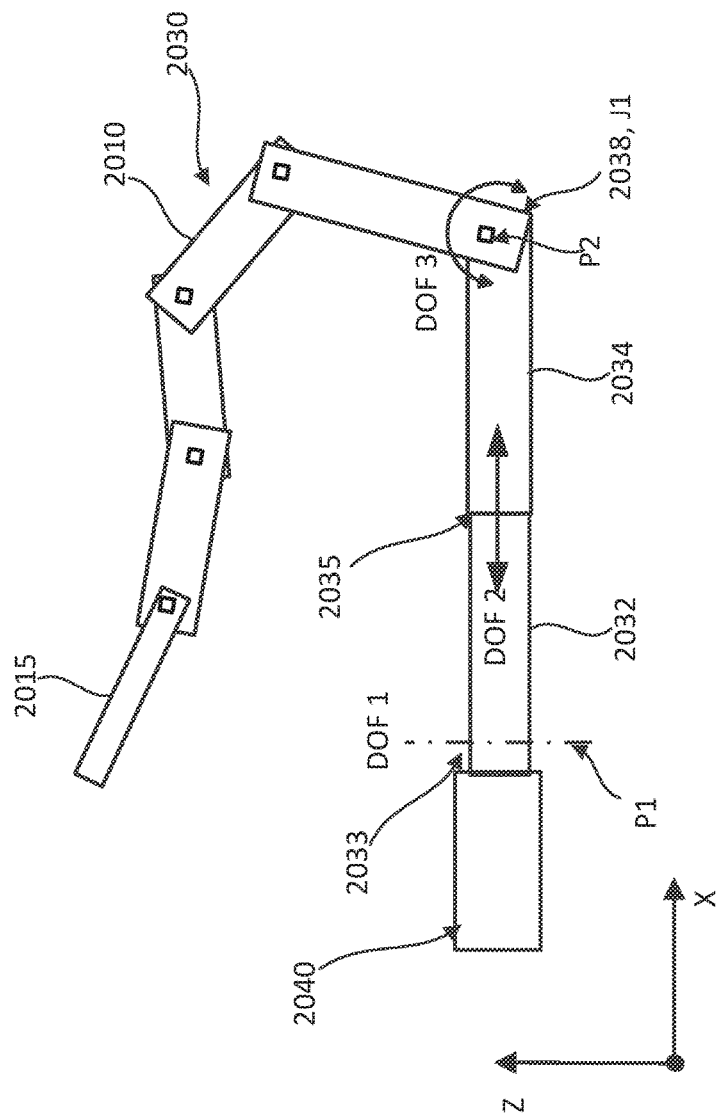
FIG. 63C is a table listing the type of degree of freedom of each of the joints.

More specifically, as shown in FIGS. 63A and 63B, the joint 2033 can provide for rotational motion of the first link members 2032 relative to the interface structure 2040 (and surgical table) about a vertical z-axis (i.e., pivot axis P1) relative to the top surface of the table top (e.g., the top surface of the torso section of the table top) and provide a first degree of freedom DOF 1. The slidable/telescoping coupling between the second link members 2034 and the first link members 2032 provides a second degree of freedom DOF 2 which is linear motion within a horizontal X-Y plane. The target joint J1 provides rotation about the axis P2 which rotates within the X-Y plane, and provides a third degree of freedom DOF 3. The target joint J1 can provide a lift mechanism to allow for vertical movement of the robotic arm 2030. The various motions provided by the motion of the first link members 2032 and second link members 2034, together with the rotation provided at the target joint J1 can provide for movement of the robotic arm 2030 along and/or about the X, Y, and/or Z axes to position the target joint J1 at a desired treatment location relative to the top surface of the table top. Although not labeled in FIGS. 63A and 63B, the various joints between links 2010 of the arm 2030 and a medical instrument 2015 disposed on the distal end of the robotic arm 2030 can provide additional motion of the arm 2030 relative to a patient (e.g., a target treatment location on the patient) disposed on the table and therefore, additional degrees of freedom.

As described above for previous embodiments, the collective motion of the various components of the adapter 2028 allow the robotic arms 2030 to move between a variety of different positions relative to the surgical table during a surgical procedure. For example, adapter 2028 and robotic arms 2030 can be moved to a stowed or folded position substantially beneath the table top (not shown). In the stowed position, the arms 2030 and adapter 2028 are each in a folded or collapsed configuration disposed beneath the table top within an outer perimeter defined by the table top. The adapter 2028 and arms 2030 can also be disposed in a parked position (not shown) and various operating positions (not shown) as described for previous embodiments. In an operating position, the target joints J1 are disposed at a desired target treatment location relative to the table top to accommodate a particular surgical procedure to be performed.

FIGS. 64-69C illustrate another embodiment of a surgical table and adapter that is similar to the table 300 and adapter 340. As shown in FIGS. 64-71C, a surgical table 2100 includes a table top 2120 (see FIG. 70 which illustrates an outline of a table top), a support 2122 (also referred to herein as pedestal) and a base 2124. As described above for previous embodiments, the support 2122 can be mounted to the base 2124, which can be fixed to the floor of an operating room, or can be movable relative to the floor. The table top 2120 can include a head section, a torso section and a leg section (each not shown). The table top 2120 can also include an arm section(s) (not shown). The table top 2120 has a top surface on which a patient can be disposed. The support 2122 can provide for movement of the table top 2120 in a desired number of degrees of freedom as described above. As described above, movement of the table top 2120 and/or its constituent sections may be performed manually, driven by motors, controlled remotely, etc. The surgical table 2100 can also include a radio-translucent window (not shown) as described for previous embodiments.

A table adapter 2128 (also referred to herein as "adapter") is shown coupled to the surgical table 2100 and includes a table interface structure 2140 coupled to the support 2122. The table interface structure 2140 includes a support plate that can be coupled to the support 2122 and/or the table top 2120. In some embodiments, the interface structure 2140 can be a single structure that can support up to six robotic arms 2130 (described below) and in some embodiments, the interface structure 2140 can support four robotic arms as shown in FIGS. 64-70. For example, the interface structure 2140 can support up to three arms on each side of the table 2100, though in most use cases no more than four arms in total are used. In some embodiments, the adapter 2128 can include two interface mechanisms 2140, each being coupleable to the table 2100 on an opposite side of the table top 2120 as shown in FIGS. 64-70. In some embodiments, the adapter 2128 can be coupled to the support 2122 such that the adapter 2128 can move vertically up and down relative to the support 2122 as described above for previous embodiments. For example, the table interface structure 2140 can be motor driven to ride along rails (e.g., such as rails 329 described above for adapter 328). In some embodiments, the table top 2120 can be moved longitudinally (in the Y-axis direction) relative to the adapter 2128, or the adapter 2128 can be moved relative to the table top 2120. For example, the adapter 2128 can be coupled to the support 2122 and when the table top 2120 moves relative to the support 2122, the table top 2120 will move relative to the adapter 2128.

In this embodiment, the adapter 2128 further includes multiple first link members 2132 that are each pivotally coupled to the table interface structures 2140 at a first joint 2133 to provide rotational movement of the first link members 2132 relative to the table 2100. A coupling member 2144 is disposed at an end of the first link members 2132 that can be used to couple a robotic arm 2130 (discussed below) to the first link member 2132. For example, the middle connector 2144 can have a coupling interface that can matingly couple to a coupling portion (not shown) at a mounting end 2136 of a robotic arm 2130. Thus, the mounting end of the robotic arm 2130 can be fixedly coupled to the first link member 2132. The robotic arm 2130 can provide for vertical movement at a joint J1 as described in more detail below. As with previous embodiments, the joint 2133 and the joint J1 can allow the adapter 2128 and robotic arm 2130 to be moved between an extended configuration for use during a surgical procedure as shown, for example, in FIGS. 64, 66-69, and a folded or collapsed configuration for storage when not in use, as shown, for example, in FIG. 70.

In an alternative embodiment, the adapter 2128 can be configured similarly to the adapter 328 and include multiple second link members (not shown) that are each coupled to one of the first link members 2132 at a second joint (not shown) that can provide the lift mechanism for moving the second link member (and thus a robotic arm coupled thereto) vertically. In such an embodiment, the second joint can include a linear motion mechanism (not shown) that allows the second link member to translate vertically, i.e. parallel to the z-axis, relative to the first link member 2132. The linear motion guide mechanism can include components similar to the linear guide mechanism 331 such as, for example, an elongate protrusion of a component coupled to the second link member 2134 that can be slidably received within a track or recess of a second component coupled to the first link member 2132. In another alternative embodiment, the vertical linear motion of such second link members relative to the first link members 2132 can be provided by a slide feature that can include, for example, a slot in the second link member that receives a mating protrusion on the first link member 2132. In some embodiments, the lift mechanism can provide for at least 6.5 inches of vertical travel. In another alternative embodiment, the second joint that provides the lift mechanism can be a pivotal joint as described herein for other embodiments.

In this embodiment, the interface mechanisms 2140 on each side of the table 2100 include mounting portions to support two sets of first link members 2132 at the joints 2133 and a middle connector 2145 disposed at a middle location between the two first joints 2133. The middle connectors 2145 can be used to mount a robotic arm 2130 directly to the interface structure 2140. For example, the middle connectors 2145 can include a coupling interface that can be matingly coupled to the coupling portion at the mounting end 2136 of a robotic arm that is the same as the coupling interface of the coupling member 2144 disposed at the end of the first link members 2132.

Figure 64:
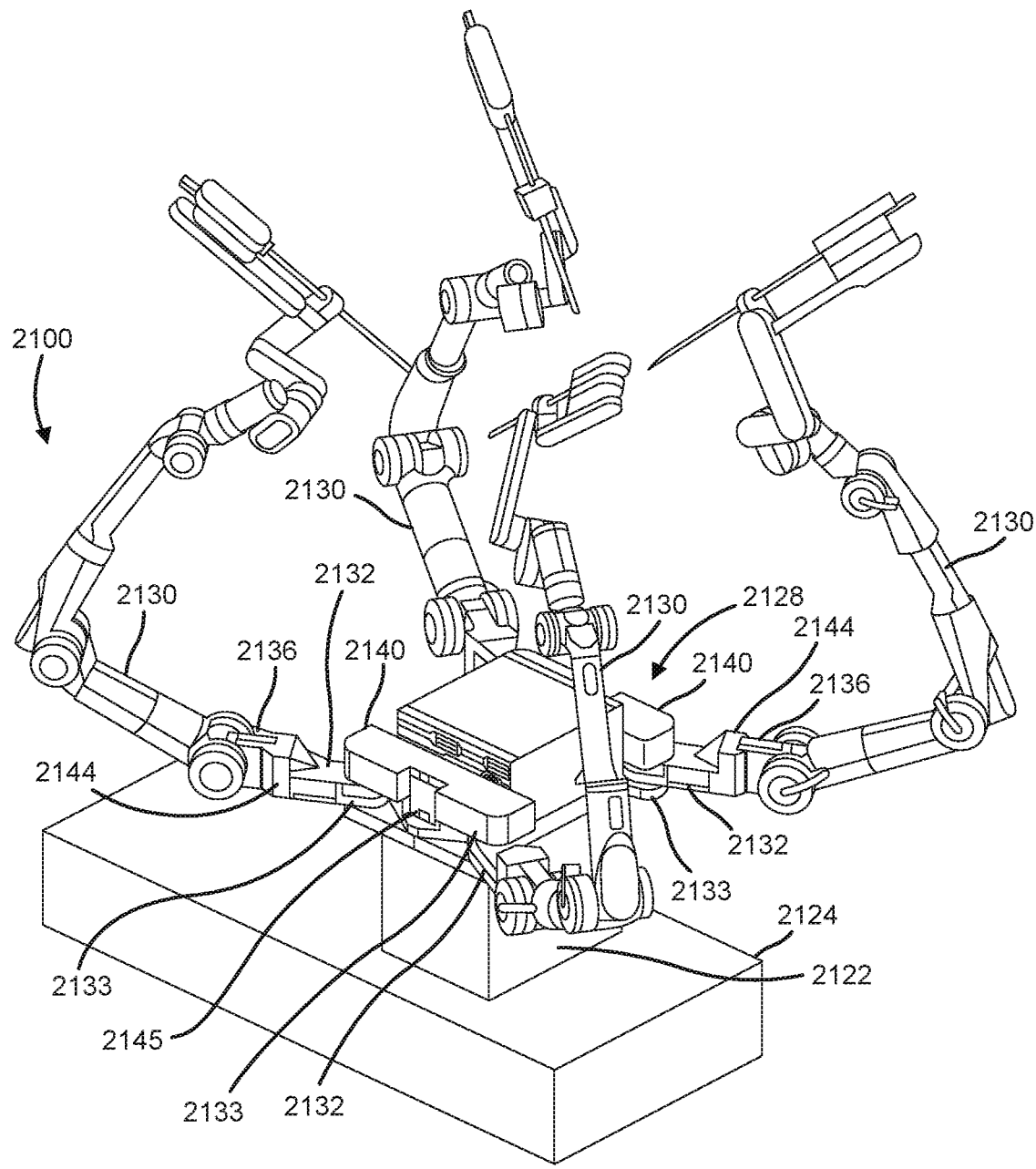
FIG. 64 is a perspective view of an adapter according to another embodiment coupled to a surgical table (with the table top removed for illustration purposes) and two robotic arms coupled to the adapter on one side of the surgical table and two robotic arms coupled to the adapter on an opposite side of the surgical table.
Figure 65:
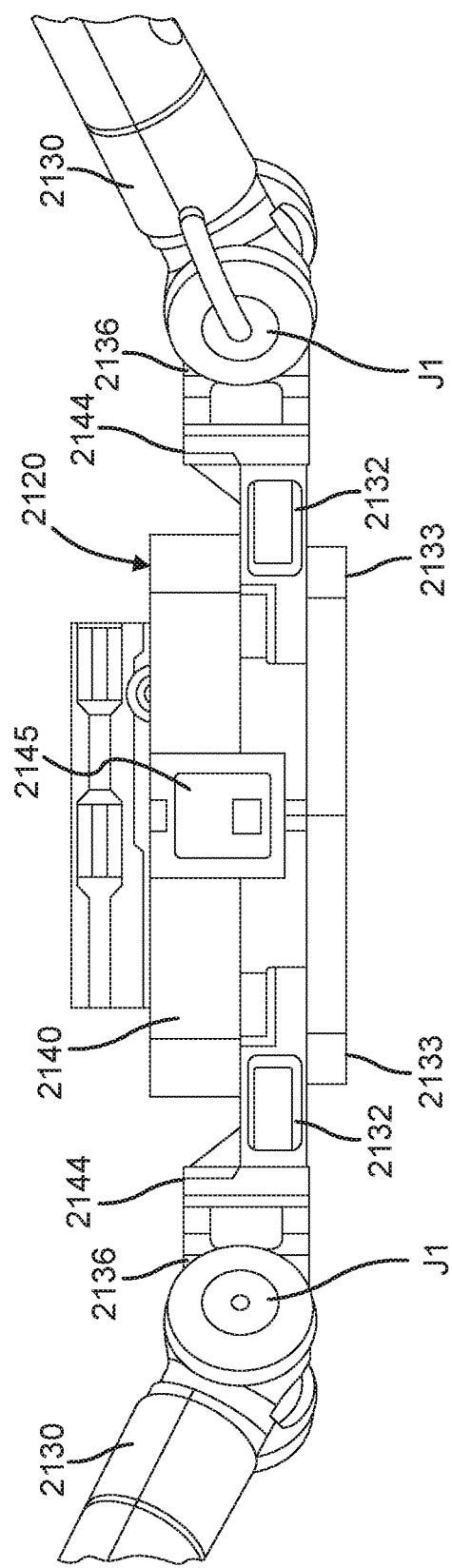
FIG. 65 is a side view of a portion of the adapter, surgical table and robotic arms of FIG. 64.
Figure 66:
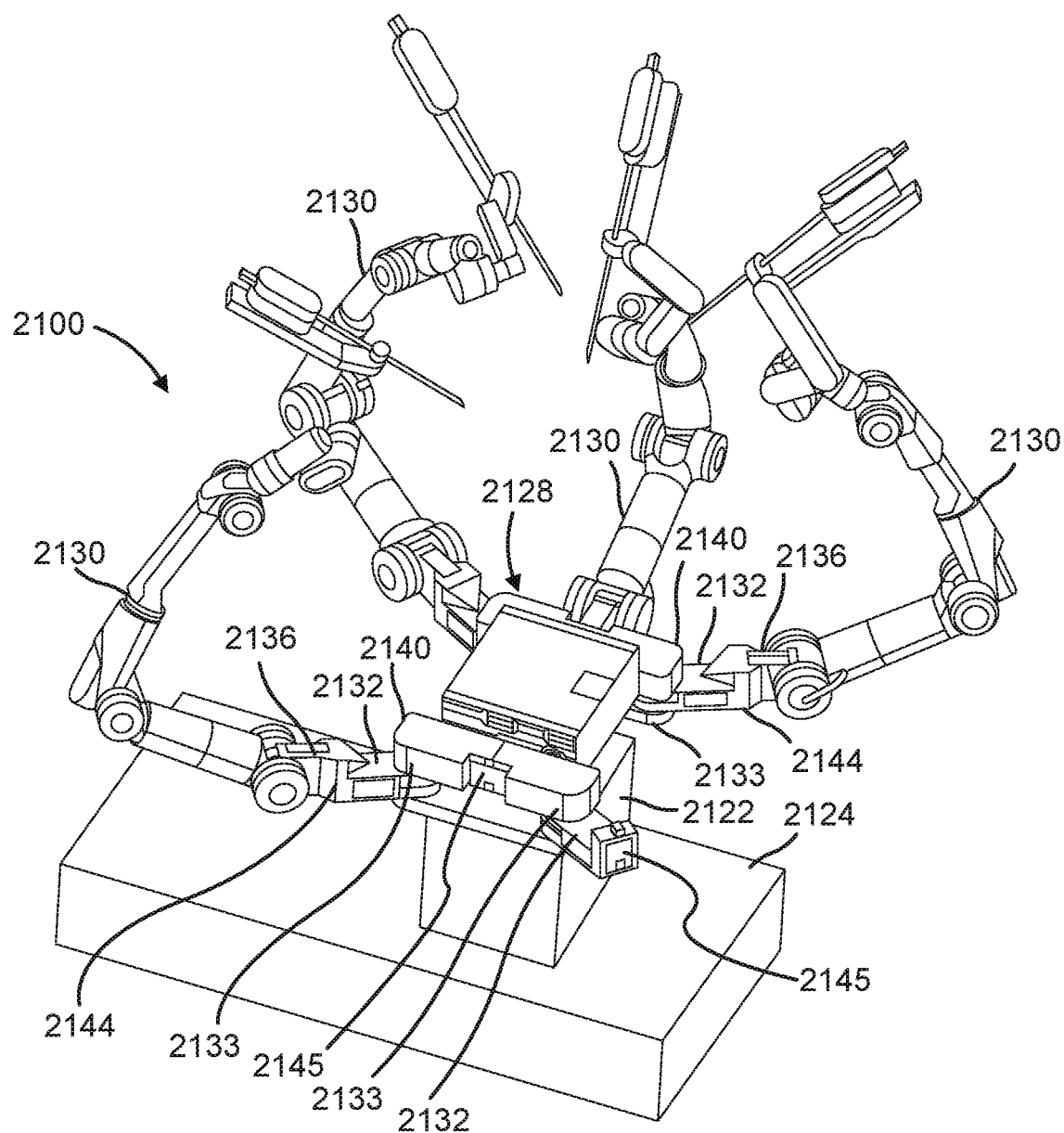
FIG. 66 is perspective view of the adapter and surgical table (with the table top removed for illustration purposes) of FIG. 64, with three robotic arms coupled to the adapter on one side of the surgical table and one robotic arm coupled to the adapter on an opposite side of the surgical table, and the robotic arms shown in an operating position.
Figure 67:
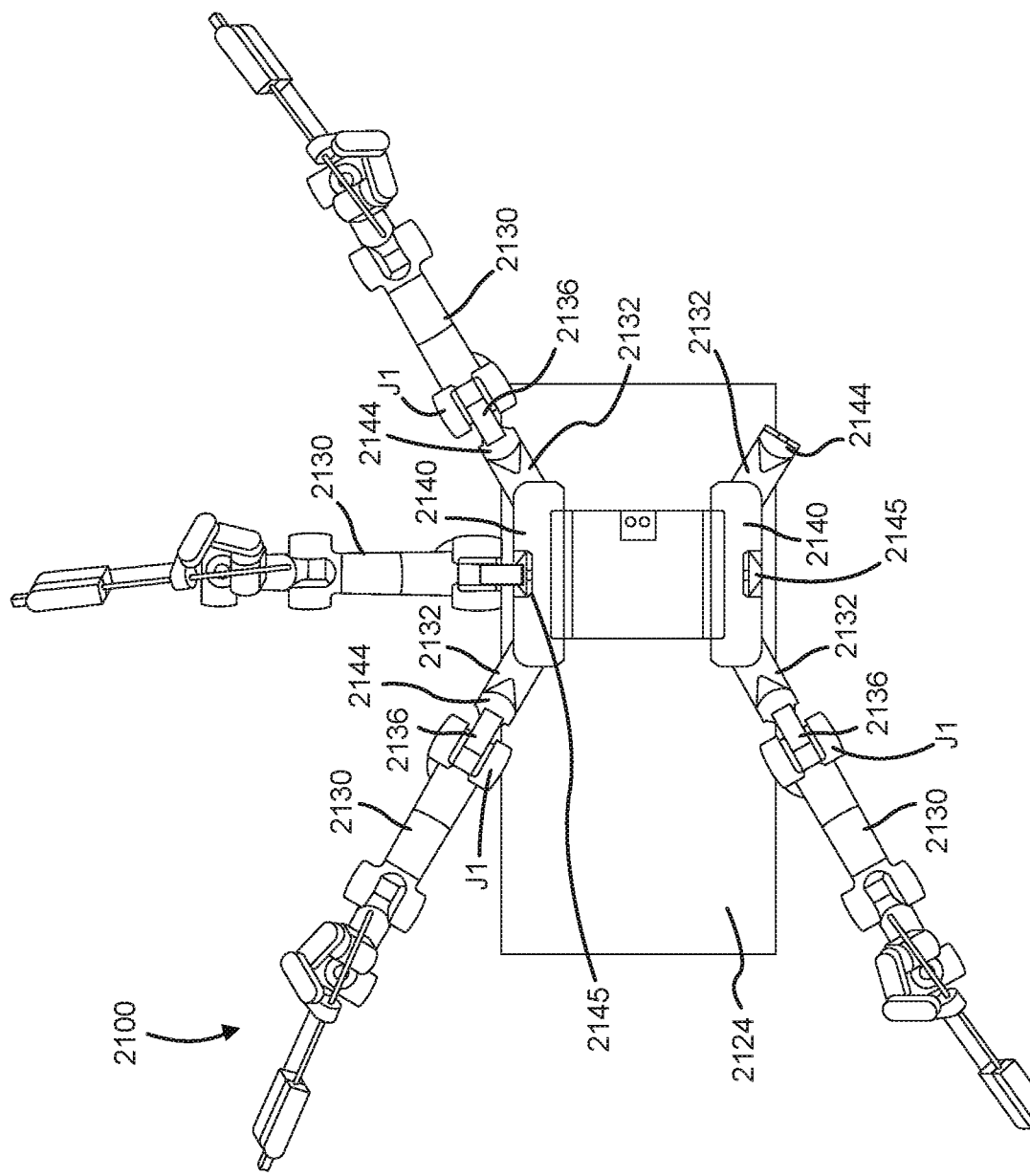
FIG. 67 is a top view of the adapter, surgical table (with the table top removed for illustration purposes) and robotic arms of FIG. 66 with the robotic arms shown in ready position.

FIG. 64 illustrates the adapter 2128 with two sets of first link members 2132 coupled to each of the interface mechanisms 2140 disposed on each side of the table 2100. Thus, in FIG. 64, the middle connectores 2145 of the interface mechanism 2140 are not being used. FIGS. 66 and 67 illustrate two first link members 2132 coupled to one interface mechanism 2140 disposed on one side of the table 2100, and one first link member 2132 coupled to the other interface mechanism 2140 disposed on an opposite side of the table 2100. Further, a robotic arm 2130 is mounted to a middle connector 2145 on one side of the table 2100. In some embodiments, each of the first link members 2132 can have varying lengths to provide further versatility.

Figure 68:
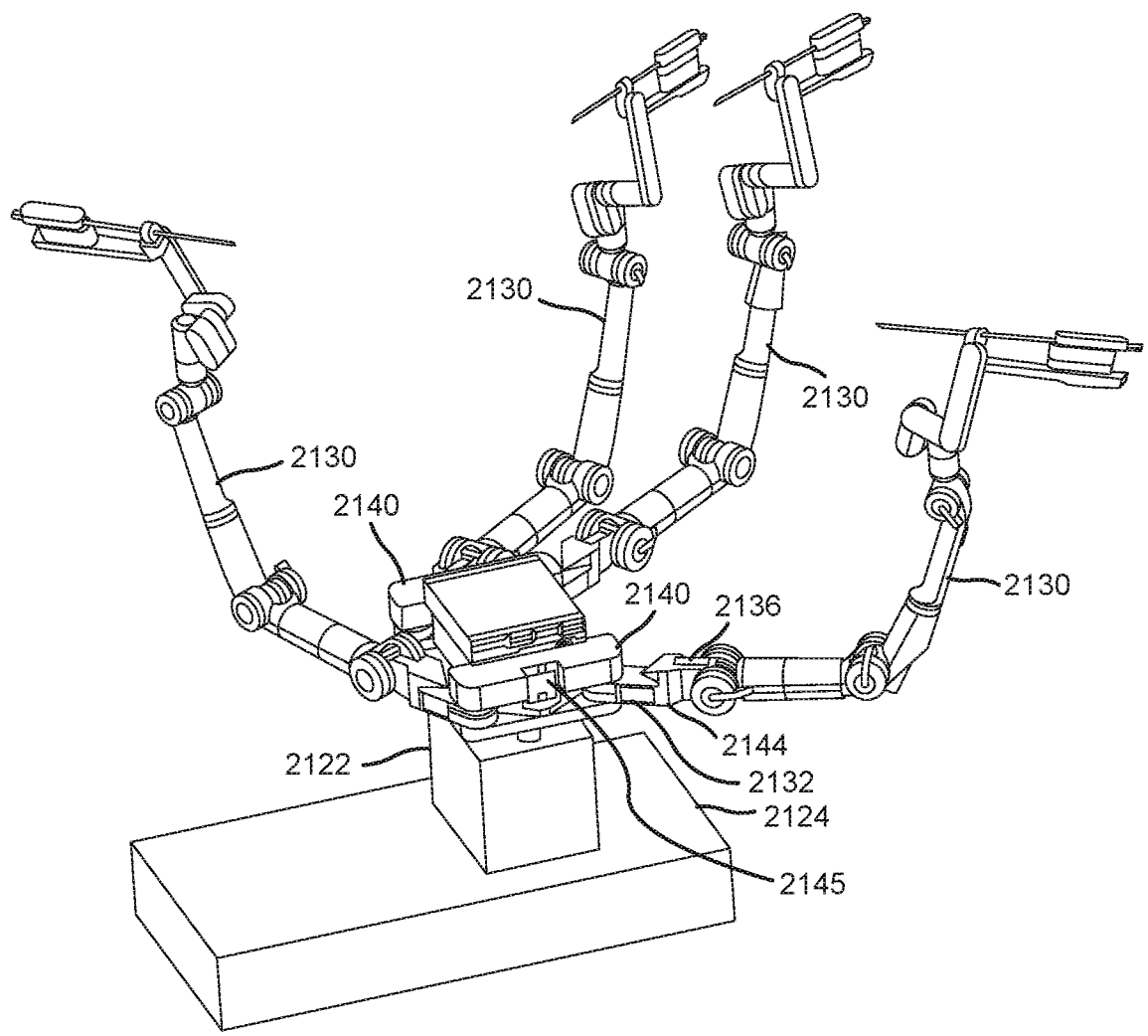
FIG. 68 is a perspective view of the adapter and surgical table (with the table top removed for illustration purposes) of FIG. 64, with two robotic arms coupled to the adapter on one side of the surgical table and two robotic arms coupled to the adapter on an opposite side of the surgical table, and the robotic arms shown in a ready position.
Figure 69:
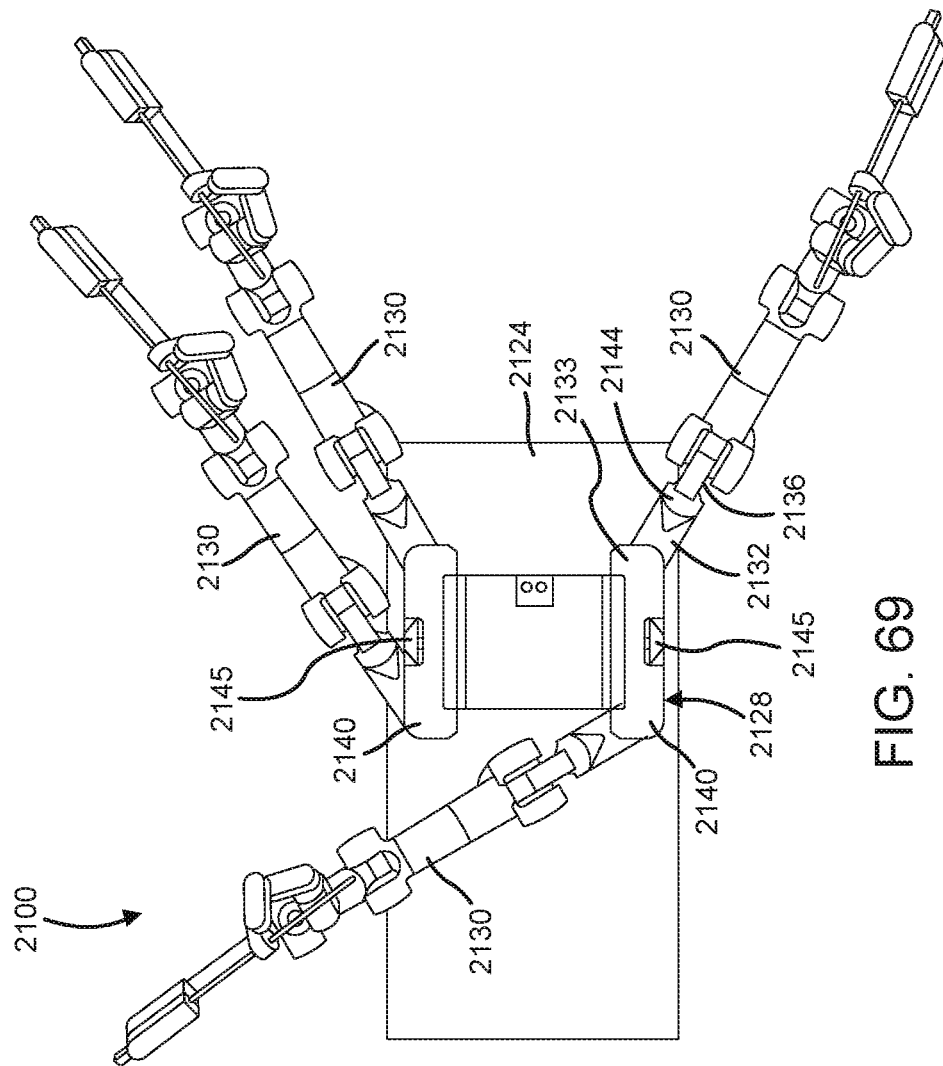
FIG. 69 is a top view of the adapter, surgical table (with the table top removed for illustration purposes) and robotic arms of FIG. 68 with the robotic arms shown in a ready position.

In this embodiment, the pivotal movement of the first joints 2133 can allow a first link member to rotate under the table top to the other side of the table as shown in FIGS. 68 and 69. FIGS. 68 and 69 illustrate two sets of first link members 2132 coupled to each of the interface mechanisms 2140 disposed on each side of the table 2100 in a similar manner as shown in FIG. 64, and no robotic arms 2130 mounted to the middle connectors 2145. Thus, if it is desired to provide for three robotic arms 2130 on one side of the table 2100, and only two arms 2130 are coupled to the adapter 2128 on each side of the table 2100, the adapter 2128 allows for one of the arms 2130 to be moved to the other side of the table 2100. Thus, if it is desired to have three arms 2130 on one side of the table 2100, the arms 2130 can be positioned on the adapter 2128 as shown in FIGS. 68 and 69, or the arms can be positioned as shown in FIGS. 66 and 67.

In this embodiment, the adapter 2128 can accommodate up to six robotic arms 2130. Each robotic arm 2130 can be releasably coupled to the adapter 2128 via the coupling members 2144 and/or the middle connectors 2145. Each robotic arm 2130 can be configured the same as or similar to, and function the same as or similar to, the robotic arms 130 described above and thus, specific details regarding the robotic arms are not discussed with respect to this embodiment. For example, as described above for robotic arms 130, the robotic arms 2130 can include multiple links or segments 2110 (see, e.g., FIGS. 71A-71B) coupled together to allow for movement of the arms 2130 between an extended configuration for use during a surgical procedure, and a folded or collapsed configuration for storage when not in use. The movement of the first link member 2132 and movement of the robotic arm at joint J1 can provide for movement of the robotic arm 2130 (and the target joint J1) along and/or about the X, Y, and/or Z axes as described in more detail below.

More specifically, as with the previous embodiments, the first joint 2133 can provide for rotational motion of the first link member 2133 relative to the table interface structure 2140 (and table 2100) about a vertical z-axis relative to a top surface of the table top, and movement of the first link member 2132 in lateral and longitudinal directions (also referred to herein as x-direction and y-direction) parallel to the top surface of the table top of the surgical table 2100 (see, e.g., X-Y axes in FIGS. 71A and 71B). 2130. Thus, the motion of the first link member 2132 and can provide for movement of the robotic arm 2130 coupled thereto along and/or about the X and/or Y axes and the joint J1 can provide for vertical movement of the remaining portion of the robotic arm 2130 (i.e., the remaining links of the robotic arm) along the Z axis, to position the target joint J1 at a desired treatment location relative to the table top.

Figure 70:
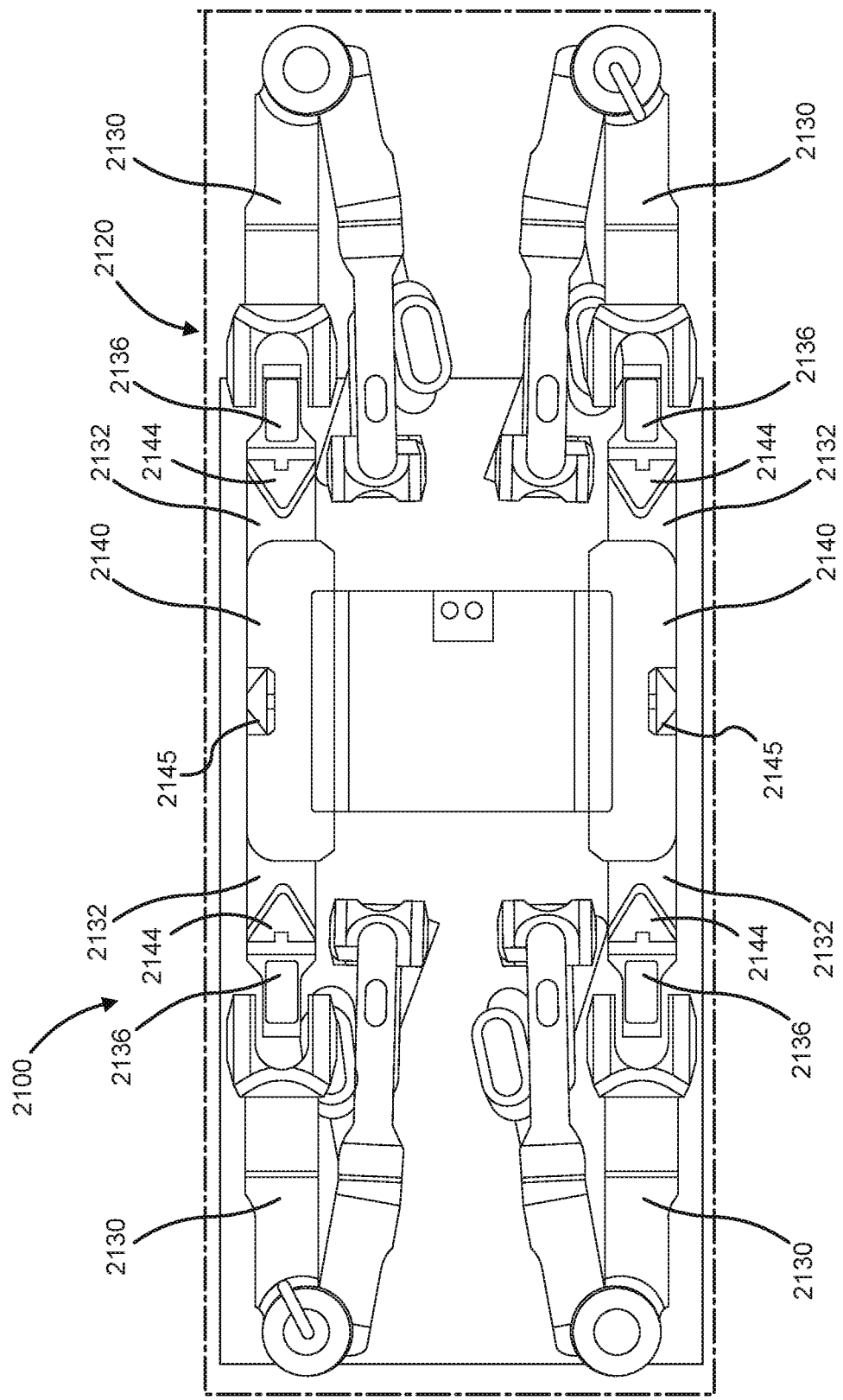
FIG. 70 is a top view of the adapter, surgical table (with the table top shown in dash line for illustration purposes) and robotic arms of FIG. 64 with the robotic arms in a stowed position.

The collective motion of the first link member 2132 and the robotic arm 2130 allows the adapter 2128 and robotic arms 2130 to move between a variety of different positions relative to the surgical table 2100 during a surgical procedure. For example, adapter 2128 and robotic arms 2130 can be moved to a stowed position substantially beneath the table top 2120 as shown, for example, in FIG. 70. FIG. 70 illustrate a stowed position with four robotic arms 2130 coupled to the adapter 2128. Thus, if more than four robotic arms 2130 are used, two of the arms 2130 may be removed in this stowed position. For example, the releasable coupling of the arms 2130 to the first link member 2132 allows for removal and recoupling of the arms 2130 at different locations on the adapter 2128 as needed. In this embodiment, the arms 2130 and the link members 2132 can be moved to the stowed position via the first joint 2133 and/or the joint J1.

For example, the arms 2130 can be lowered via the joint J1, the first link members 2132 and arms 2130 can then be pivoted to the ends via the first joints 2133. The arms 2130 can be further folded via the joints between the links/segments 2110 of the arms 2130. The arms 2130 and adapter 2128 are thus in a folded or collapsed configuration in the stowed position.

Figure 71A:
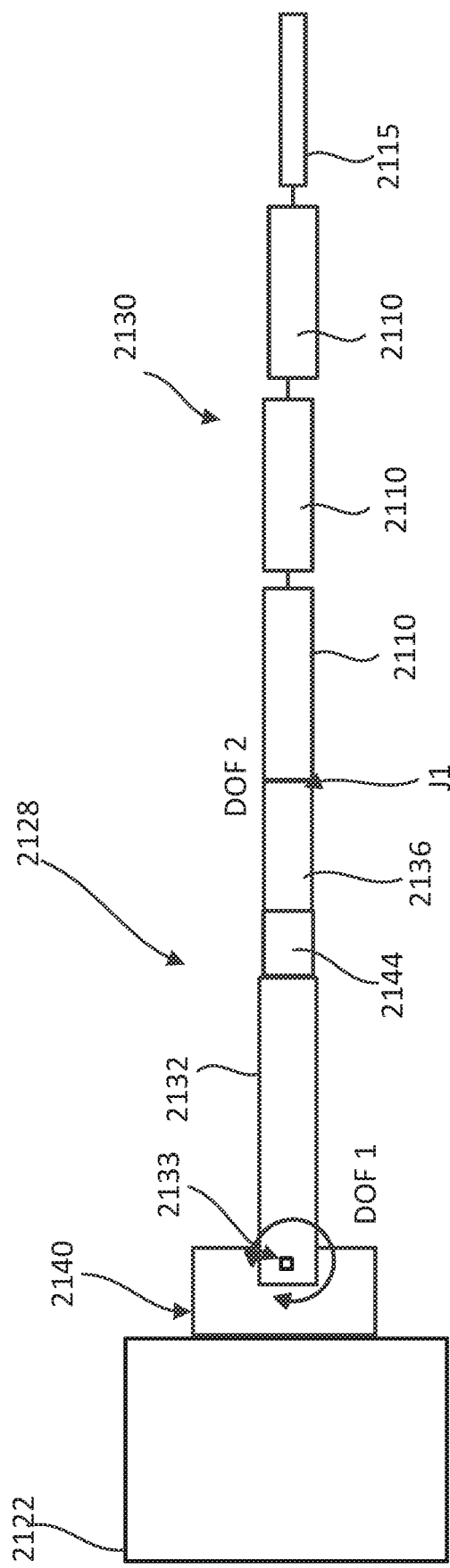

FIGS. 71A and 71B are schematic illustrations of the various degrees of freedom provided by the joints of the adapter 2128 and a robotic arm 2130, and FIG. 71C is a table listing the type of degree of freedom (e.g., rotational, linear) associated therewith. As shown in FIGS. 71A and 71B, and as described above, the interface mechanism 2140 is coupled to the support 2122 of the table 2100 and the first link members 2132 are pivotally coupled to the interface mechanism 2140 at joint 2133. The pivotal joint 2133 of the first link members 2132 to the interface mechanism 2140 allows the first link members 2132 to rotate about the z-axis and provide a first degree of freedom DOF 1. The first link members 2132 are coupled to a mounting end 2136 of a robotic arm 2130 via the coupling member 2144, and the joint J1 of the robotic arm 2130 is a pivotal joint that provides for rotational motion of the robotic arm 2130 (e.g., the remaining links/segments 2110 of the robotic arm) to pivot about a horizontal axis, i.e. an axis lying in the X-Y plane and thus provide a third degree of freedom DOF 2 (best shown in the side view illustration of FIG. 71B) that is X-Y plane rotation. Although not labeled in FIGS. 71A and 71B, the various joints between links 2110 of the arm 2130 and a medical instrument 2115 disposed on the distal end of the robotic arm 2130 can provide additional degrees of freedom relative to a patient (e.g., a target treatment location on the patient) disposed on the table 2100.

The adapter 2128 and arms 2130 can also be moved from the stowed position to various operating positions in a similar manner using the first joints 2133 and the joint J1 as described above for previous embodiments. For example, the robotic arms 2130 and adapter 2128 can be moved in various different operating positions for particular surgical procedures, such as, for example thoracic procedures and prostatectomy procedures. In the operating positions, the target joint J1 for each arm 2130 are each positioned at a target location relative to the table top 2120 such that a distal end of the arm 2130 (e.g., with medical instrument thereon) can be disposed in a desired treatment zone. As described above for FIG. 18, a range of motion or travel arc can be defined for each of the arms 2130 used for various different surgical procedures.

As described above, during a surgical procedure, the adapter 2128 and arms 2130 can also be moved to various parked positions to provide clearance for medical staff to access the patient or to provide clearance for other devices such as an imaging device. The arms 2130 and adapter 2128 can be moved to the parked position via the first joint 2133 and the second joint 2135 as described above. When the need for the clearance has passed, the arms 2130 can then be placed back into the operating position with the target joints J1 disposed at the target treatment locations relative to the table top 2120.

Figure 72:
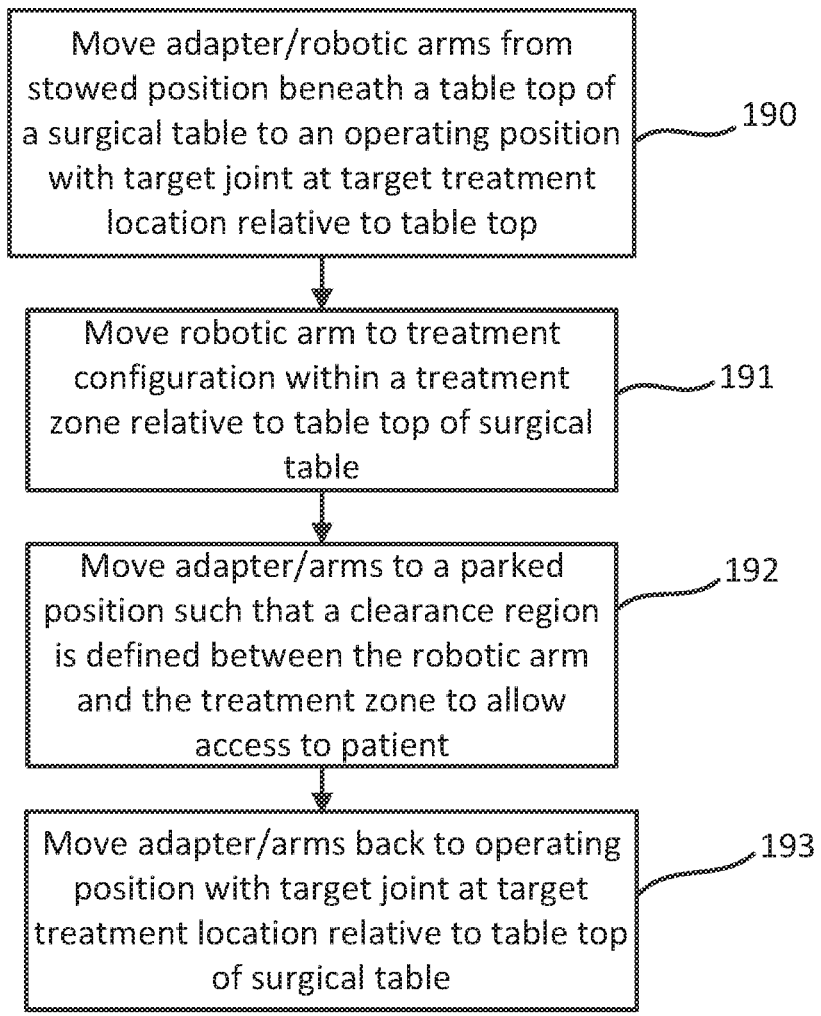
FIG. 72 is a flowchart of a method of using an adapter to move robotic arms during a surgical procedure.

FIG. 72 is a flowchart of a method of moving a robotic arm during a surgical procedure, according to an embodiment. At 190, a table adapter and a robotic arm are moved from a stowed position relative to a surgical table to an operating position where a target joint (i.e., joint J1) is positioned in a target location to perform a surgical procedure. As described herein, in the stowed position, the adapter and robotic arms can be disposed entirely beneath or substantially beneath the table top and within or substantially within an outer perimeter defined by the table top. As described herein, the operating position can be a position in which the target joint is disposed at a desired operating position relative to the table top such that a particular surgical procedure can be performed on a patient disposed on the table top using the robotic arm. At 191, while maintaining the target joint at the operating position, the robotic arm can be moved to a treatment configuration within a treatment zone relative to the table top. The treatment zone can be, for example, a target treatment area to perform a surgery on a patient disposed on the table top. At 192, during a surgical procedure, the adapter and robotic arm can be moved to a parked position relative to the table top, such that a clearance region is defined between the adapter/robotic arm and the treatment zone to allow access to the patient disposed on the table top. For example, as described herein, the robotic arm can be moved or slid longitudinally along a length of the table top, pivoted relative to the table top, and/or moved laterally away from the table top. In some cases it may be desirable to entirely remove the robotic arm from the surgical table to define the clearance area. At 193, the adapter and robotic arm can be moved back to the operating position.

Although not described for all embodiments, any of the embodiments of an adapter can be manually controlled or motor driven. For example, some or all of the motion of the various constituent components of an adapter can be operatively coupled to a drive motor that can be controlled and operated by a user (e.g., medical professional). Further, any of the embodiments can be operatively coupled to a computer system configured to operate and control the movement of the various components of an adapter as well as movement of the robotic arms coupled thereto. Although not all features of each embodiment of an adapter were described for all embodiments, it should be understood that any of the various features described herein can be included or added to any embodiment.

In addition, although not necessarily described for each embodiment, any of the embodiments described herein can include an adapter with more than two link members or only one link member. The various embodiments of a robotic surgical system described herein can include a table top on which a patient can be disposed, an adapter, and one or more link members. As described above, in some embodiments, the robotic arm can be incorporated into the adapter (e.g., an adapter/robotic arm assembly) and be coupled to a surgical table or be coupleable to a surgical table. The adapters and the robotic arms (or in the case of an adapter/robotic arm assembly) can include one or more links or link members to allow for movement of the adapter and/or arms about and/or along the X, Y, and/or Z axes, to a desired location relative to the table top and/or relative to a patient disposed thereon.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A method performed by a robotic surgical system comprising a surgical table having a table top supported by a vertical support that rises from a base that is to rest on a floor, the table top includes a left side and a right side opposite the left side, each side running a long a longitudinal axis of the table top, the method comprising:

moving at a first time period, a robotic arm and a link member of an adapter that is coupled to the robotic arm, the adapter being coupled to the surgical table via an interface structure of the adapter that is coupled to a bottom surface of the table top and is supported by the vertical support, the interface structure has at least four corners and no portion of the interface structure is outside an outer perimeter of the table top, wherein the adapter includes at least four joints, each joint is positioned at a respective one of the four corners of the interface structure and is configured to rotate about a respective vertical axis that extends through the interface structure and the table top, wherein the link member is coupled to one of the four first joints, wherein the robotic arm and the link member are moved at the first period of time from a stowed position relative to the table top, in which the robotic arm and the link member are disposed beneath a bottom surface of the table top and the robotic arm and the link member are not disposed outside the outer perimeter of the table top on at least one of the left side or the right side of the table top, to an operating position in which a target joint of the robotic arm is disposed at a target treatment location relative to the table top of the surgical table;

while maintaining the target joint at the target treatment location, moving the robotic arm to a treatment configuration within a treatment zone relative to the table top;

during a surgical procedure performed on a patient disposed on the table top, moving the robotic arm and the link member to a parked position relative to the table top such that a clearance region is defined between the robotic arm and the treatment zone to allow access to the patient disposed on the table top; and after moving the robotic arm and the link member to the parked position, moving the robotic arm and the link member to the operating position such that the target joint is disposed at the target treatment location at a second time period after the first time period.

2. The method of claim 1, further comprising:

after moving the robotic arm and the link member to the parked position, positioning an imaging device within the clearance region to take an image of a portion of the patient.

3. The method of claim 1, further comprising:

after moving the robotic arm to the treatment configuration, performing the surgical procedure on the patient using the robotic arm.

4. The method of claim 1, further comprising:

after moving the robotic arm and the link member to the operating position at the second time period, performing the surgical procedure on the patient using the robotic arm.

5. The method of claim 4, further comprising:
after moving the robotic arm and the link member to the operating position at the second time period and after performing the surgical procedure on the patient using the robotic arm, moving the robotic arm and the link member to the stowed position.

6. An adapter for coupling at least four robotic arms to a surgical table, the surgical table having a table top supported by a vertical support that rises from a base that is to rest on a floor, the adapter comprising:
an interface structure having at least four corners, the interface structure configured to be supported by the vertical support of the surgical table while affixed to a bottom side of the table top, wherein a top side of the table top is to support a patient thereon during surgery, and no portion of the interface structure is outside an outer perimeter of the table top; and
at least four joints each joint being formed at a respective one of the four corners, each joint being configured to 1) rotate about a respective vertical axis that extends through the interface structure and the table top and 2) couple to a respective one of the four robotic arms, the interface structure and the four joints being configured so that two of the at least four joints are disposed on a left side of the table top and another two of the at least four joints are disposed on a right side of the table top,
wherein the left side and the right side both run along a longitudinal axis of the table top,
wherein the interface structure and the at least four joints are configured so that each of the robotic arms can be moved independently with respect to the interface structure and each other, between i) a first position in which the robotic arms are disposed beneath a plane defined by the bottom side of the table top and all of the robotic arms are inward of the left side and the right side of the table top, and a second position in which at least a portion of at least one of the robotic arms is disposed above the plane defined by the bottom side of the table top.

7. The adapter of claim 6, wherein when in the first position, the interface structure, the at least four joints, and the robotic arms are each disposed within the outer perimeter of the table top.

8. The adapter of claim 6, wherein when in the first position, no portion of the interface structure, the at least four joints, or any of the robotic arms are disposed outside an outer perimeter of the table top on at least one of the left side of the table top and the right side of the table top.

9. The adapter of claim 6, wherein the at least four joints are first joints, wherein the adapter includes a plurality of first link members that are each pivotally coupled to the interface structure at a different first joint, at least one first link member is configured to couple to a second link member of the adapter at a second joint,
the second link member is configured to couple to a robotic arm of the at least four robotic arms via a coupling between the robotic arm and the second link member.

10. The adapter of claim 9, wherein each first joint provides for a respective first link member to rotate about the respective vertical axis relative to a top surface of the table top, the second joint provides a lift mechanism to move the second link member and a robotic arm coupled thereto in a vertical direction relative to the table top.

11. The adapter of claim 9, wherein the at least one first link member and the second link member collectively provide for movement of the robotic arm in at least one of a lateral, a longitudinal or a vertical direction relative to the table top.

12. The adapter of claim 9, wherein the second joint includes a pivotal coupling between the at least one first link member and the second link member.

13. The adapter of claim 9, wherein the second joint includes a linear motion mechanism configured to allow the second link member to slidably move relative to the at least one first link member.

14. The adapter of claim 6, wherein the adapter is configured to couple to the surgical table above the vertical support.

15. The adapter of claim 6, wherein each of the at least four joints is formed at an opening of the respective one of the four corners.

16. The adapter of claim 6, wherein each of the at least four joints is disposed between a top portion of the interface structure and a bottom portion of the interface structure.

17. An apparatus, comprising
a surgical table having a table top supported by a vertical support that rises from a base that rests on a floor, the table top having a first side and a second side opposite the first side, both sides run along a longitudinal axis of the table top; and
an adapter comprising an interface structure and at least four joints, the adapter is coupled to the surgical table via the interface structure that is fixedly coupled to a bottom surface of the table top and is supported by the vertical support, wherein the interface structure has at least four corners and no portion of the interface structure is outside an outer perimeter of the table top,
wherein each of the at least four joints is positioned at a respective one of the four corners of the interface structure, each joint being configured to 1) rotate about a respective vertical axis that extends through the interface structure and the table top and 2) couple to a respective one of four robotic arms, wherein the interface structure and the at least four joints being configured so that two of the at least four joints are disposed on the first side of the table top and another two of the at least four joints are disposed on the second side of the table top,
wherein the interface structure and the at least four joints are configured so that each of the robotic arms can be moved independently with respect to the interface structure and each other, between
a first position in which the robotic arms are disposed beneath a plane defined by the bottom surface of the table top and all of the robotic arms are inward on the first side of the table top and the second side of the table top, and
a second position in which at least a portion of at least one of the robotic arms is disposed above the plane defined by the bottom surface of the table top.

18. The apparatus of claim 17, wherein the interface structure is fixedly coupled to the bottom side of the table top in a horizontal direction with respect to the table top, wherein the apparatus further comprises one or more rails along which the interface structure is configured to move vertically up and down relative to the support.

19. The apparatus of claim 17, wherein when in the first position, the interface structure, the at least four joints, and the robotic arms are each disposed within the outer perimeter of the table top.

20. The apparatus of claim 17, wherein when in the first position, no portion of the interface structure, the at least four joints, or any of the robotic arms are disposed outside an outer perimeter of the table top on at least one of the first side of the table top and the second side of the table top.

21. The apparatus of claim 17, wherein the at least four joints are first joints, wherein the adapter includes a plurality of first link members that are each pivotally coupled to the interface structure at a different first joint, at least one first link member is configured to couple to a second link member of the adapter at a second joint,
the second link member is configured to couple to a robotic arm via a coupling between the robotic arm and the second link member.

22. The apparatus of claim 21, wherein each first joint provides for a respective first link member to rotate about the respective axis relative to atop surface of the table top, the second joint provides a lift mechanism to move the second link member and a robotic arm coupled thereto in a vertical direction relative to the table top.

23. The apparatus of claim 21, wherein the at least one first link member and the second link member collectively provide for movement of the robotic arm in at least one of a lateral, a longitudinal or a vertical direction relative to the table top.

24. The apparatus of claim 21, wherein the second joint includes a pivotal coupling between the at least one first link member and the second link member.

25. The apparatus of claim 21, wherein the second joint includes a linear motion mechanism configured to allow the second link member to slidably move relative to the at least one first link member.

26. An apparatus comprising:
a surgical table having a table top supported by a vertical support that rises from a base that rests on a floor, the table top having a left side and a right side opposite to the left side, both sides running along a longitudinal axis of the table top; and
an adapter coupled below the table top, the adapter having an interface structure with at least four corners, the interface structure configured to be supported by the vertical support of the surgical table while joined at a bottom side of the table top, wherein no portion of the interface structure is outside an outer perimeter of the table top,
at least four first joints, each formed at a respective one of the four corners and is configured to rotate about a respective vertical axis that extends through the interface structure and the table top,
for each of the first joints, 1) a first link member pivotally coupled directly to the interface structure at the first joint, and 2) a second link member that is coupled to the first link member at a second joint,
wherein each of the second link members is configured to removably couple to a respective robotic arm via a coupling between the respective robotic arm and the second link member,
wherein at least one of the at least four first joints providing for the first link member to rotate about a first axis defined in a vertical direction relative to a top surface of the table top, the second joint comprises a lift mechanism to move the second link member and the respective robotic arm coupled thereto in a vertical direction relative to the top surface of the table top,
wherein the first link member and the second link member collectively provide for movement of the respective robotic arm in at least one of a lateral, longitudinal, or vertical direction relative to the top surface of the table top.

27. The apparatus of claim 26, wherein the at least one of the at least four first joints includes a pivotal coupling between the first link member and the interface structure, the second joint includes a pivotal coupling between the first link member and the second link member.

28. The apparatus of claim 26, wherein the at least one of the at least four first joints includes a pivotal coupling between the first link member and the interface structure, the second joint includes a linear motion mechanism configured to allow the second link member to slidably move relative to the first link member.

29. The apparatus of claim 26, wherein the interface structure is fixedly attached to the surgical table between the table top and the vertical support such that a top side of the interface structure is joined to the bottom side of the table top and a bottom side of the interface structure is joined to a top side of the vertical support.

30. The apparatus of claim 26, wherein the interface structure comprises a first mounting portion on the left side that includes two first joints of the at least four joints and a second mounting portion on the right side that includes another two first joints of the at least four joints.

31. The apparatus of claim 30, wherein the respective robotic arm is a first robotic arm, wherein at least one of the mounting portions includes a middle connector disposed at a middle location between the two first joints of the at least one of the mounting portions, wherein a second robotic arm is configured to removably couple to the middle connector.

32. The apparatus of claim 26, wherein the adapter includes a third link member pivotally coupled to the interface structure at the at least one first joint, the third link member coupled to a fourth link member at a third joint,
the fourth link member coupled to another robotic arm via a coupling.

33. The apparatus of claim 32, wherein the at least one of the at least four first joints is disposed at an end portion of the vertical support.

34. The apparatus of claim 26, wherein the movement of the first link member relative to the interface structure is motor driven.

35. The apparatus of claim 26, wherein the movement of the first link member relative to the interface structure is motor driven, and movement of the second link member relative to the first link member is motor driven.

* * * * *